US007671033B2

(12) United States Patent
Percec

(10) Patent No.: US 7,671,033 B2
(45) Date of Patent: Mar. 2, 2010

(54) AMPHIPHILIC DENDRITIC DIPEPTIDES AND THEIR SELF-ASSEMBLY INTO HELICAL PORES

(75) Inventor: Virgil Percec, Philadelphia, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/171,494

(22) Filed: Jul. 1, 2005

(65) Prior Publication Data

US 2006/0088499 A1 Apr. 27, 2006

Related U.S. Application Data

(60) Provisional application No. 60/584,169, filed on Jul. 1, 2004.

(51) Int. Cl.
*A61K 9/00* (2006.01)
*A61K 38/05* (2006.01)
*A61K 47/42* (2006.01)
*G01N 33/00* (2006.01)

(52) U.S. Cl. ............... 514/19; 424/400; 424/DIG. 16; 427/2.1; 514/773; 530/345; 564/164; 564/193

(58) Field of Classification Search ................ None
See application file for complete search history.

(56) References Cited

U.S. PATENT DOCUMENTS

| | | | | |
|---|---|---|---|---|
| 5,731,095 A | | 3/1998 | Milco et al. ................ | 428/482 |
| 5,834,020 A | * | 11/1998 | Margerum et al. .......... | 424/484 |
| 5,872,255 A | | 2/1999 | Attias et al. ................ | 546/257 |
| 5,886,110 A | | 3/1999 | Gozzini et al. ............. | 525/472 |
| 6,020,457 A | | 2/2000 | Klimash et al. ............ | 528/373 |
| 6,077,500 A | | 6/2000 | Dvornic et al. ....... | 424/DIG. 16 |
| 6,136,921 A | | 10/2000 | Hsieh et al. ................ | 525/107 |
| 6,232,293 B1 | * | 5/2001 | Anderson et al. ............. | 514/19 |
| 6,312,809 B1 | | 11/2001 | Crooks et al. ............ | 428/411.1 |
| 6,733,883 B2 | | 5/2004 | Percec ....................... | 428/403 |

OTHER PUBLICATIONS

Chedid et al. Enhancement of certain biological activities . . . Proceedings of the National Academy of Sciences USA. Dec. 1979, vol. 76, No. 12, pp. 6557-6561.*
Jang et al. Dendritic Physical Gels . . . Macromolecules. Oct. 2, 2003, vol. 36, No. 22, pp. 8461-8469.*
Percec et al. Self-assembly of amphiphilic dendritic dipeptides into helical pores. Nature. Aug. 12, 2004, vol. 430, Issue 7001, pp. 764-768.*
Percec et al. Solvophobically Driven Self-Assembly Of Chiral Supramolecular Dendrimers. Polymer Preprints. 2002, vol. 43, No. 2, pp. 458-459.*
King et al. Monoclonal Antibody Conjugates of Doxorubicin . . . Journal of Medicinal Chemistry. 2002, vol. 45, No. 19, pp. 4336-4343.*

Anderson, A.G.., et al., "A convenient two-step synthesis of 2,6-Di-tert-butyl-4-methylpyridine, a sterically hindered nonnucleophilic base," J. Org. Chem., 1976, 41(18), 3034-3036.
Balagurusamy, V.S.K., et al., "Rational design of the first spherical supramolecular dendrimers silf-organized in a novel thermotropic cubic liquid-crystalline phase and the determination of their shape by x-ray analysis," J. Am. Chem. Soc., 1997, 119, 1539-1555.
Bayley, H., et al., "Stochastic sensors inspired by biology," Nature, 2001, 413, 226-230.
Bong, D.T., et al., "Self-assembling organic nanotubes," Angew. Chem. Int. Ed., 2001, 40, 989-1011.
Brunsveld, L., et al., "Hierarchical growth of chiral self-assembled structures in protic media," J. Am. Chem. Soc., 2000, 122, 6175-6182.
Chedid, L., et al., "Enhancement of certain biological activities of muramyl dipeptide derivatives after conjugation to a multi-poly(DL-alanine)-poly(L-lysine) carrier,", Proc. Of the Nat. Acad. Sci. USA, 1979, 76(12), 6557-6561.
Cornelissen, J.L.M., et al., "β-Helical polymers from isocyanopeptides," Science, 2001, 293, 676-680.
Cronin, J.S., et al., "An improved procedure for the large scale preparation of 2-chloro-4,6-dimethoxy-1,3,5-triazine," Synthetic Comm., 1996, 26(18), 3491-3494.
Doyle, D.A., et al., "The structure of the potassium channel: molecular basis of $K^+$ conduction and selectivity," Science, 1998, 280, 69-77.
Emrick, T., et al., "Self-assembly of dendritic structures," Curr. Opin. Col. & Interf. Sci., 1999, 4, 15-23.
Endres, A., et al., "X-ray absolute intensity measurement at HASYLAB ultrasmall angle x-ray scattering beamline BW4," Rev. Sci. Instr., 1997, 68(11), 4009-4013.
Engelkamp, H., et al., "Self-assembly of disk-shaped molecules to coiled-coil aggregates with tunable helicity," Science, 1999, 284, 785-788.
Fernandez-Lopez, S., et al., "Antibacterial agents based on the cyclic D,L-α-peptide architecture," Nature, 2001, 412, 452-455 (correction page for this publication is 329 attached).
Finikova, O., et al., "Porphyrin and tetrabenzoporphyrin dendrimers: tunable membrane-impermeable fluorescent pH nanosensors," JACS, 2003, 125, 4882-4893.
Gacel, G., et al., "Evidence of the preferential involvement of µ receptors in analgesia using enkephalins highly selective for peripheral µ or δ receptors," J. Med. Chem., 1981, 24, 1119-1124.
Ghadiri, M.R., et al., "Artificial transmembrane ion channels from self-assembling peptide nanotubes," Nature, 1994, 369, 301-304.
Ghadiri, M.R., et al., "Self-assembling organic nanotubes based on a cyclic peptide architecture," Nature, 1993, 366, 324-327.
Hill, D.J., et al., "A field guide to foldamers," Chem. Rev., 2001, 101, 3893-4011.
Hirschberg, J.H.K.K., et al., "Helical self-assembled polymers from cooperative stacking of hydrogen-bonded pairs," Nature, 2000, 407, 167-170.
Hudson, S.D., et al., "Direct visualization of individual cylindrical and spherical supramolecular dendrimers," Science, 1997, 278, 449-452.

(Continued)

*Primary Examiner*—Jeffrey E Russel
(74) *Attorney, Agent, or Firm*—Woodcock Washburn, LLP

(57) ABSTRACT

An amphiphilic dendritic dipeptide, comprises a dipeptide(s) comprising one or more of a naturally occurring or synthetic amino acids and a dendron. These are suitable for use in various formulations, films, coatings, membranes and sensors, among other applications.

9 Claims, 10 Drawing Sheets

OTHER PUBLICATIONS

Hue Sun Chan, et al., "Models of cooperativity in protein folding," Phil. Trans. R. Soc., Lond. B., 1995, 348, 61-70.

Hummer, G., et al., "Water conduction through the hydrophobic channel of a carbon nanotube," Nature, 2001, 414, 188-190.

Ishii, D., et al., "Chaperonin-mediated stabilization and ATP-triggered release of semiconductor nanoparticles," Nature, 2003, 423, 628-632.

Johansson, G., et al., "Molecular recognition directed self-assembly of tubular liquid crystalline and crystalline supramolecular architectures from taper shaped (15-crown-5)methyl 3,4,5-Tris(p-alkyloxybenzyloxy)benzoates and (15-crown-5)methyl 3,4,5-Tris(p-dodecyloxy)benzoate," J. Chem. Soc. Perkins 1, 1994, 447-459.

Klug, A., "From macromolecules to biological assemblies," Angew. Chem. Int. Ed. Eng., 1983, 22, 565-582.

Lehn, J.-M., ""Bouquet"-type molecules and the "chaundle" approach to molecular channels," *Supramolecular Chemistry. Concepts and Perspectives*, VCH, Weinheim, 1995, 118-120.

Murata, K., et al., "Structural determinants of water permeation through aquaporin-1," Nature, 2000, 407, 599-605.

Nelson, J.C., et al., "Solvophobically driven folding of nonbiological oligomers," Science, 1997, 277, 1793-1796.

Percec, V., et al., "Synthesis of functional aromatic multisulfonyl chlorides and their masked precursors," J. Org. Chem., 2001, 66, 2104-2117.

Percec, V., et al., "Visualizable cylindrical macromolecules with controlled stiffness from backbones containing libraries of self-assembling dendritic side groups," J. Am. Chem.. Soc., 1998, 120, 8619-8631.

Percec, V., et al., "Synethesis and structural analysis of two constitutional isomeric libraries of $AB_2$-based monodendrons and supramolecular dendrimers," J. Am. Chem. Soc., 2001, 123, 1302-1315.

Percec, V., et al., "Increasing the diameter of cylindrical and spherical supramolecular dendrimers by decreasing the solid angle of their monodendrons via periphery functionalization," J. Am. Chem. Soc., 2000, 122, 10273-10281.

Percec, V., et al., "Transformation of a spherical supramolecular dendrimer into a pyramidal columnar supramolecular dendrimer mediated by the fluorophobic effect," Angew. Chem. Int. Ed., 2003, 42, 4338-4342.

Percec, V., et al., "Controlling polymer shape through the self-assembly of dendritic side-groups," Nature, 1998, 391, 161-164.

Percec, V., et al., "Self-organization of supramolecular helical dendrimers into complex electronic materials," Nature, 2002, 419, 384-387.

Percec, et al., "Self-assembly of amphiphilic dendritic dipeptides into helical pores," Nature, 2004, 430(7001), 764-768.

Percec, et al., "Solvophobically driven self-assembly of chiral supramolecular dendrimers," Polymer Preprints, 2002, 43(2), 458-459.

Percec, V., et al., "Synthesis and NaOTf mediated self-assembly of monodendritic crown-ethers," Chem. Eur. J., 2002, 8, 2011-2025.

Rappolt, M., et al., "Mechanism of the lamellar/inverse hexagonal phase transition examined by high resolution x-ray diffraction," Biophys. J., 2003, 84, 3111-3122.

Rigaud, J.-L., et al., "Reconstitution of membrane proteins into liposomes: application to energy-transducing membrane proteins," Biophys. Acta, 1995, 1231, 223-246.

Sakai, N., et al., "Synthetic multifunctional pores: lessons from rigid-rod β-barrels," Chem. Commun., 2003, 2514-2523.

Schmitt, J.-L., et al., "Helicity-encoded molecular strands: efficient access by the hydrazone route and structural features," Helv. Chim. Acta, 2003, 86, 1598-1624.

Turner, D.C., et al., "X-ray diffraction reconstruction of the inverted hexagonal ($H_{II}$) phase in lipid-water systems," Biochemistry, 1992, 31, 1340-1355.

Ungar, G., et al., "Self-assembly of twin tapered bisamides into supramolecular columns exhibiting hexagonal columnar mesophases. Structural evidence for a microsegregated model of the supramolecular column," Liq. Cryst., 1996, 21, 73.

Vainshtein, B.K., et al., *Deffraction of X-rays by Chain Molecules*, Elsevier, NY, 1966, Table of Contents, 1-414.

van den Berg, B., et al., "X-ray structure of protein conducting channel," Nature, 2004, 427, 36-44.

Wardrop, D.J., et al., "$N$-methoxy-$N$-acylnitrenium Ions: Application to the formal synthesis of (−)-TAN1251A," Org. Lett., 2001, 3(7), 1053-1056.

Weissflog, W., et al., "From laterally branched mesogens to novel twin molecules," Liq. Cryst. 5(1), 1989, 111-122.

Woo-Dong Jang, et al., "Dendritic physical gel: hierarchical self-organization of a peptide-core dendrimer to form a micrometer-scale fibrous assembly," J. Am. Chem. Soc., 2000, 122, 3232-3233.

Woo-Dong Jang, et al., "Dendritic Physical Gels: Structural parameters for gelation with peptide-core dendrimers," Macromolecules, 2003, 36(22), 8461-8469.

Xiangbing Zeng, et al., "Lamellar structure of non-integer folded and extended long-chain n-alkanes by small-angle x-ray diffraction," Polymer, 1998, 39, 4523-4533.

\* cited by examiner

Scheme III

Scheme IV

Scheme VII A

Scheme VII B and C

AMPHIPHILIC DENDRITIC DIPEPTIDES AND THEIR SELF-ASSEMBLY INTO HELICAL PORES

This application claims the benefit of U.S. Provisional Patent Application No. 60/584,169, filed Jul. 1, 2004, the contents of which is hereby incorporated by reference in its entirety.

BACKGROUND OF THE INVENTION

1. Field of the Invention

This invention relates to amphiphilic dendritic dipeptides that are self-assembled from a dipeptide(s) and a dendron, and to their applications.

2. Description of the Background

Natural pore forming proteins act as viral helical coats and transmembrane channels, exhibit antibacterial activity and are used in synthetic systems, such as for reversible encapsulation or stochastic sensing. These diverse functions are intimately linked to protein structure. The close link between protein structure and protein function makes the design of synthetic mimics a formidable challenge, given that structure formation needs to be carefully controlled on all hierarchy levels, in solution and in the bulk. In fact, most synthetic pore structures are not simultaneously capable of forming periodically ordered assemblies that are stable in solution and in the solid state. In fact, up to the present time only closed dendrimer columns have been produced by covalent and non-covalent coating and assembly of a range of different structures.

Accordingly, there is a need for a simple and effective method of forming porous structures that form periodically ordered assemblies that are stable in solution and in the solid state, which structures have anti-microbial activity. Such structures have multiple useful applications.

SUMMARY OF THE INVENTION

This invention relates to an amphiphilic dendritic dipeptide that comprises a dipeptide(s) formed by one or more of a naturally occurring or synthetic non-polar amino acid, a polar amino acid, an aromatic amino acid and/or a sulfur-containing amino acid; and a dendron.

The amphiphilic dendritic dipeptide is also provided in the form of a composition, formulations, films, coatings, capsules, membranes and sensors, among others. These products are useful for applications in the fields of pharmaceutical, veterinary and agricultural delivery, stochastic sensors, membrane channeling, among many others.

The dendritic dipeptides of the invention may be prepared by forming a dendron comprising one or more arms, forming a dipeptide from a polar or non-polar amino acid(s) and/or an aromatic or sulfur-containing amino acid(s), and contacting the dendron and the peptide under conditions effective for operatively attaching the dipeptide to the dendron and allowing their self-assembly into a pore-comprising amphiphilic dendritic dipeptide.

Other objects, advantages and features of the present invention will become apparent to those skilled in the art from the description of the drawings that accompany this patent.

Other objects, advantages and features of the present invention will become apparent to those skilled in the art from the following discussion.

Figure 4:
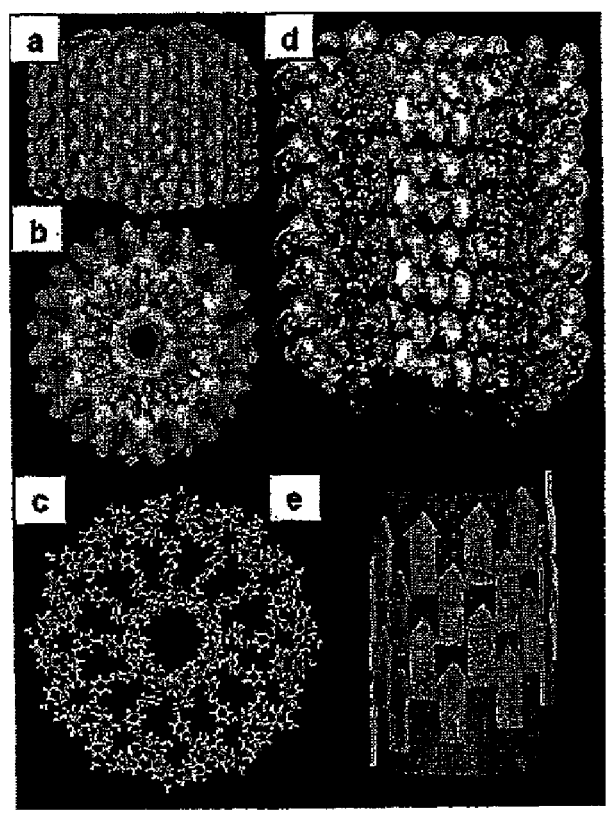

FIG. 4 shows Scheme VIII below shows the molecular models of the helical porous columns self-assembled from (4-3,4-3,5)12G2-CH2-Boc-L-Tyr-L-Ala-OMe (for simplicity n=12 was replaced with n=1). a shows a side-view of the right handed column. b shows a top-view of a. c provides a top view of a single porous column layer, d is a cross-section through the hydrophobic pore (without dendrons) showing its b-barrel structure assembled from the b-helical dipeptides, and e provides a schematic model for the self-assembly of the dipeptidic b-barrel pore.

Figure 5:
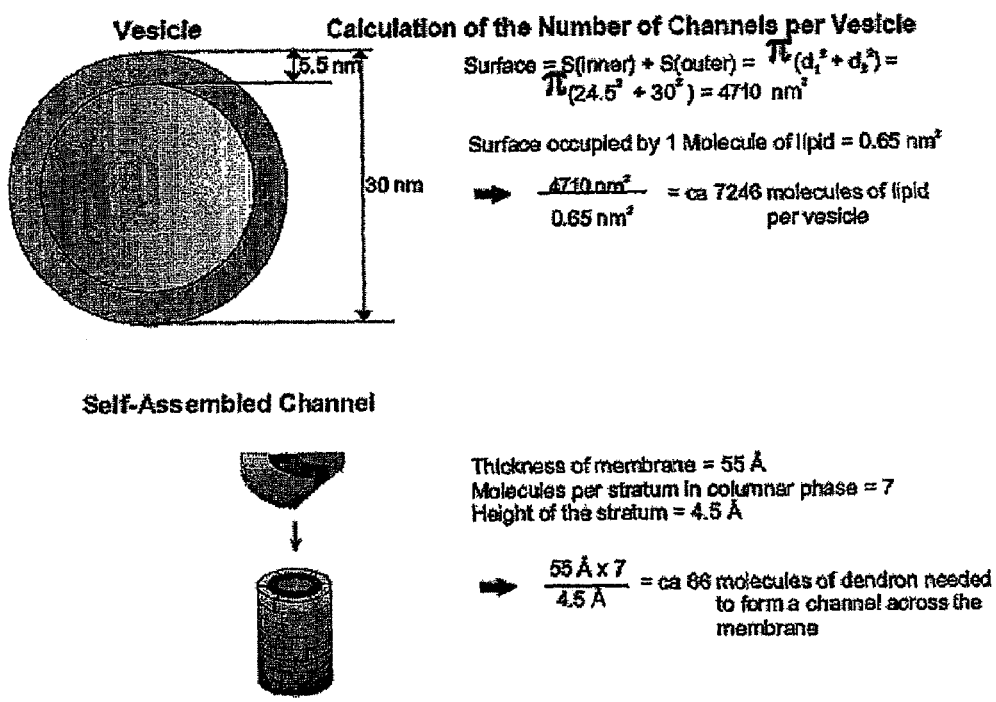

FIG. 5 shows calculation of the number of channels per vesicle.

Figure 6:
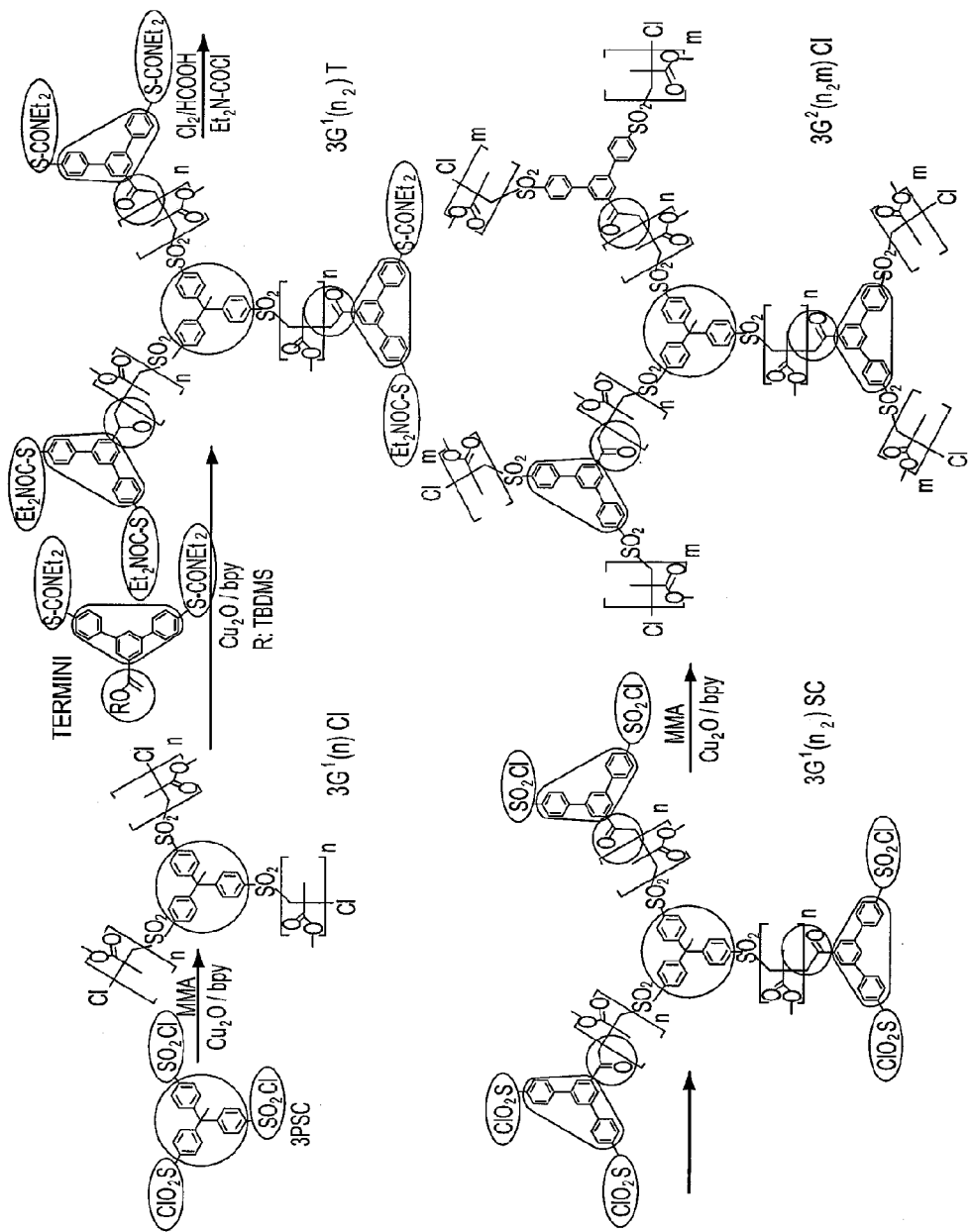

FIG. 6 depicts the synthesis of a first generation dendritic poly (methyl methacrylate) based on a TERMINI compound in conjunction with the trifunctional initiator 1,1,1-tris (4-chloro sulfonyl phenyl) ethane ("3PSC") and methyl methacrylate.

Figure 7:
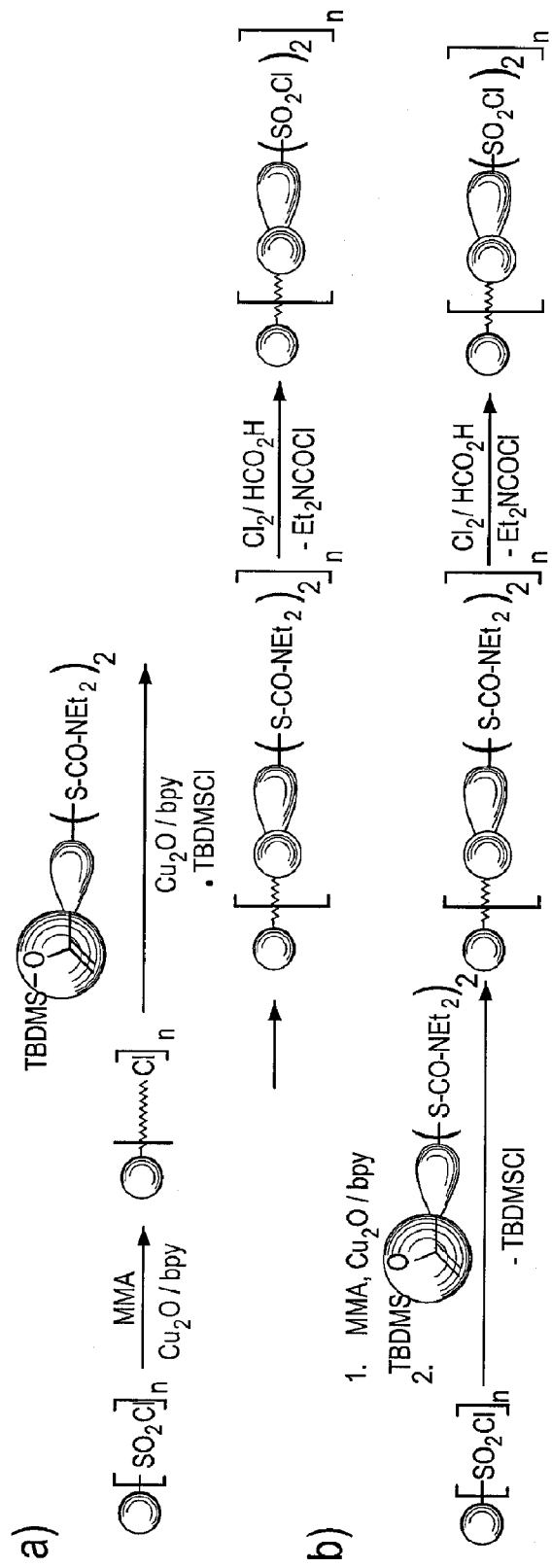

FIG. 7 illustrates one method for synthesis of dendritic macromolecules.

Figure 8:
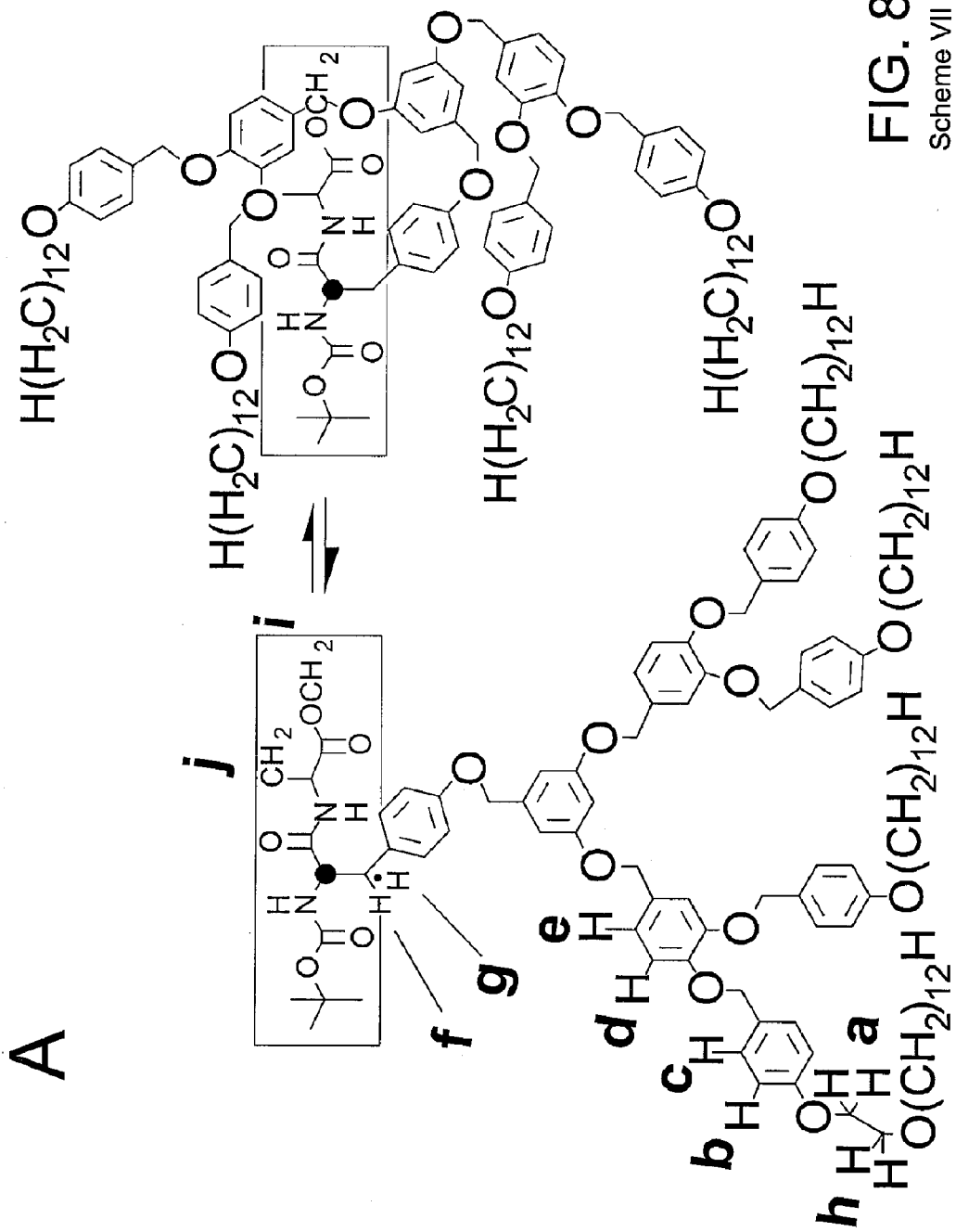

FIG. 8 shows trans-tapered low temperature (left) and a globular high temperature conformers of L-L stereoisomer (right).

Figure 9:
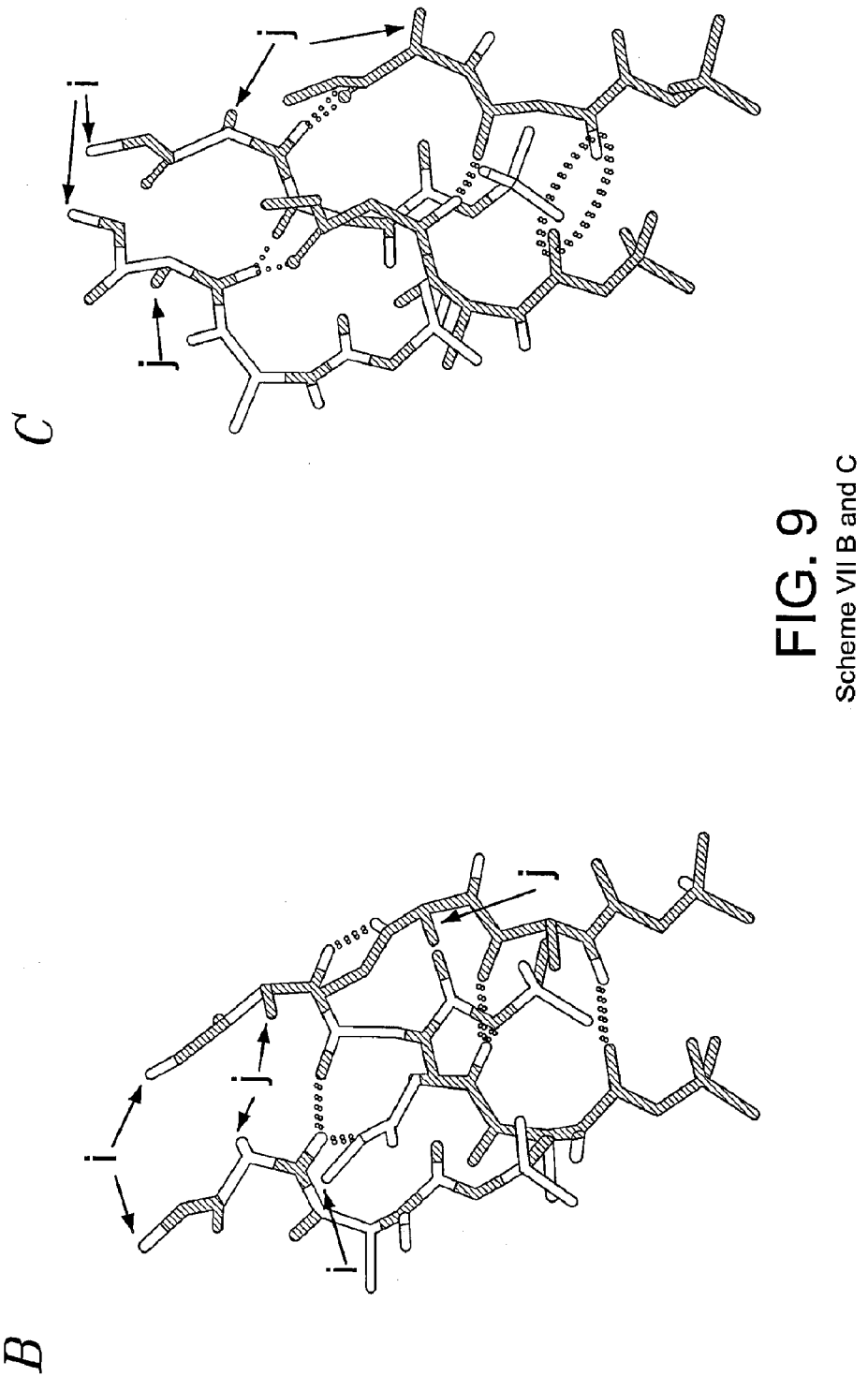

FIG. 9 depicts H bonding interactions of the L-L dipeptide forming the pore (b) and H bonding interactions of the L-D dipeptide (c).

Figure 10:
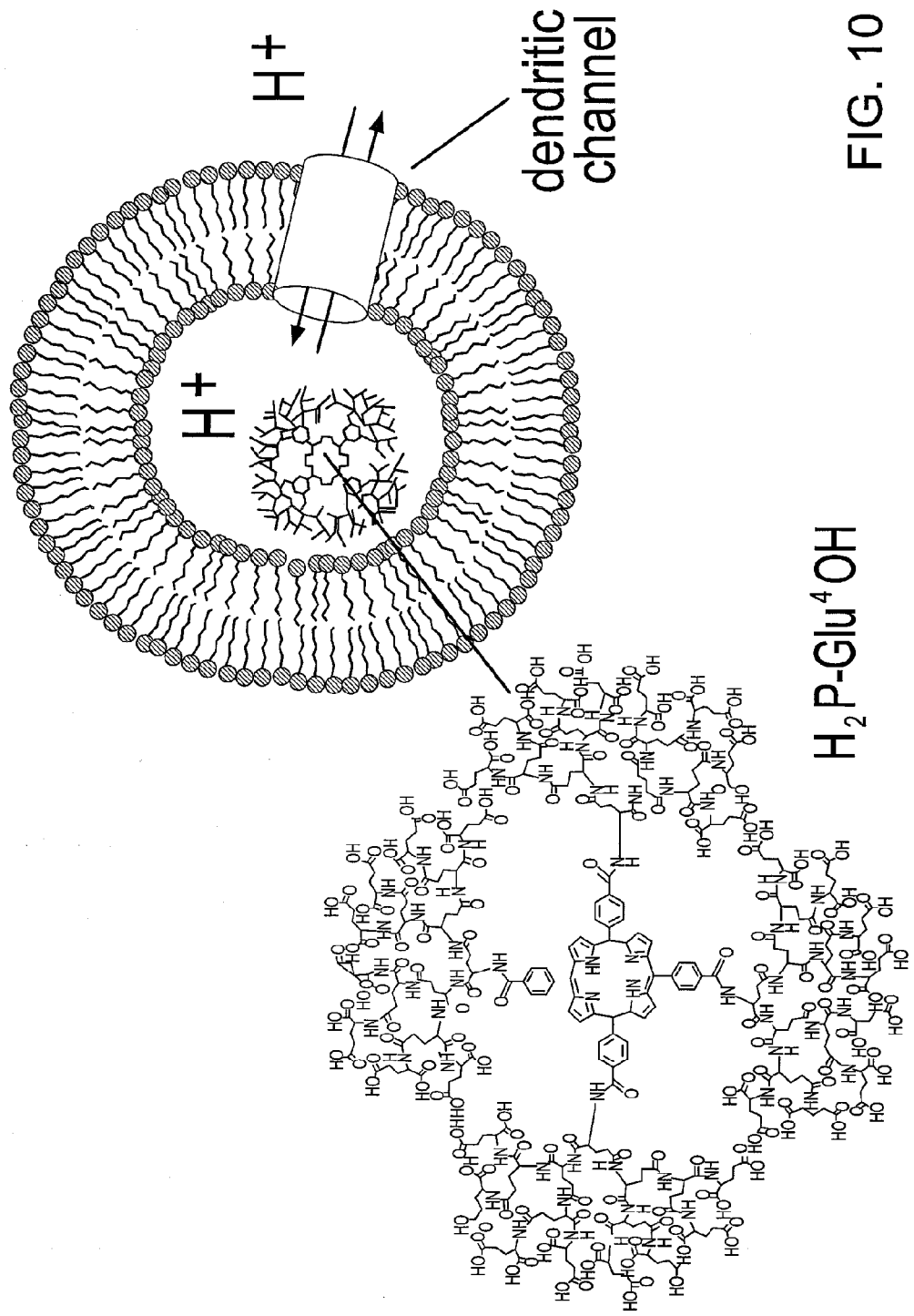

FIG. 10 illustrates incorporation of H2P-Glu$^4$OH via a dendritic channel.

DETAILED DESCRIPTION OF THE PREFERRED EMBODIMENTS

This invention arose from a desire by the inventor to overcome prior art deficiencies and provide a simple and viable approach to fabricating non-biological pores and tubular liquid crystals suitable as synthetic pore-forming structures that mimic natural macromolecules, such as proteins, that act as viral helical coats and trans-membrane channels. In this pursuit the inventor studied the effects of mixed peptide non-peptide structures and their ability to self-assemble into hybrid dendrimers of helical configurations that create their own water porous channels. This invention relates to a genus or library of amphiphilic dendritic dipeptides that self-assemble in solution and in bulk into helical pores through a complex recognition process. The nature of the molecular recognition and self-assembly process of these hybrid structures is based on the chemical formulas of the functional residues included, and permits a range of modifications to its amphiphilic structure that will result in amphiphilic products of varying natures. In addition, and as important, the dendrimers possess a porous structure, the functionality of the dendrimers' pores having been demonstrated by proton transport measurements. These self-assembling dendrimer dipeptides allow the design of a variety of biologically targeted systems with functional properties arising from their porous structure. Although broad in its reach, this invention will be described by means of example(s) described below. The synthetic methods, products' characteristics and applications mentioned in this patent by means of example apply to a broad genus of dendrimers encompassed by this patent. The following pages contain a detailed description of the preferred embodiments of the present invention, and over 100 examples. All references are cited to show the general state of the art relating to the field of the inventive subject matter and/or to enable the practice of the invention, and to the extent necessary their texts are incorporated by reference herein. The citation of a particular document is not an admission of materiality to patentability of that document to the inventive subject matter.

Glossary

The term "dendritic" as used herein refers to highly branched molecules, often having multiple layers of branching. The term "macromolecule" as used herein refers to a very large molecule, which may be composed of hundreds of thousands of atoms. Particularly relevant to the inventive subject matter, polymers are exemplary macromolecules. The term "halide" as used herein refers to a salt of any halogen acid. The term "halogen" as used herein refers to a group of non-metallic elements including fluorine, chlorine, bromine, iodine, and astatine. The term "monomer" as used herein refers to a molecular entity which, when joined together with other monomers, form a polymer. The term "polymer" as used herein refers to a long chain of repeated, covalently bonded atoms or molecules. The term "branched polymer" as used herein refers to a polymer with one or more chemical side chain(s) extending from the primary molecular backbone. The term "aryl" as used herein refers to an alicyclic or aromatic, mono-, bi- or tricyclic, carbo- or heterocyclic ring, wherein the ring is optionally substituted with one or more substituent(s) independently selected from the group consisting of alkylamino, amido, amino, aminoalkyl, azo, benzyloxy, $C_1$-$C_9$ straight or branched chain alkyl, $C_1$-$C_9$ alkoxy, $C_2$-$C_9$ alkenyloxy, $C_2$-$C_9$ straight or branched chain alkenyl, $C_3$-$C_9$ cycloalkyl, $C_5$-$C_7$ cycloalkenyl, carbonyl, carboxy, cyano, diazo, ester, formanilido, halo, haloalkyl, hydroxy, imino, isocyano, isonitrilo, nitrilo, nitro, nitroso, phenoxy, sulfhydryl, sulfonylsulfoxy, thio, thioalkyl, thiocarbonyl, thiocyano, thioester, thioformamido, trifluoromethyl, and carboxylic and heterocyclic moieties; wherein the individual alicyclic or aromatic ring contains 5-8 members and wherein said heterocyclic ring contains 1-6 heteroatom(s) independently selected from the group consisting of O, N, and S; and wherein any aromatic or tertiary alkyl amine is optionally oxidized to a corresponding oxide. The term "living polymerization" as used herein refers to a chain growth polymerization which proceeds in the absence of chain breaking terminations, and which can be used to produce essentially monodisperse polymers. The term "replaced" as used herein refers to the situation wherein an atom takes the place of another atom in the chemical formula of a compound. For example, replacement of the carbon atom at the 9-position of fluorine with a nitrogen atom produces carbazole. The term "substituent" as used herein refers to an atom or group which is added to a chemical entity by replacing one or more hydrogen atom(s); monovalent groups replace one hydrogen atom, bivalent groups replace two hydrogen atoms, and so forth.

The term "$\mu$" as used herein refers to charge carrier mobility, or velocity, in an electric field. The term "$\mu e$" as used herein refers to electron mobility in an electric field. The term "$\mu h$" as used herein refers to hole mobility in an electric field. The term "p-stack" or "$\pi$-stack" as used herein refers to the hydrophobic interaction which occurs between aromatic or aromatic heterocyclic side chains and produces a cloud of free electrons from the pi-orbitals of atoms composing the stacked structure. The term "donor" or "D" as used herein refers to a substance which produces an increase in the electron density in a material, and a corresponding decrease in the hole concentration. Similarly, the term "acceptor" or "A" as used herein refers to a substance which produces an decrease in the electron density in a material, and a corresponding increase in the hole concentration. "D-A complexes" refers to a material in which both donor and acceptor substances are present. The term "isotropic phase" as used herein refers to the phase of matter in which the molecules are randomly aligned, exhibit no long range order, and have a low viscosity. The characteristic lack of orientational order of the isotropic phase is that of a traditional liquid phase. The term "liquid crystalline phase" as used herein refers to a phase of matter in which the molecules tend to point along a common axis, exhibit long range orientational order, and wherein the average orientation may be manipulated with an electric field. The characteristic orientational order of the liquid crystal state is between the traditional solid and liquid phases.

Dendrimers

The dendrimer portion of the amphiphilic dipeptide polymer of this invention may be any type of dendrimers known in the art. Examples of dendrimeric polymers are provided in U.S. Pat. Nos. 6,733,883; 5,731,095; 5,872,255; 5,886,110; 6,020,457; 6,051,669; 6,077,500; 6,136,921 and 6,312,809, among many others known in the art. The entire texts of the exemplified patents are incorporated herein by reference in so far as the information may be needed for enablement purposes of the dendrimeric polymer and their formation and uses. Dendritic macromolecules have importance in diverse fields as nanoelectronics, e.g. electronics based on organic thin-film materials, and nanobiology. Some of these are water-soluble or water-dispersible fluorine-containing dendritic polymer surfactants or branched, dendrimeric macromolecules with a central nucleus and a series of polyoxaalkylene chains radiating from the nucleus that spread into the surrounding space, and branch in a cascade to reach a desired size. Other dendritic polymers contain disulfides that are essentially inert under non-reducing conditions, but which form sulfhydryl residues when subjected to reducing conditions. These form differentiated dendrimers suitable for application to binding reagents for diagnostics, drug delivery, gene therapy and magnetic resin imaging, and in the preparation of self-assembled dendrimer monolayers on quartz crystal resonators, e.g. for dendrimer-modified electrodes useful for ion/molecule detection. Still others may be described as higher generation radially layered co-polymeric dendrimers with a hydrophilic poly (amidoamine) or a hydrophilic poly (propyleneimine) interior and a hydrophobic organo-silicon exterior. These are suitable for delivering an active species in catalysis, pharmaceutical applications, drug delivery, gene therapy, personal care and agricultural products. Others are coupled polymers resulting from the reaction of a living alkali metal-terminated polymer and a coupling agent. Some of these polymers have good rubbery physical properties, transparency and wear resistance. Many dendritic polymers are suitable for the formation of a dendrimer monolayer film covalently bonded to the surface of a substrate, and may be used to form a chemically sensitive surface, e.g. chemical sensors. Other uses are described in this patent for their combination with peptidic fragments. Methods for the synthesis of complex chemical compounds with the shape perfection required to act as self-organizing and self-assembling building blocks to generate supramolecular objects in both novel and predictable structural lattices are known in the art, exemplified in the above listed patents, and need not further be described here. When a supramolecular object exhibits an internal ordered structure rather than a micelle-like structure, the retrostructural analysis of the lattice enables the formulation of a primary structure-activity relationship that provides molecules with designed functions. Dendritic macromolecules may be simply, efficiently, and cost effectively synthesized by the described methods. A particularly suitable method for the synthesis of complex molecular and macromolecular chemical compounds known in the art relies on a combination of living polymerization reactions employing conventional monomers and TERMINI synthesis, e.g. employing an irreversible terminator multi-functional initiator. Such process generally initiates the polymerization of a monomer using a multi-functional stilfonyl halide initiator having a number of sulfonyl halide functional groups, to produce a multi-armed branched polymer with a corresponding number of sulfonyl halide functional groups, quantitatively end-caps the thus formed branched polymer, e.g. with an excess of a thiocarbamate TERMINI compound resulting in one or more thiocarbamate-capped branched polymer, and demasks the TERMINI thiocarbamate groups to free active sulfonyl halide groups, e.g. by oxidative chlorination, capable of serving as a further initiator. In one particularly useful aspect dendritic macromolecules may be made from conventional monomers by employing a $Cu_2O$/biphenyl-2,3-diol as a catalyst in the living radical polymerization of methyl methacrylate using 3PSC as a tri-functional initiator, to produce a 3-armed star polymer 3G1(n)C1, wherein 3 stands for a tri-functional core, G1 refers to the first polymerization generation, n stands for the degree of polymerization per arm, and C1 for the functionality present at the chain ends of each arm, then quantitatively end-capping said 3G1(n)C1 using, e.g. a four times excess of the TERMINI compound to produce 3G1($n_2$)T, wherein n refers to the degree of polymerization and the subscript 2 refers to the number of new arms generated from each TERMINI branching point at the end of the poly (methyl methacrylate), and each T represents a TERMINI compound chain end, and demasks N,N'-diethyl thiocarbamate groups of the 3G1($n_2$)T, e.g. by oxidative chlorination, into sulfonyl chloride groups freeing active aryl sulfonyl chloride initiator groups in the form of 3G1(n2)SC, wherein SC stands for sulfonyl chloride that may initiate a new round of metal catalyzed living radical polymerization of methyl methacrylate to produce the second generation 3G2($n_2$m)C1, wherein m represents the degree of polymerization per arm of the second generation poly (methyl methacrylate). In this latter examples, the initiator may be a TERMINI compound such as (1,1-dimethylethyl)[[1-[3,5-bis (S-phenyl 4-N,N'-diethyl thiocarbamate)phenyl]ethenyl]oxy]dimethylsilane. Others, however, are also suitable for use with this invention.

In one embodiment the present invention employs in the formation of the dendritic macromolecule a compound of the chemical formula (I)

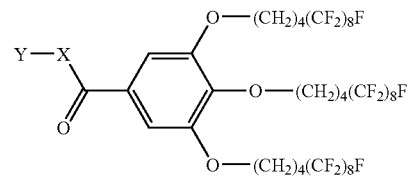

wherein X comprises Z-$CH_2CH_2O$)n, wherein n is 1 to 6, or Z-$(CH2)_mO$, where m is 1 to 9; Y comprises pentalene, indene, naphthalene, azulene, heptalene, biphenylene, indacene, acenaphthylene, fluorene, phenalene, phenanthrene, anthrcene, fluoranthene, acephenanthrylene, aceanthrylene, triphenylene, pyrene, chrysene and/or naphthacene; and may be further substituted with nitro, nitroso, carbonyl, carboxy, oxo, hydroxy, fluoro, perfluoro, chloro, perchloro, bromo, perbromo, phospho, phosphono, phosphinyl, sulfo, sulfonyl, sulfinyl, trifluoromethyl, trifluoromethylsulfonyl and/or trimethylsulfonyl; wherein 1 to 4 carbon atom(s) of Y may be further replaced by N, NH, O, or S; and Z comprises a direct bond, —C(O)O—, ($C_1$-$C_6$ alkyl)C(O)O—, ($C_2$-$C_6$ alkenyl)-C(O)O— or ($C_2$-$C_6$ alkynyl)-C(O)O—.

In another preferred embodiment X comprises Z-$CH_2CH_2O$)$_n$, wherein n is 1 to 3, or Z-$(CH_2)_mO$, wherein m is 2 to 4; Y comprises naphthalene, indacene, fluorene, phenanthrene, anthrcene or pyrene, and may be further substituted with nitro, carboxy, oxo, phosphor or sulfo; and wherein one carbon atom of Y may be further replaced by N or NH; and Z comprises a direct bond, —C(O)O— or ($C_1$-$C_6$ alkyl)-C(O)O—. In a more preferred embodiment X comprises diethylene glycol or tetraethylene glycol; Y comprises carbazole, naphthalene, pyrene or 4,5,7-trinitrofluorenone-2-carboxylic acid; and Z comprises a direct bond, —C(O)O— or —$CH_2$—C(O)O—. In still another most preferred embodiment the compound comprises one of the following chemical structures.

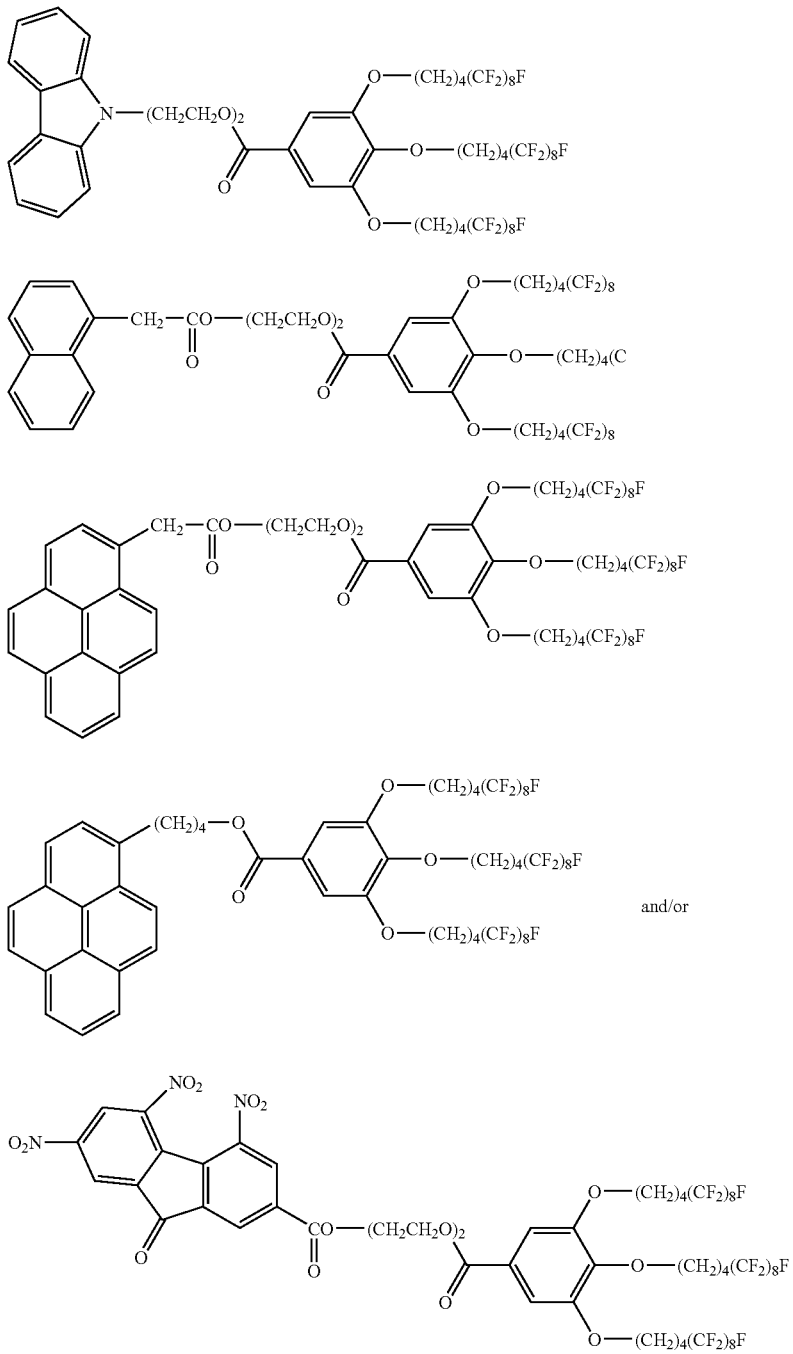

Many other compounds suitable for the formation of dendrimeric polymer structures may be used in this invention, and since they are known in the art they need not be described in greater detail in this patent.

Synthesis of Dendrimers of the Invention

The dendrimeric dipeptides of the invention may be prepared by many preparatory methods known in the art, such as that of U.S. Pat. No. 6,733,883, the entire text thereof being incorporated herein by reference for enablement purposes. By means of example a representative mobility donor dendron employed in this invention may be readily prepared by standard techniques of chemistry, utilizing the general synthetic pathway depicted below in Scheme I.

Scheme I

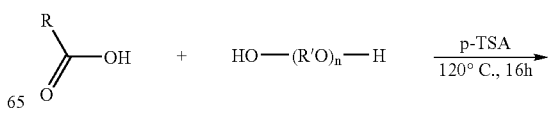

-continued

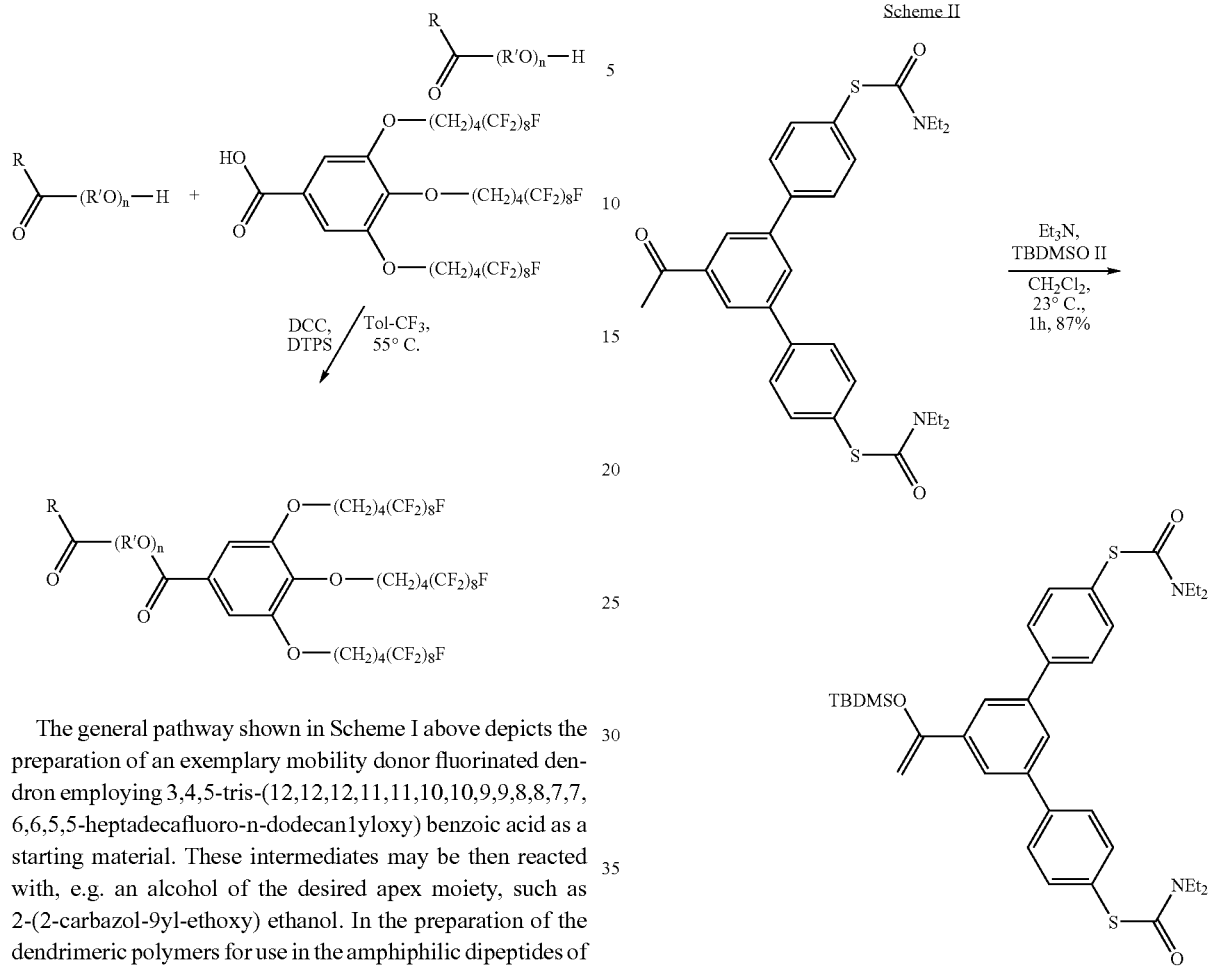

The general pathway shown in Scheme I above depicts the preparation of an exemplary mobility donor fluorinated dendron employing 3,4,5-tris-(12,12,12,11,11,10,10,9,9,8,8,7,7,6,6,5,5-heptadecafluoro-n-dodecan1yloxy) benzoic acid as a starting material. These intermediates may be then reacted with, e.g. an alcohol of the desired apex moiety, such as 2-(2-carbazol-9yl-ethoxy) ethanol. In the preparation of the dendrimeric polymers for use in the amphiphilic dipeptides of the invention an artisan will understand that various reactive functionalities on the starting compounds or intermediates may need to be protected or blocked while a desired reaction is carried out on other portions of the molecule. After the desired reactions are completed, or at any desired time, typically the protecting groups are removed by, e.g. hydrolytic or hydrogenolytic means. These protection and deprotection steps are conventional in organic chemistry, as one skilled in the art would know, as are protective residues that may be employed. See, e.g. "Protective Groups in Organic Chemistry," McOmie, Ed., Plenum Press, New York, N.Y.; "Protective Groups in Organic Synthesis," Greene, Ed., John Wiley & Sons, New York, N.Y. (1981), the relevant text of these references being incorporated herein by reference as needed for enablement purposes. The product and intermediates may be isolated or purified using one or more standard purification techniques, including, for example, one or more of simple solvent evaporation, recrystallization, distillation, sublimation, filtration, chromatography, including thin-layer chromatography (HPLC), e. g. reverse phase HPLC, column chromatography, flash chromatography, radial chromatography, trituration, and the like. Still another method for preparation of the dendrimer polymers employs standard chemical techniques as shown below in Scheme II.

Utilizing the general pathway to a representative mobility donor fluorinated dendron of the present invention as shown in Scheme II, compounds for use in the dipeptide dendrimer polymers of the invention may be prepared using 3,4,5-tris (12,12,12,11,11,10,10,9,9,8,8,7,7,6,6,5,5-heptadecafluoro-n-dodecan-1-yloxy)-benzoic acid as a starting material. These intermediates are then reacted with, for example, an alcohol of the desired apex moiety, such as 2-(2-carbazol-9yl-ethoxy)-ethanol, to obtain the compounds of the invention. In the preparation of the compounds of the invention, one skilled in the art will understand that various reactive functionalities on the starting compounds or intermediates may need to be protected or blocked while a desired reaction is carried out on other portions of the molecule. After the desired reactions are completed, or at any desired time, normally such protecting groups will be removed by, for example, hydrolytic or hydrogenolytic means. Such protection and deprotection steps are conventional in organic chemistry. See, for example, "Protective Groups in Organic Chemistry," McOmie, Ed., Plenum Press, New York, N.Y.; "Protective Groups in Organic Synthesis," Greene, Ed., John Wiley & Sons, New York, N.Y. (1981) for the teaching of protective groups which may be useful in the preparation of compounds of the present invention. The product and intermediates may be isolated or purified using one or more standard purification techniques, including, for example, one or more of simple solvent evaporation, recrystallization, distillation, sublimation, filtration, chromatography, including thin-layer chromatography, HPLC, e. g. reverse phase HPLC, column chromatography, flash chromatography, radial chromatography, trituration, and the like. Scheme II shown above depicts the final step of the synthesis of the (1,1-dimethylethyl)[[1-[3,5-bis(S-phenyl4-N,N'-diethylthiocarbamate)phenyl]ethenyl]oxy]dimethylsilane TERMINI compound. (1,1-dimethylethyl)[[1-[3,5-bis (S-phenyl4-N,NM-diethylthiocarbamate)phenyl]ethenyl]oxy]dimethylsilane may be obtained in five steps and greater than 55% overall yield starting from 4-methoxyphenylboronic acid and 3,5-dibromo acetophenone. The first four steps of this synthesis were also reported by Percec et al., "Synthesis of functional aromatic multisulfonyl chlorides and their masked precursors", J. Org. Chem. 66: 2104 (2001), the relevant text of which is incorporated herein by reference for enablement purposes. Tert-butyl dimethyl silyl trifluoro methane sulfonate ("TBDMSOTf") is typically used for the step depicted in Scheme II because it provides the t-butyl dimethyl siloxy ("TBDMS") enol ether under mild reaction conditions and in high yield. The TBDMS group offers sufficient stability to the enol ether both for long time storage and under the metal catalyzed reaction conditions selected for the end-capping process. Since enol ethers are cleaved under acidic conditions, for this step we have employed our previously developed self-regulated catalytic system based on Cu2O/biphenyl-2,3-diol. This catalytic system maintains neutral reaction conditions throughout all synthetic steps and creates only the required concentration of highly reactive, nascent CuCl species in-situ, via a self-regulated mechanism. The small concentration of highly reactive nascent CuCl facilitates the production of an extremely low concentration of radical species and thus minimizes undesirable radical side-reactions. An important aspect of the TERMINI compound is that after end-capping, the excess of the unreacted enol ether or its precursor are recovered and reused. This provides an economic synthetic method since an excess of TERMINI compound is used in each end-capping step.

The synthesis of a first generation dendritic poly (methyl methacrylate) based on a TERMINI compound in conjunction with the trifunctional initiator 1,1,1-tris (4-chloro sulfonyl phenyl) ethane ("3PSC") and methyl methacrylate, is depicted in Scheme III of FIG. 6.

Scheme III depicts a general method for the synthesis of a dendritic poly (methyl methacrylate) using a combination of living radical polymerization and TERMINI synthesis. In the first step 3PSC is typically used as a trifunctional initiator to initiate the Cu$_2$O/biphenyl-2,3-diol catalyzed living radical polymerization of methyl methacrylate and produce a star polymer 3G1(n)C1 having three arms, where 3 stands for a trifunctional core, G1 refers to the first generation, n represents the degree of polymerization (hereinafter "DP") per arm, and C1 is the functionality present at the chain ends of each arm. The inventor previously demonstrated by a combination of kinetic and structural analysis experiments that both 3PSC and the disulfonyl chloride resulted from TERMINI synthesis initiate the living radical polymerization of methyl methacrylate with 100% efficiency. During the synthesis of 3G1(n)C1 the conversion of methyl methacrylate is monitored most conveniently by 1H-NMR spectroscopy. In the second step of this sequence of reactions, 3G1(n)C1 is quantitatively end-capped using an excess of TERMINI compound. An excess is required to avoid radical side-reactions and to produce 3G1(n$_2$)T. Four times excess is preferred. Subscript 2 from 3G1(n$_2$)T is the number of new arms generated from each TERMINI compound branching point located at the end of poly (methyl methacrylate) of degree of polymerization n, and T stands for TERMINI compound chain ends. This reaction step may be monitored by a combination of $^1$H-NMR, gel permeation chromatography ("GPC"), size exclusion chromatography-multi-angle light scattering ("SEC-MALLS") and, when possible, by matrix assisted laser desorption ionization time of flight ("MALDI-TOF") spectrometry. For early generations the combination of $^1$H-NMR, GPC, and MALDI-TOF provides the most efficient method of structural analysis. However, for higher generations or for dendritic macromolecules with a high degree of polymerization of poly (methyl methacrylate) per arm, SEC-MALLS becomes the most suitable method of analysis. MALDI-TOF analysis of 3G1(62)T is used here as an example to demonstrate the perfect control of the first two reaction steps. The third step of this method involves demasking, e.g. the N,N'-diethyl thio carbamate groups of the 3G1 (n$_2$)T to free active sulfonyl chloride groups. This step may be accomplished by oxidative chlorination of 3G1(n$_2$)T under mild conditions, e. g. 7 min at 23° C., to transform quantitatively the masked TERMINI sulfonyl chlorides into the active aryl sulfonyl chloride initiator groups. The resulting 3G1(n$_2$) SC, wherein SC stands for sulfonyl chloride is a hexa-functional initiator capable to initiate the metal catalyzed living radical polymerization of methyl methacrylate to produce the second generation 3G2(n$_2$m)C1, where in stands for the degree of polymerization per arm of poly (methyl methacrylate) from the second generation. The instability of sulfonyl chlorides under MALDI-TOF analysis conditions does not allow the use of this method for the structural analysis of the 3G1(n$_2$)SC. Therefore, a combination of GPC, 500 MHz $^1$H-NMR. SEC-MALLS and kinetic analysis was employed for the structural analysis of 3G1(n$_2$)SC and for the demonstration of its structure. After the synthesis of3Gl(n$_2$)SC, the previous sequence of these reaction steps that involves metal catalyzed living radical polymerization of methyl methacrylate, end-capping with TERMINI compound and demasking may be reiterated to produce four or more generations of dendritic macromolecules. For each generation each of these reaction steps is typically monitored by a combination of 500 MHz $^1$H-NMR spectroscopy, MALDI-TOF, GPC and SEC-MALLS. Two alternate methods may be additionally employed to synthesize dendritic macromolecules suitable for use in this invention. These typically consist of three reaction steps each and utilize the general synthetic pathways depicted in Scheme IV of FIG. 7.

Scheme IV depicts two typical methods for the synthesis of dendritic macromolecules by a combination of living radical polymerization and TERMINI synthesis. The first method may be practiced as a three-step, three-pot per iteration method, and the second method as a three-step, two-pot per iteration method. The first method is based generally on an iterative process in which the required sequence of three reaction steps, i. e. living radical polymerization, end-capping and de-masking may be executed separately. In the second method the living radical polymerization and end-capping are generally combined in a two-step one-pot process. Subsequently, in the latter method a TERMINI compound is added generally to the reaction at a predetermined conversion during the living radical polymerization process. As a consequence, in this case it is as if the first two steps of the first method were combined. This eliminates the need for isolation and purification of the resulting dendritic macromolecule after the first reaction step. The latter method, therefore, requires less time for the synthesis of each generation. These two methods complement each other in terms of controlled chemical compound, functionality of the chain ends, and number of purification steps. The product and intermediates may be isolated and/or purified using one or more standard purification techniques, e.g. one or more solvent evaporation steps, recrystallization, distillation, sublimation, filtration, chromatography, thin-layer chromatography (HPLC), e. g. reverse phase HPLC, column chromatography, flash chromatography, radial chromatography, trituration, and the like.

Architectural Motifs

Dendritic macromolecules of various architectures may be produced by the combination of living radical polymerization of methyl methacrylate and the bi-functional TERMINI compound starting from a multi-branched initiator, e.g. 3PSC-trifunctional initiator. Examples are those containing various degrees of polymerization of the monomer, e. g. poly (methyl methacrylate), per arm, having a zero degree of polymerization of poly (methyl methacrylate, and having a degree of polymerization of poly (methyl methacrylate) equal to one. In the structure of the fourth generation 3G4(n2m2p2q2)C1 when the degree of polymerization of the monomer, e.g. poly (methyl methacrylate), in each generation is zero, the resulting dendritic macromolecule may have a perfect structure of relatively uniform size that resembles the structure of conventional dendrimers prepared by traditional divergent methods. This structure may be synthesized by eliminating the polymerization step from Scheme IV by deleting the poly (methyl methacrylate) branches from the 3G4(n2m2p2q2)C1 structure. A structure of relatively uniform size may be also obtained when the degree of polymerization, e.g. of poly (methyl methacrylate), from each branch is equal to one in each generation. Prior synthetic methods also permit the addition of only one monomer unit to any sulfonyl chloride initiator to enable the synthesis of these structures.

At least three different classes of dendritic macromolecules may be envisioned when the degree of polymerization of poly (methyl methacrylate) per branch is larger than one. The resulting dendritic macromolecules will have typically a perfect degree of branching with a branching multiplicity equal to two and, therefore, they differ from hyperbranched polymers for which there is no control over their degree of branching. At the same time they have generally a narrow molecular weight distribution (Mw/Mn), e.g. of the poly (methyl methacrylate) segments. As a consequence, these dendritic macromolecules differ from conventional monodisperse dendrimers synthesized by either divergent or convergent methods. Dendritic macromolecules containing a small degree of polymerization of poly (methyl methacrylate) provide short and stiff chains between branching points. Those with a medium degree of polymerization provide flexible random coil conformation between the branching points, those with a large degree of polymerization provide long entangled chains between branching points. In the first class of dendritic macromolecules prepared by the combination of living radical polymerization and TERMINI synthesis the degree of polymerization per branch is typically larger than one but lower than the degree of polymerization that defines the persistence length of the repeating units, e.g. of poly (methyl methacrylate). In this case the repeat units between branches are typically stiff and as a consequence each branch is generally fully elongated. The second class of polymers includes DPs larger than the one corresponding to the persistence length of the unit, e.g. poly (methyl methacrylate), but lower than the degree of polymerization that corresponds to the Mn that produces entangled chains. In this case the poly (methyl methacrylate) branches adopt typically a random-coil conformation. The third case produces DPs that correspond to Mn values that are larger than the entanglement molecular weight. These three classes of dendritic macromolecules exhibit completely different physical properties amongst themselves, and in comparison to classic dendrimers. In addition to these three classes, combinations of different degree of polymerization per branch may be incorporated within a single dendritic macromolecule. Finally, within any of the above-mentioned chemical compounds the structure of each generation may be changed by simply employing a different monomer. In addition, the structure of the outer shell of these dendritic macromolecules may be functionalized with different groups. Last but not least, the structures of these dendritic macromolecules may be modified by performing a diversity of chemical reactions on their repeat units.

Amphiphilic Dendritic Dipeptides

The peptides of the product of this invention may comprise any amino acid in accordance with this invention. The combination and selection of amino acids is relevant to the properties of the present amphiphilic dendrimer peptides. In order to address the need for self-organized dipeptide dendrimer polymers with controlled properties the present patent provides a library based on a dipeptide dendrons that is suitable for the different applications described here. The resulting functional dendrons are programmed to self-assemble into appropriate structures the provide channels such as helical pores that permit the access of water molecules when placed in the appropriate environment, among other functions. Other embodiments of the invention employ different monomers for making the dendrimer. For example, the monomer may be a methacrylate, acrylate, acrylonitrile, methacrylonitrile, styrene or combination thereof, preferably the monomer comprises methyl methacrylate. In another embodiment the dendromer may comprise a sulfonyl halide such as an aryl sulfonyl halide, such as chloride. Others however are also contemplated. In yet another embodiment the dendrimer may be prepared starting from a multi-functional sulfonyl halide initiator, e.g. a tri-functional initiator such as 1,1,1-tris(4-chloro sulfonyl phenyl)ethane. In another aspect the dendrimer may be provided with a terminus(i) such as (1,1-dimethyl ethyl)[[1-[3,5-bis(S-phenyl4-N,N'-diethyl thiocarbamate)phenyl]ethenyl]oxy]dimethyl silane. The combination of self-assembly and ease of processability provides a construct of unexpected characteristics that has multiple uses described below. This provides an unprecedented, simple, and practical strategy that permits the combination of these dendrimers with appropriate peptides into the unexpected polymeric structures that mimic the characteristics of proteins in a biological system. A typical synthetic route for the preparation of Moc protected dendritic peptides of the invention are shown in Scheme V below.

Scheme V
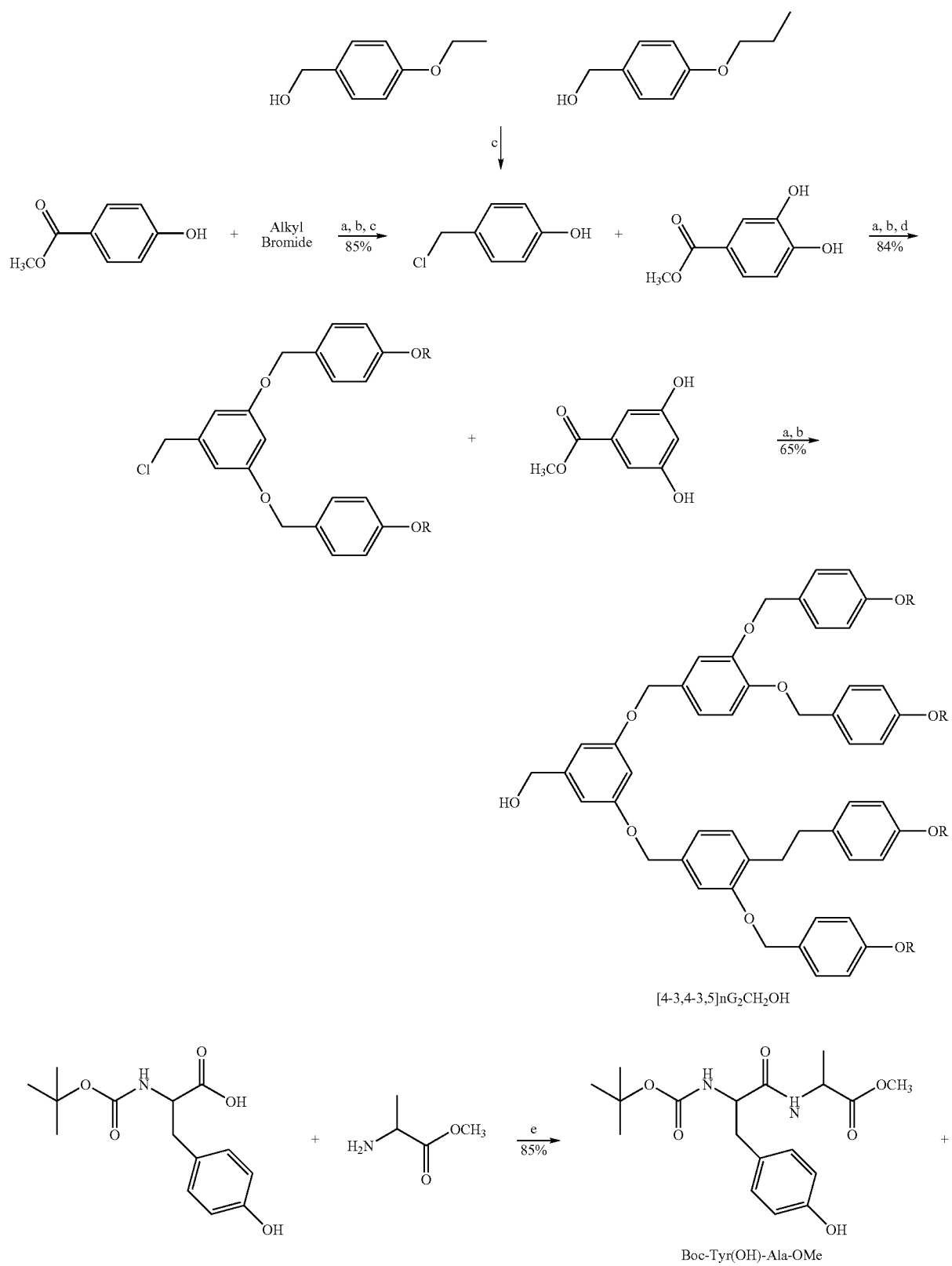

-continued

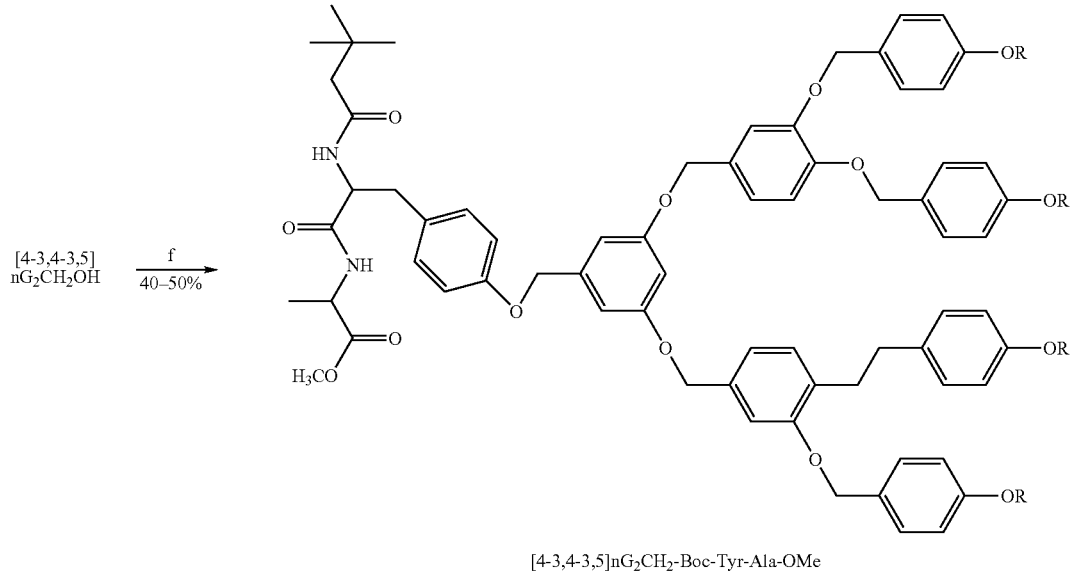

[4-3,4-3,5]nG₂CH₂-Boc-Tyr-Ala-OMe $R = C_{17}H_{(2n+1)}$
n = 1, 2, 6, 8, 10, 12, 14, 16

Reagents and Conditions: a) K₂CO₃, DMF, 70° C., 2–12 hr. b) LiAlH₄, THF, RT. 2 hr. c) SOCl₂, CH₂Cl₂, Cat. DMF, RT, 5 min. d) SOCl₂, DTBMP, CH₂Cl₂, RT, 5 min. e) CDMT, NMM, EtOAc, RT, 2 hr. f) DAD, PPh₃, THF, RT, 3–8 hr.

CDMT = 2-Chloro-4,6-dimethoxy-1,3,5-triazene    DTBMP = 2,6-Di-tert-butyl-i-methylpyridine
NMM = N-Methyl morpholine
DIAD = Diisopropyl azodicarboxylate Yet another typical route for preparation of the amphiphilic dendritic dipeptides of the invention is shown in Scheme VI below.

Scheme VI

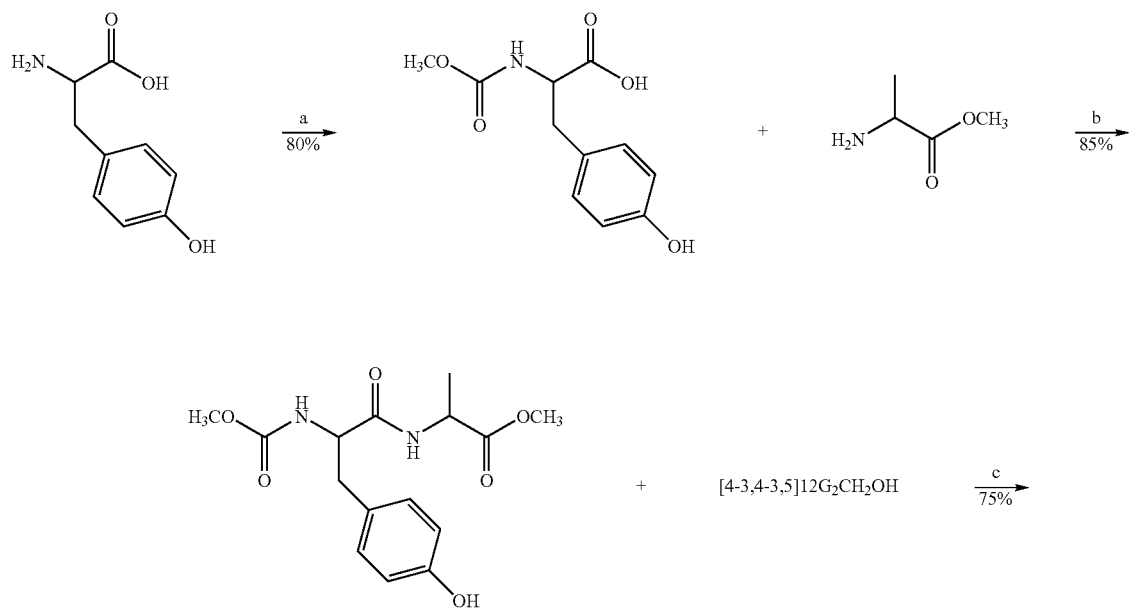

-continued

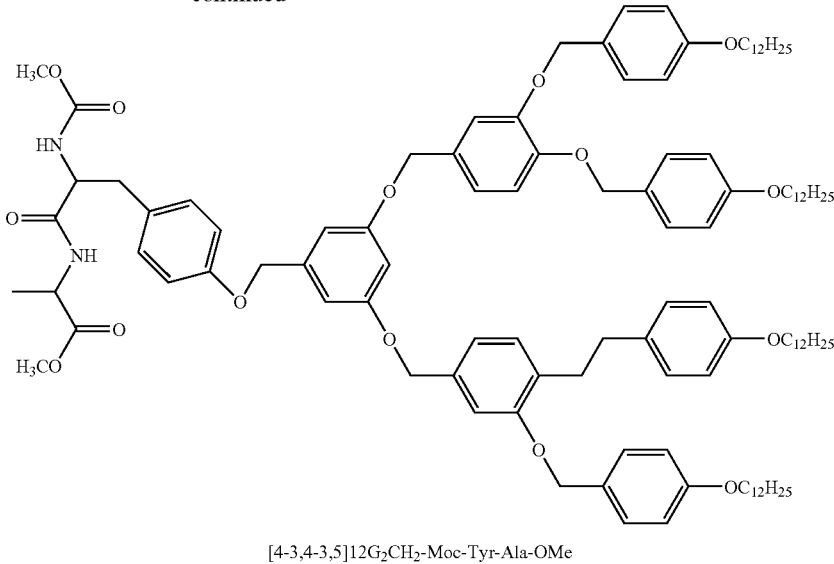

[4-3,4-3,5]12G₂CH₂-Moc-Tyr-Ala-OMe

Reagents and Conditions: a) CH₃OCOCl, NaHCO₃, THF/H₂O, RT, 12 hr. b) CDMT, NMM, EtOAc, RT, 2 hr. c) PPh₃, DIAD, THF, RT, 12 hr.

CDMT = 2-Chloro-4,6-dimethoxy-1,3,5-triazene
NMM = N-Methyl morpholine
DIAD = Diisopropyl azodicarboxylate Schemes V and VI above show examples of preparative routes for these polymers. The invention will now be described with reference to certain examples, although its teachings apply broadly to all classes of dendritic polymers and peptides employed in the formation of the amphiphilic products of this invention. IN general terms, the dendritic segment of the molecules are typically synthesized separately from the peptides that are then protected prior to reaction with the dendrimers.

The present invention thus provides for an amphiphilic dendritic dipeptide, comprising a dipeptide(s) comprising one or more of a naturally occurring or synthetic non-polar amino acid, a polar amino acid, an aromatic amino acid and/or a sulfur-containing amino acid; and a dendron. In one embodiment, the dipeptide and the dendron are assembled into a pore-comprising amphiphilic dendritic dipeptide. In another, the dipeptide and the dendron are self-assembled into a pore-comprising amphiphilic dendritic dipeptide. In one preferred form, the dipeptide and the dendron are assembled into a channel-comprising amphiphilic dendritic dipeptide. IN another, they are assembled into closed supramolecular columns. One very preferred embodiment comprises a dendritic dipeptide, where the dendron comprises the chemical formula $$m G_n\text{-}Y,$$

wherein
G represents the dendron generation and comprises about 1 to about 30;
n represents the degree of polymerization and comprises about 2 to about 30;
m represents the number of arms and comprises about 2 to about 20; and
Y comprises a terminal residue for the dendron.

Preferred forms of the dendritic dipeptide are those where the dendron comprises the chemical formula (4-3,4-3,5) 12G₂-Y, wherein Y comprises COOCH₃ or COOH, or (4-3, 4-3,5)n G₂-CH₂OH, wherein n comprises about 10 to about 16. However, many others are also included in this patent. One of these is the dendritic dipeptide, where the dendron comprises (4-3,4-3,5)12G₂-Boc, (4-3,4-3,5)12G₂-Moc. In another preferred form of the present product, the dendritic dipeptide comprises the chemical formula $$mG_n\text{-}X,$$

wherein
G refers to the dendron generation and comprises about 1 to about 30;
n represents the degree of polymerization and comprises about 2 to about 30;
m represents the number of arms and comprises about 2 to about 20; and
X comprises a dipeptide.

The dendritic dipeptide may also comprise the chemical formula (4-3,4-3,5)12G₂-CH₂—X, wherein G, n, and m are as before, and X comprises Boc-L-Tyr-L-Ala-O-CH3, Moc-L-Tyr-L-Ala-O-CH3, Boc-D-Tyr-D-Ala-O-CH3, Boc-L-Tyr-D-Ala-O-CH3, Boc-D-Tyr-L-Ala-O-CH3, Boc-DL-Tyr-DL-Ala-O—CH3 or Moc-L-Tyr-L-O-CH3. The dipeptide of the invention may be comprised of an L-amino acid(s), an R-amino acid(s), or their combinations. Clearly any amino acid, whether naturally occurring or synthetic, may be employed in the dendritic dipeptides of this invention. Preferred examples are amino acids such as L-Ala, R-Ala, Gly, L-Val, R-Val, L-Phen, R-Phen, L-Ser, R-Ser, L-Tyr, R-Tyr, L-Cys and R-Cys. Any combination of these is within the four corners of this invention. The dendritic dipeptide of the invention is also provided in the form of a composition, a coating, membrane or film, among other article forms into which it may be developed. Examples of applications are a viral helical coating, a pharmaceutical formulation further comprising a pharmaceutically, veterinarily or agriculturally acceptable carrier and a pharmaceutically, veterinarily or agriculturally active agents), an encapsulation formulation, preferably a reverse encapsulation formulation, a stochastic sensor, a trans-membrane channel(s), among man y other applications. Examples of agents for the formulation, whether for encapsulation or otherwise, are an anti-viral, anti-bacterial and/or anti-fungal agent(s). Other types of agents are also contemplated for inclusion in the present products.

Although the present dendritic dipeptides may be prepared by any method known in the art, one that may be employed comprises obtaining a dendron comprising one or more arms; forming a dipeptide from a polar or non-polar amino acid(s) and/or an aromatic or sulfur-containing amino acid(s); and contacting the dendron and the peptide under conditions effective for operatively attaching the dipeptide to the dendron and allow their self-assembly into a pore-comprising amphiphilic dendritic dipeptide.

As an artisan would understand, the present method may further comprise protecting non-reacting residues at either the amino acid(s) in the dipeptide or the dendron prior to the contacting step. Method for protecting functional residues from reacting are known in the art and need not be described herein. Examples of protecting groups are Boc and Moc. However, others are also known and are considered suitable for use in this invention. In one preferred form the present method further comprises allowing the dendritic dipeptide to self-assemble into a synthetic viral helical coat, a synthetic trans-membrane channel(s), a pharmaceutically, veterinarily or agriculturally active composition, an encapsulation composition, preferably a reversible encapsulation composition, or a composition for stochastic sensing, among many other applications. In one important form, the pore comprises a helical channel. However, other forms of self-assembly are also possible and fall within the scope of the invention.

Exemplary Dipeptide Polymers

One of the present exemplary amphiphilic dendritic dipeptides of the invention comprises a dendron (4-3,4-3,5)12$G_2$-X. wherein X comprises $CO_2CH_3$ or COOH, and a dendron (4-3,4-3,5)$_n$ $G_2$-$CH_2OH$, wherein n comprises about 10 to about 16. The dendromer self-assembles into closed supramolecular columns. A (4-3,4-3,5)12$G_2$-$CH_2$—X dendritic dipeptide was synthesized, wherein X comprises Boc (Moc)-L-Tyr-L-Ala-OMe, Boc-D-Tyr-D-Ala-OMe, Boc-L-Tyr-D-Ala-OMe, Boc-D-Tyr-L-Ala-OMe, Boc-DL-Tyr-DL-Ala-OMe or Moc-L-Tyr-L-OMe as described below. The dipeptide groups, i.e. Boc-L-Tyr-L-Ala-OMe, L-Tyr-L-Ala, and L-L dipeptides were followed as tags to monitor self-assembly and expression of chirality in solution and in bulk. In solvents allowing H-bonding, such as $CHCl_3$, $CH_2Cl_2$ and tetrahydrofuran (THF), self-assembly was not detected by temperature- or concentration-dependent $^1$H-NMR, UV spectroscopy or circular dichroism (CD). Is surmised therefrom that the equilibrium between the trans and gauche conformers of the benzyl ether moiety may favors a globular dendron conformation encapsulating the dipeptide in its focal point, such as the one shown in Scheme VII (FIGS. 8 and 9). Scheme VII shows the structure, conformations and H-bonding of (4-3,4-3,5)12G2-CH2-Boc-L-Tyr-L-Ala-OMe and (4-3,4-3,5)12G2-CH2-Boc-L-Tyr-D-Ala-OMe during self-assembly, a Top left shows trans-tapered low temperature and Top right shows globular high temperature conformers of L-L stereoisomer. The letters (a, b, . . ., j) indicate protons with $^1$H-NMR chemical shifts. Yellow indicates the region of the dendritic dipeptide where functional groups capable of taking part in H bonding are accessible (left), and the corresponding region that sterically prevents the same type of H bonding in the globular structure (right). b H bonding interactions of the L-L dipeptide forming the pore according to the model. c H bonding interactions of the L-D dipeptide. In a and b four dipeptides from two layers (top layer has one peptide with carbons-light blue and one with carbons-silver, bottom layer has one peptide with carbons-green and one with carbons-dark blue; oxygen-red, hydrogen-white, nitrogen-purple; phenyl of Tyr and hydrogens not shown except in H-bonding N—H) are illustrated. L-D dipeptide does not exhibit (dotted oval) the bottom H-bonding of L-L dipeptide. This explains the lower transition temperature of L-D dendritic dipeptide assembly. H-bonding distances are in supplementary SF 14.

Figure 1:
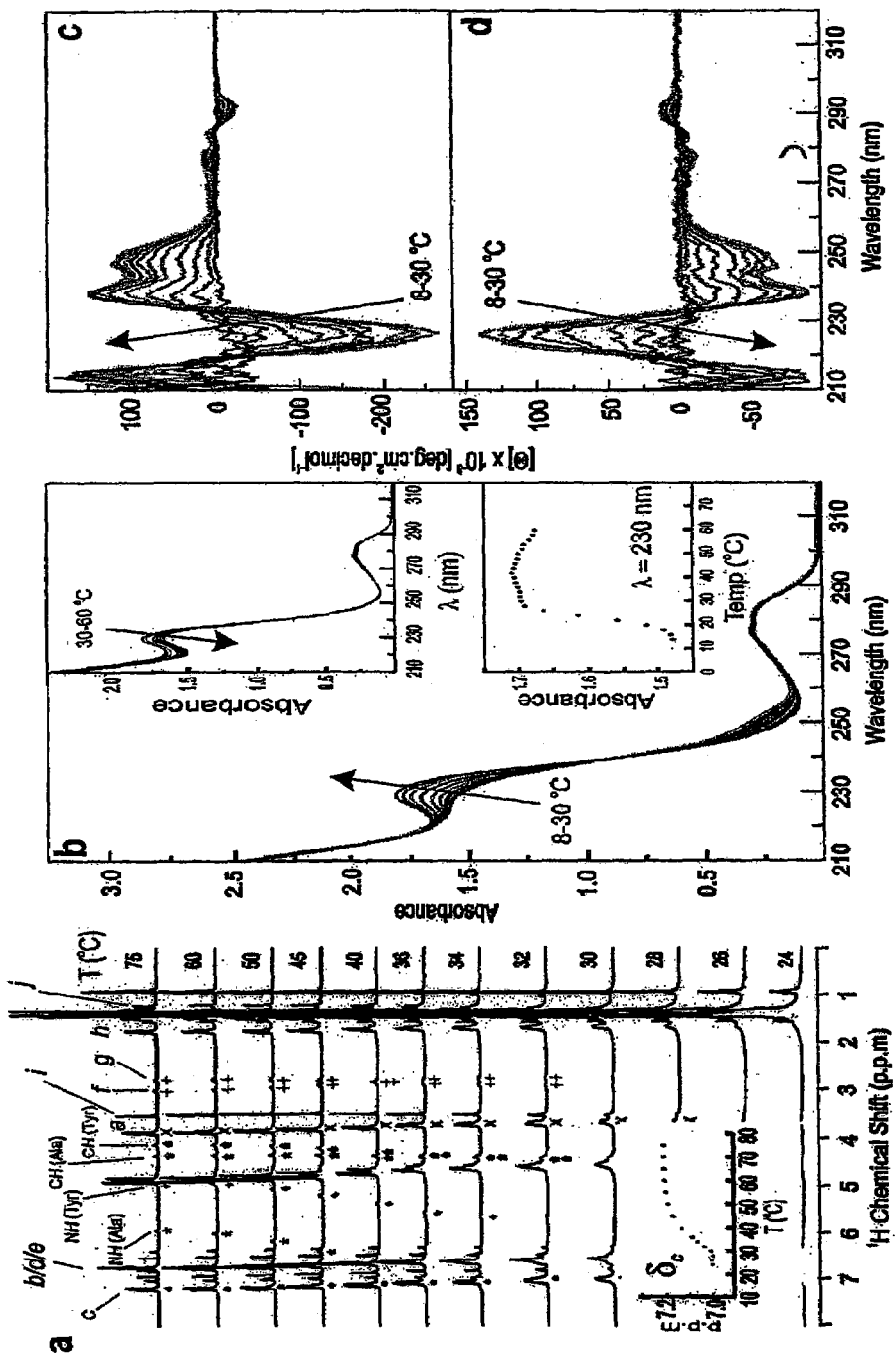
FIG. 1 shows the spectroscopic analysis of dendritic dipeptide self-assembly in solvophobic solution. a $^1$H-NMR (500 MHz) spectra of (4-3,4-3,5)12G$_2$-CH$_2$-Boc-L-Tyr-L-Ala-OMe in C6D12 (2.0×10$^{-3}$M). Inset shows the plot of chemical shift, dc, as a function of temperature. Proton assignments are shown in Scheme VII. b UV spectra of (4-3,4-3,5)12G$_2$-CH$_2$-Boc-L-Tyr-L-Ala-OMe in cyclohexane (1.6×10$^{-4}$ M) exhibiting an isosbestic point at 240 nm. Insets are spectra at higher temperature and a plot of A230 as a function of temperature. c CD spectra of (4-3,4-3,5)12G$_2$-CH$_2$-Boc-L-Tyr-L-Ala-OMe in cyclohexane (1.6×10$^{-4}$M). d CD spectra of (4-3,4-3,5)12G2-CH2-Boc-D-Tyr-D-Ala-OMe in cyclohexane (1.6×10$^{-4}$M). In all parts arrows indicate trends upon increasing temperature.
Figure 2:
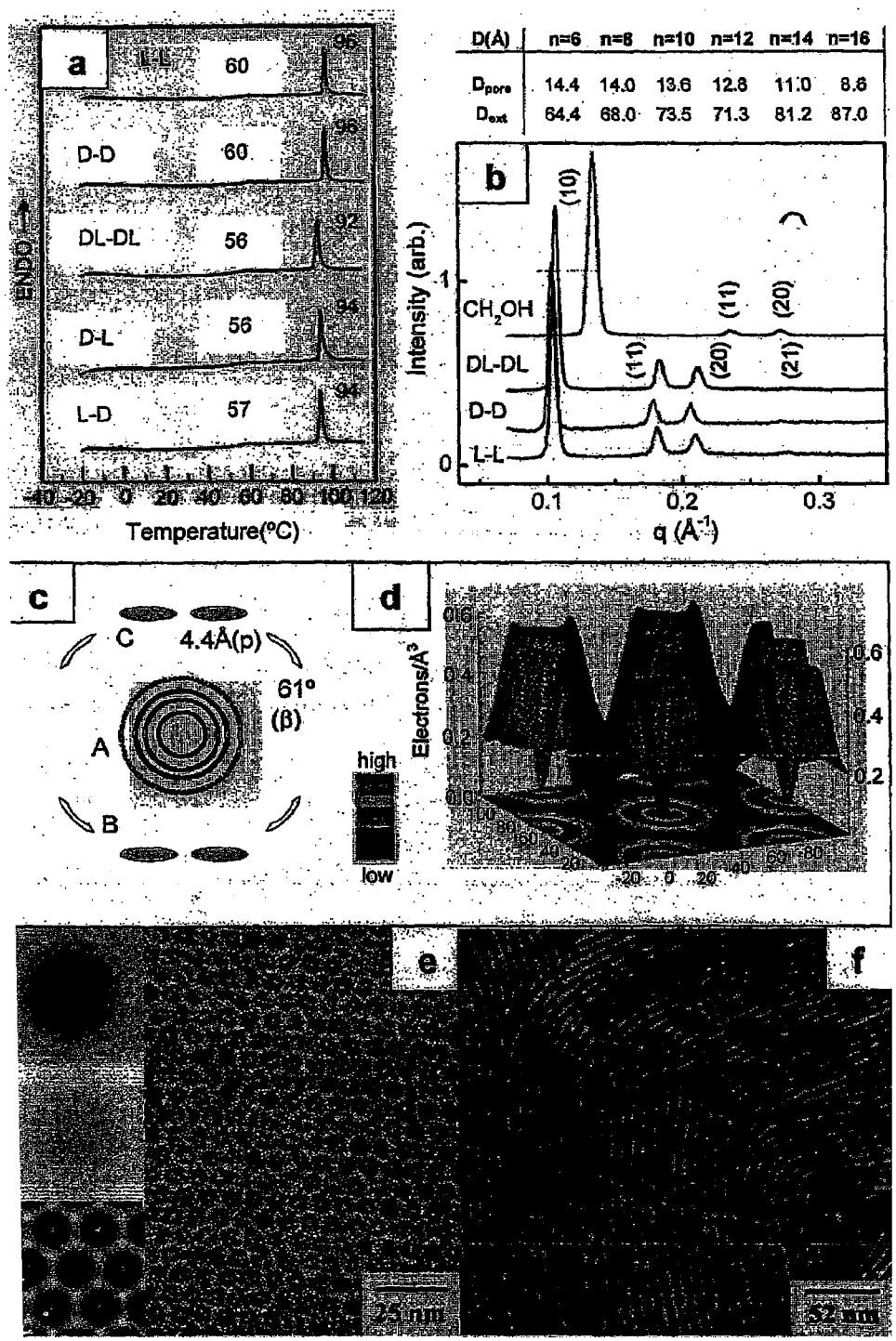
FIG. 2 shows the structural analysis of dendritic dipeptide pore in bulk. a DSC showing the glassy and isotropization temperatures of L-L, D-D, DL-DL, D-L, L-D stereoisomers of (4-3,4-3,5)12G$_2$-CH2-Boc-Tyr-Ala-OMe. b Powder X-Ray Diffraction of L-L, D-D, DL-DL stereoisomers of (4-3,4-3,5)12G$_2$-CH2-Boc-Tyr-Ala-OMe and of (4-3,4-3,5) 12G2-CH20H. Dext and Dpore (Å) of (4-3,4-3,5)nG$_2$-CH2-Boc-L-Tyr-L-Ala-OMe with n=6 to 16 (top table). c Wide and small-angle fiber XRD pattern. (A) column to column distance, long-range order, (B) molecular tilt (b), (C) short-range helical correlation along column axis, short-range pitch. d Electron density maps of (4-3,4-3,5)12G2-CH2-Boc-L-Tyr-L-Ala-OMe columns. Profile shows variation of electron density in a plane perpendicular to columns. Colored contour maps show change in electron density in the same plane. e TEM of (4-3,4-3,5)12G2-CH2-Boc-L-Tyr-L-Ala-OMe along the column axis. Insets from top are: electron diffraction pattern, Fourier transform power spectrum, image reconstructed from the (10), (11) and (20) Fourier components with phases: +, −, −. f, SFM of columns parallel to pyrolytic graphite substrate. Dislocations and disclinations of the focal conic like texture are observed.

Typically, this conformation sterically precludes intermolecular H-bonding. In contrast, H-bonding and self-assembly more easily occur in solvophobic solvents, i.e. cyclohexane, regardless of the dipeptide stereochemistry. In this instance, a decrease in temperature from 60° C. to 30° C. lead to a downfield shift of the NH protons of tyrosine (Tyr) and Ala and of the CH of Tyr (de-shielding). It also lead to an up-field shift of the aromatic, benzyl and methylenic ether protons of the dendron, the latter taken as indicative of H-bonding and shielding effects attributed to inter-molecular interactions. The chemical shifts of the methyl, methoxy and CH groups of alanine (Ala) appear to remain unaffected. Below 30° C., the $^1$H-NMR spectrum broadens. This corresponds to a stiffening of the supra-molecular structure of the compound. Except for the alkyl groups, no NMR spectrum was detected below 24° C. This is taken as indicative of decreased molecular motion. On cooling from 60° C. to 42° C. in cyclohexane, a blue shift and a hyper-chromic -effect were seen in the form of an increase in the absorption at 230 nm ($A_{230}$) of the UV spectrum. The absorption $A_{230}$ remained constant between 42° C. and 30° C. Upon cooling from 30° C. to 12° C., however, an isosbestic point an a hypochromic shift in the form of a second blue shift of the $A_{230}$ peak are observed. The hypochromic effect, indicative of oriented chromophores, varies with their conformation and distance. Below 12° C., the UV absorption spectrum showed no observable changes. Plotting $A_{230}$ as a function of temperature yielded a sigmoidal curve, which was taken as indicative of a cooperative two-state assembly process. In addition, the increase of $A_{230}$ from 60° C. to 42° C. was associated with the transition from a globular dendron containing a mixture of trans and gauche benzyl ether conformers to an all trans-tapered dendron that facilitated self-assembly as is seen in Scheme VII above. During this process, intramolecular interactions within the globular dendron were eliminated, which caused the hyperchromic effect. In addition, the trans-tapered dendron underwent intermolecular H-bonding as shown in FIGS. 2a and 2b. Below 32° C. the hypochromic and blue shifts and the appearance of an isosbestic point were taken as an indication of an equilibrium between the tapered dendron and its aggregate. Upon reaching a temperature of about 12° C. this equilibrium was shifted entirely to the supramolecular aggregate.

CD experiments detect chirality in the supramolecular structure and, thus, are a good complement to the $^1$H-NMR and UV analyses. When chiral dipeptides were placed in THF, and chiral dendritic dipeptides are placed in THF, $CH_2Cl_2$, $CHCl_3$ and $ClCH_2CH_2Cl$ their respective CD spectra between 60° C. and 8° C. all showed only the ellipticity of the dipeptide chromophore at l=232 nm. This is taken as indicative of molecular solutions, i.e. supplementary material in the form of SF1 to SF3. Regardless of temperature and concentration, the CD of the racemic (4-3,4-3,5)12G2-CH2-(DL-Tyr-DL-Ala) did not exhibit any signal in cyclohexane or in any other solvents, which is indicative of SF2. From 60° C. to 30° C., both the L-L and D-D dendritic dipeptides exhibited in cyclohexane only the ellipticity of the dipeptide. These results, together with the UV and NMR data were taken to indicate that the dendron may be adopting an all-trans tapered conformation and may be in fast exchange with its aggregate. Below 30° C. only the trans-tapered conformer is believed to exist in molecular solution. Within this temperature range, what is observed is a transfer of chirality from the dipeptide to the aromatic part of the dendron, an amplification of the Cotton effects, and an isodichroic point. The supramolecular aggregate, therefore, appears to have the ability of amplifying the stereochemical informatin of the dipeptide. The chemical shifts plots, and the ellipticity [Q] at 248 nm (SF4) as a function of temperature are believed to reflect only the equilibrium between the trans-tapered dendron and its aggregate. On the other hand, UV analysis demonstrated the progression of the conformational order of the dendron. For the aggregate in cyclohexane ($1.6 \times 10^{-4}$ M), a transition temperature Tm of 22° C. was calculated from UV, CD and NMR plots as a function of temperature. For clarity, the NMR data are reported at a higher concentration ($2.0 \times 10^{-3}$ M) and show a higher $T_m$ (32° C.).

Figure 3:
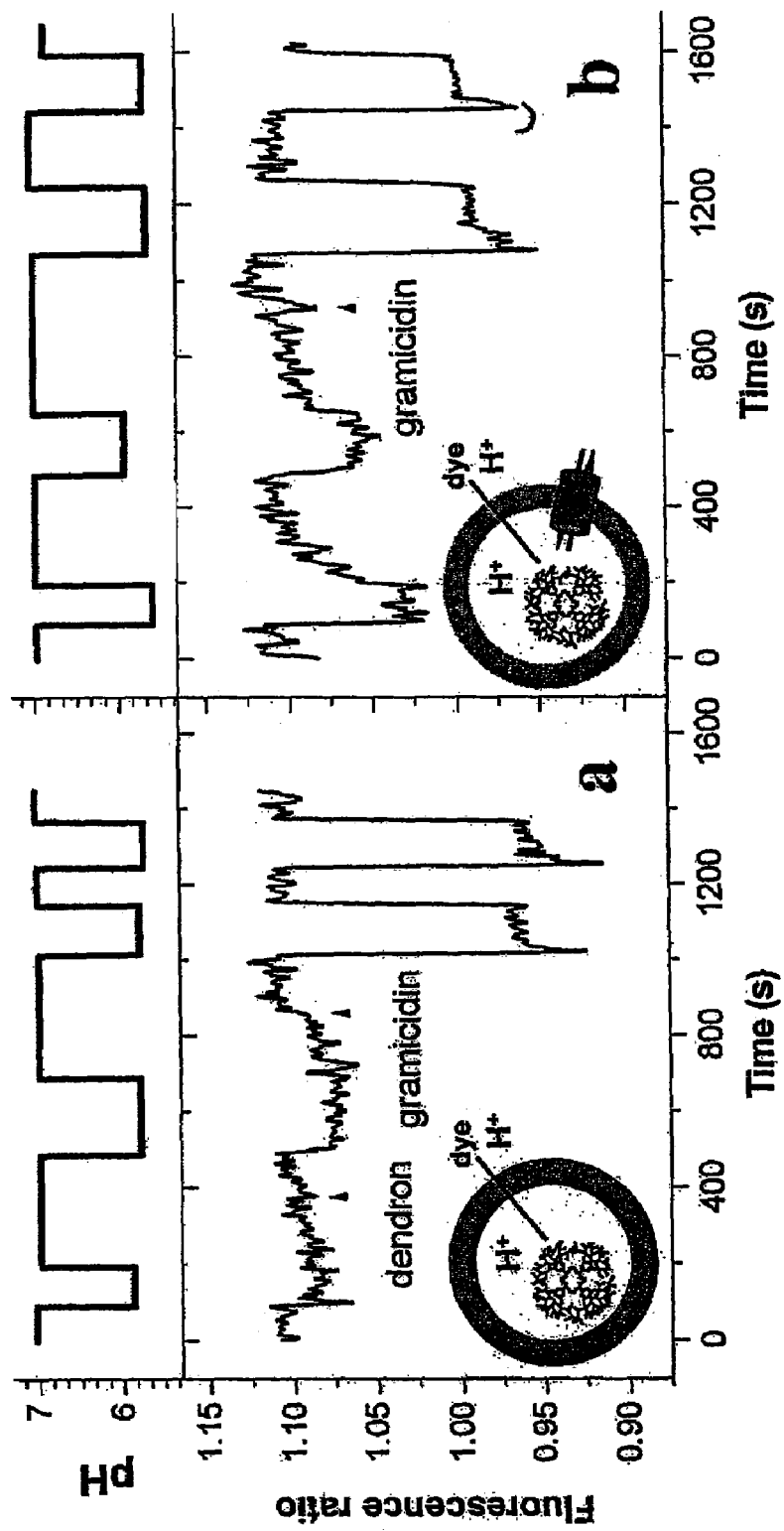
FIG. 3 shows the proton transport through (4-3,4-3,5) 12G2-CH2-(Boc-L-Tyr-L-Ala-OMe) pores reconstituted in phospholipid liposomes (pH-jumps experiments). a Liposomes containing only the membrane-impermeable pH indicator inside. b Liposomes containing the pH indicator inside and the dendritic dipeptide pores. In both cases arrows indicate the addition of the dendritic dipeptide or gramicidin as DMSO/THF solutions. pH-jumps at 20° C. outside the liposome (induced by adding aliquots, about 10 mL of HCl or KOH) were recorded by pH-microelectrodes (upper graphs). pH-jumps inside liposomes were assessed by fluorescence (I647/I670) (lower graphs). The signal of the total amount of captured pH dye was estimated by adding excess of gramicidine.

Differential scanning calorimetry (DSC) data shown in FIG. 3a, small angle powder data, and wide angle oriented fiber x-ray diffraction (XRD) indicated that the supramolecular structures assembled in bulk from (4-3,4-3,5)12G2-CH$_2$-L-Tyr-L-Ala) and (4-3,4-3,5)12G2-CH$_2$-(D-Tyr-D-Ala) and exhibited identical transition temperatures and structure as seen in FIGS. 3a, 3b, 3c and ST2. The control CD spectrum, tested for the absence of linear dichroism, and the dendrons' UV spectra were recorded from both a cyclohexane solution and as thin films on quartz (SF5). Both were identical except for the L-L and D-D dendritic dipeptides, which showed mirror-image Cotton effects as may be observed in FIGS. 2c and 2d. The similarity of the UV and CD spectra obtained from solution and in bulk indicates the presence of similar supramolecular structures in both states. The DL-DL, D-L, and L-D dendritic dipeptides exhibited similar structures as the L-L and D-D as is shown in FIGS. 3a, 3b and 3c. The DL-DL, D-L and L-D dendritic dipeptides, however, had slightly lower transition temperatures. The helical sense of the dipeptides is determined by the Tyr stereochemistry. Thin film CD spectra show this helical columnar structure in both ordered glassy and liquid crystalline states as evidenced in SF5. Although the DL-DL derived supramolecular structure is racemic, its fiber X-Ray Diffraction demonstrates columns with short-range helical order. The presence of helicity in the columns of the racemic DL-DL dendritic dipeptide indicates that helix conformation is induced by the achiral dendrons, with the chiral peptide attached to the dendron only selecting the helix' twist sense. This assembly behavior relates to other examples of stereocenters determining the twist sense of racemic helical structures, in contrast to systems where a stereocenter induces helicity in an achiral non-helical supramolecular structure.

The data confirmed and complemented the data obtained from X-Ray Diffraction (XRD) analysis. The data also showed transmission electron micrographs (TEM) and electron diffraction patterns (ED) of the homeotropically aligned. Scanning force microscopy (SFM) images showed a planar-aligned 2-D hexagonal columnar lattice. Moreover, the TEM images and their Fourier reconstructions evidenced columns with low electron density both in the core and in their aliphatic periphery. These images contrast with previously observed TEM for closed-core columns with a high electron density in their core. The low electron density in the core is associated with the hollow structure of the cylinder and explains the anomalously enhanced intensities of the higher order diffraction peaks (11), (20) and (21) observed in X-Ray Diffraction, and in ED. Absolute electron density profiles were computed from the XRD data (seen in SF10 and SF11) assuming an intra-molecular phase segregated column. The phases of the (10), (11) and (20) reflections were established from the Fourier analysis of the TEM images (SF7, SF8), and those of higher resolution (21) and (30) were phase combinations that resulted in nearly constant electron density for the aromatic and aliphatic regions satisfying the intra-molecular segregated model. The converted electron density profiles of the assembly shown in SF10 and SF11 exhibit significantly lower electron density in the core than the average aliphatic density in the periphery (approximately 0.30 electrons/Å$^3$ for a mass density of 0.86 g/cm$^3$), and demonstrate hollow columns. Form-factor calculations were performed for a column model with three levels of electron density, i.e. hollow core, high density peptide-aromatic region and low density aliphatic periphery, distribution. These calculations in combination with experimental densities, electron density profiles and molecular modeling experiments were performed for the entire series of supramolecular structures generated from L-L X-Ray Diffraction dendritic dipeptides, wherein n=6, 8, 10, 12, 14 or 16 to determine their pore diameters ($D_{pore}$) and structure. The external diameters ($D_{ext}$) were calculated from the peak positions. $D_{pores}$ were obtained from the least-squares fit of the diffraction amplitudes calculated from the three level electron density model to the measured X-Ray Diffraction amplitudes. The dendritic dipeptides, wherein n=12, and the D-D, D-L, L-D, DL-DL stereochemistry have $D_{pore}$ of 13.6, 12.8, 13.7 and 12.80 Å.

Scheme VIII below shows the molecular models of the helical porous columns self-assembled from (4-3,4-3,5) 12G2-CH2-Boc-L-Tyr-L-Ala-OMe (for simplicity n=12 was replaced with n=1). a shows a side-view of the right handed column. b shows a top-view of a. c provides a top view of a single porous column layer, d is a cross-section through the hydrophobic pore (without dendrons) showing its b-barrel structure (CH$_3$ of Ala is white, CH$_3$ of Boc are blue, O is red, C—N of dipeptide are green, aromatic groups are gray) assembled from the b-helical dipeptides, and e provides a schematic model for the self-assembly of the dipeptidic b-barrel pore. The green arrow indicates the dipeptide.

Scheme VIII (a, b, c and d) below shows a side-view of the supramolecule generated from (4-3,4-3,5)12G2-CH$_2$-L-Tyr-L-Ala), its top view (only methyl groups are shown as the alkyl groups of the dendron), the top view of a single layer of the pore, and the pore cross-section without the dendron, respectively. It may be seen in Scheme VIII that a right-handed column self-assembled from the L-L dendritic dipeptide, and a left-handed column self-assembled from the D-D stereoisomer. The pore interior was hydrophobic, and contained the Ala methyl group (white) and one Boc methyl group (blue) on the pore surface. The hydrophilic part of the dipeptide was seen to segregate between the hydrophobic dendron and the hydrophobic pore. Hydrophobic channels are important since they facilitate the transport of ions and water, both at high rate and with selectivity. The conformation of the dendritic dipeptide and the hydrogen bonding interactions that generated the supramolecular assembly and the inner part of the pore are illustrated in Scheme VII shown above. The dipeptide formed an inter-digitated and H-bonded b-helix in response to the self-assembly of its dendritic fragment; the structure of the pore resembling a b-barrel. In elucidating the structure, the classic anti-parallel dipeptide model was eliminated first since it would not form a column. Eight additional structures of pore assembly (4 helical and 4 non-helical) were considered initially. See, Table 12 below.

The model shown in FIG. 4 (Scheme VIIIe) was finally selected because it may be stabilized via an H-bonding network that is shown in Scheme VII b and c. This model is unrelated to that of the single crystal structure of a dipeptide without dendron. Scheme VII b and c, and Scheme VIII provide methods to redesign pore architecture by retro-structural analysis of its X-Ray Diffraction-generated structure. By means of example, a replacement of Boc with Moc in (4-3,4-3,5)12G2-CH$_2$-(L-Tyr-L-Ala) reduced the pore diameter from 12.8 Å to 10.2 Å. The conformation of the Tyr phenyl was anti versus its Boc group and was tilted in the opposite direction. Attaching the dendron to a Tyr via an ester bond rather than a benzyl ether was expected to restrict its dynamics. This was demonstrated for (4-3,4-3,5)12G2-CO$_2$-(L-Tyr-L-Ala), which despite a D$_{pore}$=12.4 Å required longer annealing to achieve structural order as measured by X-Ray Diffraction. The replacement of L-Ala from (4-3,4-3,5-)12G2-CH$_2$-(L-Tyr-L-Ala) with other non-polar or polar amino acids, e.g. Gly, L-Val, L-Phen and L-Ser, of L-Tyr with L-Cys, of (L-Tyr-L-Ala) with (L-Ala-L-Tyr), and of (4-3,4-3,5)12G2-with other dendrons produced building blocks that self-assemble into related porous columns as may be seen in ST6 and ST8. The smaller D$_{pore}$ of (4-3,4-3,5)12G2-CH$_2$-[Boc-L-Cys-L-Ala-OMe] (10.0 vs. 13 Å for the same dendritic dipeptide with Boc-L-Tyr-L-Ala-OMe dipeptide) indicated that the Tyr phenyl group may play an important role in the self-assembly of porous columns.

In view of the above, the inventor designed a library of self-assembling dendrons containing additional phenyl and biphenyl groups in their apex and/or branches to produce 20 non-peptidic porous columns with a D$_{pore}$ of about 2 to 24 Å. These structures together with those generated from the 19 dendritic di-peptides demonstrated the simplicity and versatility of the method of this invention to producing non-biological pores and tubular liquid crystals. The successful self-assembly of dendritic dipeptides in cyclohexane indicates that they may also assemble in phospholipid membranes, and the suitable decoration of their alkyl groups most likely mediates their assembly in, or on, the surface of microbial cell membranes. As a first step in this direction, the inventor reconstructed the porous structure of (4-3,4-3,5)12G2-CH$_2$-[Boc-L-Tyr-L-Ala-OMe] in both a thermotropic bilayer lamellar phase, and in liposomes produced from phospholipids. The proton translocation mediated by dendritic pores and gramicidin channels was evaluated by monitoring the emission intensity of a pH sensitive fluorescent dye captured inside the liposomes. The proton permeability of liposomes containing an average 2-3 reconstituted dendritic pores (14/1 mass ratio phospholipid to dendritic dipeptide) was comparable in efficiency to those containing gramicidin channels. These results illustrate that supramolecular dendrimer chemistry allows the controlled design of a range of periodic non-biological porous structures forming in solution and as films.

(4-3,4-3,5)12G$_2$-CH$_2$-(Boo-Tyr-Ala-OMe)

| Dipeptide Core | Column Diameter (Å) D$_{ext}$ | Pore Diameter (Å) D$_{pore}$ |
|---|---|---|
| Boo-L-Tyr-L-Ala-OMe | 71.3 ± 0.2 | 12.8 ± 0.4 |
| Boo-O-Tyr-O-Ala-OMe | 72.6 ± 0.2 | 13.8 ± 1.0 |
| Boo-O-tyr-L-Ala-OMe | 72.0 ± 0.2 | 12.8 ± 3.0 |
| Boo-L-tyr-O-Ala-OMe | 71.3 ± 0.2 | 13.4 ± 1.8 |
| Boo-OL-tye-OL-Ala-OMe | 80.0 ± 0.2 | 12.5 ± 0.8 |

Supramolecular Porous Dendritic Dipeptides vs. Amino Acid Stereochemistry

Scheme X: Supramolecular Porous Dendritic Dipeptides vs. Amino Acids/Protecting Groups

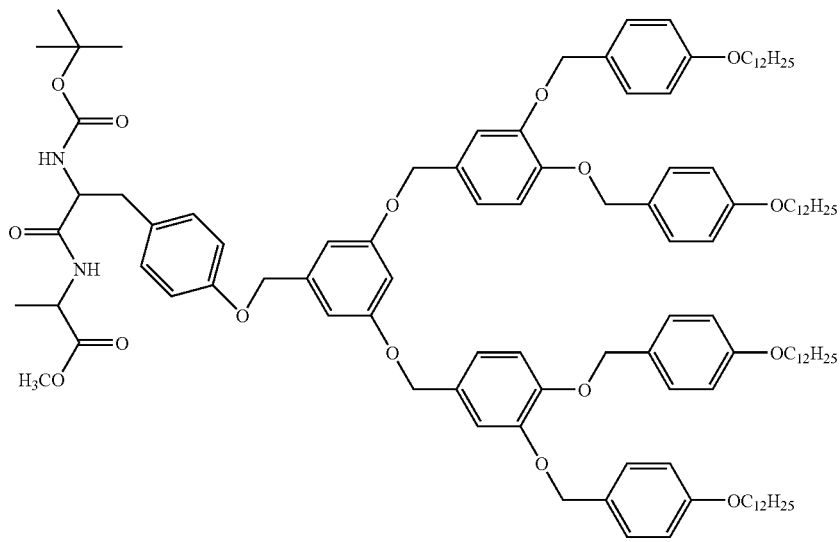

(4-3,4-3,5)12G$_2$-CH$_2$-(Boc-L-Tyr-L-Ala-OMe)
D$_{ext}$ = 71.3 ± 0.2 Å; D$_{pore}$ = 12.8 ± 0.4 Å

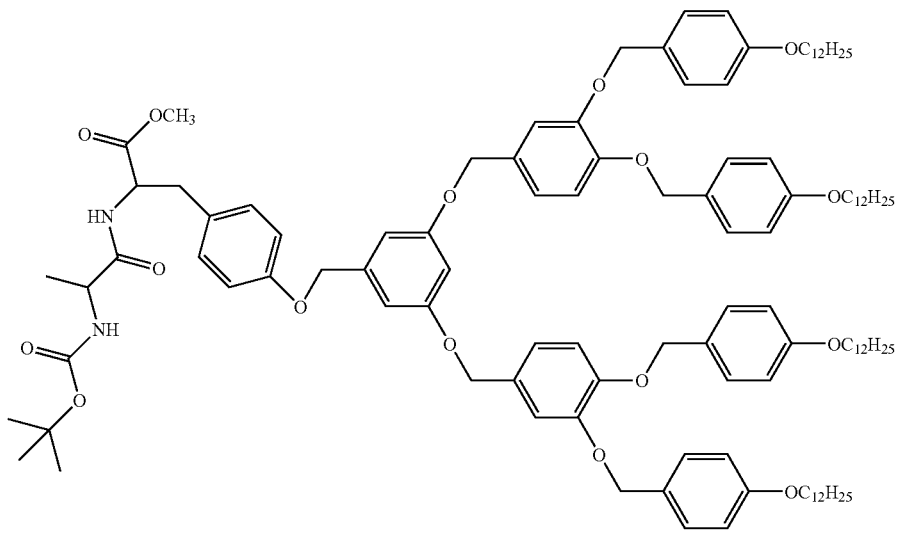
(4-3,4-3,5)12G$_2$-CH$_2$-(Boc-L-Ala-L-Tyr-OMe)
D$_{ext}$ = 73.2 ± 0.5 Å; D$_{pore}$ = 13.8 ± 2.0 Å
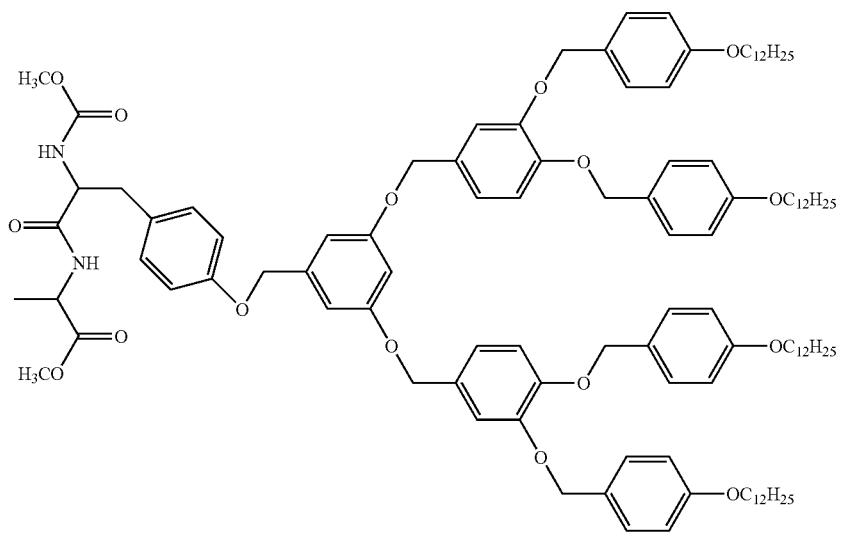
(4-3,4-3,5)12G$_2$-CH$_2$-(Moc-L-Tyr-L-Ala-OMe)
D$_{ext}$ = 74.4 ± 0.5 Å; D$_{pore}$ = 12.2 ± 2.0 Å

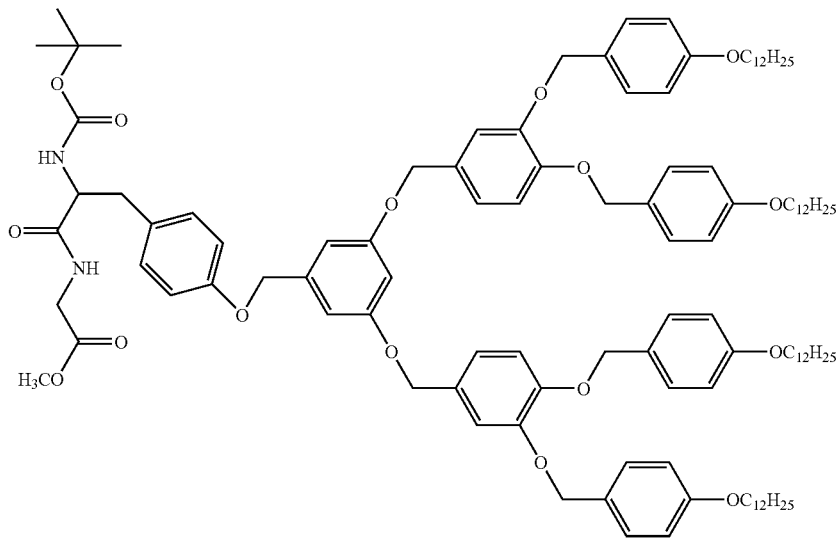
(4-3,4-3,5)12G$_2$-CH$_2$-(Boc-L-Tyr-Gly-OMe)
D$_{ext}$ = 70.1 ± 0.4 Å; D$_{pore}$ = 11.8 ± 1.4 Å
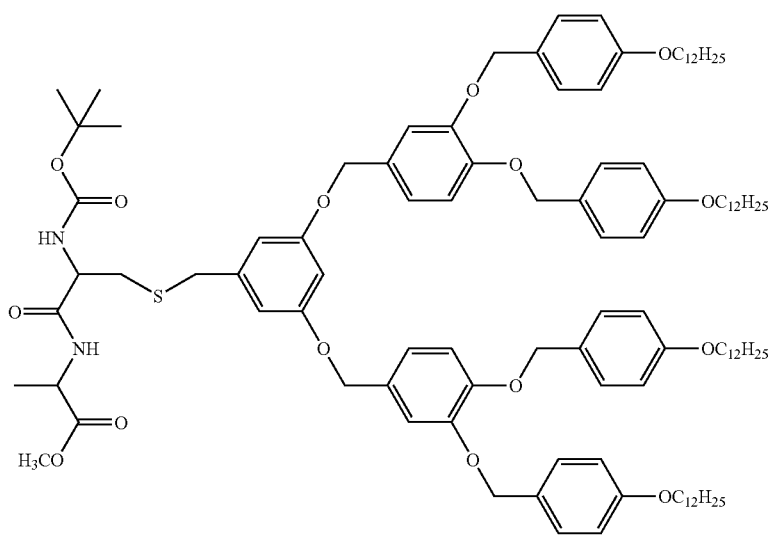
(4-3,4-3,5)12G$_2$-CH$_2$-(Boc-L-Cys-L-Ala-OMe)
D$_{ext}$ = 69.5 ± 0.2 Å; D$_{pore}$ = 10.0 ± 1.6 Å

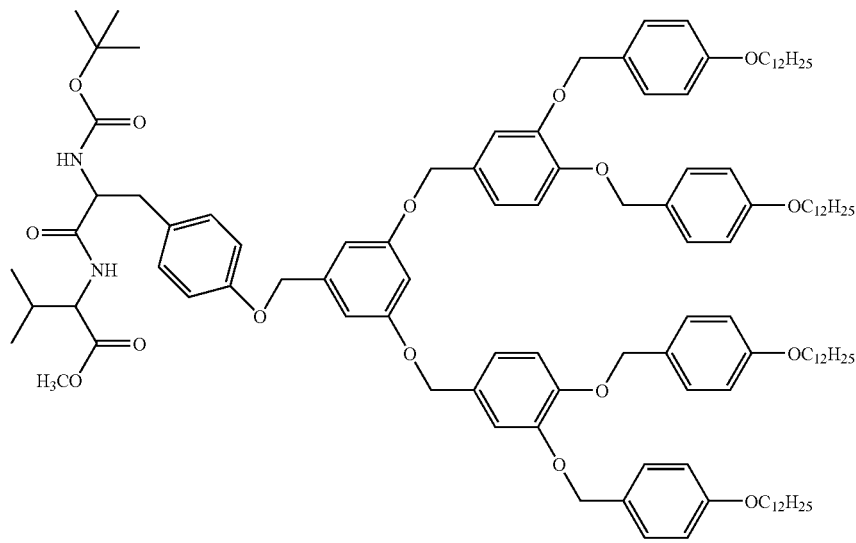
(4-3,4-3,5)12G$_2$-CH$_2$-(Boc-L-Tyr-L-Val-OMe)
D$_{ext}$ = 74.2 ± 0.2 Å°; D$_{pore}$ = 14.2 ± 2.0 Å
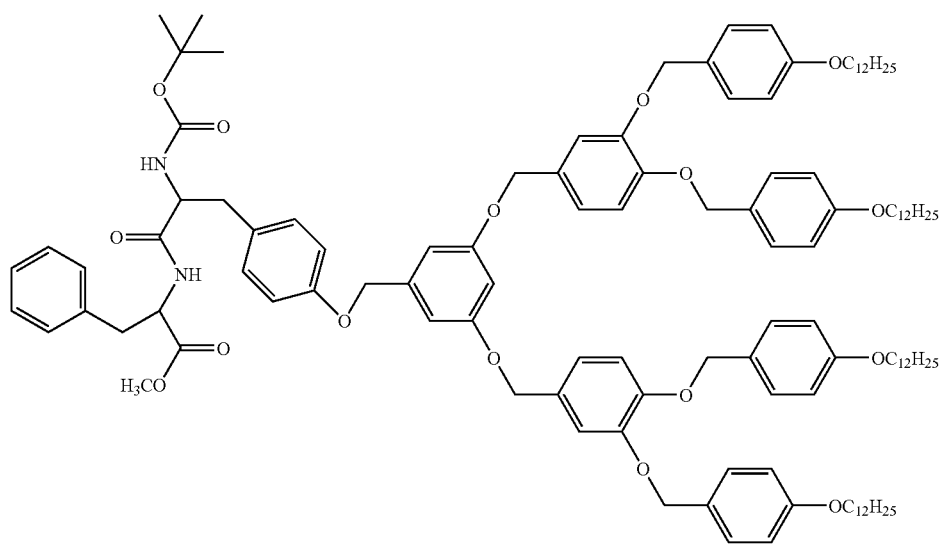
(4-3,4-3,5)12G$_2$-CH$_2$-(Boc-L-Tyr-L-Phe-OMe)
D$_{ext}$ = 62.1 ± 0.8 Å; D$_{pore}$ = 9.4 ± 0.4 Å

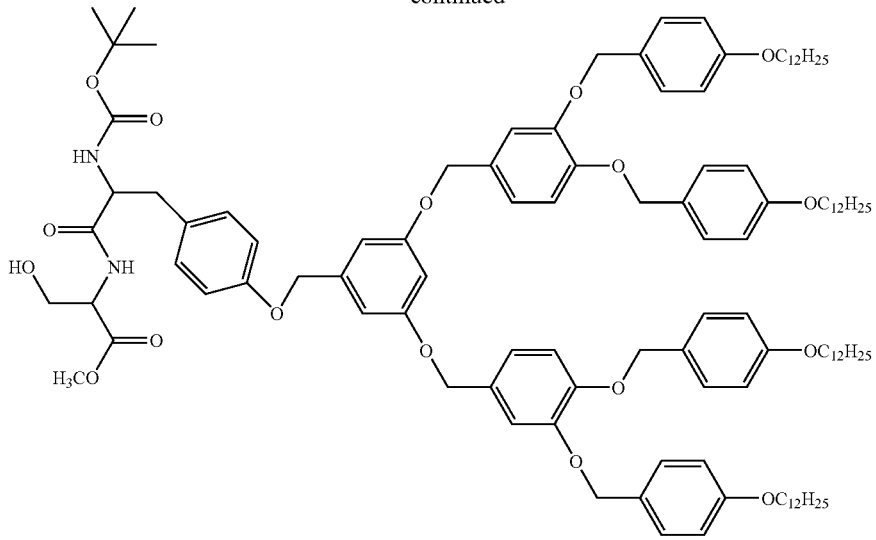

(4-3,4-3,5)12G$_2$-CH$_2$-(Boc-L-Tyr-L-Ser-OMe)
D$_{ext}$ = 68.3 ± 2.2 Å; D$_{pore}$ = 11.5 ± 1.6 Å

Schemes IX through XVI presented above and below show representative examples of amphiphilic dendritic dipeptides of the invention with different dendrons, peptides and substituents. These are merely representative species of the polymers of this invention and, by no means, preclude the inclusion of other species encompassed by the general definitions included in the Glossary and the claims.

Scheme XI: Supramolecular Porous Dendritic Dipeptides with Dendron Periphery Alkyl

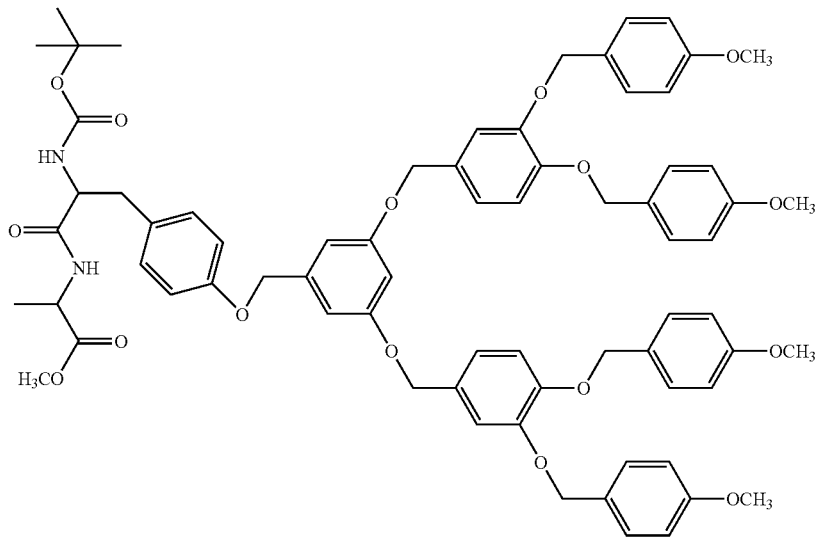

(4-3,4-3,5)1G$_2$-CH$_2$-(Boc-L-Tyr-L-Ala-OMe)
D$_{ext}$ = 66.7 Å Columnar Nematic (N$_c$)

-continued
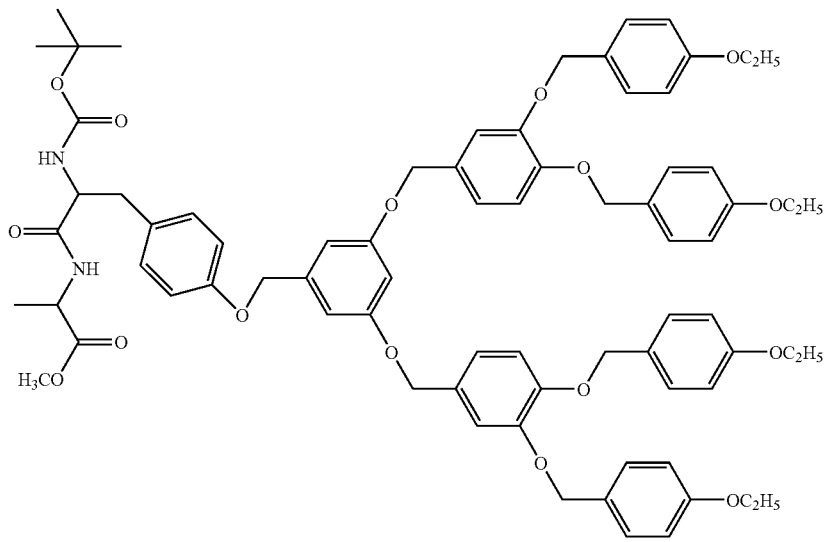
(4-3,4-3,5)2G$_2$-CH$_2$-(Boc-L-Tyr-L-Ala-OMe)
D$_{ext}$ = 27.4 Å Columnar Nematic (N$_c$)
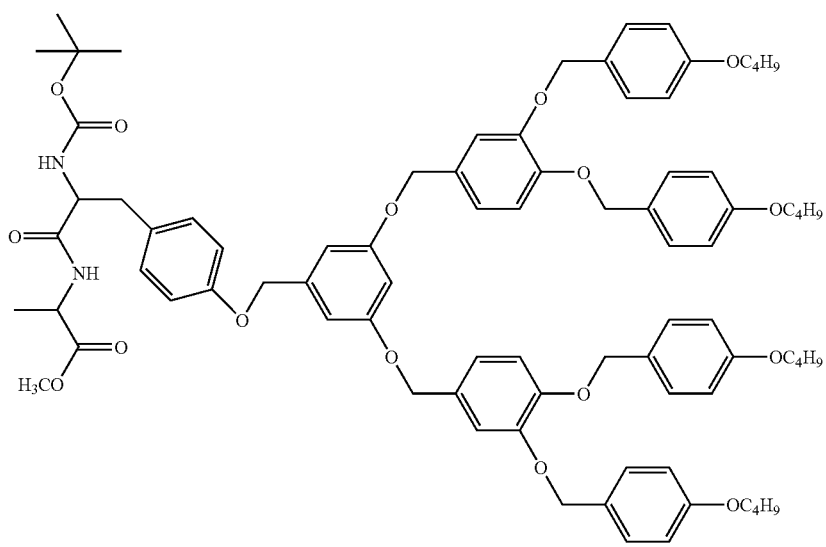
(4-3,4-3,5)4G$_2$-CH$_2$-(Boc-L-Tyr-L-Ala-OMe)
Crystalline -continued
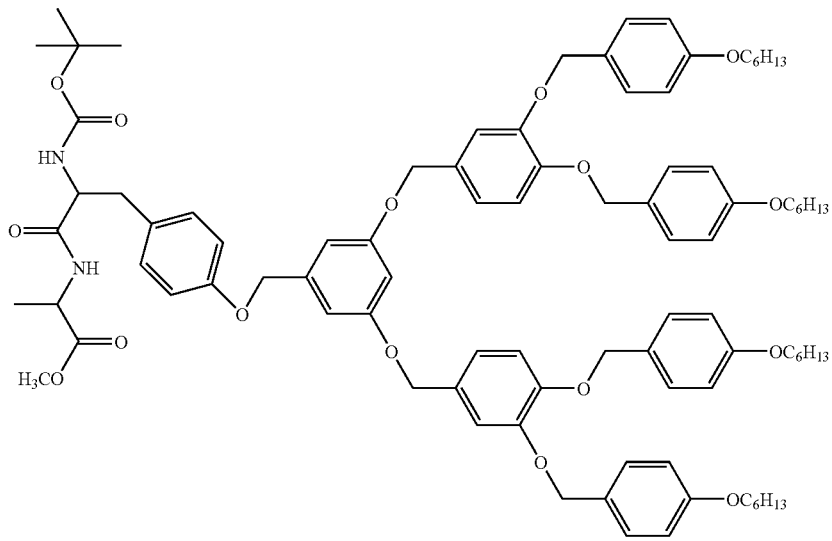
(4-3,4-3,5)6G$_2$-CH$_2$-(Boc-L-Tyr-L-Ala-OMe)
D$_{ext}$ = 64.4 ± 0.6 Å; D$_{pore}$ = 14.4 ± 0.8 Å
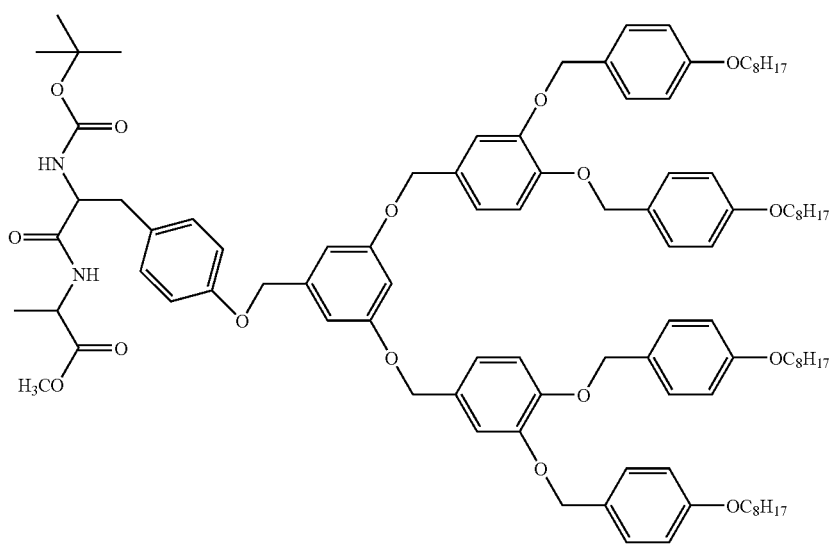
(4-3,4-3,5)8G$_2$-CH$_2$-(Boc-L-Tyr-L-Ala-OMe)
D$_{ext}$ = 68.0 ± 0.4 Å; D$_{pore}$ = 14.0 ± 1.2 Å

-continued
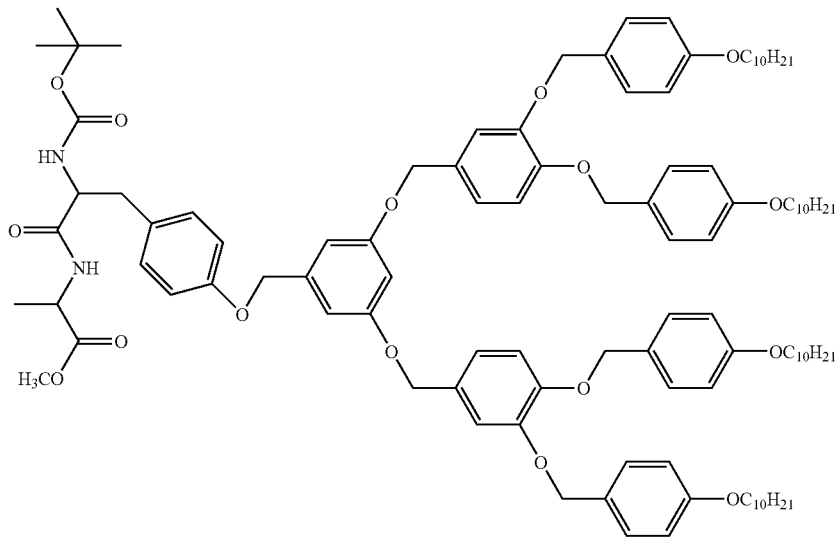
(4-3,4-3,5)10G$_2$-CH$_2$-(Boc-L-Tyr-L-Ala-OMe)
D$_{ext}$ = 73.5 ± 0.4 Å; D$_{pore}$ = 13.6 ± 1.8 Å
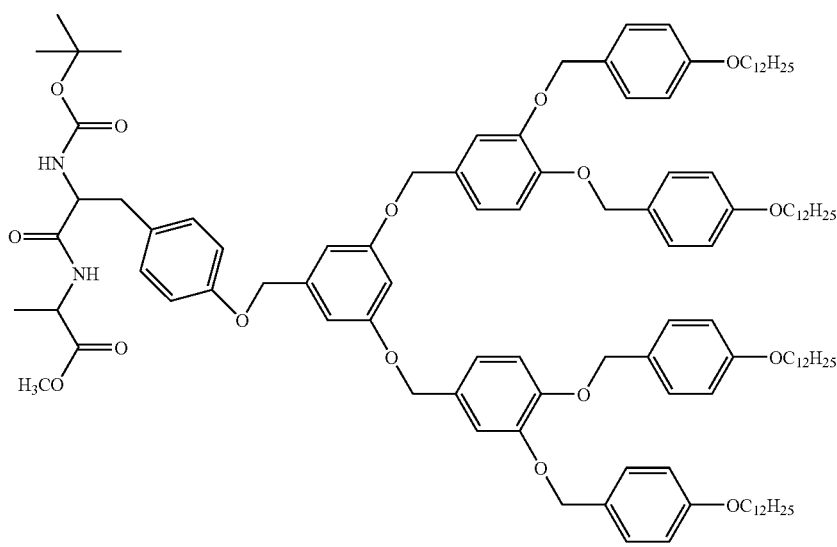
(4-3,4-3,5)12G$_2$-CH$_2$-(Boc-L-Tyr-L-Ala-OMe)
D$_{ext}$ = 71.3 ± 0.2 Å; D$_{pore}$ = 12.8 ± 0.4 Å

-continued
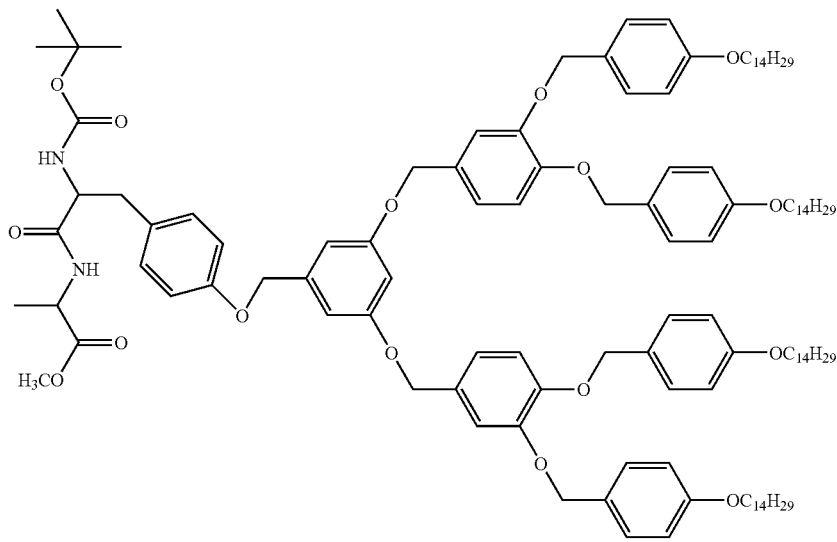
(4-3,4-3,5)14G$_2$-CH$_2$-(Boc-L-Tyr-L-Ala-OMe)
D$_{ext}$ = 81.2 ± 0.3 Å; D$_{pore}$ = 11.0 ± 2.6 Å
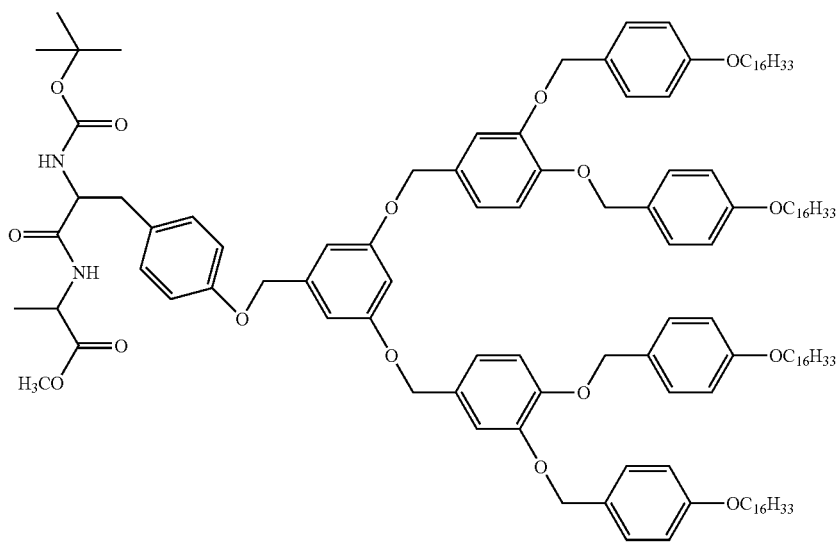
(4-3,4-3,5)16G$_2$-CH$_2$-(Boc-L-Tyr-L-Ala-OMe)
D$_{ext}$ = 87.0 ± 0.3 Å; D$_{pore}$ = 8.6 ± 2.0 Å

Scheme XII: Supramolecular Porous Dendritic Dipeptides from Different Dendrons
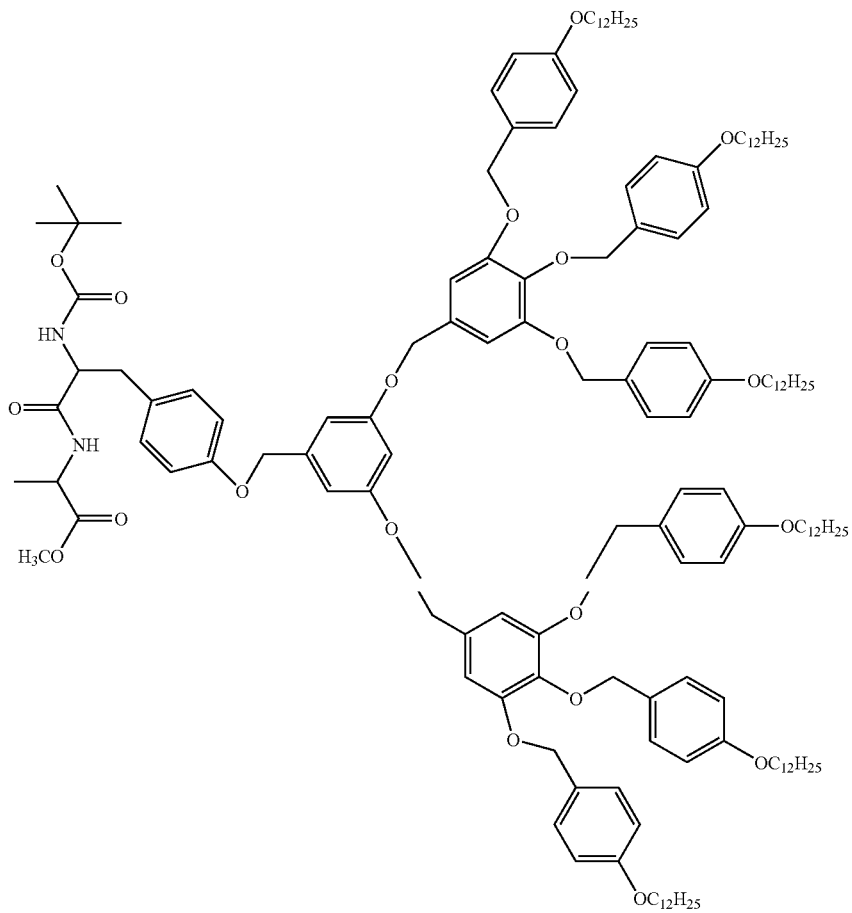
(4-3,4-3,5)12G$_2$-CH$_2$-(Boc-L-Tyr-L-Ala-OMe)
D$_{ext}$ = 52.0 Å Columnar Nematic (N$_c$)
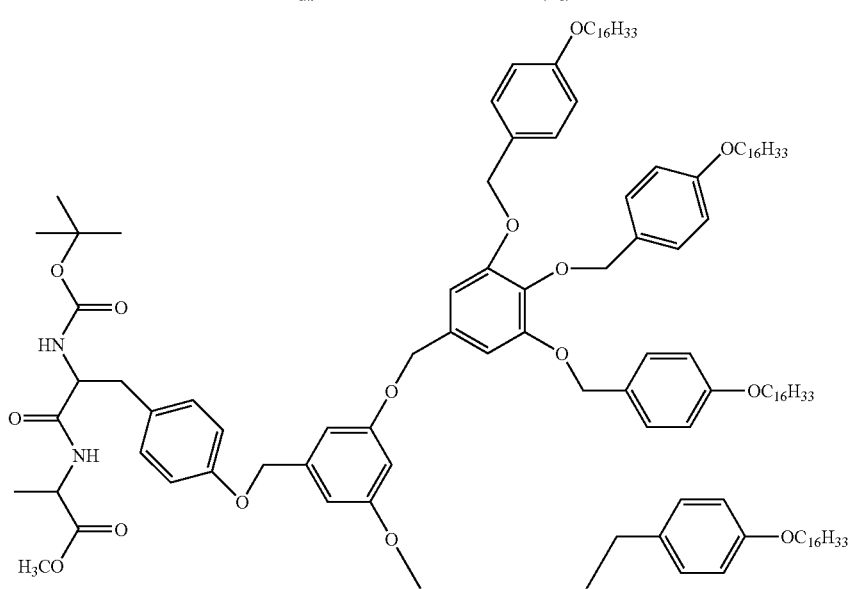

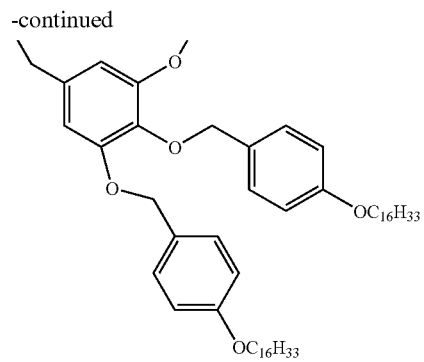
(4-3,4-3,5)16G$_2$-CH$_2$-(Boc-L-Tyr-L-Ala-OMe)
D$_{ext}$ = 65.8 ± 0.3 Å; D$_{pore}$ = 9.2 ± 2.4 Å
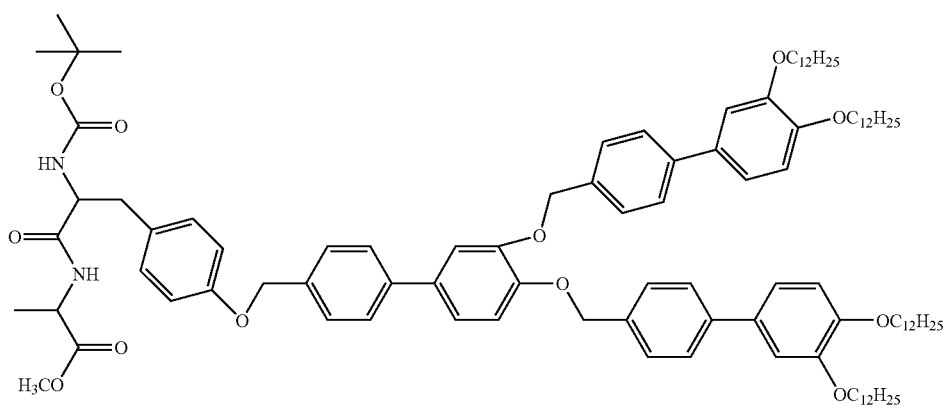
[(3,4Bp)$^2$]12G$_2$-CH$_2$-(Boc-L-Tyr-L-Ala-OMe)
D$_{ext}$ = 83.2 ± 0.3 Å; D$_{pore}$ = 13.0 ± 4.0 Å
Scheme XIII: Supramolecular Porous Dendrimers with Additional Focal Point Benzyl Ethers
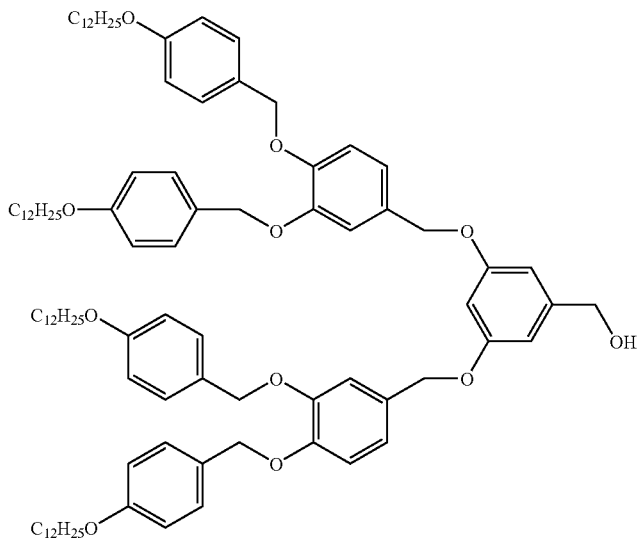
(4-3,4-3,5)12G2-CH$_2$OH
D$_{ext}$ = 53.1 Å; D$_{pore}$ = 0 Å

-continued
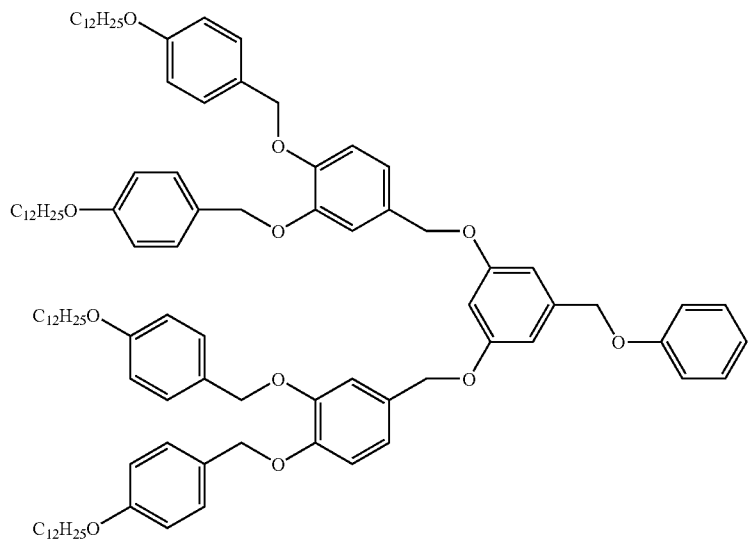
(4-3,4-3,5)12G2-H
$D_{ext} = 62.6$ Å; $D_{pore} = 4.5 \pm 1.6$ Å
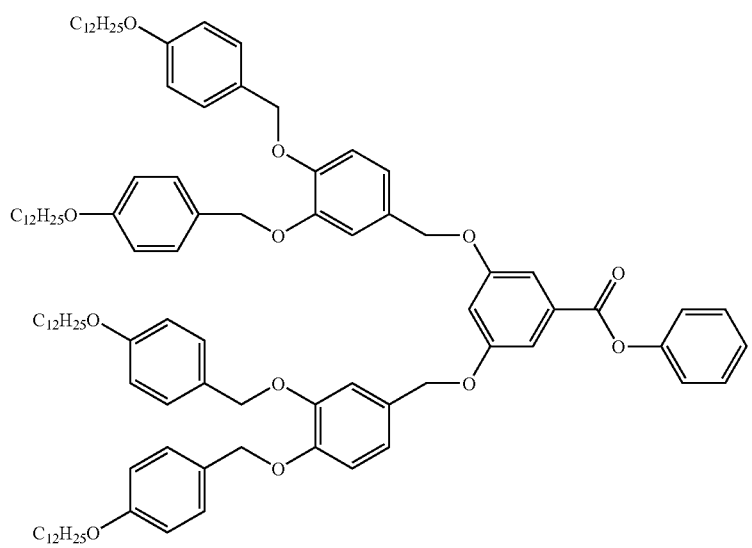
(4-3,4-3,5)12G2-CO$_2$Ph
$D_{ext} = 44.0$ Å; $D_{pore} = 6.9 \pm 3.2$ Å

-continued
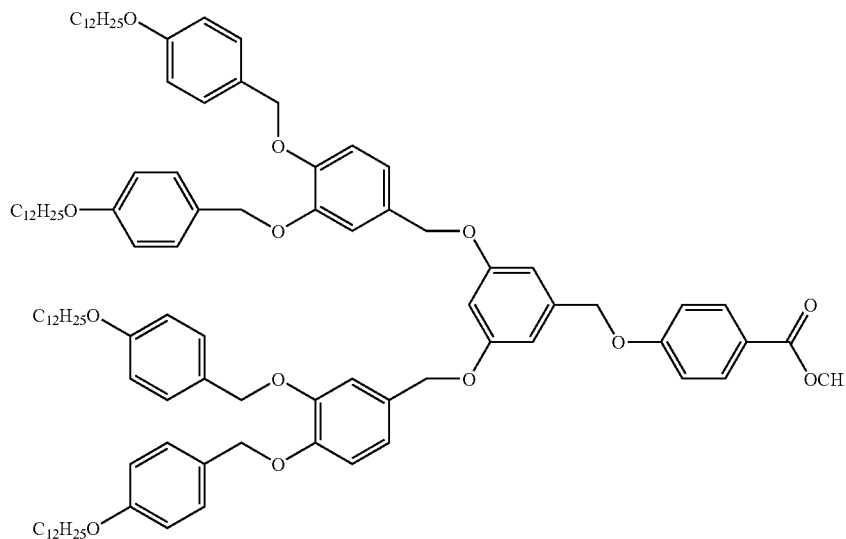
(4-3,4-3,5)12G2-CO$_2$CH$_3$
D$_{ext}$ = 64.4 Å; D$_{pore}$ = 3.6 ± 0.7 Å
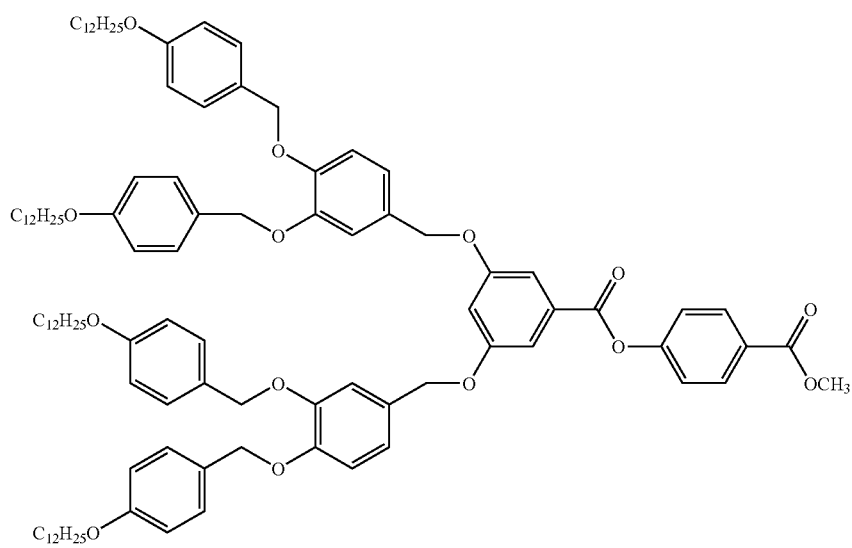
(4-3,4-3,5)12G2-CO$_2$PhCO$_2$CH$_3$
D$_{ext}$ = 64.4 Å; D$_{pore}$ = 3.1 ± 2.8 Å

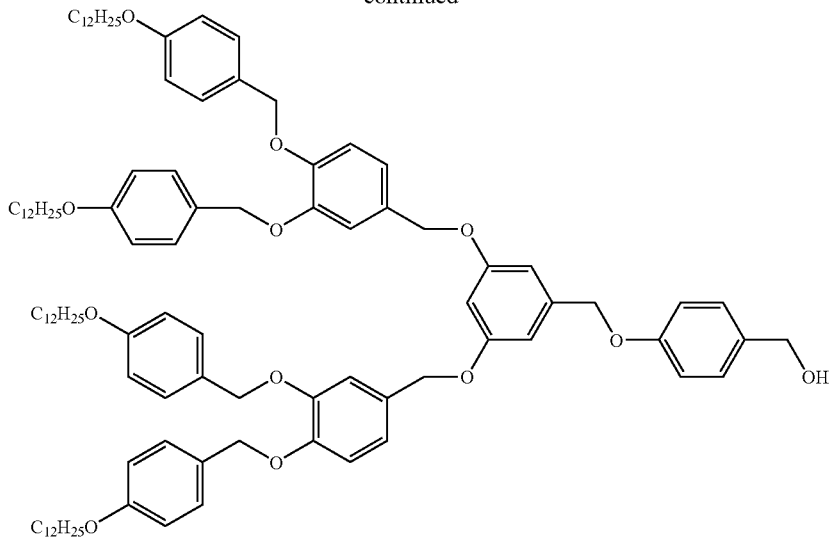
(4-3,4-3,5-4)12G2-CO₂OH
$D_{ext}$ = 62.6 Å; $D_{pore}$ = 2.3 ± 0.7 Å
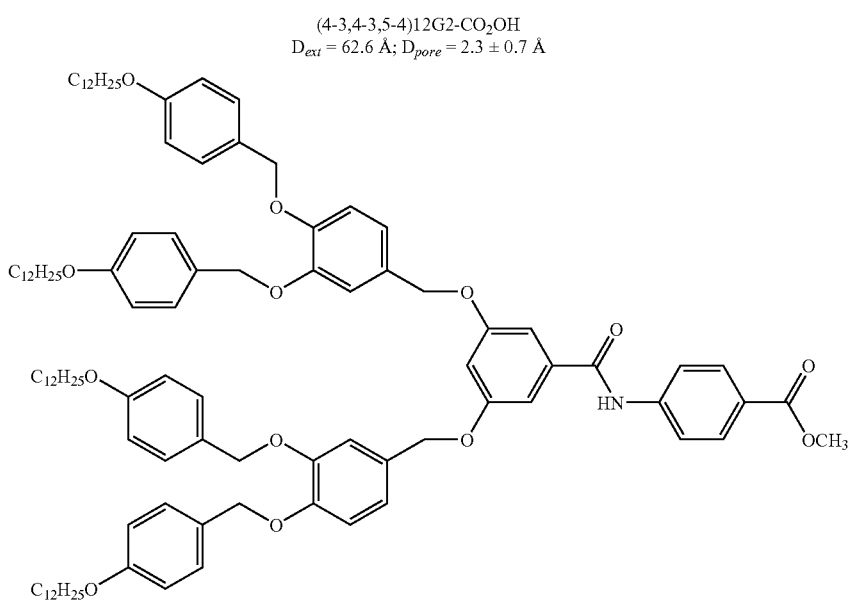
(4-3,4-3,5)12G2-CONHPhCO₂CH₃
$D_{ext}$ = 63.2 Å; $D_{pore}$ = 2.0 ± 1.0 Å
Scheme XIV: Supramolecular Porous Dendrimers with Multiple Focal Point Benzyl Ethers
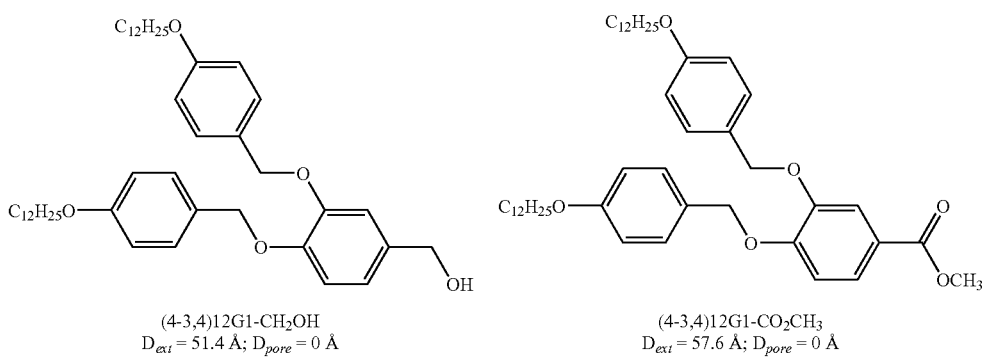
(4-3,4)12G1-CH₂OH
$D_{ext}$ = 51.4 Å; $D_{pore}$ = 0 Å
(4-3,4)12G1-CO₂CH₃
$D_{ext}$ = 57.6 Å; $D_{pore}$ = 0 Å

-continued
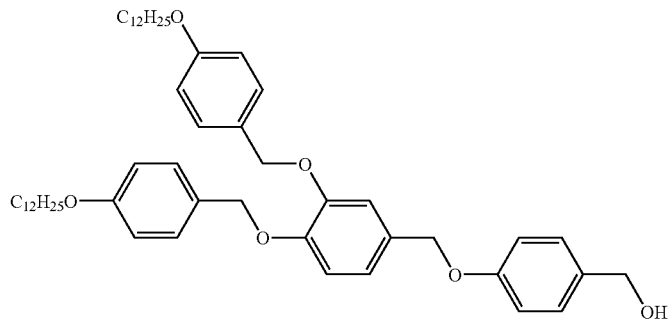
(4-3,4-4)12G1-CH$_2$OH
$D_{ext}$ = 61.2 Å; $D_{pore}$ = 4.0 ± 2.5 Å
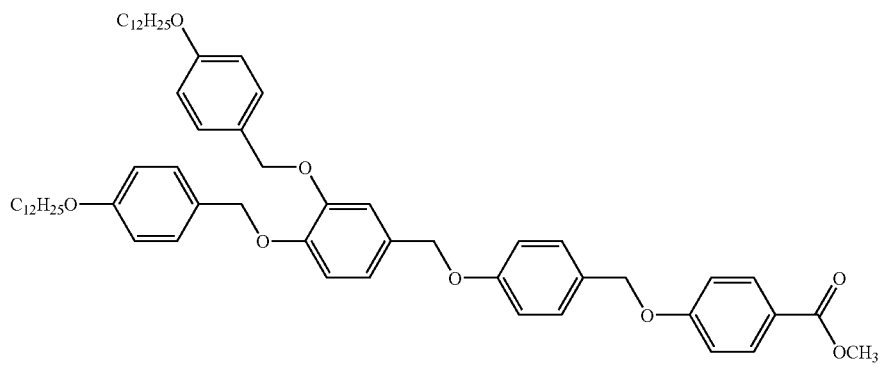
(4-3,4-(4)$^2$]12G1-CO$_2$CH$_3$
$D_{ext}$ = 72.1 Å; $D_{pore}$ = 4.5 ± 2.4 Å
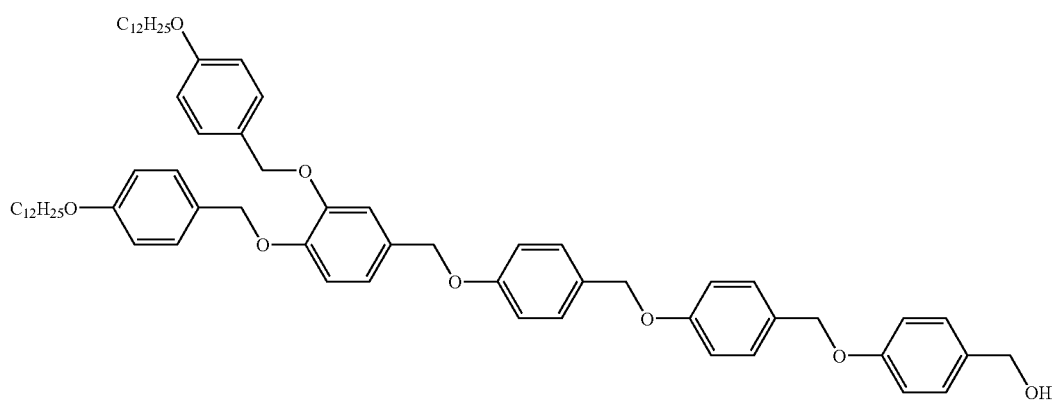
(4-3,4(4)$^3$]12G1-CH$_2$OH
$D_{ext}$ = 81.8 Å; $D_{pore}$ = 13.2 ± 1.6 Å

Scheme XV
Supramolecular Porous Dendrimers with
Additional Focal Point/Branch Benzyl Ethers
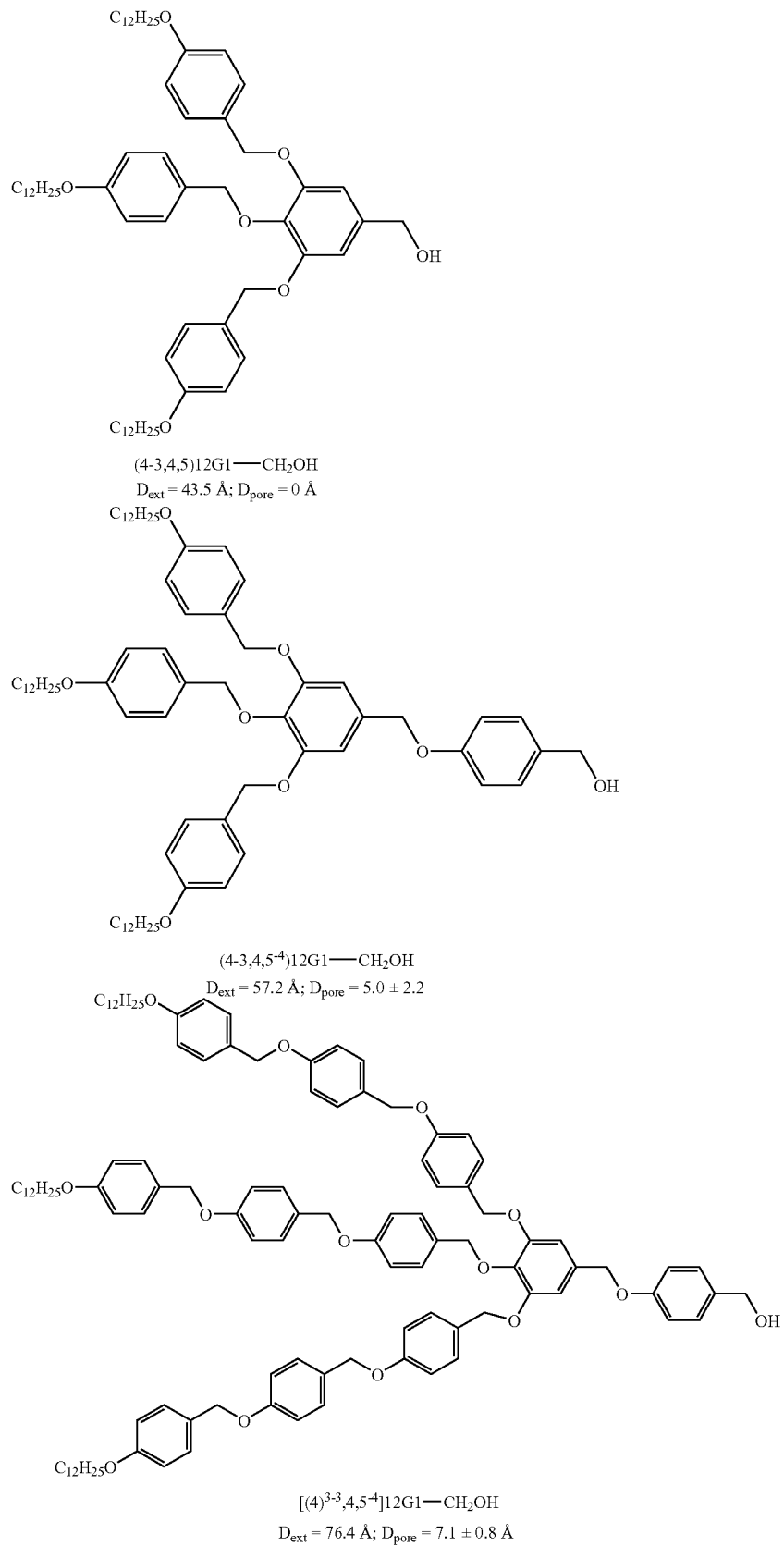
(4-3,4,5)12G1—CH$_2$OH
$D_{ext}$ = 43.5 Å; $D_{pore}$ = 0 Å
(4-3,4,5$^{-4}$)12G1—CH$_2$OH
$D_{ext}$ = 57.2 Å; $D_{pore}$ = 5.0 ± 2.2
[(4)$^{3-3}$,4,5$^{-4}$]12G1—CH$_2$OH
$D_{ext}$ = 76.4 Å; $D_{pore}$ = 7.1 ± 0.8 Å

Scheme XVI:
Supramolecular Porous Dendrimers with Focal Point Biphenyls
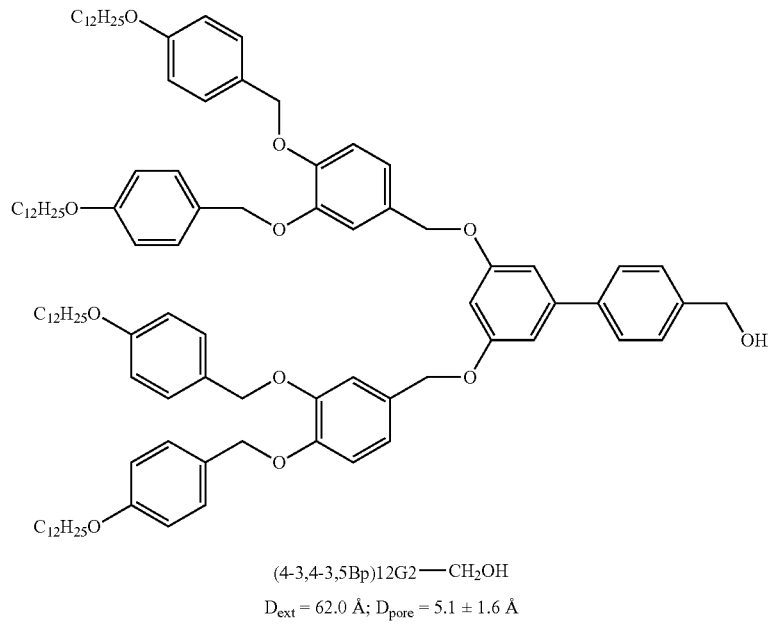
(4-3,4-3,5Bp)12G2—CH$_2$OH
$D_{ext}$ = 62.0 Å; $D_{pore}$ = 5.1 ± 1.6 Å
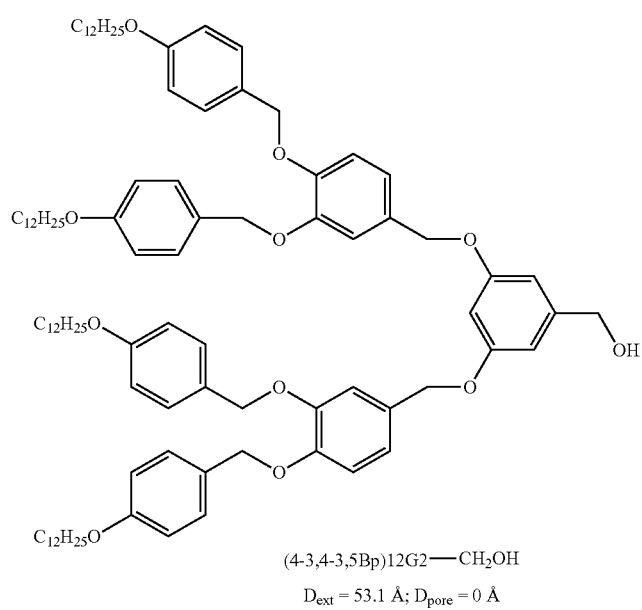
(4-3,4-3,5Bp)12G2—CH$_2$OH
$D_{ext}$ = 53.1 Å; $D_{pore}$ = 0 Å

-continued
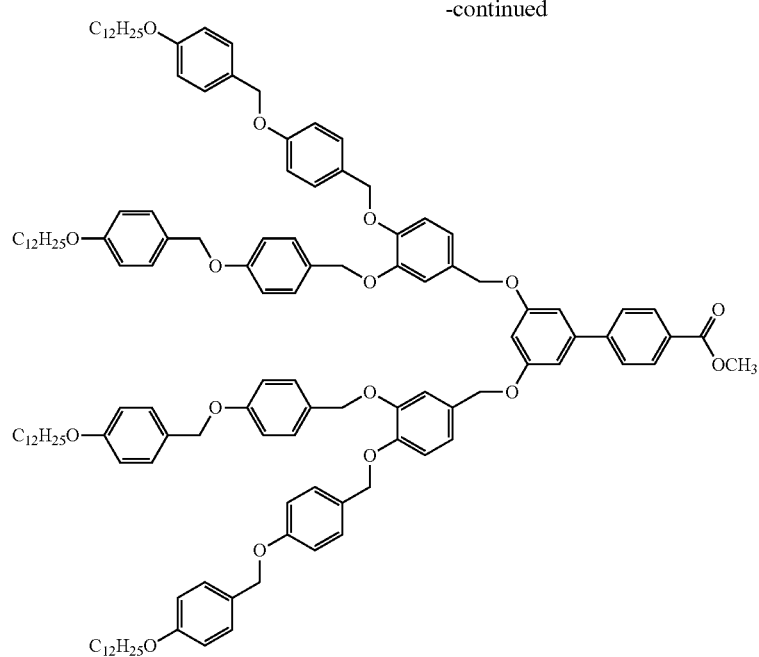
[(4)²-3,4-3,5Bp]12G2—CO₂CH₃
$D_{ext}$ = 76.1 Å; $D_{pore}$ = 10.4 ± 1.0 Å
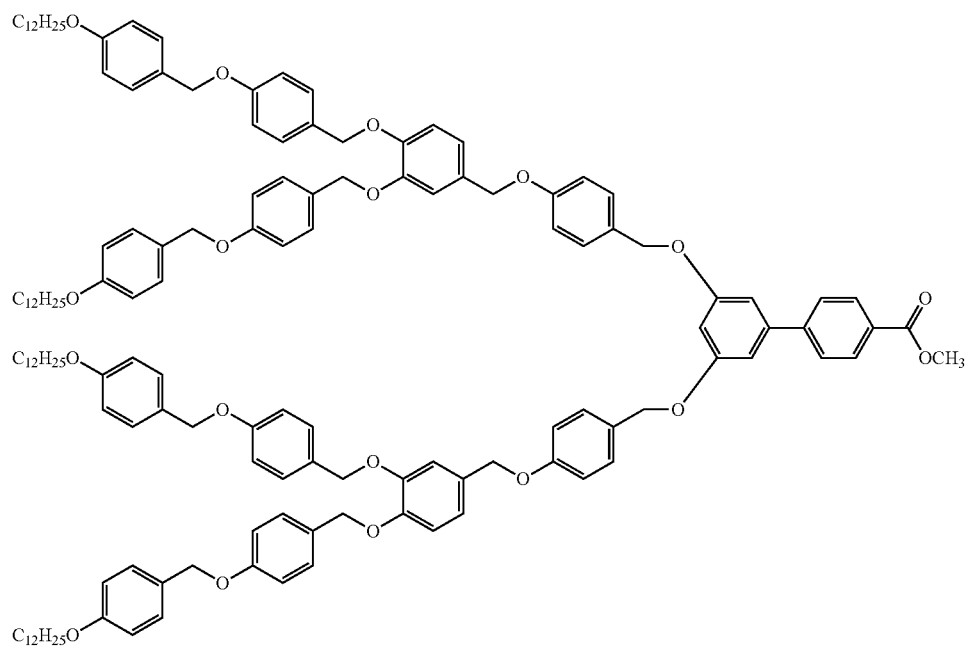
[(4)²-3,4-4-3,5Bp]12G2—CO₂CH₃
$D_{ext}$ = 91.9 Å; $D_{pore}$ = 11.1 ± 4.0 Å

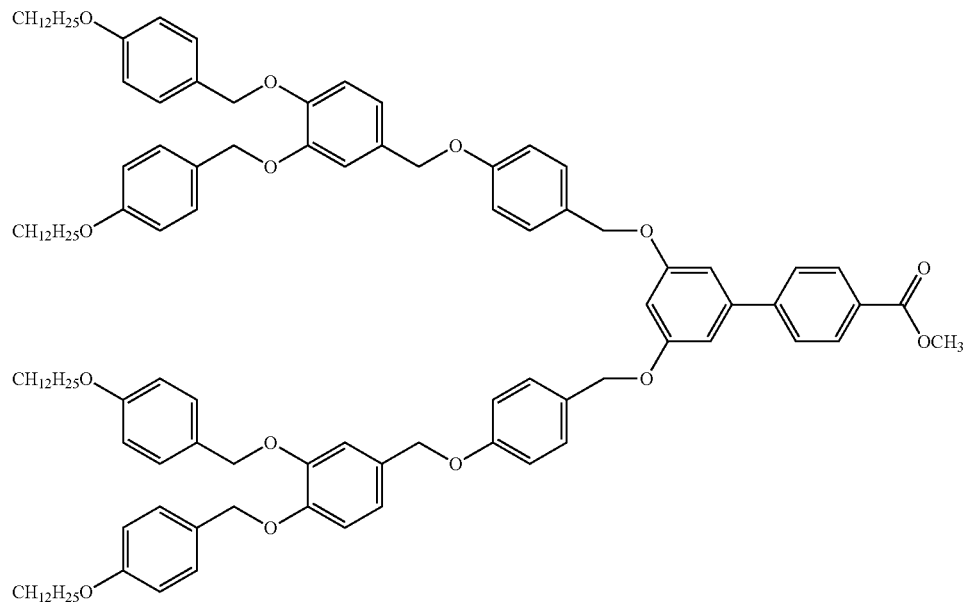
(4-3,4-4-3,5Bp)12G2—CO$_2$CH$_3$
D$_{ext}$ = 76.4 Å; D$_{pore}$ = 11.5 ± 1.8 Å
Scheme XVII
Supramolecular Porous Dendrimers with Focal
Point/Branch Biphenyls
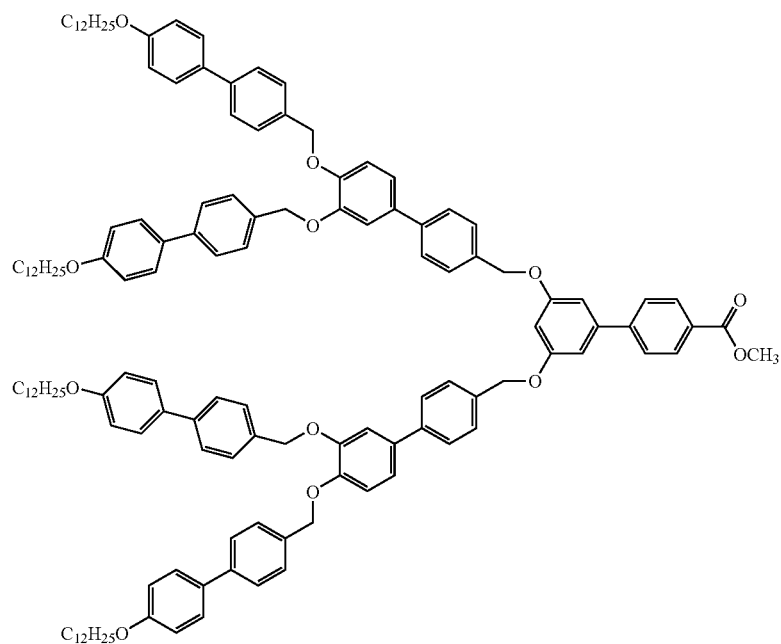
(4Bp$^{-3}$,4Bp$^{-3}$,5Bp)12G2—CO$_2$CH$_3$
D$_{ext}$ = 87.5 Å; D$_{pore}$ = 13.2 ± 1.8 Å

-continued
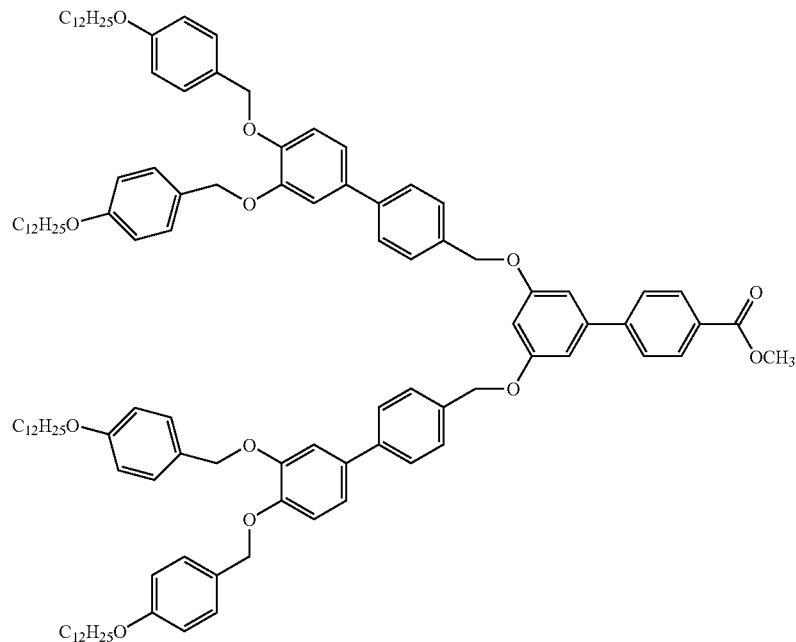
(4⁻³,4Bp⁻³,5Bp)12G2—CO$_2$CH$_3$
$D_{ext}$ = 73.4 Å; $D_{pore}$ = 11.5 ± 0.8 Å
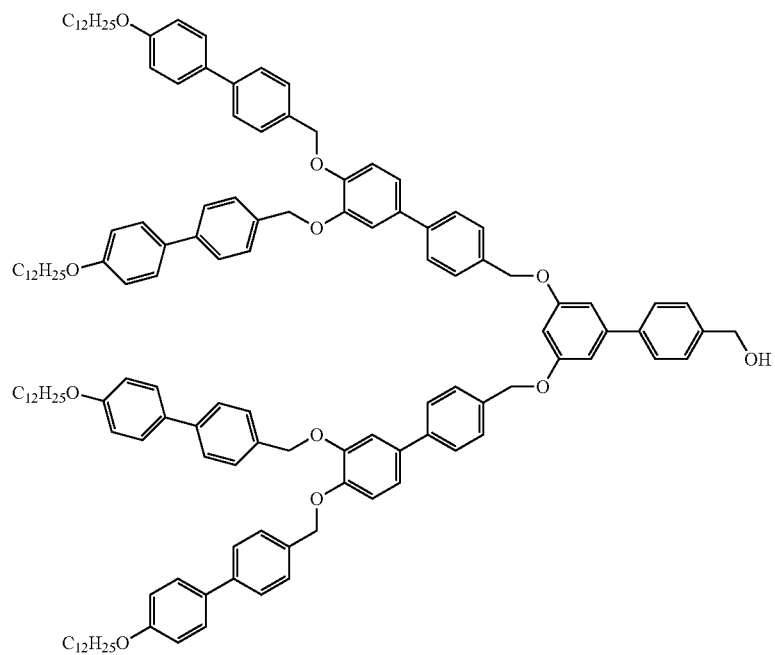
(4Bp-3,4Bp)12G2—CH$_2$OH
$D_{ext}$ = 81.0 Å; $D_{pore}$ = 12.4 ± 1.8 Å;

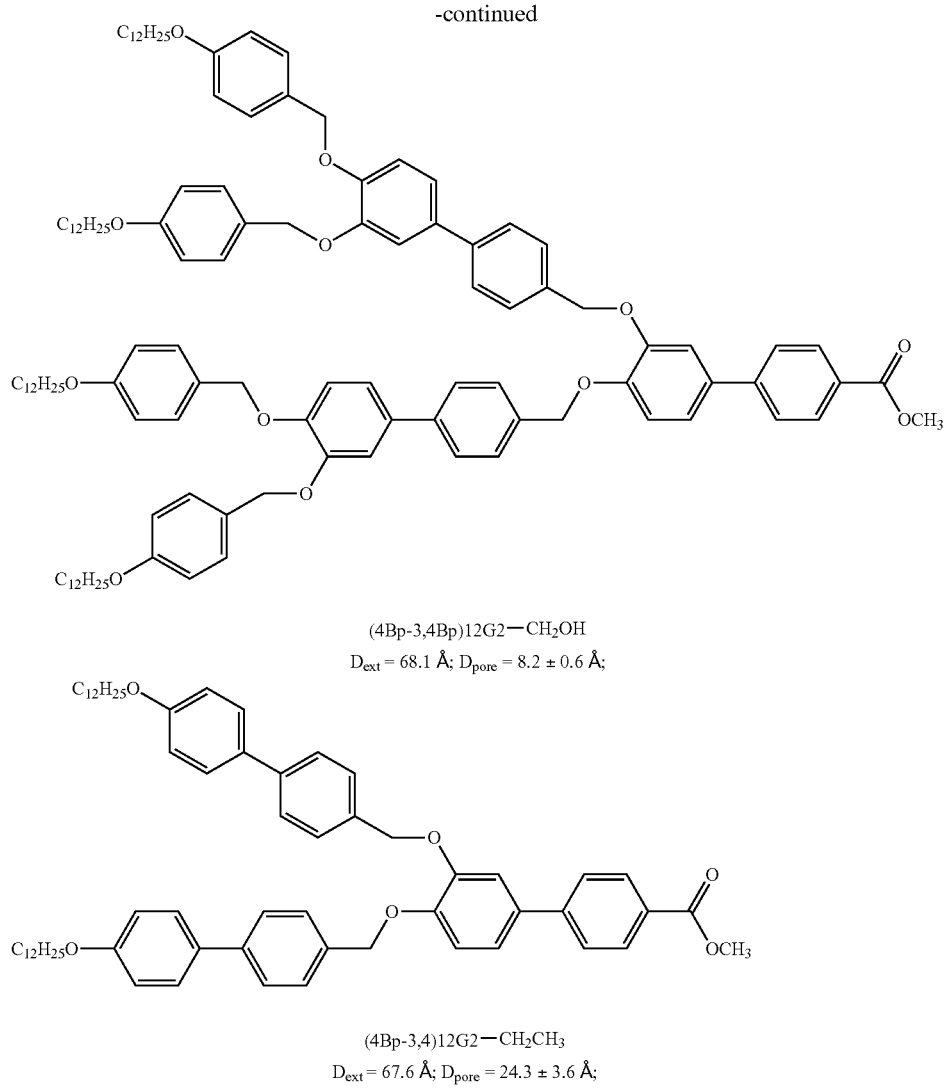

(4Bp-3,4Bp)12G2—CH$_2$OH
D$_{ext}$ = 68.1 Å; D$_{pore}$ = 8.2 ± 0.6 Å;

(4Bp-3,4)12G2—CH$_2$CH$_3$
D$_{ext}$ = 67.6 Å; D$_{pore}$ = 24.3 ± 3.6 Å;

Having now generally described this invention, the same will be better understood by reference to certain specific examples, which are included herein for purposes of illustration only and are not intended to be limiting of the invention or any embodiment thereof, unless so specified.

EXAMPLES

Materials

Methyl 4-hydroxybenzoate (99%), 1-bromohexane (98%), 1bromotetradecane (97%), 1-bromohexadecane (98%) (all from Lancaster Synthesis), 4-methoxybenzyl chloride (98%), thionyl chloride (99.5%), LiAlH4 (95%), diisopropyl azodicarboxylate (DIAD) (95%), N-methyl morpholine (NMM) (99%), methyl chloroformate (98%), anhydrous K$_2$CO$_3$ (all from Aldrich), 3,4-dihydroxybenzoic acid (97%), 3,5-dihydroxybenzoic acid (97%), 1-bromooctane (99%), 1-bromodecane (98%), 1-bromododecane (98%), 4-ethoxybenzyl alcohol (98%), 4-butoxybenzyl alcohol (98%), tyrosine (99%), cyanuric chloride (99%), triphenylphosphene (99%) (all form Acros Organics), Boc-L-Tyr-OH (99%), Boc-D-Tyr-OH (99%), Boc-DL-Tyr-OH (99%), H$_2$N-L-Ala-OMe·HCl (99%), H$_2$N-D-Ala-OMe.HCl (99%), H2N-DL-Ala-OMe·HCl (99%), (all from Bachem Peptides) were used as received, 2,6-di-tert-butyl-4-methylpyridine (DTBMP) was prepared following the literature procedure by Stang et. al. 2-chloro-4,6-dimethoxy-1,3,5-triazene (CDMT) was prepared from cyanuric chloride following the procedure by Crinin. Deuterated cyclohexane (Cambridge Isotope Laboratories) was used freshly from ampoules. Cyclohexane for CD experiments (Fisher, HPLC grade) was refluxed over CaH$_2$ and freshly distilled to ensure absence of moisture. N,N-dimethyl formamide, methanol, tetrahydrofuran, dichloromethane, MgSO$_4$, acetone, ethyl acetate (all from Fisher, ACS reagents), silica gel (Sorbent Technology) were used as received. Tetrahydrofuran (Fisher, ACS reagent grade) was refluxed over sodium/benzophenone and freshly distilled before use, dichloromethane (Fisher, ACS reagent grade) was refluxed over CaH$_2$ and freshly distilled before use. All other chemicals were commercially available and were used as received.

$^1$H NMR and $^{13}$C NMR Spectra $^1$H NMR (500 MHz) and $^{13}$C NMR (125 MHz) spectra were recorded on a Bruker DRX 500 instrument and $^1$H NMR (300 MHz) and $^{13}$C NMR (75 MHz) spectra were recorded on a Bruker DMX 300 instrument. The purity of the products was determined by a combination of thin-layer chromatography (TLC) on silica gel coated aluminum plates (with F254 indicator; layer thickness, 200 μm; particle size, 225 μm; pore size 60 Å, SIGMA-Aldrich) and high pressure liquid chromatography (HPLC) using a Perkin-Elmer Series 10 high pressure liquid chromatograph equipped with a LC-100 column oven, Nelson Analytical 900 Series integrator data station and two Perkin-Elmer PL gel columns of $5\times10^2$ and $1\times10^4$ Å. THF was used as solvent at the oven temperature of 40° C. Detection was by UV absorbance at 254 nm.

Thermal Transitions

Thermal transitions, and corresponding enthalpy changes, were measured on a Thermal Analysis (TA) Instrument 2920 modulated differential scanning calorimeter (DSC). In all cases, the heating and the cooling rates were 10° C. min$^{-1}$. The transition temperatures were measured as the maxima and minima of their endothermic and exothermic peaks. Indium was used as calibration standard. An Olympus BX-40 polarized optical microscope (10×/50× magnification) equipped with a Mettler FP 82HT hot stage and a Mettler FP 80 central processor was used to verify thermal transitions and examine the textures in various phases.

Circular Dichroism

Circular dichroism (CD) spectra were recorded in a Jasco J-720 spectrophotometer equipped with a RTE-111 variable temperature circulator. Data were processed using Jasco Spectra Manager V. 1.51, optical rotations were determined on a Jasco P-1010 polarimeter, and UV analysis was performed on a Shimadzu UV-1601 instrument, equipped with a variable temperature sample holder.

MALDI-TOF Mass Spectrometry

Matrix-assisted laser desorption/ionization time-of-flight (MALDI-TOF) mass spectrometry was carried out on a Per-Septive Biosystems-Voyager-DE (Framingham, Mass.) mass spectrometer operating in linear mode. The spectrometer equipped with a nitrogen laser (337 nm) was calibrated using Angiotensin II and Bombesin as standards. The laser steps and voltages applied were adjusted as a function of the molecular weight and the nature of the compound. The matrix used in MALDI-TOF mass spectrometry was 3,5-dimethoxy-4-hydroxy-trans-cinnamic acid. The solvent used for both matrix and sample was tetrahydrofuran (THF). A typical procedure used for sample preparation was as follows. The matrix (10 mg) was dissolved in 1 mL of THF. The sample concentration was 5-10 mg/mL. The matrix solution (25 μL) and the sample solution (5 μL) were mixed well, and then 0.5 μL of the resulting solution was loaded into the MALDI-plate and dried before inserting into the vacuum chamber of the MALDI machine.

Transmission Electron Microscopy

Images of unstained samples were recorded on Fuji image plates, using 100 and 120 kV (JEOL 100 CX and Philips EM400T) and low-dose procedures. AFM imaging was performed with a Dimension 5000 scanning probe microscope (Digital Instruments/Veeco Metrology Group), using etched Si probes with a stiffness of 1N/m. X-ray diffraction measurements were performed with Cu—Kα1 radiation from a Bruker-Nonius FR-591 rotating anode X-ray source with a 0.2×2.0 mm$^2$ filament operated at 3.4 kW. The beam was collimated and focused by a single bent mirror and sagitally focusing Ge(111) monochromator, resulting in a 0.2×0.2 mm$^2$ spot on a Bruker-AXS Hi-Star multiwire area detector. To minimize attenuation and background scattering, an integral vacuum was maintained along the length of the flight tube and the sample chamber. The samples were kept either inside a Linkham hot stage or home-made oven that was mounted inside the sample chamber and the sample temperature was controlled within ±0.1° C. Oriented fibers were obtained from either the liquid crystalline phase or the melt. Both bulk samples as well as the fiber samples were held in Lindeman-type capillaries during X-ray experiments. Electron density profiles were computed using computer programs developed by us with Silicon graphics (SGI) machines.

Molecular Modeling

Molecular modeling studies were carried out with Silicon graphics (SGI) machines using Macromodel 7.2 (Columbia University, New York, U.S.A), and Materials Studio (Accelrys Inc, San Diego, Calif., U.S.A) software suite. X-ray intensity data from L-L dipeptide single crystals were collected on a Rigaku Mercury CCD area detector-employing graphite monochromated Mo—Kα radiation (λ=0.71069 Å) at a temperature of 143K. Indexing was performed from a series of four 0.5° oscillation images with exposures of 30 seconds per frame.

Example 1

Preparation of Liposomes and Loading

Liposomes were prepared by sonicating a 1/14 mass ratio of dendritic dipeptide in L-a-phosphatidylcholine (P5638 from Sigma 2004-2005), and a fluorescent membrane-impermeable pH indicator (G4 polyglutamic porphyrin-dendrimer)$^{29}$ in a phosphate buffer (10 mM K2HPO4, 50 mM KCl, pH=7.0). A control experiment (a) was conducted in the absence of dendron. The liposomes were purified from untrapped indicator by gel-filtration on Sephadex G200, and on anion exchange resin QAE Sepharose A50, and placed in a fluorimetric cell equipped with stirrer.

As expected from its hydrophobicity (un-optimized experiment a), A solution of the dendritic dipeptide in DMSO/THF was added to liposomes to assess its loading and delivery. The dipeptide was not delivered very effectively, resulting in only a slight increase in permeability. More effective delivery was attained using an amphiphilic carrier. Liposomes were made of a lipid dendritic dipeptide mixture$^{27}$ employing a 14/1 mass ratio of lipid to dendron equivalent to an average of one to two pores per vesicle. See, figure S10. The permeability of the thus prepared vesicles increased significantly (b) when compared to control. The addition of gramicidin (10 mL of DMSO alone does not affect permeability) increased slightly the magnitude of the jumps, suggesting that a small fraction of vesicles did not contain dendritic channels.

Example 2

Synthesis of Methyl 4-dodecyloxybenzoate

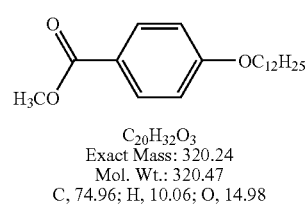

$C_{20}H_{32}O_3$
Exact Mass: 320.24
Mol. Wt.: 320.47
C, 74.96; H, 10.06; O, 14.98

To a thoroughly degassed suspension of K2CO3 (127 g, 921 mmol) in DMF (600 mL) was added methyl-4-hydroxybenzoate (70 g, 461 mmol) and the mixture heated to 70° C. after which was added bromododecane (126 g, 507 mmol)

and the reaction allowed to stir at 70° C. under argon for 3 hours, after which TLC (CH2Cl2) showed completion. Reaction was cooled to room temperature and precipitated into cold water. The precipitate was collected by suction filtration and purified by re-crystallization from acetone to give the title compound (140 g, 95%).

mp 56-57° C. (literature[3] 57-58° C.)

$^1$H NMR (500 MHz, CDCl3) δ=7.97 (d, 2H, J=8.8 Hz), 6.88 (d, 2H, J=8.9 Hz), 3.97 (t, 2H, J=6.6 Hz), 3.86 (s, 3H), 1.85-1.75 (m, 2H), 1.47-1.41 (n, 2H), 1.34-1.26 (m, 16H), 0.88 (t, 3H, J=6.8 Hz). $^{13}$C NMR (125 MHz, CDCl3) δ=167.0, 163.1, 131.7, 122.4, 114.1, 68.3, 51.8, 32.1, 29.8 (×2), 29.7 (×2), 29.5 (×3), 29.2, 26.2, 26.1, 26.0, 22.8, 14.3.

Example 3

Preparation of Methyl 4-hexyloxybenzoate

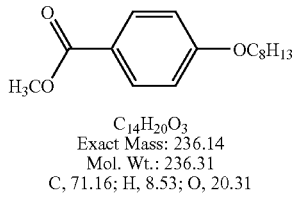

C$_{14}$H$_{20}$O$_3$
Exact Mass: 236.14
Mol. Wt.: 236.31
C, 71.16; H, 8.53; O, 20.31

This chemical structure was synthesized following the same general procedure as that for the preparation of methyl 4-dodecyloxybenzoate, K2CO3 (18.1 g, 132 mmol), methyl 4-hydroxybenzoate (10.0 g, 65.8 mmol), 1-bromohexane (10.88 g, 65.9 mmol), DMF (100 mL).

TLC (CH2Cl2), 15.1 g (97%) as an oil.

$^1$H NMR (300 MHz, CDCl3) δ=7.97 (d, 2H, J=6.9 Hz), 6.89 (d, 2H, J=6.9 Hz), 3.99 (t, 2H, J=6.6 Hz), 3.88 (s, 3H), 1.81-1.76 (m, 2H), 1.46 (m, 2H), 1.36-1.32 (m, 4H), 0.91 (t, 3H, J=6.3 Hz). $^{13}$C NMR (75 MHz, CDCl3) δ=167.1, 163.2, 131.8, 122.5, 114.2, 68.4, 52.0, 31.7, 29.3, 25.9, 22.8, 14.2.

Example 4

Preparation of Methyl 4-octyloxybenzoate

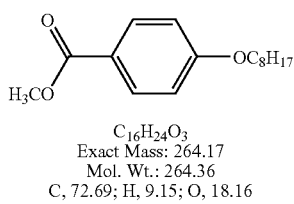

C$_{16}$H$_{24}$O$_3$
Exact Mass: 264.17
Mol. Wt.: 264.36
C, 72.69; H, 9.15; O, 18.16

This compound was synthesized following the same general procedure as that for the preparation of methyl 4-dodecyloxybenzoate, K2CO3 (18.1 g, 132 mmol), methyl 4-hydroxybenzoate (10.0 g, 65.8 mmol), 1-bromooctane (12.7 g, 65.9 mmol), DMF (100 mL).

TLC (CH2Cl2), 12.4 g (71%) as an oil.

$^1$H NMR (300 MHz, CDCl3) δ=7.97 (d, 2H, J=6.9 Hz), 6.89 (d, 2H, J=6.9 Hz), 3.99 (t, 2H, J=6.0 Hz), 3.87 (s, 3H), 1.81-1.75 (m, 2H), 1.47 (m, 2H), 1.31-1.28 (m, 8H), 0.89 (t, 3H, J=6.3 Hz).

$^{13}$C NMR (75 MHz, CDCl3) δ=167.1, 163.2, 131.7, 122.5, 114.2, 68.4, 52.0, 32.0, 29.5, 29.4, 29.3, 26.2, 22.8, 14.3.

Example 5

Preparation of Methyl 4-decyloxybenzoate

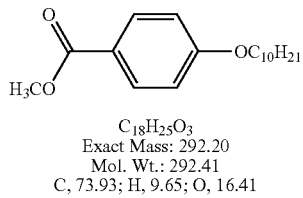

C$_{18}$H$_{28}$O$_3$
Exact Mass: 292.20
Mol. Wt.: 292.41
C, 73.93; H, 9.65; O, 16.41

This compound was synthesized following the same general procedure as that for the preparation of methyl 4-dodecyloxybenzoate, K2CO3 (18.1 g, 132 mmol), methyl 4-hydroxybenzoate (10.0 g, 65.8 mmol), 1-bromodecane (16.0 g, 72.3 mmol), DMF (120 mL).

TLC (CH2Cl2), 13.4 g (70%) as a white solid. mp 44-45° C. (literature[3] 47-48° C.).

$^1$H NMR (500 MHz, CDCl3) δ=7.97 (d, 2H, J=9.5 Hz), 6.89 (d, 2H, J=9.0 Hz), 3.99 (t, 2H, J=6.0 Hz), 3.87 (s, 3H), 1.81-1.77 (m, 2H), 1.44 (m, 2H), 1.31-1.27 (m, 12H), 0.88 (t, 3H, J=6.4 Hz).

$^{13}$C NMR (125 MHz, CDCl3) δ=167.2, 163.0, 131.5, 122.5, 114.0, 68.2, 51.7, 31.9, 29.5, 29.3 (×2), 29.1, 25.9, 22.6, 14.0.

Example 6

Preparation of Methyl 4-tetradecyloxybenzoate

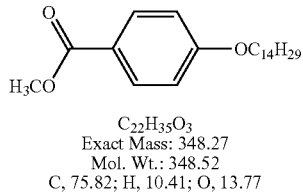

C$_{22}$H$_{36}$O$_3$
Exact Mass: 348.27
Mol. Wt.: 348.52
C, 75.82; H, 10.41; O, 13.77

This molecule was synthesized following the same general procedure as that for the preparation of methyl 4-dodecyloxybenzoate, K2CO3 (18.1 g, 132 mmol), methyl 4-hydroxybenzoate (10.0 g, 65.8 mmol), 1-bromotetradecane (19.9 g, 71.6 mmol), DMF (120 mL).

TLC (CH2Cl2), 20.9 g (92%) as a white solid. mp 64-66° C. (literature[3] 65-66° C.)

$^1$H NMR (500 MHz, CDCl3) δ=7.97 (d, 2H, J=8.8 Hz), 6.88 (d, 2H, J=8.8 Hz), 3.97 (t, 2H, J=6.6 Hz), 3.86 (s, 3H), 1.81-1.77 (n, 2H), 1.44 (m, 2H), 1.31-1.25 (m, 16H), 0.87 (t, 3H, J=6.8 Hz).

$^{13}$C NMR (125 MHz, CDCl3) δ=167.0, 163.1, 131.7, 122.4, 114.1, 68.3, 51.9, 32.1, 29.8 (×2), 29.7, 29.6, 29.5 (×2), 29.3, 26.3, 26.1, 26.0, 22.9, 14.3.

Example 7

Preparation of Methyl 4-hexadecyloxybenzoate

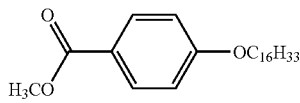

$C_{24}H_{60}O_3$
Exact Mass: 376.30
Mol. Wt.: 376.57
C, 76.55; H, 10.71; O, 12.75

This compound was synthesized following the same general procedure as that for the preparation of methyl 4-dodecyloxybenzoate, K2CO3 (18.1 g, 132 mmol), methyl 4-hydroxybenzoate (10.0 g, 65.8 mmol), 1-bromohexadecane (21.1 g, 69.0 mmol), DMF (120 mL).

TLC (CH2Cl2), 24.2 g (98%) as a white solid. nip 69-71° C. (literature[3] 70-72° C.).

$^1$H NMR (500 MHz, CDCl3) δ=7.97 (d, 2H, J=10.0 Hz), 6.90 (d, 2H, J=10.0 Hz), 3.99 (t, 2H, J=6.5 Hz), 3.88 (s, 3H), 1.82-1.76 (m, 2H), 1.44 (m, 2H), 1.35-1.27 (m, 24H), 0.88 (t, 3H, J=7.0 Hz).

$^{13}$C NMR (125 MHz, CDCl3) δ=167.1, 163.2, 131.8, 122.5, 114.3, 68.4, 52.0, 32.2, 29.9 (×3), 29.8 (×2), 29.6, 29.4, 29.2, 26.2, 22.9, 14.3.

Example 8

Preparation of 4-Dodecyloxybenzyl Alcohol

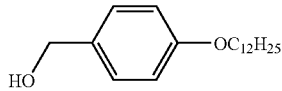

$C_{19}H_{32}O_2$
Exact Mass: 292.24
Mol. Wt.: 292.46
C, 78.03; H, 11.03; O, 10.94

To a 0° C. slurry of LAH (13.0 g, 343 mmol) in dry THF (400 mL) was added slowly methyl 4-dodecyloxybenzoate (100 g, 312 mmol) in dry THF (350 mL) over 1.5 hours. Upon addition, the mixture was stirred at room temperature for one hour, after which TLC (CH2Cl2) showed completion. Reaction was cooled to 0° C. and quenched by successive addition of H2O (13 mL), 15% NaOH (13 mL), and H2O (39 mL), and stirring continued until H2 evolution ceased. Reaction mixture was then filtered and the lithium salts rinsed generously with CH2Cl2. The filtrate was dried over MgSO4 and concentrated to give the title benzyl alcohol (80 g, 88%), which was taken to the next step without further purification.

mp 64-65° C. (literature[3] 67° C.).

$^1$H NMR (500 MHz, CDCl3) δ=7.13 (d, 2H, J=8.4 Hz), 6.76 (d, 2H, J=8.4 Hz), 4.45 (s, 2H), 3.83 (t, 2H, J=6.6 Hz), 2.20 (s, 1H), 1.67 (m, 2H), 1.35 (m, 2H), 1.35-1.23 (m, 16H), 0.80 (t, 3H, J=6.8 Hz).

$^{13}$C NMR (125 MHz, CDCl3) δ=158.8, 133.1, 128.7, 114.6, 68.2, 65.0, 32.1, 29.8 (×2), 29.7 (×2), 29.5 (×2), 29.4, 26.2, 22.9, 14.3.

Example 9

4-Hexyloxybenzyl Alcohol

$C_{13}H_{20}O_2$
Exact Mass: 208.15
Mol. Wt.: 208.30
C, 74.96; H, 9.68; O, 15.36

This compound was synthesized following the same general procedure as that for the preparation of 4-dodecyloxybenzyl alcohol; LAH (3.60 g, 95.3 mmol) in dry THF (75 mL), methyl 4-hexyloxybenzoate (15.0 g, 63.6 mmol) in dry THF (75 mL).

TLC (CH2Cl2), white solid 11.3 g (85%). mp 33-34° C. (literature[4] 34-36° C.).

$^1$H NMR (300 MHz, CDCl3) δ=7.25 (d, 2H, J=6.6 Hz), 6.87 (d, 2H, J=6.6 Hz), 4.58 (d, 2H, J=5.4 Hz), 3.94 (t, 2H, J=6.6 Hz), 1.81-1.74 (m, 2H), 1.45 (m, 2H), 1.35-1.29 (m, 4H), 0.91 (t, 3H, J=6.3 Hz).

$^{13}$C NMR (75 MHz, CDCl3) δ=159.0, 133.1, 128.8, 114.7, 68.3, 65.2, 31.8, 29.4, 25.9, 22.8, 14.2.

Example 10

Preparation of 4-Octyloxybenzyl Alcohol

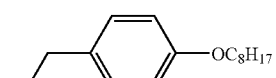

$C_{16}H_{24}O_2$
Exact Mass: 236.18
Mol. Wt.: 236.35
C, 76.23; H, 10.24; O, 13.54

This chemical entity was synthesized following the same general procedure as that for the preparation of 4-dodecyloxybenzyl alcohol; LAH (3.50 g, 92.1 mmol) in dry THF (70 mL), methyl 4-octyloxybenzoate (16.2 g, 61.4 mmol) in dry THF (75 mL).

TLC (CH2Cl2), white solid 12.6 g (87%). mp 47-48° C. (literature[5] 49° C.).

$^1$H NMR (300 MHz, CDCl3) δ=7.25 (d, 2H, J=6.6 Hz), 6.87 (d, 2H, J=6.6 Hz), 4.57 (d, 2H, J=5.7 Hz), 3.94 (t, 2H, J=6.6 Hz), 1.80-1.74 (m, 2H), 1.44 (m, 2H), 1.35-1.29 (m, 8H), 0.88 (t, 3H, J=6.9 Hz).

$^{13}$C NMR (75 MHz, CDCl3) δ=158.0, 133.1, 128.8, 114.7, 68.2, 65.2, 32.0, 29.6, 29.4 (×2), 26.2, 22.8, 14.3.

Example 11

Preparation of 4-Decyloxybenzyl Alcohol

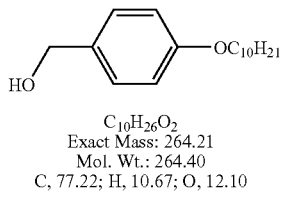

C$_{10}$H$_{26}$O$_2$
Exact Mass: 264.21
Mol. Wt.: 264.40
C, 77.22; H, 10.67; O, 12.10

This compound was synthesized following the same general procedure as that for the preparation of 4-dodecyloxybenzyl alcohol; LAH (1.61 g, 42.5 mmol) in dry THF (60 mL), methyl 4-decyloxybenzoate (11.3 g, 38.6 mmol) in dry THF (50 mL).

TLC (CH2Cl2), white solid 10.0 g (98%). mp 58-59° C. (literature[3] 59-60° C.).

$^1$H NMR(500 MHz, CDCl3) δ=7.24 (d, 2H, J=8.5 Hz), 6.86 (d, 2H, J=8.5 Hz), 4.57 (d, 2H, J=6.0 Hz), 3.93 (t, 2H, J=6.5 Hz), 1.81-1.75 (m, 2H), 1.44 (m, 2H), 1.34-1.26 (m, 12H), 0.88 (t, 3H, J=6.9 Hz).

$^{13}$C NMR (125 MHz, CDCl3) δ=158.7, 133.1, 128.5, 114.5, 68.0, 65.0, 31.8, 29.5 (×2), 29.3 (×2), 29.2, 26.0, 22.6, 14.0.

Example 12

Preparation of 4-Tetradecyloxybenzyl Alcohol

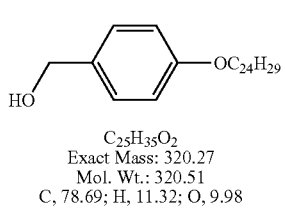

C$_{25}$H$_{35}$O$_2$
Exact Mass: 320.27
Mol. Wt.: 320.51
C, 78.69; H, 11.32; O, 9.98

This molecule was synthesized following the same general procedure as that for the preparation of 4-dodecyloxybenzyl alcohol; LAH (2.40 g, 63.1 mmol) in dry THF (60 mL), methyl 4-tetradecyloxybenzoate (20.0 g, 57.4 mmol) in dry THF (60 mL).

TLC (CH2Cl2), white solid 17.2 g (93%). mp 76° C. (literature[3] 76-78° C.).

$^1$H NMR (500 MHz, CDCl3) δ=7.26 (d, 2H, J=9.0 Hz), 6.87 (d, 2H, J=9.0 Hz), 4.60 (d, 2H, J=6.0 Hz), 3.95 (t, 2H, J=6.8 Hz), 1.80-1.74 (m, 2H), 1.44 (m, 2H), 1.34-1.22 (m, 20H), 0.88 (t, 3H, J=6.8 Hz).

$^{13}$C NMR (125 MHz, CDCl3) δ=158.8, 132.9, 128.6, 114.6, 68.1, 65.1, 31.9, 29.7, 29.6 (×2), 29.4, 29.3 (×2), 26.0, 22.7, 14.1.

Example 13

4-Hexadecyloxybenzyl Alcohol

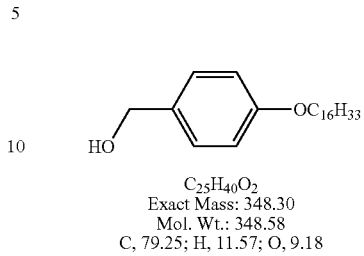

C$_{25}$H$_{40}$O$_2$
Exact Mass: 348.30
Mol. Wt.: 348.58
C, 79.25; H, 11.57; O, 9.18

This molecule was synthesized following the same general procedure as that for the preparation of 4-dodecyloxybenzyl alcohol; LAH (2.22 g, 58.4 mmol) in dry THF (80 mL), methyl 4-hexadecyloxybenzoate (20.0 g, 53.1 mmol) in dry THF (70 mL).

TLC (CH2Cl2), white solid 18.0 g (97%). mp 78-79° C. (literature[3] 79-80° C.).

$^1$H NMR (500 MHz, CDCl3) δ=7.25 (d, 2H, J=8.5 Hz), 6.87 (d, 2H, J=8.5 Hz), 4.59 (d, 2H, J=5.5 Hz), 3.94 (t, 2H, J=6.5 Hz), 1.81-1.75 (m, 2H), 1.44 (m, 2H), 1.34-1.22 (m, 24H), 0.88 (t, 3H, J=6.5 Hz).

$^{13}$C NMR (125 MHz, CDCl3) δ=159.0, 133.1, 128.8, 114.8, 68.3, 65.3, 32.1, 29.9 (×3), 29.8, 29.6 (×2), 29.5 (×2), 26.3, 22.9, 14.3.

Example 14

Preparation of 4-Ethoxybenzyl Chloride

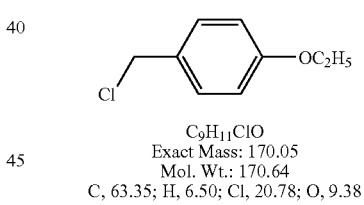

C$_9$H$_{11}$ClO
Exact Mass: 170.05
Mol. Wt.: 170.64
C, 63.35; H, 6.50; Cl, 20.78; O, 9.38

Thionyl chloride (10.4 g, 87.7 mmol) was added dropwise to a 0° C. solution of 4-ethoxybenzyl alcohol (11.0 g, 72.4 mmol) in dry CH2Cl2 (150 mL) with a catalytic amount of DMF (1 mL). Upon addition, reaction was allowed to stir for 5-10 minutes, while monitoring through TLC (CH$_2$Cl$_2$) for completion. Reaction mixture was concentrated under reduced pressure and the residue dissolved in minimal THF and then precipitated in cold H$_2$O to yield a white precipitate. The solid was collected, taken up in CH$_2$Cl$_2$, dried and concentrated. The resulting oil was solidified by cooling with CO$_2$/acetone. The compound as a white solid, which decomposes upon melting 11.3 g(92%).

$^1$H NMR (300 MHz, CDCl3) δ=7.28 (d, 2H, J=6.6 Hz), 6.86 (d, 2H, J=6.6 Hz), 4.55 (s, 2H), 4.01 (q, 2H, J=6.9 Hz), 1.40 (t, 3H, J=6.9 Hz).

$^{13}$C NMR (75 MHz, CDCl3) δ=159.0, 130.2, 129.7, 114.8, 63.7, 46.6, 15.0.

Example 15

Preparation of 4-Butoxybenzyl Chloride

C₁₁H₁₅ClO
Exact Mass: 198.08
Mol. Wt.: 198.69
C, 66.49; H, 7.61; Cl, 17.84; O, 8.05

Was synthesized following the same general procedure as that for the preparation of 4-ethoxybenzyl chloride; thionyl chloride (7.42 g, 69.2 mmol), 4-butoxybenzyl alcohol (9.45 g, 52.4 mmol), CH₂Cl₂ (145 mL).

Oil, 10.4 g (99%).

¹H NMR (300 MHz, CDCl3) δ=7.28 (d, 2H, J=6.6 Hz), 6.86 (d, 2H, J=6.6 Hz), 4.56 (s, 2H), 3.95 (t, 2H, J=6.6 Hz), 1.76 (m, 2H), 1.48 (m, 2H), 0.97 (t, 3H, J=7.5 Hz).

¹³C NMR (75 MHz, CDCl3) δ=159.5, 130.2, 129.7, 114.9, 67.9, 46.6, 31.5, 19.4, 14.0.

Example 16

Preparation of 4-Hexyloxybenzyl Chloride

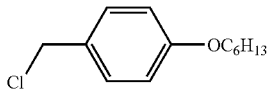

C₁₃H₁₉ClO
Exact Mass: 226.11
Mol. Wt.: 226.74
C, 68.86; H, 8.45; Cl, 15.64; O, 7.06

This molecule was synthesized following the same general procedure as that for the preparation of 4-ethoxybenzyl chloride; thionyl chloride (7.17 g, 60.3 mmol), 4-hexyloxybenzyl alcohol (11.3 g, 54.3 mmol), CH₂Cl₂ (150 mL).

Oil, 10.8 g (99%).

¹H NMR (300 MHz, CDCl3) δ=7.28 (d, 2H, J=8.7 Hz), 6.85 (d, 2H, J=8.7 Hz), 4.55 (s, 2H), 3.94 (t, 2H, J=6.6 Hz), 1.75 (m, 2H), 1.34 (m, 2H), 1.31 (m, 4H), 0.90 (t, 3H, J=6.9 Hz).

¹³C NMR (75 MHz, CDCl3) δ=159.5, 130.2, 129.7, 114.9, 68.3, 46.6, 31.8, 29.4, 25.9, 22.8, 14.2.

Example 17

Preparation of 4-Octyloxybenzyl Chloride

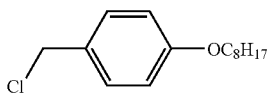

C₁₅H₂₃ClO
Exact Mass: 254.14
Mol. Wt.: 254.80
C, 70.71; H, 9.10; Cl, 13.91; O, 6.28

This compound was synthesized following the same general procedure as that for the preparation of 4-ethoxybenzyl chloride; thionyl chloride (6.36 g, 53.4 mmol), 4-octyloxybenzyl alcohol (12.4 g, 52.5 mmol), CH₂Cl₂ (150 mL).

Oil, 13.1 g (97%).

¹H NMR (300 MHz, CDCl3) δ=7.28 (d, 2H, J=6.6 Hz), 6.86 (d, 2H, J=6.6 Hz), 4.56 (s, 2H), 3.95 (t, 2H, J=6.3 Hz), 1.77 (m, 2H), 1.34 (m, 2H), 1.28 (m, 8H), 0.89 (t, 3H, J=6.9 Hz).

¹³C NMR (75 MHz, CDCl3) δ=159.5, 130.2, 129.7, 114.9, 68.3, 46.6, 32.0, 29.6, 29.4 (×2), 26.2, 22.9, 14.3.

Example 18

Preparation of 4-Dodecyloxybenzyl Chloride

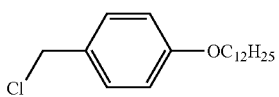

C₁₉H₃₁ClO
Exact Mass: 310.21
Mol. Wt.: 310.90
C, 73.40; H, 10.05; Cl, 11.40; O, 5.15

Thionyl chloride (38.8 g, 328 mmol) was added dropwise to a 0° C. solution of 4-Dodecyloxybenzyl alcohol (80.0 g, 274 mmol) in dry CH2Cl2 (900 mL) with a catalytic amount of DMF. Upon addition, reaction was allowed to stir for 5-10 minutes, while monitoring through TLC (CH2Cl2) for completion. Reaction mixture was concentrated under reduced pressure and the resulting residue re-crystallized from acetone to give the title benzyl chloride, decomposes upon melting. 77g (92%).

¹H NMR (500 MHz, CDCl3) δ=7.31 (d, 2H, J=8.6 Hz), 6.89 (d, 2H, J=8.6 Hz), 4.58 (s, 2H), 3.97 (t, 2H, J=6.4 Hz), 1.81 (m, 2H), 1.48 (m, 2H), 1.35-1.23 (m, 16H), 0.93 (t, 3H, J=6.6 Hz).

¹³C NMR (125 MHz, CDCl3) δ=159.5, 130.2, 129.6, 114.8, 68.2, 46.5, 32.1, 29.8 (×3), 29.7, 29.5 (×2), 29.4, 26.2, 22.8, 14.3.

Example 19

Preparation of 4-Decyloxybenzyl Chloride

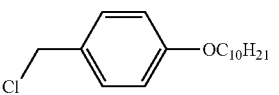

C₁₂H₂₇ClO
Exact Mass: 282.18
Mol. Wt.: 282.85
C, 72.19; H, 9.62; Cl, 12.53; O, 5.66

Was synthesized following the same general procedure as that for the preparation of 4-dodecyloxybenzyl chloride; thionyl chloride (5.00 g, 42.4 mmol), 4-decyloxybenzyl alcohol (10.2 g, 38.6 mmol), CH₂Cl₂ (100 mL). 9.87 g (90%) white solid which decomposes upon melting.

¹H NMR (500 MHz, CDCl3) δ=7.27 (d, 2H, J=9.5 Hz), 6.85 (d, 2H, J=9.5 Hz), 4.54 (s, 2H), 3.93 (t, 2H, J=6.5 Hz), 1.76 (m, 2H), 1.44 (m, 2H), 1.35-1.25 (m, 12H), 0.88 (t, 3H, J=6.5 Hz).

¹³C NMR (125 MHz, CDCl3) δ=159.5, 130.2, 129.6, 114.8, 68.2, 46.5, 32.1, 29.8 (×2), 29.7, 29.5, 29.4, 26.2, 22.8, 14.3.

Example 20

Preparation of 4-Tetradecyloxybenzyl Chloride

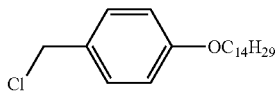

C$_{21}$H$_{35}$ClO
Exact Mass: 338.24
Mol. Wt.: 338.95
C, 74.41; H, 10.41; Cl, 10.46; O, 4.72

This one was synthesized following the same general procedure as that for the preparation of 4-dodecyloxybenzyl chloride; thionyl chloride (7.45 g, 63.1 mmol), 4-tetradecyloxybenzyl alcohol (18.4 g, 57.4 mmol), CH$_2$Cl$_2$ (150 mL). 16.28 g (84%) white solid which decomposes upon melting.

$^1$H NMR (500 MHz, CDCl3) δ=7.28 (d, 2H, J=9.0 Hz), 6.86 (d, 2H, J=8.5 Hz), 4.56 (s, 2H), 3.94 (t, 2H, J=6.5 Hz), 1.77 (m, 2H), 1.44 (m, 2H), 1.34-1.25 (m, 20H), 0.88 (t, 3H, J=6.5 Hz).

$^{13}$C NMR (125 MHz, CDCl3) δ=159.3, 130.0, 129.0, 114.7, 68.1, 46.4, 31.9, 29.7, 29.6 (×2), 29.4, 29.3, 29.2, 26.0, 22.7, 14.1.

Example 21

Preparation of 4-Hexadecyloxybenzyl Chloride

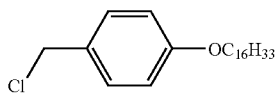

C$_{23}$H$_{39}$ClO
Exact Mass: 366.27
Mol. Wt.: 367.01
C, 75.27; H, 10.71; Cl, 9.66; O, 4.36

In this case the synthesis followed the same general procedure as that for the preparation of 4-dodecyloxybenzyl chloride; thionyl chloride (7.07 g, 60.0 mmol), 4-hexadecyloxybenzyl alcohol (19.0 g, 54.5 mmol), CH2Cl2 (150 mL). 19.0 g (95%) white solid which decomposes upon melting.

$^1$H NMR (500 MHz, CDCl3) δ=7.27 (d, 2H, J=8.5 Hz), 6.84 (d, 2H, J=8.5 Hz), 4.53 (s, 2H), 3.92 (t, 2H, J=6.5 Hz), 1.77 (m, 2H), 1.44 (m, 2H), 1.35-1.20 (m, 24H), 0.88 (t, 3H, J=6.5 Hz).

$^{13}$C NMR (125 MHz, CDCl3) δ=159.5, 130.2, 129.6, 114.8, 68.2, 46.5, 32.1, 29.9 (×3), 29.8 (×2), 29.6 (×2), 29.4, 26.2, 25.8, 22.9, 14.3.

Example 22

Preparation of [4-3,4]MeG1COOCH$_3$ Dendrimer

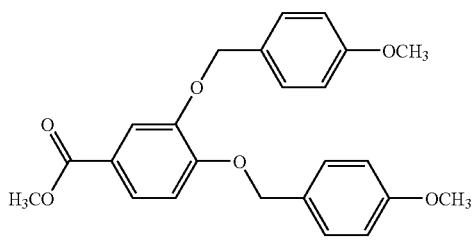

C$_{24}$H$_{24}$O$_8$
Exact Mass: 408.16
Mol. Wt.: 408.44
C, 70.57; H, 5.92; O, 23.50

To a thoroughly degassed suspension of K2CO3 (4.92 g, 138 mmol) in DMF (25 mL) was added methyl 3,4-dihydroxybenzoate (1.00 g, 5.95 mmol) and the mixture heated to 70° C. after which was added 4-methoxybenzyl chloride (1.86 g, 11.9 mmol) and the reaction allowed to stir at 70° C. under argon for 4 hours, after which TLC (CH2Cl2) showed completion. Reaction was cooled to room temperature and the reaction mixture partitioned between ethyl acetate and water. The organic layer was washed with water (5x's) and brine, dried over MgSO4 and concentrated. The crude product was purified by flash column chromatography: silica gel/CH2Cl2 to give the first generation dendron as a clear oil which crystallizes to a white solid upon standing (2.40 g, 98%).

mp 27-28° C.

$^1$H NMR (500 MHz, CDCl3) δ=7.64 (m, 2H), 7.35 (m, 4H), 6.93 (d, 1H, J=8.5 Hz), 6.89 (d, 4H, J=6.5 Hz), 5.11 (d, 4H, J=9.0 Hz), 3.87 (s, 3H), 3.80 (s, 6H).

$^{13}$C NMR (125 MHz, CDCl3) δ=166.7, 159.4, 153.1, 148.4, 128.9, 123.9, 123.0, 115.9, 113.8, 113.5, 71.1, 70.7, 55.2, 51.8. OC2H5

Example 23

Preparation of [4-3,4]2G1COOCH$_3$ Dendrimer

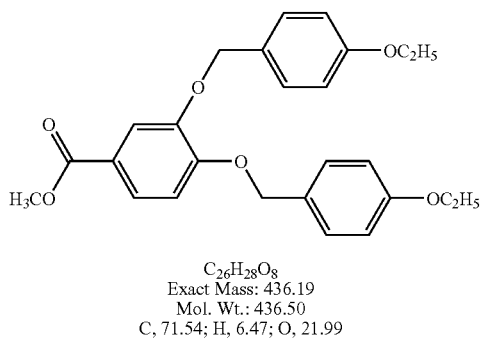

C$_{26}$H$_{28}$O$_8$
Exact Mass: 436.19
Mol. Wt.: 436.50
C, 71.54; H, 6.47; O, 21.99

This molecule was synthesized following the same general procedure as that for the preparation of [4-3,4] MeG1CO2CH3; K2CO3 (20.6 g, 149 mmol), methyl 3,4-dihydroxybenzoate (5.58 g, 33.2 mmol), 4-ethoxybenzyl chloride (11.3 g, 66.4 mmol), DMF (120 mL). TLC (CH2Cl2), flash column chromatography: silica gel CH2Cl2, yield: 11.45 g (79%) of the title compound as a white solid.

mp 31-33° C.

$^1$H NMR (300 MHz, CDCl3) δ=7.63 (m, 2H), 7.34 (t, 4H, J=8.7 Hz), 6.92 (d, 1H, J=8.4 Hz), 6.87 (d, 4H, J=6.6 Hz), 5.10 (d, 4H, J=7.5 Hz), 4.01 (q, 4H, J=6.9 Hz), 3.86 (s, 3H), 1.41 (t, 6H, J=6.9 Hz).

$^{13}$C NMR (75 MHz, CDCl3) δ=167.0, 158.9, 153.2, 148.6, 129.3, 129.1, 129.0, 128.6, 124.1, 123.1, 115.9, 114.7, 113.6, 71.3, 70.9, 63.6, 52.1, 15.0.

Example 24

Preparation of [4-3,4]4G1COOCH$_3$ Dendrimer

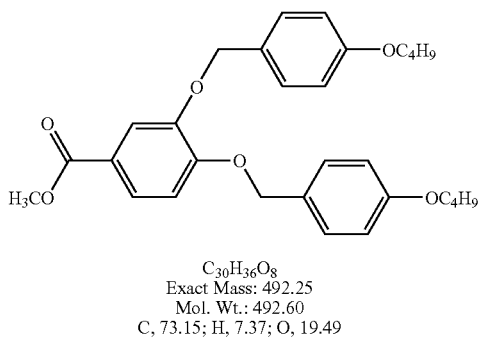

C$_{30}$H$_{36}$O$_8$
Exact Mass: 492.25
Mol. Wt.: 492.60
C, 73.15; H, 7.37; O, 19.49

In this case the synthesis followed the same general procedure as that for the preparation of [4-3,4]MeG1CO2CH3; K2CO3 (15.7 g, 114 mmol), methyl 3,4-dihydroxybenzoate (4.40 g, 26.2 mmol), 4-butoxybenzyl chloride (10.4 g, 52.3 mmol), DMF (120 mL). TLC (CH2Cl2), flash column chromatography: silica gel/ CH2Cl2, yield: 10.5 g (81%) of the title compound as a white solid.

mp 33° C.

$^1$H NMR (300 MHz, CDCl3) δ=7.63 (m, 2H), 7.33 (t, 4H, J=9.0 Hz), 6.92 (d, 1H, J=8.1 Hz), 6.87 (d, 4H, J=6.9 Hz), 5.09 (d, 4H, J=6.6 Hz), 3.95 (t, 4H, J=6.6 Hz), 3.86 (s, 3H), 1.79-1.72 (m, 4H), 1.54-1.43 (m, 4H), 0.97 (t, 6H, J=7.2 Hz).

$^{13}$C NMR (75 MHz, CDCl3) δ=167.0, 159.2, 153.2, 148.6, 129.3, 129.1, 128.9, 128.6, 124.1, 123.1, 115.9, 114.7, 113.6, 71.3, 70.9, 67.9, 52.1, 31.5, 19.4, 14.0.

Example 25

Preparation of [4-3,4]6G1COOCH$_3$ Dendrimer

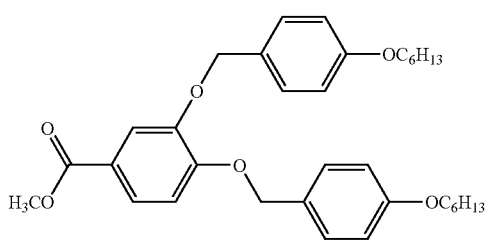

C$_{34}$H$_{44}$O$_8$
Exact Mass: 548.31
Mol. Wt.: 548.71
C, 74.42; H, 8.08; O, 17.49

This one was synthesized following the same general procedure as that for the preparation of [4-3,4]MeG1CO2CH3; K2CO3 (20.0 g, 144 mmol), methyl 3,4-dihydroxybenzoate (4.40 g, 26.2 mmol), 4-hexyloxybenzyl chloride (12.0 g, 53 mmol), DMF (120 mL). TLC (CH2Cl2), flash column chromatography: silica gel/ CH2Cl2, yield: 13 g (91%) of the title compound as a white solid.

mp 38-39° C.

$^1$H NMR (300 MHz, CDCl3) δ=7.63 (m, 2H), 7.33 (t, 4H, J=9.0 Hz), 6.92 (d, 1H, J=8.4 Hz), 6.87 (d, 4H, J=6.6 Hz), 5.09 (d, 4H, J=6.9 Hz), 3.94 (t, 4H, J=6.3 Hz), 3.86 (s, 3H), 1.79-1.72 (m, 4H), 1.45 (m, 4H), 1.38-1.29 (m, 8H), 0.91 (t, 6H, J=6.5 Hz).

$^{13}$C NMR (75 MHz, CDCl3) δ=167.0, 159.2, 153.2, 148.6, 129.3, 129.1, 128.9, 128.6, 124.1, 123.1, 115.9, 114.7 (×2), 113.6, 71.3, 70.9, 68.2, 52.1, 31.8, 29.4, 25.9, 22.8, 14.2.

Example 26

Preparation of [4-3,4]8G1COOCH$_3$ Dendrimer

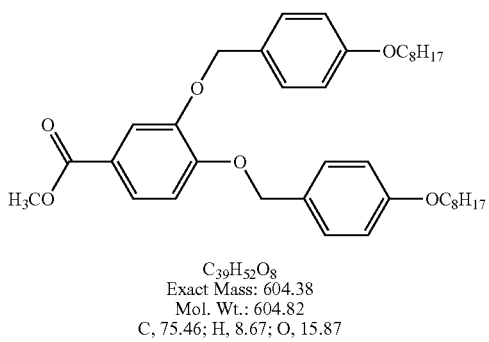

C$_{39}$H$_{52}$O$_8$
Exact Mass: 604.38
Mol. Wt.: 604.82
C, 75.46; H, 8.67; O, 15.87

This compound was synthesized following the same general procedure as that for the preparation of [4-3,4] MeG1CO2CH3; K2CO3 (15.7 g, 114 mmol), methyl 3,4-dihydroxybenzoate (4.29 g, 25.5 mmol), 4-octyloxybenzyl chloride (13.0 g, 51 mmol), DMF (120 mL). TLC (CH2Cl2), flash column chromatography: silica gel/CH2Cl2, yield: 12.4 g (80%) of the title compound as a white solid.

mp 42-44° C.

$^1$H NMR (300 MHz, CDCl3) δ=7.63 (m, 2H), 7.33 (t, 4H, J=8.7 Hz), 6.92 (d, 1H, J=8.1 Hz), 6.87 (d, 4H, J=6.9 Hz), 5.09 (d, 4H, J=6.6 Hz), 3.94 (t, 4H, J=6.6 Hz), 3.86 (s, 3H), 1.79-1.72 (m, 4H), 1.43 (m, 4H), 1.38-1.27 (m, 16H), 0.87 (t, 6H, J=6.5 Hz).

$^{13}$C NMR (75 MHz, CDCl3) δ=167.0, 159.2, 153.2, 148.6, 129.3, 129.1, 128.9, 128.5, 124.1, 123.1, 115.9, 114.7 (×2), 113.6, 71.3, 70.9, 68.2, 52.1, 32.0, 29.6, 29.5, 29.4, 26.2, 22.8, 14.3.

Example 27

Preparation of [4-3,4]12G1COOCH$_3$ Dendrimer

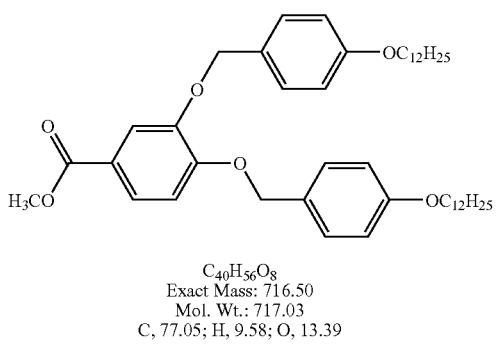

C$_{40}$H$_{56}$O$_8$
Exact Mass: 716.50
Mol. Wt.: 717.03
C, 77.05; H, 9.58; O, 13.39

To a thoroughly degassed suspension of K2CO3 (72 g, 516 mmol) in DMF (400 mL) was added methyl 3,4-dihydroxybenzoate (17 g, 113 mmol) and the mixture heated to 70° C. after which was added 4-dodecyloxybenzyl chloride (70.2 g, 226 mmol) and the reaction allowed to stir at 70° C. under argon for 8 hours, after which TLC (7:1 Hex:EtOAc) showed completion. Reaction was cooled to room temperature and precipitated into cold water. The precipitate was collected by suction filtration and purified by flash column chromatography: silica gel/CH2Cl2, followed by re-crystallization from acetone to give the title compound (57 g, 71%).

mp 98-100° C. (literature[6] 99° C.).

$^1$H NMR (500 MHz, CDCl3) δ=7.64 (m, 2H), 7.36 (d, 2H, J=8.8 Hz), 7.32 (d, 2H, J=8.8 Hz), 6.93 (d, 1H, J=8.4 Hz), 6.88 (d, 4H, J=8.1 Hz), 5.10 (d, 4H, J=8.8 Hz), 3.95 (t, 4H, J=5.1 Hz), 3.87 (s, 3H), 1.79 (m, 4H), 1.46 (m, 4H), 1.40-1.21 (m, 32H), 0.90 (t, 6H, J=6.9 Hz).

$^{13}$C NMR (125 MHz, CDCl3) δ=167, 159.1 (×2), 153.2, 148.6, 129.3, 129.0, 129.8, 128.5, 124.0, 123.1, 115.9, 114.6 (×3), 113.5, 71.2, 70.8, 68.2 (×2), 52.0, 32.1, 29.8 (×3), 29.7, 29.6, 29.5, 29.4, 26.2, 22.8, 14.3.

Example 28

Preparation of [4-3,4]10G$_1$COOCH$_3$Dendrimer

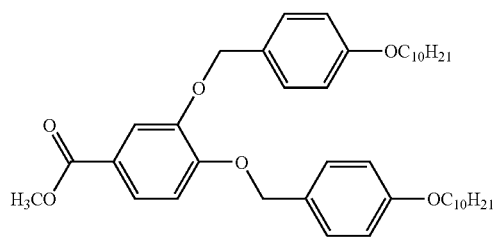

C$_{42}$H$_{50}$O$_8$
Exact Mass: 660.44
Mol. Wt.: 660.92
C, 76.33; H, 9.15; O, 14.52

This synthesis followed the same general procedure as that for the preparation of [4-3,4]12G1CO2CH3; K2CO3 (8.64 g, 62.2 mmol), methyl 3,4-dihydroxybenzoate (1.75 g, 10.4 mmol), 4-decyloxybenzyl chloride (5.90 g, 20.9 mmol), DMF (60 mL). TLC (CH$_2$Cl$_2$), flash column chromatography: silica gel/CH$_2$Cl$_2$, yield: 5.4 g (79%) of the title compound as a white solid.

mp 48-50° C.

$^1$H NMR (500 MHz, CDCl3) δ=7.62 (m, 2H), 7.32 (m, 4H), 6.92 (d, 1H, J=8.0 Hz), 6.86 (d, 4H, J=6.5 Hz), 5.09 (d, 4H, J=6.6 Hz), 3.94 (t, 4H, J=6.5 Hz), 3.86 (s, 3H), 1.77 (m, 4H), 1.43 (m, 4H), 1.38-1.25 (m, 24H), 0.88 (t, 6H, J=7.0 Hz).

$^{13}$C NMR (125 MHz, CDCl3) δ=166.8, 159.0, 153.1, 148.5, 129.1, 128.9, 128.7, 128.4, 123.9, 123.0, 115.9, 114.6, 114.5, 113.6, 71.2, 70.8, 68.1, 51.9, 31.9, 29.5, 29.4, 29.3, 26.1, 22.7, 14.1.

Example 29

Preparation of [4-3,4]14G$_1$COOCH$_3$ Dendrimer

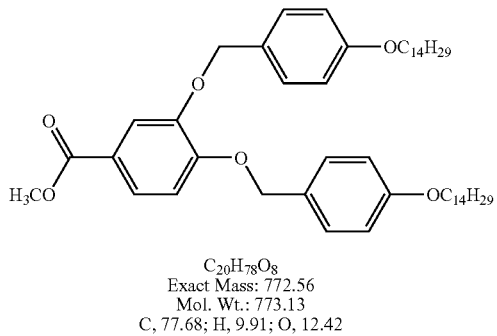

C$_{20}$H$_{78}$O$_8$
Exact Mass: 772.56
Mol. Wt.: 773.13
C, 77.68; H, 9.91; O, 12.42

This compound was synthesized following the same general procedure as that for the preparation of [4-3,4]12G1CO2CH3; K2CO3 (7.33 g, 53.1 mmol), methyl 3,4-dihydroxybenzoate (1.49 g, 8.85 mmol), 4-tetradecyloxybenzyl chloride (6.00 g, 17.7 mmol), DMF (40 mL). TLC (CH2Cl2), flash column chromatography: silica gel/CH2Cl2, yield: 5.9 g (86%) of the title compound as a white solid.

mp 82° C.

$^1$H NMR (500 MHz, CDCl3) δ=7.62 (m, 2H), 7.32 (m, 4H), 6.92 (d, 1H, J=8.5 Hz), 6.87 (d, 4H, J=8.5 Hz), 5.10 (d, 4H, J=8.6 Hz), 3.94 (t, 4H, J=6.5 Hz), 3.86 (s, 3H), 1.77 (m, 4H), 1.45 (m, 4H), 1.38-1.23 (m, 40H), 0.88 (t, 6H, J=8.0 Hz).

$^{13}$C NMR (125 MHz, CDCl3) δ=166.8, 159.0, 153.1, 148.5, 129.1, 128.9, 128.7, 128.4, 123.9, 123.0, 115.9, 114.5 (×2), 113.6, 71.2, 70.8, 68.1, 51.9, 31.9, 29.7, 29.6 (×2), 29.4, 29.3 (×2), 26.1, 22.7, 14.1.

Example 30

Preparation of [4-3,4]16G$_1$COOCH$_3$ Dendrimer

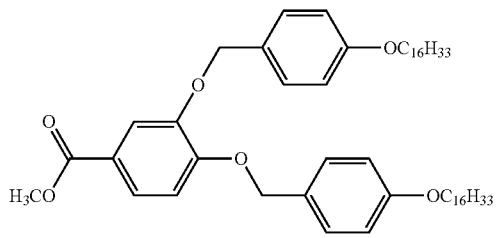

C$_{54}$H$_{84}$O$_6$
Exact Mass: 828.63
Mol. Wt.: 829.24
C, 78.21; H, 10.21; O, 11.58

This synthesis followed the same general procedure as that for the preparation of [4-3,4]12G1CO2CH3; K2CO3 (6.77 g, 49.0 mmol), methyl 3,4-dihydroxybenzoate (1.37 g, 8.17 mmol), 4-hexadecyloxybenzyl chloride (6.00 g, 16.3 mmol), DMF (50 mL). TLC (CH2Cl2), flash column chromatography: silica gel/CH2Cl2, yield: 6.28 g (93%) of the title compound as a white solid.

mp 66° C.

$^1$H NMR (500 MHz, CDCl3) δ=7.63 (m, 2H), 7.32 (m, 4H), 6.92 (d, 1H, J=8.5 Hz), 6.86 (d, 4H, J=8.5 Hz), 5.09 (d, 4H, J=9.0 Hz), 3.95 (t, 4H, J=6.5 Hz), 3.86 (s, 3H), 1.77 (m, 4H), 1.45 (m, 4H), 1.38-1.23 (m, 48H), 0.88 (t, 6H, J=7.0 Hz).

$^{13}$C NMR (125 MHz, CDCl3) δ=167.0, 159.2, 153.3, 148.6, 129.3, 129.1, 128.9, 128.6, 128.4, 124.1, 123.1, 116.0, 114.7 (×2), 113.6, 71.3, 70.9, 68.2, 52.1, 32.1, 29.9 (×2), 29.8 (×2), 29.6 (×2), 29.5 (×2), 26.3, 22.9, 14.3.

Example 31

Preparation of [4-3,4]1G$_1$CH$_2$OH Dendrimer

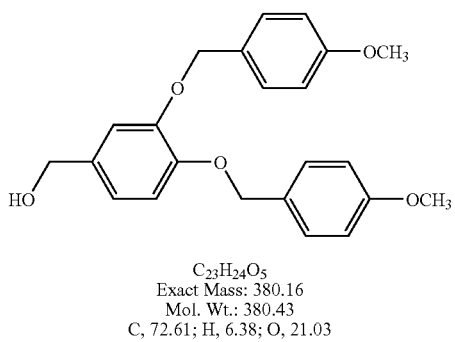

C$_{23}$H$_{24}$O$_5$
Exact Mass: 380.16
Mol. Wt.: 380.43
C, 72.61; H, 6.38; O, 21.03

This molecule was synthesized following the same general procedure as that for the preparation of 4-dodecyloxybenzyl alcohol; LAH (250 mg, 6.54 mmol) in dry THF (10 mL), [4-3,4]1G1CO2CH3 (2.43 g, 5.95 mmol) in dry THF (15 mL).

TLC (CH2Cl2), white solid 2.20 g (97%). mp 64° C.

$^1$H NMR (500 MHz, CDCl3) δ=7.33 (t, 4H, J=8.5 Hz), 6.97 (s, 1H), 6.90-6.82 (m, 6H), 5.04 (s, 4H), 4.54 (s, 2H), 3.77 (s, 6H), 1.73 (s, 1H).

$^{13}$C NMR (125 MHz, CDCl3) δ=159.3, 149.3, 148.6, 134.5, 133.2, 129.4 (×2), 129.0, 120.1, 115.6, 114.4, 113.9, 113.8, 71.3, 71.2, 65.1, 55.2.

Example 32

Preparation of [4-3,4]2G$_1$CH$_2$OH Dendrimer

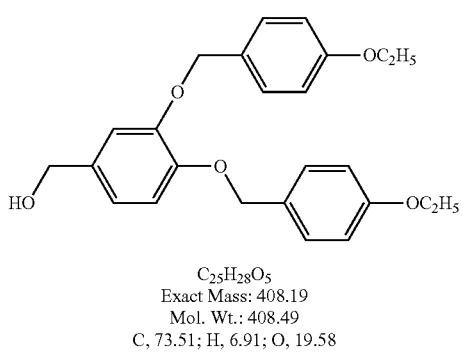

C$_{25}$H$_{28}$O$_5$
Exact Mass: 408.19
Mol. Wt.: 408.49
C, 73.51; H, 6.91; O, 19.58

This synthesis followed the same general procedure as that for the preparation of 4-dodecyloxybenzyl alcohol; LAH (1.50 g, 39.5 mmol) in dry THF (60 mL), [4-3,4]2G1CO2CH3 (11.45 g, 26.2 mmol) in dry THF (60 mL).

TLC (CH2Cl2), white solid 9.00 g (84%). mp 99° C.

$^1$H NMR (300 MHz, CDCl3) δ=7.33 (t, 4H, J=8.0 Hz), 6.97 (s, 1H), 6.90-6.81 (m, 6H), 5.04 (s, 4H), 4.53 (d, 2H, J=5.7 Hz), 4.02 (q, 4H, J=6.9 Hz), 1.73 (s, 1H), 1.40 (t, 6H, J=6.9 Hz).

$^{13}$C NMR (75 MHz, CDCl3) δ=158.9, 149.5, 148.8, 129.4, 129.3, 129.2, 120.3, 115.7, 114.6, 114.5, 71.5, 71.3, 65.3, 63.6, 15.0.

Example 33

Preparation of [14-3,4]4G$_1$CH$_2$OH Dendrimer

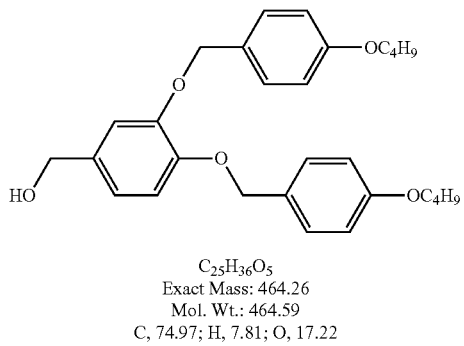

C$_{25}$H$_{36}$O$_5$
Exact Mass: 464.26
Mol. Wt.: 464.59
C, 74.97; H, 7.81; O, 17.22

This compound was synthesized following the same general procedure as that for the preparation of 4-dodecyloxybenzyl alcohol; LAH (1.20 g, 31.6 mmol) in dry THF (60 mL), [4-3,4]4G1CO2CH3 (10.5 g, 21.3 mmol) in dry THF (60 mL).

TLC (CH2Cl2), white solid 9.90 g (99%). mp 89° C.

$^1$H NMR (300 MHz, CDCl3) δ=7.31 (m, 4H), 6.96 (s, 1H), 6.90-6.81 (m, 6H), 5.02 (s, 4H), 4.51 (d, 2H, J=5.7 Hz), 3.93 (t, 4H, J=6.3 Hz), 1.88 (t, 1H, J=5.7 Hz), 1.74 (m, 4H), 1.47 (m, 4H), 0.97 (t, 6H, J=7.2 Hz).

$^{13}$C NMR (75 MHz, CDCl3) δ=159.0, 149.4, 148.7, 134.6, 129.3, 129.2 (×2), 120.4, 115.6, 114.6, 114.4, 71.5, 71.3, 67.8, 65.2, 31.5, 19.4, 14.0.

Example 34

Synthesis of [14-3,4]6G$_1$CH$_2$OH Dendrimer

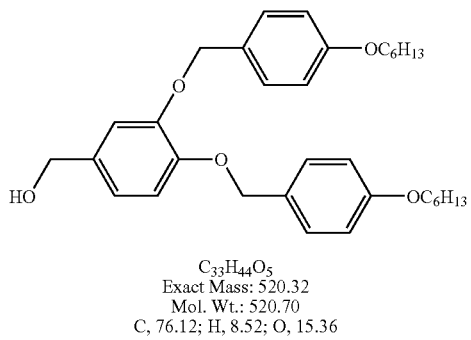

C$_{33}$H$_{44}$O$_5$
Exact Mass: 520.32
Mol. Wt.: 520.70
C, 76.12; H, 8.52; O, 15.36

This compound was synthesized following the same general procedure as that for the preparation of 4-dodecyloxybenzyl alcohol; LAH (1.35 g, 35.5 mmol) in dry THF (60 mL), [4-3,4]6G1CO2CH3 (13.0 g, 23.7 mmol) in dry THF (60 mL).

TLC (CH$_2$Cl$_2$), white solid 12.0 g (97%). mp 88° C.

$^1$H NMR (300 MHz, CDCl3) δ=7.30 (m, 4H), 6.96 (s, 1H), 6.89-6.81 (m, 6H), 5.03 (s, 4H), 4.52 (d, 2H, J=5.7 Hz), 3.93 (t, 4H, J=6.6 Hz), 1.82-1.74 (m, 5H), 1.44 (m, 4H), 1.32 (m, 8), 0.90 (t, 6H, J=6.9 Hz).

$^{13}$C NMR (75 MHz, CDCl3) δ=159.0, 149.4, 148.7, 134.6, 129.3, 129.2 (×2), 120.3, 115.6, 114.6, 114.4, 71.5, 71.3, 68.2, 65.3, 31.8, 29.4, 25.9, 22.8, 14.2.

Example 35

Preparation of [4-3,4]8G$_1$CH$_2$OH Dendrimer

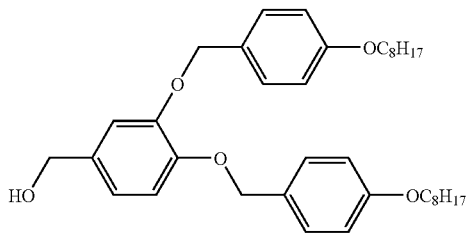

C$_{27}$H$_{50}$O$_5$
Exact Mass: 576.38
Mol. Wt.: 576.81
C, 77.04; H, 9.09; O, 13.87

The synthesis followed the same general procedure as that for the preparation of 4-dodecyloxybenzyl alcohol; LAH (1.17 g, 30.8 mmol) in dry THF (60 mL), [4-3,4] 6G1CO2CH3 (12.4 g, 20.5 mmol) in dry THF (60 mL).

TLC (CH2Cl2), white solid 11.8 g (97%). mp 92° C.

$^1$H NMR (300 MHz, CDCl3) δ=7.32 (t, 4H, J=8.7 Hz), 6.98.(s, 1H), 6.89-6.83 (m, 6H), 5.05 (s, 4H), 4.55 (d, 2H, J=5.7 Hz), 3.94 (t, 4H, J=6.6 Hz), 1.77 (m, 4H), 1.59 (m, 1H), 1.60 (m, 4H), 1.34-1.25 (m, 16H), 0.87 (t, 6H, J=6.9 Hz).

$^{13}$C NMR (75 MHz, CDCl3) δ=159.1, 149.5, 148.8, 134.6, 129.3, 129.2 (×2), 120.3, 115.7, 114.6, 114.5, 71.5, 71.3, 68.2, 65.4, 32.0, 29.6, 29.5, 26.3, 22.9, 14.3.

Example 36

Preparation of [43,4]10G$_1$CH$_2$OH Dendrimer

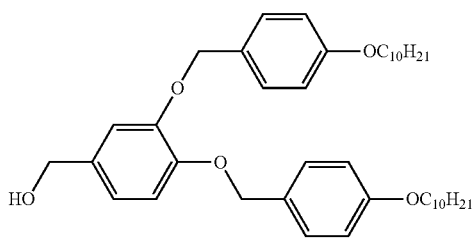

C$_{41}$H$_{60}$O$_5$
Exact Mass: 632.44
Mol. Wt.: 632.91
C, 77.81; H, 9.56; O, 12.64

This dendrimer was synthesized following the same general procedure as that for the preparation of 4-dodecyloxy-benzyl alcohol; LAH (127 mg, 3.33 mmol) in dry THF (15 mL), [4-3,4]10G1COOCH$_3$ (2.0 g, 3.03 mmol) in dry THF (20 mL).

TLC (CH2Cl2), white solid 1.82 g (95%). mp 94° C.

$^1$H NMR (500 MHz, CDCl3) δ=7.31 (t, 4H, J=8.5 Hz), 6.97 (s, 1H), 6.89-6.83 (m, 6H), 5.03 (s, 4H), 4.54 (d, 2H, J=5.5 Hz), 3.94 (t, 4H, J=6.5 Hz), 1.77 (m, 4H), 1.59 (m, 1H), 1.43 (m, 4H), 1.34-1.25 (m, 24H), 0.88 (t, 6H, J=7.5 Hz).

$^{13}$C NMR (125 MHz, CDCl3) δ=158.9, 149.4, 148.7, 134.5, 129.2, 129.1, 129.0 (×2), 120.1, 115.6, 114.4, 71.4, 71.2, 68.0, 65.1, 31.9, 29.5, 29.4, 29.3, 26.0, 22.6, 14.0.

Example 37

Preparation of [4-3,4]12G$_1$CH$_2$OH Dendrimer

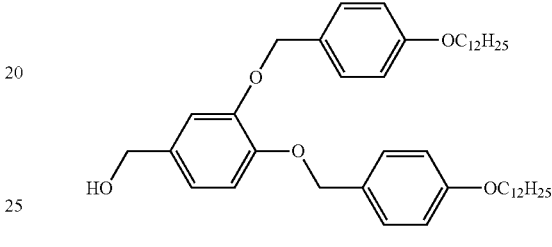

C$_{45}$H$_{68}$O$_5$
Exact Mass: 688.51
Mol. Wt.: 689.02
C, 78.44; H, 9.95; O, 11.61

This dendrimer was synthesized following the same general procedure as that for the preparation of 4-dodecyloxy-benzyl alcohol; LAH (3.27 g, 86 mmol) in dry THF (200 mL), [4-3,4]12G1CO2CH3 (56.4 g, 81.2 mmol) in dry THF (250 mL).

TLC (CH2Cl2), white solid 48.0 g (92%). mp 96° C. (literature$^7$ 97° C.).

$^1$H NMR (500 MHz, CDCl3) δ=7.33 (t, 4H, J=9.3 Hz), 6.98 (s, 1H), 6.87 (m, 6H), 5.06 (d, 4H, J=4.6 Hz), 4.60 (s, 1H), 4.56 (d, 2H, J=5.1 Hz), 3.94 (m, 4H), 1.77 (m, 4H), 1.45 (m, 4H), 1.39-1.21 (m, 32H), 0.88 (t, 6H, J=6.6 Hz).

$^{13}$C NMR (125 MHz, CDCl3) δ=159.1, 149.6, 148.8, 134.7, 133.2, 129.4 (×2), 120.4, 115.8, 114.8, 114.7 (×2), 114.6, 71.4, 68.3 (×2), 65.4.(×2), 32.2, 29.9 (×3), 29.8 (×2), 29.6 (×2), 29.5 (×2), 26.3 (×2), 22.9, 14.4.

Example 38

Synthesis of [4-3,4]14G$_1$CH$_2$OH Dendrimer

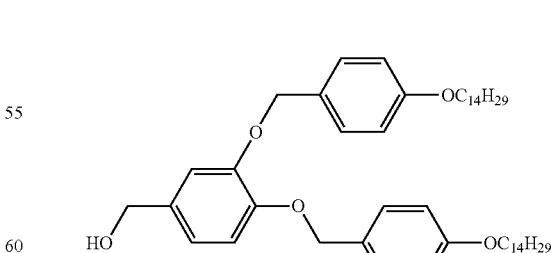

C$_{49}$H$_{76}$O$_5$
Exact Mass: 744.57
Mol. Wt.: 745.12
C, 78.98; H, 10.28; O, 10.74

This dendrimer was synthesized following the same general procedure as that for the preparation of 4-dodecyloxybenzyl alcohol; LAH (108 mg, 2.85 mmol) in dry THF (20 mL), [4-3,4]14G1CO2CH3 (2.00 g, 2.59 mmol) in dry THF (20 mL).

TLC (7:1 Hex:EtOAc), white solid 1.88 g (98%).

$^1$H NMR (500 MHz, CDCl3) δ=7.31 (t, 4H, J=9.5 Hz), 6.97 (s, 1H), 6.90-6.82 (m, 6H), 5.04 (d, 4H, J=4.5 Hz), 4.54 (d, 2H, J=6.0 Hz), 3.93 (m, 4H), 1.77 (m, 4H), 1.45 (m, 4H), 1.39-1.21 (m, 40H), 0.88 (t, 6H, J=7.0 Hz).

$^{13}$C NMR (125 MHz, CDCl3) δ=158.9, 149.4, 148.7, 134.4, 129.2, 129.1, 129.0, 129.0, 120.1, 115.7, 114.5, 114.4, 71.4, 71.2, 68.1, 65.2, 31.9, 29.7, 29.6 (×2), 29.4, 29.3 (×2), 26.1, 22.7, 14.1.

Example 39

Preparation of [4-3,4]16G$_1$CH$_2$OH Dendrimer

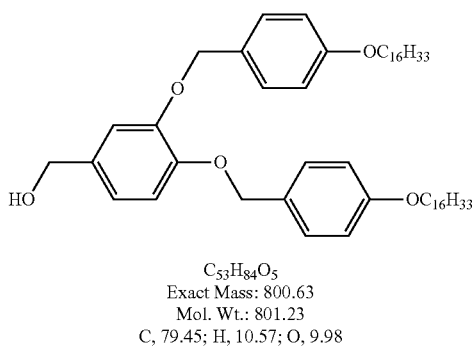

C$_{53}$H$_{84}$O$_5$
Exact Mass: 800.63
Mol. Wt.: 801.23
C, 79.45; H, 10.57; O, 9.98

This particular dendrimer was synthesized following the same general procedure as that for the preparation of 4-dodecyloxybenzyl alcohol; LAH (275 mg, 7.24 mmol) in dry THF (20 mL), [4-3,4]16G1CO2CH3 (6.00 g, 7.24 mmol) in dry THF (35 mL).

TLC (7:1 Hex:EtOAc), white solid 1.88 g (98%). mp 95° C.

$^1$H NMR (500 MHz, CDCl3) δ=7.32 (t, 4H, J=9.0 Hz), 6.98 (s, 1H), 6.90-6.82 (m, 6H), 5.04 (d, 4H, J=4.5 Hz), 4.55 (d, 2H, J=5.5 Hz), 3.93 (m, 4H), 1.77 (m, 4H), 1.62 (t, 1H, J=5.5 Hz), 1.43 (m, 4H), 1.39-1.21 (m, 48H), 0.88 (t, 6H, J 6.5 Hz).

$^{13}$C NMR (125 MHz, CDCl3) δ=159.0, 149.5, 148.8, 134.6, 129.3 (×2), 129.2, 120.3, 115.7, 114.6 (×2), 114.5, 71.5, 71.4, 68.2, 65.4, 32.1, 30.5, 29.9 (×2), 29.8 (×2), 29.6 (×2), 29.5, 26.3, 22.9, 14.3.

Example 40

Synthesis of [4-3,4]12G$_1$CH2Cl Dendrimer

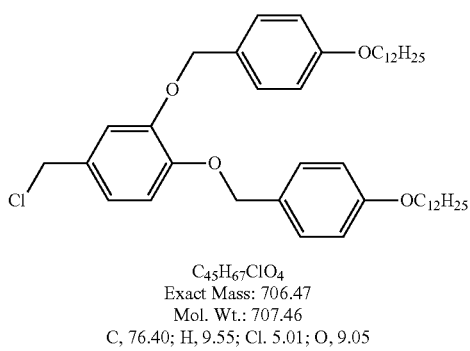

C$_{45}$H$_{67}$ClO$_4$
Exact Mass: 706.47
Mol. Wt.: 707.46
C, 76.40; H, 9.55; Cl. 5.01; O, 9.05

Thionyl chloride (3.95 g, 33.5 mmol) was added dropwise to a chilled solution of [4-3,4]12G1CH2OH (20 g, 29.1 mmol) and DTBMP (8.95 g, 43.7 mmol) in dry CH2Cl2 (200 mL). Upon addition, reaction was allowed to stir for 5-10 minutes, while monitored by TLC (3:1 Hex:EtOAc) for completion. Solvent was removed under reduced pressure and the resulting residue re-crystallized from acetone to give the title benzyl chloride which was used without further purification and characterization (20 g, 98%).

$^1$H NMR (500 MHz, CDCl3) δ=7.33 (m, 4H), 6.98 (s, 1H), 6.87(m, 6H), 5.06 (s, 4H), 4.51 (s, 2H), 3.95 (m, 4H), 1.78 (m, 4H), 1.45 (m, 4H), 1.39-1.21 (m, 32H), 0.88 (t, 6H, J=6.7 Hz).

$^{13}$C NMR (125 MHz, CDCl3) δ=159.1, 129.3, 129.1 (x3), 122.0, 115.9, 115.2, 114.7, 71.5, 71.4, 68.2, 46.7, 32.1, 29.8 (×3), 29.7, 29.6, 29.5, 29.4, 26.3, 22.9, 14.3.

Example 41

Preparation of [43,4]1G$_1$CH$_2$Cl Dendrimer

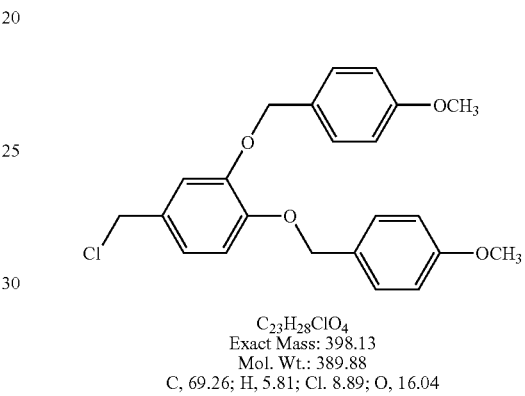

C$_{23}$H$_{28}$ClO$_4$
Exact Mass: 398.13
Mol. Wt.: 389.88
C, 69.26; H, 5.81; Cl. 8.89; O, 16.04

This dendrimer was synthesized following the same general procedure as that for the preparation of [4-3,4] 12G1CH2Cl; SOCl2 (682 mg, 5.78 mmol), DTBMP (1.62 g, 7.89 mmol), [4-3,4]MeG1CH2OH (2.00 g, 5.26 mmol), CH2Cl2 (35 mL), TLC (3:1 Hex:EtOAc). Triturated from Et2O/Hex to give a white powder, which was used without further purification and characterization, 1.81 g (87%).

$^1$H NMR (500 MHz, CDCl3) δ=7.34 (m, 4H), 6.99 (s, 1H), 6.87 (m, 6H), 5.06 (s, 4H), 4.50 (s, 2H), 3.80 (s, 6H).

$^{13}$C NMR(125MHz, CDCl3)δ=159.4, 130.7, 129.2, 129.1, 129.0, 121.9, 115.9, 115.2, 113.9, 71.3, 71.2; 55.3, 46.5.

Example 42

Preparation of [4-3,4]2G$_1$CH$_2$Cl Dendrimer

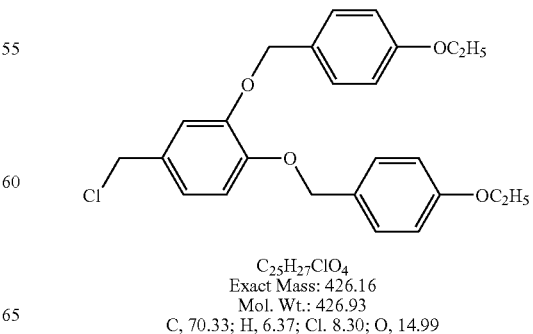

C$_{25}$H$_{27}$ClO$_4$
Exact Mass: 426.16
Mol. Wt.: 426.93
C, 70.33; H, 6.37; Cl. 8.30; O, 14.99

This dendrimer was synthesized following the same general procedure as that for the preparation of [4-3,4] 12G1CH2Cl; SOCl2 (245 mg, 2.07 mmol), DTBMP (570 mg, 2.78 mmol), [4-3,4]2G1CH₂OH (750 mg, 1.84 mmol), CH₂Cl₂ (20 mL), TLC (3:1 Hex:EtOAc). Unstable oil that was further processed directly without further characterization or purification.

Example 43

Preparation of [4-3,4]4G₁CH₂Cl Dendrimer

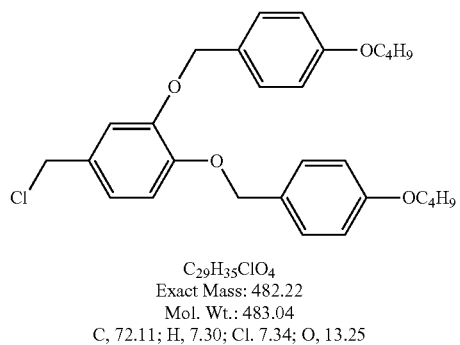

C$_{29}$H$_{35}$ClO$_4$
Exact Mass: 482.22
Mol. Wt.: 483.04
C, 72.11; H, 7.30; Cl. 7.34; O, 13.25

This dendrimer was synthesized following the same general procedure as that for the preparation of [4-3,4] 12G1CH2Cl; SOCl2 (293 mg, 2.49 mmol), DTBMP (573 mg, 2.80 mmol), [4-3,4]4G1CH2OH (1.00 g, 2.15 mmol), CH2Cl2 (20 mL), TLC (3:1 Hex:EtOAc). Unstable oil which was taken directly to the next step without further characterization or purification.

Example 44

Synthesis of [4-3,4]6G1CH₂Cl Dendrimer

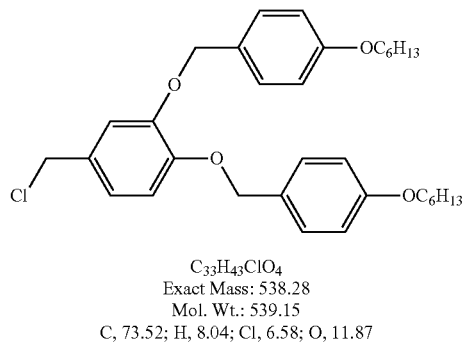

C$_{33}$H$_{43}$ClO$_4$
Exact Mass: 538.28
Mol. Wt.: 539.15
C, 73.52; H, 8.04; Cl, 6.58; O, 11.87

This dendrimer was synthesized following the same general procedure as that for the preparation of [4-3,4] 12G₁CH₂Cl; SOCl2 (326 mg, 2.76 mmol), DTBMP (630 mg, 3.07 mmol), [4-3,4]6G₁CH₂OH (1.00 g, 2.45 mmol), CH2Cl2 (20 mL), TLC (3:1 Hex:EtOAc). Unstable oil which was taken directly to the next step without further characterization or purification.

Example 45

Preparation of [4-3,4]8G₁CH₂Cl Dendrimer

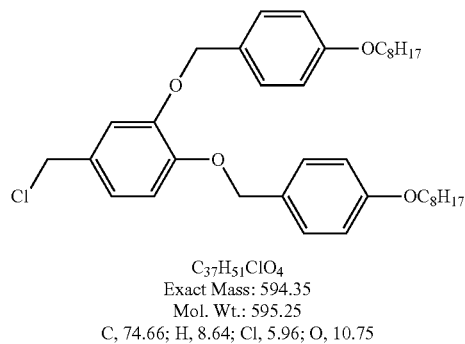

C$_{37}$H$_{51}$ClO$_4$
Exact Mass: 594.35
Mol. Wt.: 595.25
C, 74.66; H, 8.64; Cl, 5.96; O, 10.75

This dendrimer was synthesized following the same general procedure as that for the preparation of [4-3,4] 12G1CH2Cl; SOCl2 (228 mg, 1.90 mmol), DTBMP (475 mg, 2.3 mmol), [4-3,4]8G1CH2OH (1.00 g, 1.70 mmol), CH2Cl2(20 mL), TLC (3:1 Hex:EtOAc). Unstable oil which was taken directly to the next step without further characterization or purification.

Example 46

Preparation of [4-3,4]10G₁CH₂Cl Dendrimer

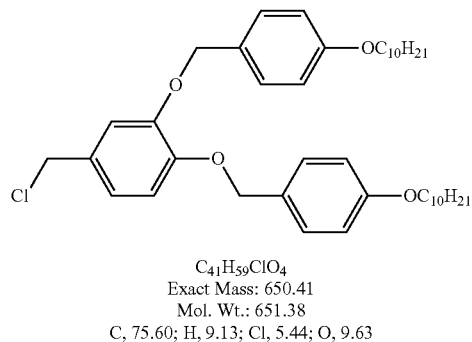

C$_{41}$H$_{59}$ClO$_4$
Exact Mass: 650.41
Mol. Wt.: 651.38
C, 75.60; H, 9.13; Cl, 5.44; O, 9.63

This dendrimer was synthesized following the same general procedure as that for the preparation of [4-3,4] 12G1CH2Cl; SOCl2 (436 mg, 3.16 mmol), DTBMP (884 mg, 4.31 mmol), [4-3,4]10G1CH2OH (1.82 g, 2.87 mmol), CH₂Cl₂ (25 mL). TLC (7:1 Hex:EtOAc). Crude residue was taken up in minimal CH2Cl2 and product precipitated in CH3OH, filtered to yield the title compound as a white solid, which was used without further purification and characterization, 1.79 g (96%).

$^1$H NMR (500 MHz, CDCl3) δ=7.31 (t, 4H, J=8.0 Hz), 6.98 (s, 1H), 6.88-6.83 (m, 6H), 5.04 (d, 4H, J=3.5 Hz), 4.49 (s, 2H), 3.93 (m, 4H), 1.77 (m, 4H), 1.45 (m, 4H), 1.34-1.26 (m, 24H), 0.88 (t, 6H, J=7.0 Hz).

$^{13}$C NMR (125 MHz, CDCl3) δ=159.0, 149.4, 149.2, 130.6, 129.1, 129.0, 128.9, 121.8, 115.9, 115.2, 114.5, 71.3, 71.2, 68.1, 46.4, 31.9, 29.6, 29.5, 29.4, 29.3, 26.0, 22.6, 14.1.

Example 47

Preparation of [4-3,4]14G$_1$CH$_2$Cl Dendrimer

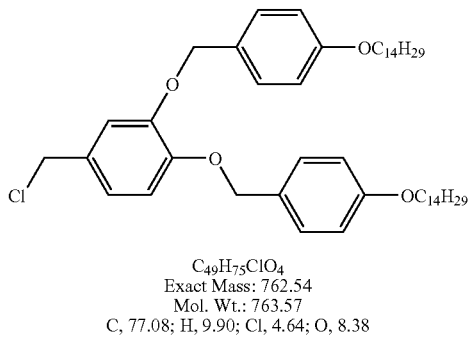

C$_{49}$H$_{75}$ClO$_4$
Exact Mass: 762.54
Mol. Wt.: 763.57
C, 77.08; H, 9.90; Cl, 4.64; O, 8.38

This dendrimer was synthesized following the same general procedure as that for the preparation of [4-3,4] 12G1CH$_2$Cl; SOCl$_2$ (327 mg, 2.77 mmol), DTBMP (776 mg, 3.78 mmol), [4-3,4]14G1CH$_2$OH (1.88 g, 2.52 mmol), CH$_2$Cl$_2$ (25 mL), TLC (7:1 Hex:EtOAc). Crude residue was taken up in minimal CH2Cl2 and product precipitated in CH3OH, filtered to yield the title compound as a white solid, which was used without further purification and characterization, 1.80 g (94%).

$^1$H NMR (500 MHz, CDCl3) δ=7.32 (t, 4H, J=8.0 Hz), 6.98 (s, 1H), 6.88-6.83 (m, 6H), 5.05 (d, 4H, J=3.0 Hz), 4.49 (s, 2H), 3.94 (m, 4H), 1.77 (m, 4H), 1.44 (m, 4H), 1.34-1.26 (m, 40H), 0.88 (t, 6H, J=7.0 Hz).

$^{13}$C NMR (125 MHz, CDCl3) δ=159.0, 149.4, 149.3, 130.7, 129.1, 129.0, 128.9, 121.8, 115.9, 115.2, 114.5, 114.4, 71.4, 71.2, 68.1, 46.5, 31.9, 29.7 (×2), 29.6, 29.4, 29.3 (×2), 26.1, 22.7, 14.1.

Example 48

Preparation of [4-3,4]16G$_1$CH$_2$Cl Dendrimer

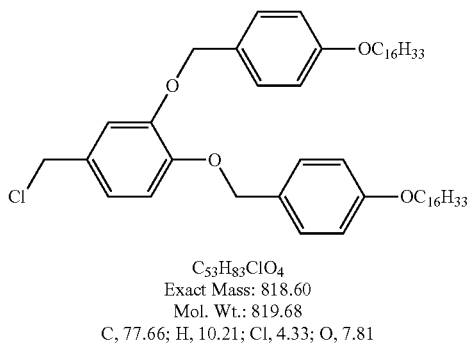

C$_{53}$H$_{83}$ClO$_4$
Exact Mass: 818.60
Mol. Wt.: 819.68
C, 77.66; H, 10.21; Cl, 4.33; O, 7.81

This dendrimer was synthesized following the same general procedure as that for the preparation of [4-3,4] 12G1CH2Cl; SOCl2 (938 mg, 7.95 mmol), DTBMP (2.22 g, 10.8 mmol), [4-3,4]16G1CH2OH (5.79 g, 7.23 mmol), CH2Cl2 (60 mL), TLC (7:1 Hex:EtOAc). Crude residue was taken up in minimal CH$_2$Cl$_2$ and product precipitated in CH3OH, filtered to yield the title compound as a white solid, which was used without further purification and characterization, 5.60 g (95%).

$^1$H NMR (500 MHz, CDCl3) δ=7.32 (t, 4H, J=8.0 Hz), 6.98 (s, 1H), 6.88-6.84 (m, 6H), 5.05 (d, 4H, J=3.0 Hz), 4.49 (s, 2H), 3.94 (m, 4H), 1.77 (m, 4H), 1.44 (m, 4H), 1.34-1.23 (m, 48H), 0.88 (t, 6H, J=7.0 Hz).

$^{13}$C NMR (125 MHz, CDCl3) δ=159.0, 149.5, 149.4, 130.8, 129.3, 129.1 (×3), 122.0, 115.9, 115.2, 114.7, 71.5, 71.4, 68.2, 46.7, 31.1, 29.9, 29.8, 29.6 (×2), 29.5, 26.3, 26.2, 22.9, 14.3.

Example 49

Preparation of [4-3,4-3,5]12G$_2$COOCH$_3$ Dendrimer

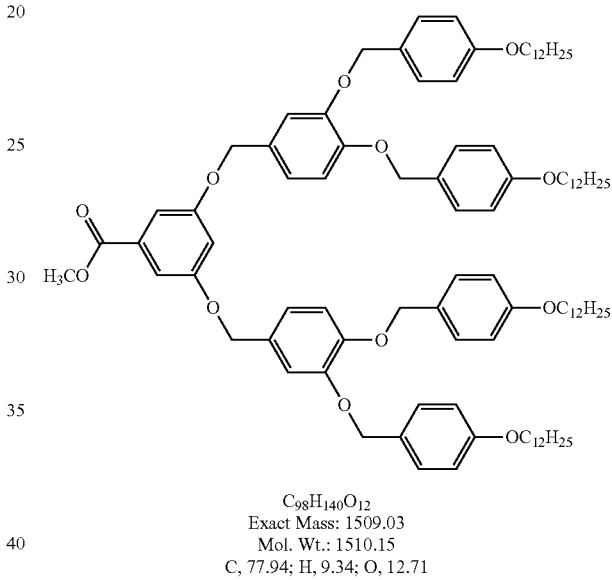

C$_{98}$H$_{140}$O$_{12}$
Exact Mass: 1509.03
Mol. Wt.: 1510.15
C, 77.94; H, 9.34; O, 12.71

To a thoroughly degassed suspension of K2CO3 (7.64 g, 55.4 mmol) in DMF (50 mL) was added methyl 3,5-dihydroxybenzoate (2.33 g, 13.9 mmol) and the mixture heated to 70° C. after which was added [4-3,4]12G1CH2Cl (19.6 g, 27.7 mmol) and the reaction allowed to stir at 70° C. under argon for 12 hours, after which TLC (7:1 Hex:EtOAc) showed completion. Reaction flask was cooled to room temperature and product precipitated into cold water. The precipitate was collected by suction filtration and purified by flash column chromatography: silica get/CH$_2$Cl$_2$, followed by re-crystallization from acetone to give the title compound (17.1 g, 78%).

mp 103° C. (literature[6] 103-104° C.).

$^1$H NMR (500 MHz, CDCl3) δ=7.34 (m, 8H), 7.30 (d, 2H, J=2.4 Hz), 7.06 (s, 2H), 6.94 (s, 4H), 6.89 (d, 8H, J=8.3 Hz), 6.77 (t, 1H, J=2.4 Hz), 5.07 (s, 8H), 4.96 (s, 4H), 3.96 (m, 8H), 3.92 (s, 3H), 1.79 (m, 8H), 1.47 (m, 8H), 1.39-1.21 (m, 64H), 0.91 (t, 12H, J=6.8 Hz).

$^{13}$C NMR (125 MHz, CDCl3) δ=166.9, 159.3, 159.0 (×2), 149.4, 149.2, 132.1, 129.7, 129.4, 129.2 (×3), 121.1, 115.4, 115.0, 114.8, 114.6, 109.7, 108.5, 107.4, 71.4 (×2), 70.4, 68.2, 52.4, 32.1, 29.8 (×4), 29.6 (×2), 29.4, 26.3, 26.1, 22.3, 14.3.

Example 50

Preparation of [4-3,4-3,5]1G$_2$CO$_2$CH$_3$ Dendrimer

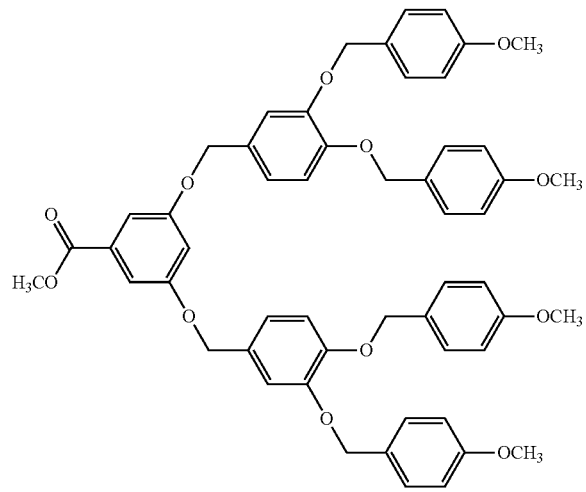

C$_{54}$H$_{52}$O$_{12}$
Exact Mass: 892.35
Mol. Wt.: 892.98
C, 72.63; H, 5.87; O, 21.50

This dendrimer was synthesized following the same general procedure as that for the preparation of [4-3,4-3,5] 12G2CO2CH3; K2CO3 (1.76 g, 12.8 mmol), methyl 3,5-dihydroxybenzoate (358 mg, 2.13 mmol), [4-3,4] MeG1CH2Cl (1.70 g, 4.26 mmol), DMF (40 mL). TLC (CH2Cl2), flash column chromatography: silica gel/CH2Cl2 followed by precipitation in Et2O from minimal CH2Cl2 to give the title compound as a light blue solid, 1.39 g (73%).

mp 25° C.

$^1$H NMR (500 MHz, CDCl3) δ=7.33 (d, 8H, J=7.5 Hz), 7.26 (d, 2H, J=2.5 Hz), 7.03 (s, 2H), 6.92 (s, 4H), 6.88-6.84 (m, 8H), 6.73 (t, 1H, J=2.5 Hz), 5.06 (s, 8H), 4.94 (s, 4H), 3.89 (s, 3H), 3.78 (d, 12H, J=5.0 Hz).

$^{13}$C NMR (125 MHz, CDCl3) δ=159.8, 159.4, 149.3, 149.1, 132.0, 129.8, 129.4, 129.3, 129.1, 129.0, 121.0, 115.5, 115.0, 113.9, 108.4, 107.3, 71.3, 70.2, 55.3, 55.2, 52.2.

Example 52

Preparation of [4-3,4-3,5]2G$_2$COOCH$_3$ Dendrimer

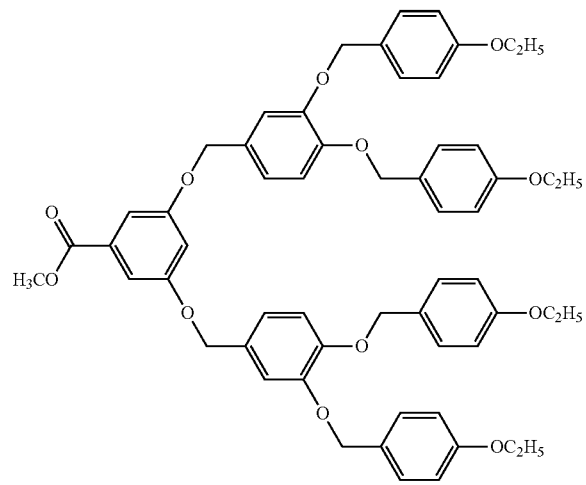

C$_{58}$H$_{60}$O$_{12}$
Exact Mass: 948.41
Mol. Wt.: 949.09
C, 73.40; H, 6.37; O, 20.23

This dendrimer was synthesized following the same general procedure as that for the preparation of [4-3,4-3,5] 12G2CO2CH3; K2CO3 (510 mg, 3.7 mmol), methyl 3,5-dihydroxybenzoate (140 mg, 0.83 mmol), [4-3,4]2G1CH2Cl (785 mg, 1.83 mmol), DMF (20 mL). TLC (CH2Cl2), flash column chromatography: silica gel/CH$_2$Cl$_2$ followed by precipitation in Et$_2$O from minimal CH$_2$Cl$_2$ to give the title compound as a white solid, 530 mg (67%).

mp 42° C.

$^1$H NMR (300 MHz, CDCl3) δ=7.33 (d, 8H, J=1.8 Hz), 7.30 (s, 2H), 7.03 (s, 2H), 6.92 (s, 4H), 6.87 (d, 8H, J=8.7 Hz), 6.74 (t, 1H, J=2.5 Hz), 5.06 (s, 8H), 4.93 (s, 4H), 4.06-3.98 (m, 8H), 3.90 (s, 3H), 1.43-1.36 (m, 12H).

$^{13}$C NMR (75 MHz, CDCl3) δ=167.0, 160.0, 158.9, 149.5, 149.2, 132.2, 129.8, 129.3 (×2), 129.2, 121.2, 115.5, 115.1, 114.6, 108.5, 107.4, 71.4, 70.4, 63.6, 52.5, 15.0.

Example 53

Preparation of [4-3,4-3,5]4G$_2$COOCH$_3$ Dendrimer

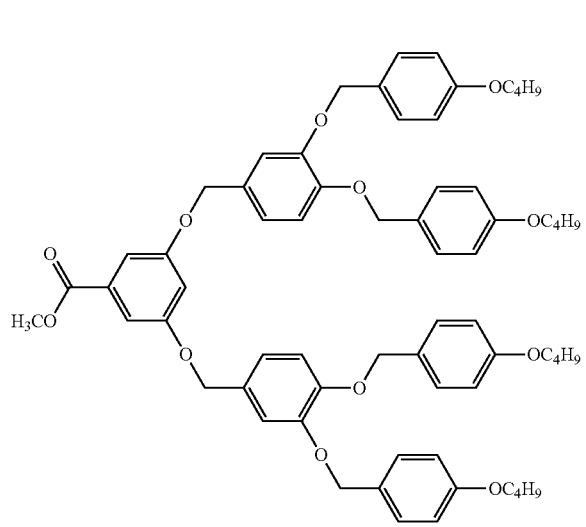

C$_{66}$H$_{76}$O$_{12}$
Exact Mass: 1060.53
Mol. Wt.: 1061.30
C, 74.69; H, 7.22; O, 18.09

This dendrimer was synthesized following the same general procedure as that for the preparation of [4-3,4-3,5] 12G2CO2CH3; K2CO3 (600 mg, 4.3 mmol), methyl 3,5-dihydroxybenzoate (165 mg, 0.98 mmol), [4-3,4]4G1CH2Cl (1.04 g, 2.15 mmol), DMF (20 mL). TLC (CH2Cl2), flash column chromatography: silica gel/CH2Cl2 followed by precipitation in hexanes from minimal CH2Cl2 to give the title compound as a white solid, 690 mg (66%).

mp 64-65° C.

$^1$H NMR (300 MHz, CDCl3) δ=7.31 (m, 8H), 7.27 (s, 2H), 7.03 (s, 2H), 6.91 (s, 4H), 6.88 (d, 8H, J=8.7 Hz), 6.74 (t, 1H, J=2.5 Hz), 5.05 (s, 8H), 4.93 (s, 4H), 3.93 (t, 8H, J=6.6 Hz), 3.89 (s, 3H), 1.75 (m, 8H), 1.47 (m, 8H), 0.97 (t, 12H, J=7.2 Hz).

$^{13}$C NMR (75 MHz, CDCl3) δ=167.0, 159.9, 159.1, 149.4, 149.2, 132.1, 129.8, 129.3, 129.2 (×2), 121.1, 115.5, 115.1, 114.6, 108.5, 107.4, 71.4, 70.4, 67.9, 52.4, 31.5, 19.4, 14.0.

Example 54

Preparation of [4-3,4-3,5]6G$_2$COOCH$_3$ Dendrimer

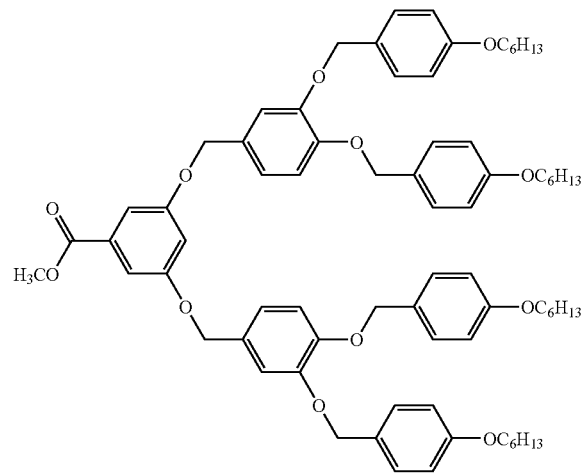

C$_{24}$H$_{92}$O$_{12}$
Exact Mass: 1172.66
Mol. Wt.: 1173.52
C, 75.74; H, 7.90; O, 16.38

This dendrimer was synthesized following the same general procedure as that for the preparation of [4-3,4-3,5] 12G2CO2CH3; K2CO3 (650 mg, 4.7 mmol), methyl 3,5-dihydroxybenzoate (185 mg, 1.10 mmol), [4-3,4]6G1CH2Cl (1.32 g, 2.45 mmol), DMF (20 mL). TLC (CH2Cl2), flash column chromatography: silica gel/CH2Cl2 followed by precipitation in hekanes from minimal CH$_2$Cl$_2$ to give the title compound as a white solid, 670 mg (52%).

mp 77° C.

$^1$H NMR (300 MHz, CDCl3) δ=7.33 (d, 8H, J=8.7 Hz), 7.27 (s, 2H), 7.03 (s, 2H), 6.91 (s, 4H), 6.86 (d, 8H, J=8.4 Hz), 6.75 (t, 1H, J=2.5 Hz), 5.06 (s, 8H), 4.94 (s, 4H), 3.94 (t, 8H, J=6.6 Hz), 3.90 (s, 3H), 1.75 (m, 8H), 1.47 (m, 8H), 1.36-1.29 (m, 16H), 0.87 (t, 12H, J=7.0 Hz).

$^{13}$C NMR (75 MHz, CDCl3) δ=167.0, 160.0, 159.1, 149.5, 149.2, 132.2, 129.8, 129.3 (×2), 129.2, 121.2, 115.5, 115.1, 114.6, 108.6, 107.4, 71.4, 70.4, 68.2, 52.5, 31.8, 29.4, 25.9, 22.8, 14.2.

Example 55

Preparation of [4-3,4-3,5]8G$_2$COOCH$_3$

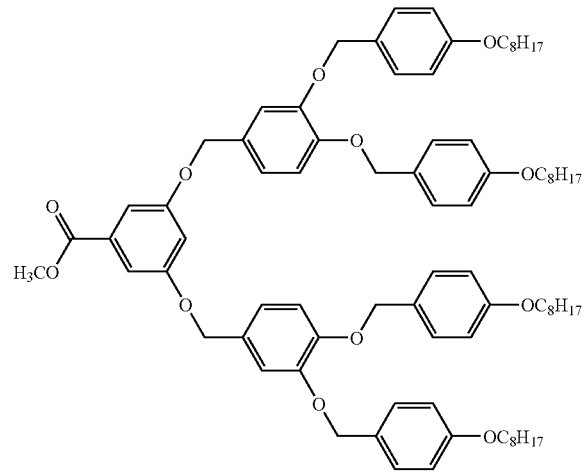

C$_{32}$H$_{108}$O$_{12}$
Exact Mass: 1284.78
Mol. Wt.: 1285.73
C, 76.60; H, 8.47; O, 14.93

This dendrimer was synthesized following the same general procedure as that for the preparation of [4-3,4-3,5] 12G2CO2CH3; K2CO3 (480 mg, 3.5 mmol), methyl 3,5-dihydroxybenzoate (131 mg, 0.78 mmol), [4-3,4]8G1CH2Cl (1.01 g, 1.7 mmol), DMF (20 mL). TLC (CH2Cl2), flash column chromatography: silica gel/CH2Cl2 followed by precipitation in CH3OH from minimal CH2Cl2 to give the title compound as a white solid, 840 mg (84%).

mp 89° C.

$^1$H NMR (300 MHz, CDCl3) δ=7.33 (m, 8H), 7.27 (s, 2H), 7.03 (s, 2H), 6.92 (s, 4H), 6.87 (d, 8H, J=8.7 Hz), 6.74 (t, 1H, J=2.5 Hz), 5.06 (s, 8H), 4.94 (s, 4H), 3.93 (t, 8H, J=6.6 Hz), 3.90 (s, 3H), 1.77 (m, 8H), 1.46 (m, 8H), 1.35-1.26 (m, 32H), 0.88 (t, 12H, J=7.2 Hz).

$^{13}$C NMR (75 MHz, CDCl3) δ=167.0, 160.0, 159.1, 149.5, 149.2, 132.2, 129.8, 129.3 (×2), 129.2, 121.2, 115.5, 115.1, 114.6, 108.6, 107.4, 71.4, 70.4, 68.2, 52.5, 32.0, 29.6, 29.5, 29.4, 26.3, 22.9, 14.3.

Example 56

Preparation of [4-3,43,5]10G$_2$COOCH$_3$ Dendrimer

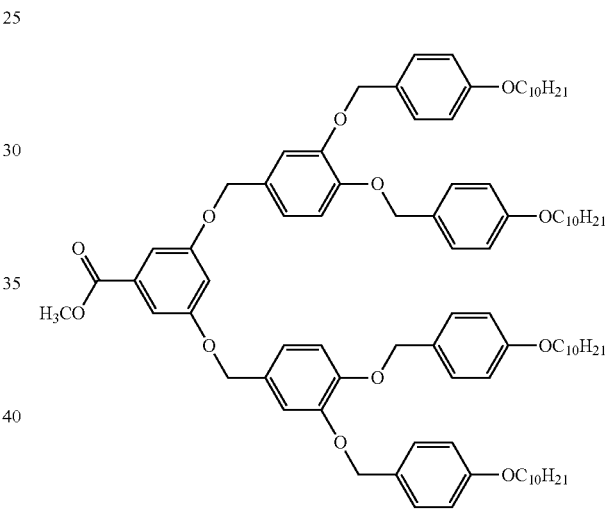

C$_{82}$H$_{108}$O$_{12}$
Exact Mass: 1396.91
Mol. Wt.: 1397.94
C, 77.33; H, 8.94; O, 13.73

This dendrimer was synthesized following the same general procedure as that for the preparation of [4-3,4-3,5] 12G2CO2CH3; K2CO3 (674 mg, 4.88 mmol), methyl 3,5-dihydroxybenzoate (113 mg, 0.814 mmol), [4-3,4] 10G1CH2Cl (1.06 g, 1.63 mmol), DMF (15 mL). TLC (7:1 ex:EtOAc), flash column chromatography: silica gel/CH2Cl2 followed by precipitation in CH3OH from minimal CH2Cl2 to give the title compound as a white solid, 850 mg (77%).

mp 92-93° C. $^1$H NMR (500 MHz, CDCl3) δ=7.31 (m, 8H), 7.26 (s, 2H), 7.03 (s, 2H), 6.92 (s, 4H), 6.85 (d, 8H, J=8.0 Hz), 6.74 (t, 1H, J=2.5 Hz), 5.05 (s, 8H), 4.94 (s, 4H), 3.93 (m, 8H), 3.89 (s, 3H), 1.44 (m, 8H), 1.38-1.21 (m, 48H), 0.88 (t, 12H, J=7.0 Hz). $^{13}$C NMR (125 MHz, CDCl3) δ=167.0, 159.8, 158.9, 149.4, 149.1, 132.2, 129.7, 129.1 (×2), 129.0, 121.0, 115.5, 115.1, 114.5, 108.4, 107.3, 71.3, 70.2, 68.1, 52.2, 31.9, 29.5, 29.4, 29.3, 26.1, 22.7, 14.1.

Example 57

Preparation of [4-3,4-3,5]14G$_2$COOCH$_3$ Dendrimer

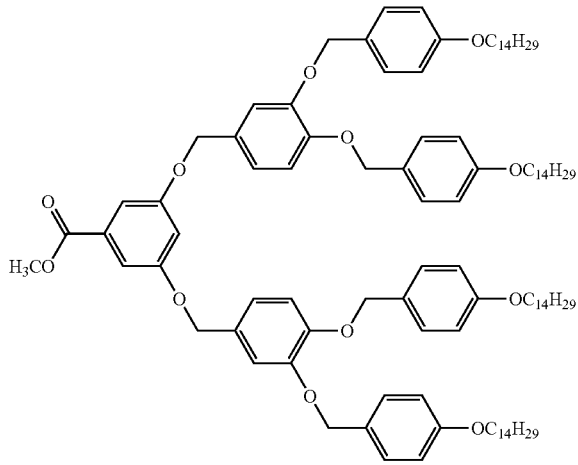

C$_{109}$H$_{198}$O$_{12}$
Exact Mass: 1621.16
Mol. Wt.: 1622.37
C, 78.47; H, 9.69; O, 11.83

This dendrimer was synthesized following the same general procedure as that for the preparation of [4-3,4-3,5] 12G2CO2CH3; K2CO3 (556 mg, 4.03 mmol), methyl 3,5-dihydroxybenzoate (113 mg, 0.674 mmol), [4-3,4] 14G1CH2Cl (1.03 g, 1.35 mmol), DMF (20 mL). TLC (7:1 Hex:EtOAc), flash column chromatography: silica gel/ CH2Cl2 followed by precipitation in CH3OH from minimal CH2Cl2 to give the title compound as a white solid, 950 mg (87%).

mp 100-101° C.

$^1$H NMR (500 MHz, CDCl3) δ=7.31 (m, 8H), 7.26 (s, 2H), 7.03 (s, 2H), 6.92 (s, 4H), 6.85 (d, 8H, J=9.0 Hz), 6.74 (t, 1H, J=2.5 Hz), 5.04.(s, 8H), 4.94 (s, 4H), 3.93 (m, 8H), 3.89 (s, 3H), 1.76 (m, 8H), 1.44 (m, 8H), 1.39-1.21 (m, 80H), 0.88 (t, 12H, J=7.0 Hz).

$^{13}$C NMR (125 MHz, CDCl3) δ=166.7, 159.8, 159.0, 149.4, 149.1, 132.0, 129.7, 129.1 (×2), 129.0, 121.0, 115.5, 115.1, 114.5, 108.4, 107.3, 71.3, 70.2, 68.1, 52.2, 31.9, 29.7, 29.6, 29.4, 29.3 (×2), 26.1, 22.7, 14.1.

Example 58

Preparation of [4-3,4-3,5]16G$_2$COOCH$_3$ Dendrimer

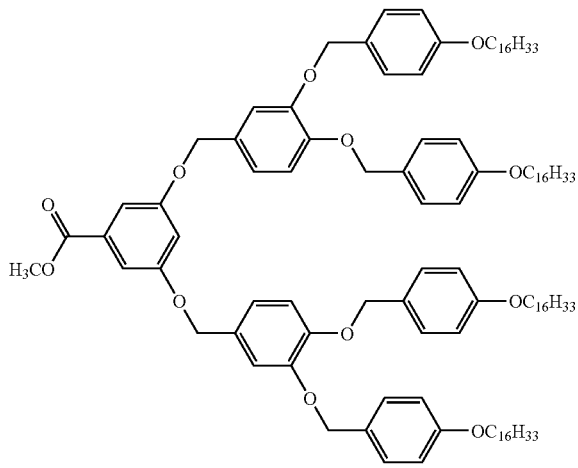

C$_{114}$H$_{132}$O$_{12}$
Exact Mass: 1733.28
Mol. Wt.: 1734.58
C, 78.94; H, 9.99; O, 11.07

This dendrimer was synthesized following the same general procedure as that for the preparation of [4-3,4-3,5] 12G2CO2CH3; K2CO3 (2.81 g, 20.3 mmol), methyl 3,5-dihydroxybenzoate (570 mg, 3.39 mmol), [4-3,4] 16G1CH2Cl (5.56 g, 6.78 mmol), DMF (50 mL). TLC (7:1 Hex:EtOAc), flash column chromatography: silica gel/ CH2Cl2 followed by precipitation in CH3OH from minimal CH2Cl2 to give the title compound as a white solid, 4.88 g (82%).

mp 98-100° C. $^1$H NMR,(500 MHz, CDCl3) δ=7.32 (m, 8H), 7.26 (s, 2H), 7.03 (s, 2H), 6.92 (s, 4H), 6.86 (d, 8H, J=8.5 Hz), 6.75 (t, 1H, J=2.5 Hz), 5.06 (s, 8H), 4.94 (s, 4H), 3.93 (m, 8H), 3.89 (s, 3H), 1.76 (m, 8H), 1.43 (m, 8H), 1.39-1.26 (m, 134H), 0.88 (t, 12H, J=7.0 Hz). $^{13}$C NMR (125 MHz, CDCl3) δ=167.0, 160.0, 159.1 (×2), 149.5, 149.1, 132.2, 129.8, 129.6, 129.3 (×2), 129.2, 121.2, 115.6, 115.2, 114.6, 108.6, 107.4, 81.0, 76.8, 71.5, 70.4, 68.2, 52.5, 32.1, 29.9, 29.8, 29.7, 29.6, 29.5, 26.3, 22.9, 14.3.

Example 59

Preparation of [4-3,4-3,5]1G$_2$CH$_2$OH Dendrimer

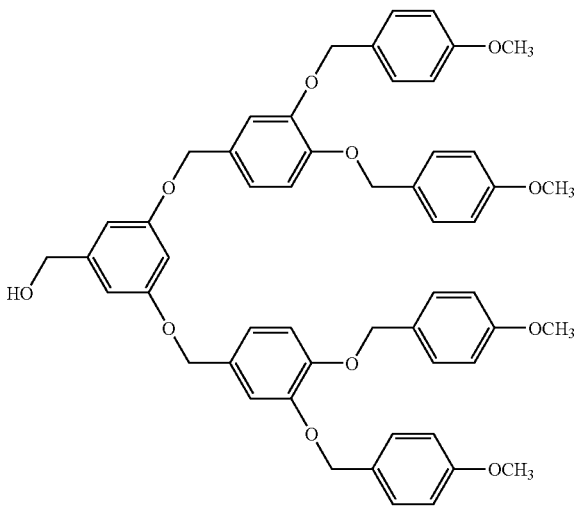

C$_{33}$H$_{22}$O$_{11}$
Exact Mass: 864.35
Mol. Wt.: 864.97
C, 73.59; H, 6.06; O, 20.35

[4-3,4-3,5]1G2CO2CH3 (1.39 g, 1.56 mmol) in dry THF (20 mL) was added slowly to a suspension of LAH (65 mg, 1.71 mmol) in dry THF (10 mL) and the reaction allowed to stir at room temperature for 2 hours after which TLC (2:1 Hex:EtOAc) showed completion. Reaction was quenched by slow successive addition of H2O (65 μL), 15% NaOH (65 μL), H2O (200 μL). The lithium salts were filtered and rinsed generously with CH2Cl2, the filtrate was dried over MgSO4 and concentrated to give the title alcohol as an oil which solidified upon standing 1.33 g (99%).

mp 22° C.

$^1$H NMR (500 MHz, CDCl3) δ=7.33 (d, 8H, J=8.5 Hz), 7.01 (s, 2H), 6.91 (m, 4H), 6.86 (m, 8H), 6.56 (s, 2H), 6.48 (t, 1H, J=2.0 Hz), 5.06 (s, 8H), 4.91 (s, 4H), 4.60 (d, 2H, J=6.0 Hz), 3.80 (d, 12H, J=5.0 Hz).

$^{13}$C NMR (125 MHz, CDCl3) δ=160.2, 159.4, 149.3, 149.0, 132.0, 130.2, 129.4 (×2), 129.1, 129.0, 120.9, 115.5, 115.1, 113.9, 105.8, 101.4, 71.3 (×2), 70.0, 65.3, 55.3.

Example 60

Preparation of [4-3,4-3,5]2G₂CH₂OH Dendrimer

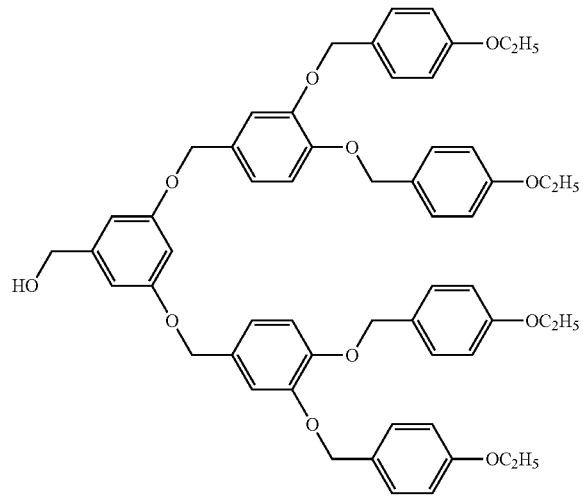

C₅₇H₆₀O₁₁
Exact Mass: 920.41
Mol. Wt.: 921.08
C, 74.33; H, 6.57; O, 19.11

This dendrimer was synthesized following the same general procedure as that for the preparation of [4-3,4-3,5] 1G₂CH₂OH; LAH (27 mg, 0.71 mmol) in dry THF (5 mL), [4-3,4-3,5]2G2CO2CH3 (450 mg, 0.47 mmol) in dry THF (8 mL).

TLC (7:1 Hex:EtOAc), white solid 438 mg (98%). mp 71° C.

m¹H NMR (300 MHz, CDCl3) δ=7.30 (d, 8H, J=8.4 Hz), 7.01 (s, 2H), 6.90 (s, 4H), 6.85 (d, 8H, J=4.5 Hz), 6.56 (s, 2H), 6.48 (t, 1H, J=2.5 Hz), 5.05 (s, 8H), 4.89 (s, 4H), 4.58 (d, 2H, J=6 Hz), 4.05-3.97 (m, 8H), 1.40 (t, 12H, J=6.9 Hz).
¹³C NMR (75 MHz, CDCl3) δ=160.3, 158.9, 149.4, 149.1, 143.6, 130.2, 129.4, 129.3, 129.2, 121.1, 115.5, 115.1, 114.6, 105.9, 101.4, 71.4 (×2), 70.2, 65.5, 63.6, 15.0.

Example 61

Preparation of [4-3,4-3,5]4G₂CH₂OH Dendrimer

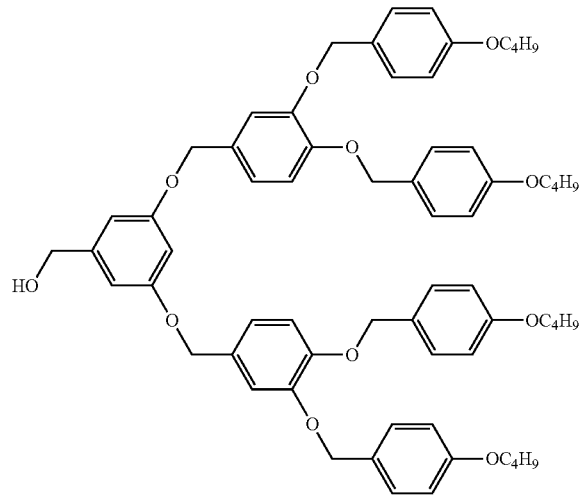

C₆₅H₇₆O₁₁
Exact Mass: 1032.54
Mol. Wt.: 1033.29
C, 75.55; H, 7.41; O, 17.03

This dendrimer was synthesized following the same general procedure as that for the preparation of [4-3,4-3,5] 1G2CH2OH; LAH (35 mg, 0.92 mmol) in dry THF (5 mL), [4-3,4-3,5]4G2CO2CH3 (650 mg, 0.61 mmol) in dry THF (8 mL).

TLC (7:1 Hex:EtOAc), white solid 620 mg (98%). mp 101° C.

¹H NMR (300 MHz, CDCl3) δ=7.31 (d, 8H, J=8.1 Hz), 7.01 (s, 2H), 6.90 (s, 4H), 6.85 (d, 8H, J=4.5 Hz), 6.56 (s, 2H), 6.48 (t, 1H, J=2.5 Hz), 5.04 (s, 8H), 4.89 (s, 4H), 4.58 (d, 2H, J=6 Hz), 3.94 (t, 8H, J=6.6 Hz), 1.80-1.71 (m, 8H), 1.53-1.43 (m, 8H), 0.97 (t, 12H, J=7.2 Hz). 13C NMR (75 MHz, CDCl3) δ=160.3, 159.1, 149.4, 149.1, 143.6, 130.2, 129.3, 129.2 (×2), 121.1, 115.5, 115.1, 114.6, 105.9, 101.4, 71.4 (×2), 70.2, 67.9 (×2), 65.5, 31.5, 19.4, 14.1.

Example 62

Preparation of [4-3,4-3,5]6G₇CH₂OH Dendrimer

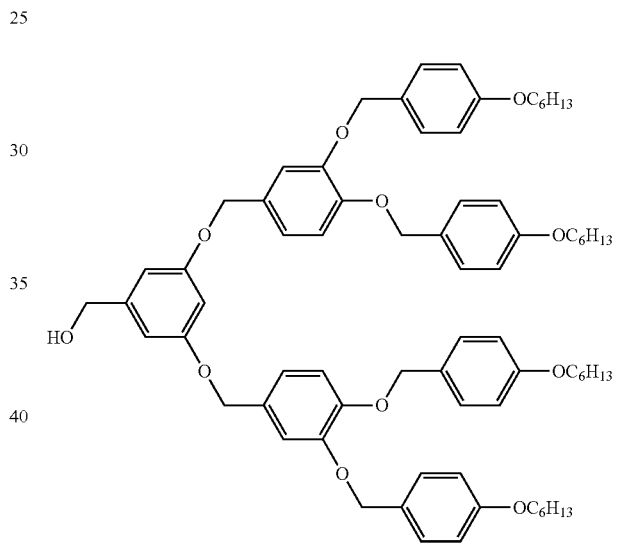

C₇₃H₈₂O₁₁
Exact Mass: 1144.66
Mol. Wt.: 1145.50
C, 76.54; H, 8.10; O, 15.36

This dendrimer was synthesized following the same general procedure as that for the preparation of [4-3,4-3,5] 1G2CH2OH; LAH (14 mg, 0.37 mmol) in dry THF (5 mL), [4-3,4-3,5]6G2CO2CH3 (280 mg, 0.24 mmol) in dry THF (5 mL).

TLC (7:1 Hex:EtOAc), white solid 270 mg (98%). mp 116° C.

¹H NMR (300 MHz, CDCl3) δ=7.31 (d, 8H, J=7.8 Hz), 7.02 (s, 2H), 6.90 (s, 4H), 6.85 (d, 8H, J=4.5 Hz), 6.57 (s, 2H), 6.49 (t, 1H, J=2.5 Hz), 5.05 (s, 8H), 4.90 (s, 4H), 4.59 (d, 2H, J=6 Hz), 3.93 (t, 8H, J=6.6 Hz), 1.80-1.71 (m, 8H), 1.48-1.41 (m, 8H), 1.38-1.29 (m, 16H), 0.90 (t, 12H, J=7.2 Hz). ¹³C NMR (75 MHz, CDCl3) δ=160.3, 159.1, 149.4, 149.1, 143.6, 130.2, 129.3, 129.2 (×2), 121.1, 115.5, 115.1, 114.6, 105.9, 101.4, 71.4 (×2), 70.2, 68.2, 65.5, 31.8, 29.4, 25.9, 22.8, 14.2.

Example 63

Preparation of [4-3,4-3,5]8G₂CH₂OH Dendrimer

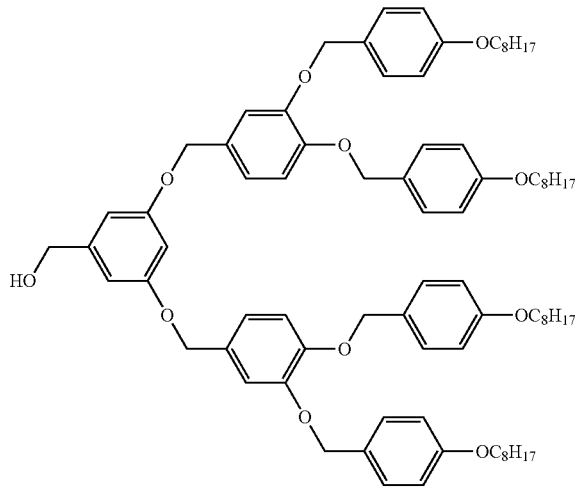

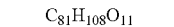

C$_{81}$H$_{108}$O$_{11}$
Exact Mass: 1256.79
Mol. Wt.: 1257.72
C, 77.35; H, 8.06; O, 13.99

This dendrimer was synthesized following the same general procedure as that for the preparation of [4-3,4-3,5]1G2CH2OH; LAH (36 mg, 0.95 mmol) in dry THF (5 mL), [4-3,4-3,5]8G2CO2CH3 (820 mg, 0.64 mmol) in dry THF (10 mL).

TLC (7:1 Hex:EtOAc), white solid 800 mg (98%). mp 126° C.

$^1$H NMR (300 MHz, CDCl3) δ=7.30 (d, 8H, J=7.5 Hz), 7.01 (s, 2H), 6.89 (s, 4H), 6.84 (d, 8H, J=8.7 Hz), 6.55 (s, 2H), 6.48 (t, 1H, J=2.5 Hz), 5.03 (s, 8H), 4.88 (s, 4H), 4.56 (d, 2H, J=6 Hz), 3.93 (t, 8H, J=6.6 Hz), 1.80-1.73 (m, 8H), 1.48-1.41 (m, 8H), 1.38-1.27 (m, 32H), 0.89 (t, 12H, J=7.0 Hz).

$^{13}$C NMR (75 MHz, CDCl3) δ=160.3, 159.0, 149.4, 149.1, 143.6, 130.2, 129.3, 129.2 (×2), 121.0, 115.5, 115.0, 114.6, 105.8, 101.4, 71.4 (×2), 70.1, 68.2, 65.4, 32.0, 29.6, 29.5, 29.4, 26.2, 22.8, 14.3.

Example 64

Preparation of [4-3,4-3,5]10G₂CH₂OH Dendrimer

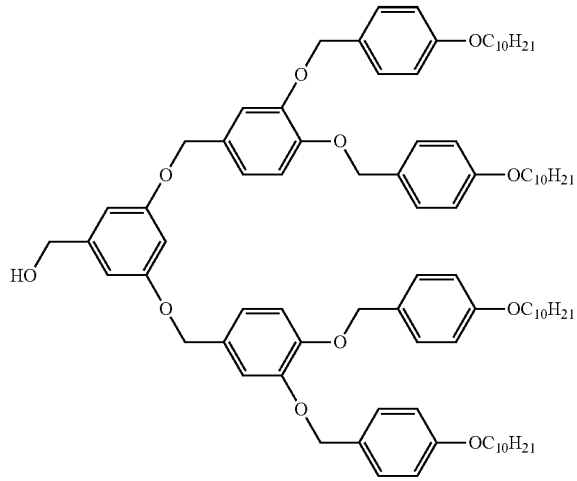

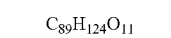

C$_{89}$H$_{124}$O$_{11}$
Exact Mass: 1368.91
Mol. Wt.: 1369.93
C, 78.03; H, 9.12; O, 12.85

This dendrimer was synthesized following the same general procedure as that for the preparation of [4-3,4-3,5]1G2CH2OH; LAH (24 mg, 0.63 mmol) in dry THF (5 mL), [4-3,4-3,5]10G2CO2CH3 (800 mg, 0.57 mmol) in dry THF (10 mL).

TLC (7:1 Hex:EtOAc), white solid 780 mg (98%). mp 130° C.

$^1$H NMR (500 MHz, CDCl3) δ=7.30 (d, 8H, J=7.5 Hz), 7.01 (s, 2H), 6.89 (s, 4H), 6.84 (d, 8H, J=8.7 Hz), 6.55 (s, 2H), 6.48 (t, 1H, J=2.5 Hz), 5.03 (s, 8H), 4.88 (s, 4H), 4.56 (d, 2H, J=6 Hz), 3.93 (t, 8H, J=6.6 Hz), 1.81-1.72 (m, 8H), 1.48-1.40 (m, 8H), 1.38-1.27 (m, 48H), 0.89 (t, 12H, J=7.0 Hz).

$^{13}$C NMR (125 MHz, CDCl3) δ=160.3, 159.8, 158.9, 149.4, 149.1, 132.2, 129.7, 129.1 (×2), 129.0, 121.0, 115.5, 115.1, 114.5, 108.4, 107.3, 71.3, 70.2, 68.1, 52.2, 31.9, 29.5, 29.4, 29.3, 26.1, 22.7, 14.1.

Example 65

Preparation of [4-3,4-3,5]12G₂CH₂OH Dendrimer

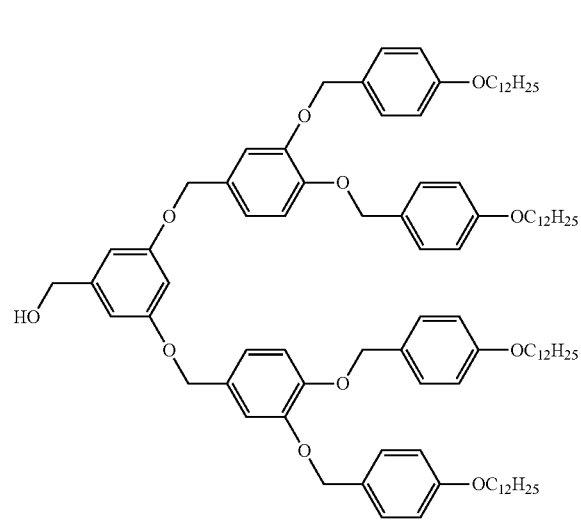

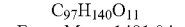

C$_{97}$H$_{140}$O$_{11}$
Exact Mass: 1481.04
Mol. Wt.: 1482.14
C, 78.60; H, 9.52; O, 11.87

This dendrimer was synthesized following the same general procedure as that for the preparation of [4-3,4-3,5]1G2CH2OH; LAH (101 mg, 2.42 mmol) in dry THF (10 mL), [4-3,4-3,5]12G2CO2CH3 (3.65 g, 2.42 mmol) in dry THF (15 mL).

TLC (7:1 Hex:EtOAc), white solid 3.50 g (97%). mp 132-133° C. (literature[6] 133° C.).

$^1$H NMR (500 MHz, CDCl3) δ=7.34 (d, 8H, J=6.6 Hz), 7.05 (d, 2H, J=1.5 Hz), 6.93 (s, 4H), 6.89 (m, 8H), 6.58 (s, 2H), 6.51 (t, 1H, J=2.2 Hz), 5.06 (s, 8H), 4.91 (s, 4H), 4.59 (s, 2H), 3.96 (m, 8H), 2.00 (s, 1H), 1.80 (m, 8H), 1.47 (m, 8H), 1.40-1.20 (m, 64H), 0.92 (t, 12H, J=6.7 Hz).

$^{13}$C NMR (125 MHz, CDCl3) δ=160.2, 159.0, 149.4, 149.1, 143.6, 130.2, 129.2 (×4), 121.0, 115.5, 115.0, 114.6, 105.8, 101.4, 71.4 (×2), 70.1, 68.2 (×2), 65.4, 32.1, 30.5, 29.8 (×4), 29.6, 29.5 (×2), 26.2, 22.9, 14.3.

Example 66

Preparation of [4-3,4-3,5]14G$_2$CH$_2$OH Dendrimer

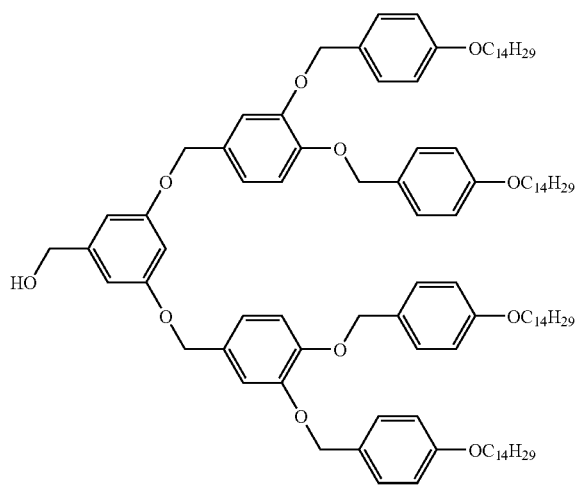

C$_{105}$H$_{339}$O$_{11}$
Exact Mass: 1593.16
Mol. Wt.: 1594.36
C, 79.10; H, 9.86; O, 11.04

This dendrimer was synthesized following the same general procedure as that for the preparation of [4-3,4-3,5] 1G2CH2OH; LAH (26 mg, 0.678 mmol) in dry THF (10 mL), [4-3,4-3,5]14G2CO2CH3 (1.00 g, 0.616 mmol) in dry THF (15 mL).

TLC (7:1 Hex:EtOAc), white solid 900 mg (92%). mp 132° C.

$^1$H NMR (500 MHz, CDCl3) δ=7.34 (d, 8H, J=6.6 Hz), 7.05 (d, 2H, J=1.5 Hz), 6.94 (s, 4H), 6.89 (m, 8H), 6.58 (s, 2H), 6.51 (t, 1H, J=2.2 Hz), 5.05 (s, 8H), 4.91 (s, 4H), 4.59 (s, 2H), 3.95 (m, 8H), 2.00 (s, 1H), 1.80 (m, 8H), 1.46 (m, 8H), 1.40-1.21 (m, 80H), 0.92 (t, 12H, J=6.5 Hz). $^{13}$C NMR (125 MHz, CDCl3) δ=160.2, 159.8, 159.0, 149.4, 149.1, 132.0, 129.7, 129.1 (×2), 129.0, 121.0, 115.5, 115.1, 114.5, 108.4, 107.3, 71.3, 70.2, 68.1, 52.2, 31.9, 29.7, 29.6, 29.4, 29.3 (×2), 26.1, 22.7, 14.1.

Example 67

Preparation of [4-3,4-3,5]16G$_2$CH$_2$OH Dendrimer

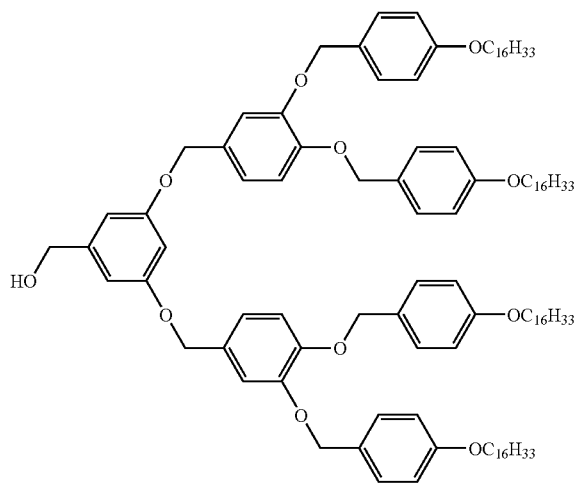

C$_{112}$H$_{172}$O$_{11}$
Exact Mass: 1705.29
Mol. Wt.: 1706.57
C, 79.53; H, 10.16; O, 10.31

This dendrimer was synthesized following the same general procedure as that for the preparation of [4-3,4-3,5] 1G$_2$CH$_2$OH; LAH (51 mg, 1.33 mmol) in dry THF (10 mL), [4-3,4-3,5]16G$_2$COOCH$_3$ (2.10 g, 1.21 mmol) in dry THF (20 mL).

TLC (7:1 Hex:EtOAc), white solid 1.95 g (95%). mp 128° C.

$^1$H NMR (500 MHz, CDCl3) δ=7.31 (d, 8H, J=6.6 Hz), 7.02 (s, 2H), 6.91 (s, 4H), 6.84 (m, 8H), 6.56 (s, 2H), 6.48 (t, 1H, J=2.2 Hz), 5.04 (s, 8H), 4.90 (s, 4H), 4.59 (s, 2H), 3.93 (m, 8H), 1.79-1.74 (m, 8H), 1.46-1.40 (m, 8H), 1.34-1.26 (m, 120H), 0.88 (t, 12H, J=6.5 Hz).

$^{13}$C NMR (125 MHz, CDCl3) δ=160.3, 159.1, 159.0, 149.5, 149.1, 143.6, 130.2, 129.3, 129.3, 129.2 (×2), 121.1, 115.5, 115.1, 101.5, 71.5, 71.4, 70.2, 68.2, 65.5, 32.1, 30.5, 29.9, 29.8, 29.6 (×2), 29.5, 26.3, 22.9, 14.3.

Example 68

Preparation of [4-3,4-3,5]1G$_2$CH$_2$Cl Dendrimer

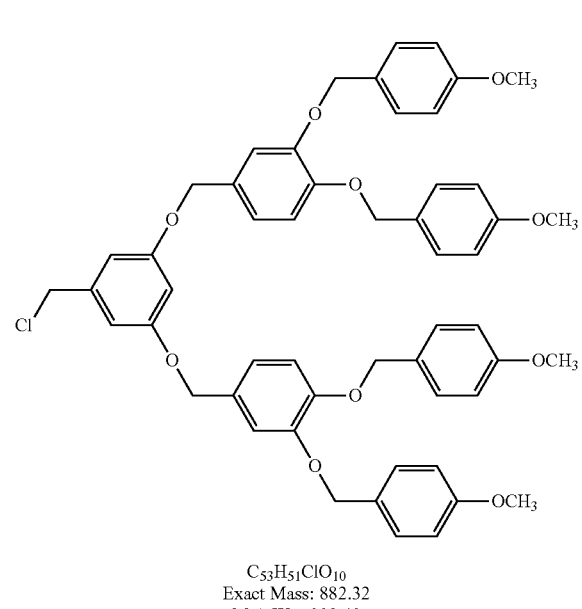

C$_{53}$H$_{51}$ClO$_{10}$
Exact Mass: 882.32
Mol. Wt.: 883.42
C, 72.06; H, 5.82; Cl, 4.01; O, 18.11

This dendrimer was synthesized following the same general procedure as that for the preparation of [4-3,4] 12G1CH2Cl; SOCl2 (142 mg, 1.21 mmol), DTBMP (335 mg, 1.63 mmol), [4-3,4-3,5]1G2CH2OH (950 mg, 1.09 mmol), CH2Cl2 (15 mL), TLC (1:1 Hex:EtOAc). Product chloride was precipitated in Et2O from minimal CH2Cl2, and was used without further purification and characterization, 837 mg (87%).

$^1$H NMR (500 MHz, CDCl3) δ=7.33 (d, 8H, J=8.5 Hz), 7.01 (s, 2H), 6.91 (m, 4H), 6.86 (m, 8 H), 6.56 (s, 2H), 6.48 (t, 1H, J=2.0 Hz), 5.06.(s, 8H), 4.91 (s, 4H), 4.48 (s, 2H), 3.80 (d, 12H, J=5.0 Hz). $^{13}$C NMR (125 MHz, CDCl3) δ=160.1, 159.4, 149.3, 149.1, 139.5, 130.0, 129.4, 129.3, 129.1, 129.0, 121.0, 115.5, 115.1, 113.9, 107.7, 102.2, 71.3 (×2), 70.1, 55.2, 46.3.

Example 69

Preparation of [4-3,4-3,5]10G$_2$CH$_2$Cl Dendrimer

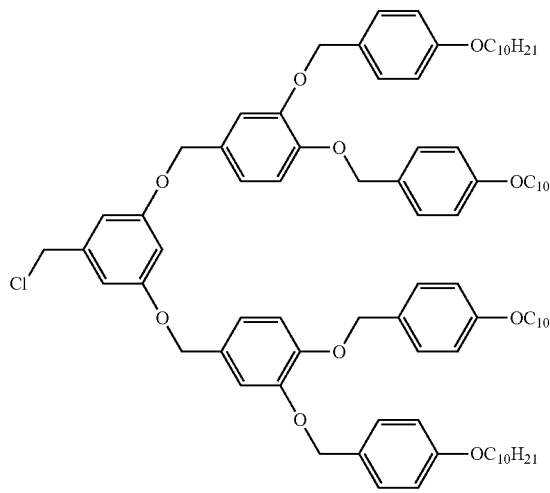

C$_{89}$H$_{123}$ClO$_{10}$
Exact Mass: 1386.88
Mol. Wt.: 1388.38
C, 76.99; H, 8.93; Cl, 2.55; O, 11.52

This dendrimer was synthesized following the same general procedure as that for the preparation of [4-3,4] 12G1CH2Cl; SOCl2 (24 mg, 0.207 mmol), DTBMP (58 mg, 0.282 mmol), [4-3,4-3,5]10G2CH2OH (258 mg, 0.182 mmol), CH2Cl2 (8 mL), TLC (7:1 Hex:EtOAc). Product chloride was precipitated in CH3OH from minimal CH2Cl2, and was used without further purification and characterization, 240 mg (92%).

$^1$H NMR (500 MHz, CDCl3) δ=7.30 (d, 8H, J=7.5 Hz), 7.01 (s, 2H), 6.89 (s, 4H), 6.84 (d, 8H, J=8.7 Hz), 6.55 (s, 2H), 6.48 (t, 1H, J=2.5 Hz), 5.03 (s, 8H), 4.88 (s, 4H), 4.49 (s, 2H), 3.93 (t, 8H, J=6.6 Hz), 1.81-1.72 (m, 8H), 1.48-1.40(m, 8H), 1.38-1.27 (m, 48H), 0.89 (t, 12H, J=7.0 Hz).

$^{13}$C NMR (125 MHz, CDCl3) δ=160.3, 159.8, 158.9, 149.4, 149.1, 132.2, 129.7, 129.1 (×2), 129.0, 121.0, 115.5, 115.1, 114.5, 108.4, 107.3, 71.3, 70.2, 68.1, 52.2, 31.9, 29.5, 29.4, 29.3, 26.1, 22.7, 14.1.

Example 70

Preparation of [4-3,4-3,5]12G$_2$CH$_2$Cl Dendrimer

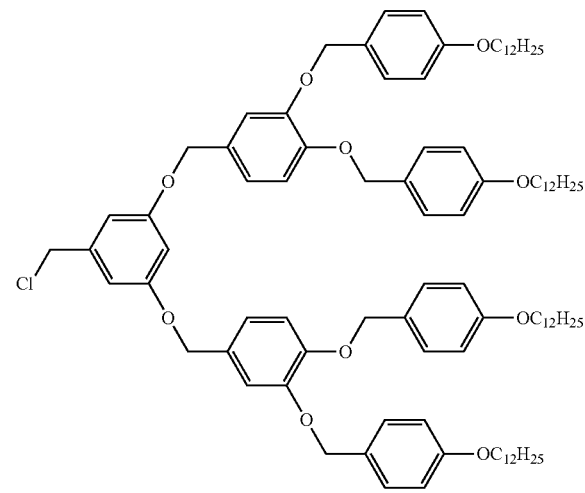

C$_{97}$H$_{139}$ClO$_{10}$
Exact Mass: 1499.01
Mol. Wt.: 1500.59
C, 77.64; H, 9.34; Cl, 2.36; O, 10.66

Thionyl chloride (0.263 g, 2.23 mmol) was added dropwise to a chilled solution of [4-3,4-3,5]12G$_2$CH$_2$OH (3 g, 2.03 mmol) and DTBMP (0.623 g, 3.03 mmol) in dry CH2Cl2 (80 mL). Upon addition, reaction was allowed to stir for 5-10 minutes, while monitoring through TLC (7:1 Hex:EtOAc) for completion. Reaction mixture was concentrated under reduced pressure and the resulting residue re-crystallized from acetone to give the title benzyl chloride, which was used without further purification and characterization (2.58 g, 85%).

$^1$H NMR (500 MHz, CDCl3) δ=7.35 (m, 8H), 7.05 (s, 2H), 6.93 (m, 4H), 6.89 (d, 8H, J=8.6 Hz), 6.62 (d, 2H, J=2.2 Hz), 6.54 (t, 1H, J=2.2 Hz), 5.08 (s, 8H), 4.92 (s, 4H), 4.51 (s, 2H), 3.96 (m, 8H), 1.80 (m, 8H), 1.47 (m, 8H), 1.40-1.21 (m, 64H), 0.91 (t, 12H, J=6.8 Hz).

$^{13}$C NMR (125 MHz, CDCl3) δ=160.4, 159.1 (×2), 149.5, 149.3, 139.8, 130.1, 129.4 (×2), 129.3 (×2), 121.2, 115.6, 115.2, 114.7, 107.9, 102.3, 71.5 (×2), 70.4, 68.3, 53.7, 46.6, 32.2, 29.9 (×4), 29.7 (×2), 29.6, 29.5, 26.4, 23.0, 14.4.

Example 71

Preparation of [4-3,4-3,5]14G₂CH₂Cl Dendrimer

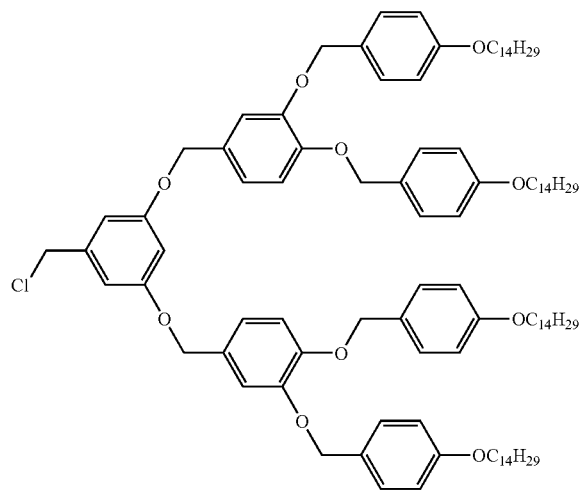

C₁₀₈H₁₈₅ClO₁₀
Exact Mass: 1611.13
Mol. Wt.: 1612.8
C, 78.19; H, 9.69; Cl, 2.20; O, 9.92

This dendrimer was synthesized following the same general procedure as that for the preparation of [4-3,4-3,5] 12G₂CH₂Cl; SOCl₂ (16.3 mg, 0.138 mmol), DTBMP (38 mg, 0.188 mmol), [4-3,4-3,5]14G₂CH₂OH (200 mg, 0.125 mmol), CH2Cl2 (8 mL), TLC (7:1 Hex:EtOAc). Product chloride was precipitated in CH₃OH from minimal CH₂Cl₂, and was used without further purification and characterization, 180 mg (89%).

¹H NMR (500 MHz, CDCl3) δ=7.34 (d, 8H, J=6.6 Hz), 7.05 (d, 2H, J=1.5 Hz), 6.94 (s, 4H), 6.89 (m, 8H), 6.58 (s, 2H), 6.51 (t, 1H, J=2.2 Hz), 5.05 (s, 8H), 4.91 (s, 4H), 4.52 (s, 2H), 3.95 (m, 8H), 2.00 (s, 1H), 1.80 (m, 8H), 1.46 (m, 8H), 1.40-1.21 (m, 80H), 0.92 (t, 12H, J=6.5 Hz).

¹³C NMR (125 MHz, CDCl3) δ=160.2, 159.8, 159.0, 149.4, 149.1, 132.0, 129.7, 129.1 (×2), 129.0, 121.0, 115.5, 115.1, 114.5, 108.4, 107.3, 71.3, 70.2, 68.1, 52.2, 31.9, 29.7, 29.6, 29.4, 29.3 (×2), 26.1, 22.7, 14.1.

Example 72

Preparation of [4-3,4-3,5]16G₂CH₂Cl Dendrimer

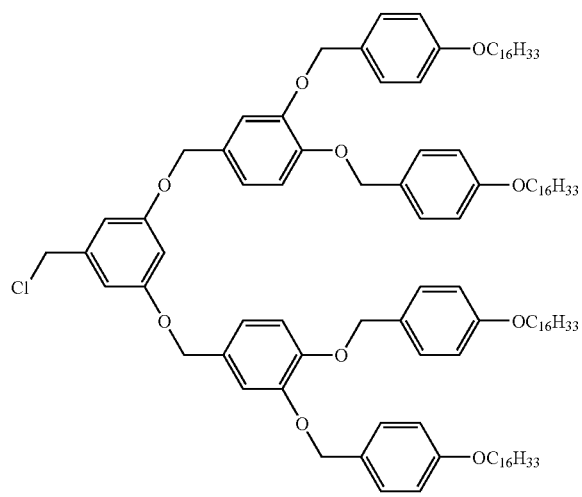

C₁₅₃H₁₇₁ClO₁₀
Exact Mass: 1723.26
Mol. Wt.: 1725.01
C, 78.68; H, 9.99; Cl, 2.06; O, 9.27

This dendrimer was synthesized following the same general procedure as that for the preparation of [4-3,4-3,5] 12G2CH2Cl; SOCl2 (16.3 mg, 0.138 mmol), DTBMP (38 mg, 0.188 mmol), [4-3,4-3,5]16G2CH2OH (200 mg, 0.125 mmol), CH2Cl2 (8 mL), TLC (7:1 Hex:EtOAc). Product chloride was precipitated in CH3OH from minimal CH2Cl2, and was used without further purification and characterization, 180 mg (89%).

¹H NMR (500 MHz, CDCl3) δ=7.32 (m, 8H), 7.02 (s, 1H), 6.91 (m, 4H), 6.85 (d, 8H, J=8.5 Hz), 6.59 (s, 2H), 6.50 (t, 1H, J=2.2 Hz), 5.05 (s, 8H), 4.90 (s, 4H), 4.49 (s, 2H), 3.93 (m, 8H), 1.82-1.70 (m, 8H), 1.43 (m, 8H), 1.33-1.22 (m, 140H), 0.88 (t, 12H, J=6.5 Hz). ¹³C NMR (125 MHz, CDCl3) δ=160.3, 159.1, 149.5, 139.7, 130.0, 129.3, 129.2 (×2), 129.0, 121.1, 115.6, 115.1, 114.6, 107.9, 107.3, 71.5, 71.4, 68.3, 46.5, 32.1, 29.9, 29.8, 29.6 (×2), 29.5, 26.3, 22.9, 14.3.

Example 73

Preparation of Boc-Tyr(OH)-Ala-OMe Dipeptide Derivative

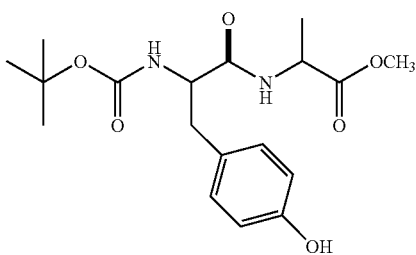

C₁₃H₂₆N₂O₆
Exact Mass: 366.18
Mol. Wt.: 366.41
C, 59.00; H, 7.15; N, 7.65; O, 26.20

N-methyl morpholine (NMM) (1.37 g, 13.5 mmol) was added slowly to a 0° C. solution of Boc-Tyr(OH)COOH (1.52 g, 5.40 mmol), HCl.H₂N-Ala-OMe (752 mg, 5.40 mmol) and 2-chloro-4,6-dimethoxy-1,3,5-triazene (CDMT) (949 mg, 5.40 mmol) in EtOAc (15 mL), and the reaction allowed to stir at room temperature for 2 hours, after which mixture was taken up in EtOAc and washed with H₂O (1×), 1M HCl (2×), saturated NaHCO₃ (2×), H₂O (1×), brine, dried over MgSO₄ and concentrated. Crude product was purified by flash column chromatography: silica gel/gradient 2 to 4% MeOH in CHCl3 to give the dipeptide as a white solid.

Example 74

Properties of Boc-L-Tyr(OH)-L-Ala-OMe Dipeptide Derivative

The L-Tyr L-Ala dipeptide derivative has a product mass:: 1.62g (82%).

mp 180-183° C. (literature[8] 78-80° C.). [α]_D^{20}=−3.6 (c. 0.05, THF).

¹H NMR (500 MHz, CDCl3) δ=7.04 (d, 2H, J=8.4 Hz), 6.74 (d, 2H, J=8.6 Hz), 6.40 (d, 1H, J=7.7 Hz), 5.66 (s, 1H), 5.03 (s, 1H), 4.51 (qt, 1H, J=7.3 Hz), 4.28 (s, 1H), 3.70 (s, 3H), 2.98 (m, 2H), 1.42 (s, 9H), 1.34 (d, 3H, J=7.2 Hz).

¹³C NMR (125 MHz, CDCl3) δ=173.1, 171.2, 155.8, 155.6, 130.6, 127.7, 115.8, 80.7, 56.0, 52.7, 48.3, 37.8, 34, 28.4, 25.0, 18.3.

Example 75

Properties of Boc-D-Tyr(OH)-D-Ala-OMe Dipeptide Derivative

The D-Tyr D-Ala dipeptide derivative has a product mass: 1.50 g (76%).

mp 180-181° C. $[\alpha]D^{20}$=+4.0 (c. 0.05, THF).

$^1$H NMR (500 MHz, CDCl3) δ=7.04 (d, 2H, J=8.4 Hz), 6.74 (d, 2H, J=8.6 Hz), 6.40 (d, 1H, J=7.7 Hz), 5.66 (s, 1H), 5.03 (s, 1H), 4.51 (qt, 1H, J=7.3 Hz), 4.28 (s, 1H), 3.70 (s, 3H), 2.98 (m, 2H), 1.42 (s, 9H), 1.34 (d, 3H, J=7.2 Hz).

$^{13}$C NMR(125 MHz, CDCl3) δ=173.1, 171.2, 155.8, 155.6, 130.6, 127.7, 115.8, 80.7, 56.0, 52.7, 48.3, 37.8, 34, 28.4, 25.0, 18.3.

Example 76

Preparation of Boc-L-Tyr(OH)-D-Ala-OMe Dipeptide Derivative

This L-Tyr D-Ala dipeptide derivative has a product mass: 1.65 g (83%).

mp 175-177° C. $[\alpha]D^{20}$=−1.8 (c.0.05, THF).

$^1$H NMR (500 MHz, CDCl$_3$)δ=7.04 (d,2H,J=8.4 Hz),6.74 (d,2H,J=8.6 Hz), 6.40 (d, 1H, J=7.7 Hz), 5.66 (s, 1H), 5.03 (s, 1H), 4.51(qt, 1H, J=7.3 Hz), 4.28 (s, 1H), 3.70 (s, 3H), 2.98 (m, 2H), 1.42 (s, 9H), 1.34 (d, 3H, J=7.2 Hz).

$^{13}$C NMR (125 MHz, CDCl3) δ=173.1, 171.2, 155.8, 155.6, 130.6, 127.7, 115.8, 80.7, 56.0, 52.7, 48.3, 37.8, 34, 28.4, 25.0, 18.3.

Example 77

Preparation of Boc-D-Tyr(OH)-L-Ala-OMe Dipeptide Derivative

This D-Tyr L-Ala dipeptide derivative has a product mass: 1.68 g (84%).

mp 175-177° C. $[\alpha]D^{20}$=+2.2 (c. 0.05, THF).

$^1$H NMR (500 MHz, CDCl3) δ=7.04 (d, 2H, J=8.4 Hz), 6.74 (d, 2H, J=8.6 Hz), 6.40 (d, 1H, J=7.7 Hz), 5.66 (s, 1H), 5.03 (s, 1H), 4.51 (qt, 1H, J=7.3 Hz), 4.28 (s, 1H), 3.70 (s, 3H), 2.98 (m, 2H), 1.42 (s, 9H), 1.34 (d, 3H, J=7.2 Hz).

$^{13}$C NMR (125 MHz, CDCl$_3$) δ=173.1, 171.2, 155.8, 155.6, 130.6, 127.7, 115.8, 80.7, 56.0, 52.7, 48.3, 37.8, 34 28.4, 25.0, 18.3.

Example 78

Preparation of Boc-DL-Tyr(OH)-DL-Ala-OMe Dipeptide Derivative

This DL-Tyr DL-Ala dipeptide derivative has a product mass: 1.45 g (73%).

mp 174-176° C. $[\alpha]_D{}^{20}$=+0.1 (c.0.05, THF).

$^1$H NMR (500 MHz, CDCl3) δ=7.04 (d, 2H, J=8.4 Hz), 6.74 (d, 2H, J=8.6 Hz), 6.40 (d, 1H, J=7.7 Hz), 5.66 (s, 1H), 5.03 (s, 1H), 4.51 (qt, 1H, J=7.3Hz), 4.28 (s, 1H), 3.70 (s, 3H), 2.98 (m, 2H), 1.42 (s, 9H), 1.34 (d, 3H, J=7.2 Hz).

$^{13}$C NMR (125 MHz, CDCl3) δ=173.1, 171.2, 155.8, 155.6, 130.6, 127.7, 115.8, 80.7, 56.0, 52.7, 48.3, 37.8, 34, 28.4, 25.0, 18.3.

Example 79

Preparation of Moc-Tyr(OH)-COOH Dipeptide Derivative

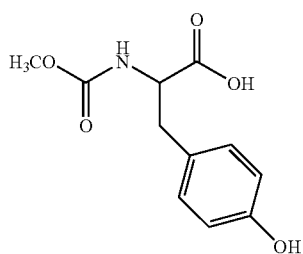

$C_{11}H_{13}NO_5$
Exact Mass: 239.08
Mol. Wt.: 239.22
C, 55.23; H, 5.48; N, 5.86; O, 33.44

Methyl chloroformate (2.87 g, 30.3 mmol) was added to a solution of tyrosine (5.00 g, 27.6 mmol) and NaHCO$_3$ (6.95g, 82.8mmol) in a THF:H$_2$O system (1:1 v:v, 280 mL). After stirring at room temperature overnight, the reaction mixture was diluted with H2O, and washed with Et2O. The aqueous layer was then acidified with concentrated HCl and extracted with EtOAc (3×'s). The combined organic layers were washed with H2O and brine, dried over MgSO$_4$ and concentrated to give the N-protected tyrosine as a glassy solid which was taken to the next step without further purification, 5.94 g (90%).

mp 86-88° C. (literature[9] 89-90° C.).

$^1$H NMR (500 MHz, CDCl3) δ=7.12 (d, 2H, J=8.5 Hz), 6.77 (d, 2H, J=8.5 Hz), 6.33 (d, 1H, J=8.5 Hz), 4.43 (m, 1H), 3.55 (s, 3H), 3.11 (m, 1H), 2.91 (m, 1H), 1.97 (s, 1H).

$^{13}$C NMR (125 MHz, CDCl3) δ=227.7, 194.6, 178.0, 152.0, 149.8, 142.7, 136.9, 73.1, 58.3, 41.8, 35.4.

Example 80

Preparation of Moc-Tyr(OH)-Ala-OMe Dipeptide Derivative

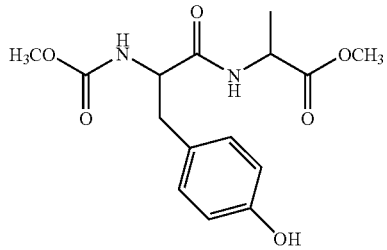

$C_{15}H_{20}N_2O_6$
Exact Mass: 324.13
Mol. Wt.: 324.33
C, 55.55; H, 6.22; N,8.64; O, 29.60

This dipeptide derivative was synthesized following the same general procedure as that for the preparation of Boc-Tyr (OH)-Ala-OMe; Moc-Tyr(OH)-COOH (1.52 g, 6.35 mmol), HCl.H2N-Ala-OMe (884 mg, 6.35 mmol), CDMT (1.23 g, 6.99 mmol), N-methyl morpholine (1.61 g, 15.9 mmol), EtOAc (10 mL). Crude product was purified by flash column chromatography: silica gel/5% MeOH in CH2Cl2 to give the dipeptide as a white solid, 1.80 g (88%).

mp 150-151° C. $[\alpha]D^{20}$=−5.6 (c. 0.05, THF).

$^1$H NMR (500 MHz, CDCl3) δ=7.05 (d, 2H, J=8.0 Hz), 6.74 (d, 2H, J=9.0 Hz), 6.30 (d, 1H, J=7.0 Hz), 5.43 (s, 1H), 5.24 (s, 1H), 4.50 (m, 1H), 4.34 (s, 1H), 3.75 (s, 3H), 3.67 (s, 3H), 3.06-2.92 (m, 2H), 1.35 (d, 3H, J=7.5 Hz).

$^{13}$C NMR (125 MHz, CDCl3) δ=194.6, 170.6, 152.0, 149.8, 142.7, 130.5, 115.6, 73.1, 52.5, 48.2, 37.8, 18.3.

Example 81

Preparation of [4-3,4-3,5]12G$_2$CH$_2$-Boc-Tyr-Ala-OMe

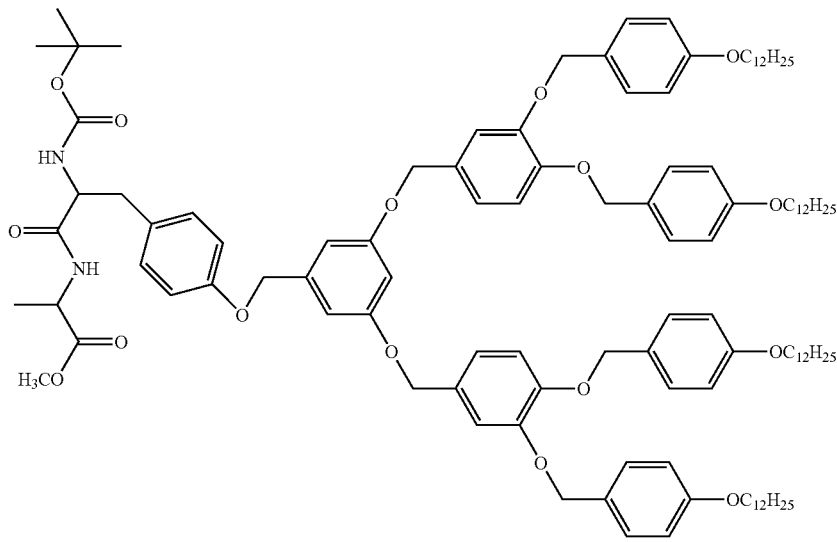

$C_{115}H_{164}N_2O_{16}$
Exact Mass: 1829.21
Mol. Wt.: 1830.54
C, 75.45; H, 9.03; N, 1.53; O, 13.98

This amphiphilic dendritic dipeptide was synthesized by modifying Aida's procedure[10], used for the synthesis of a non self-assembling dendritic dipeptide; Boc-Tyr(OH)-Ala-OMe (64 mg, 0.175 mmol) was added to a degassed suspension of K2CO$_3$ (73 mg, 0.524 mmol) in DMF (5 mL) and the mixture heated to 70° C. after which was added [4-3,4-3,5] 12G$_2$CH$_2$Cl (262 mg, 0.175 mmol) and the reaction allowed to stir overnight at 70° C. under argon. Reaction flask was allowed to cool to room temperature and the product precipitated into cold water, filtered and purified by flash column chromatography silica/1% MeOH in CH$_2$Cl$_2$, followed by precipitation in MeOH from minimal CH$_2$Cl$_2$ to give the title compound (130 mg, 41%).

mp 95.0-96.1° C. $[\alpha]D^{20}$=−14.0 (c. 0.05, THF). MALDI-TOF for C115H164N2O16 m/z calcd: 1853.53 [M+Na$^+$]; found 1852.26. HPLC: >99%.

$^1$H NMR (500 MHz, CDCl3) δ=7.33 (m, 8H), 7.12 (d, 2H, J=8.0 Hz), 7.04 (s, 2H), 6.92-6.85 (m, 14H), 6.65 (s, 2H), 6.52 (s, 1H), 6.40 (d, 1H, J=7.5 Hz), 5.05 (s, 8H), 4.96 (s, 2H), 4.90 (s, 4H), 4.53 (m, 1H), 4.31 (s, 1H), 3.94 (m, 8H), 3.70 (s, 3H), 3.08-2.91 (m, 2H), 1.81-1.72 (m, 8H), 1.44 (m, 8H), 1.41 (s, 9H), 1.36-1.24 (m, 67H), 0.88 (t, 12H, J=7.0 Hz).

$^{13}$C NMR (125 MHz, CDCl3) δ=160.4, 159.1, 149.5, 149.1, 139.6, 130.6, 130.1, 129.3 (×2), 129.2 (×2), 121.2, 115.6, 115.2, 115.1, 114.6, 106.5, 101.6, 71.5 (×2), 70.3, 70.2, 68.2, 52.6, 48.3, 37.6, 32.1, 30.6, 29.9 (×3), 29.8 (×2), 29.6 (×3), 28.5, 26.3, 23.0, 18.6, 14.3. Anal. Calc. for C115H164N2O16: C, 75.45; H, 903; N, 1.53. Found: C, 75.53; H, 9.16; N, 1.59.

Example 82

Preparation of [4-3,4-3,5]12G$_2$CH$_2$-Boc-D-Tyr-D-Ala-OMe

This dipeptide derivative was prepared in a similar manner as that of Example 80.

mp 95-96° C. $[\alpha]D^{20}$=+13.4 (c. 0.05, THF). MALDI-TOF for C115H164N2O16 m/z calcd: 1853.53 [M+Na$^+$]; found 1852.72. HPLC:>99%.

$^1$H NMR (500 MHz, CDCl3) δ=7.33 (m, 8H), 7.12 (d, 2H, J=8.0 Hz), 7.03 (s, 2H), 6.92-6.85 (m, 14H), 6.65 (s, 2H), 6.52 (s, 1H), 6.40 (d, 1H, J=7.5 Hz), 5.05 (s, 8H), 4.96 (s, 2H), 4.91 (s, 4H), 4.53 (m, 1H), 4.31 (s, 1H), 3.94 (m, 8H), 3.71 (s, 3H), 3.08-2.91 (m, 2H), 1.81-1.72 (m, 8H), 1.45 (m, 8H), 1.41 (s, 9H), 1.36-1.24 (m, 67H), 0.88 (t, 12H, J=7.0 Hz). $^{13}$C NMR (125 MHz, CDCl3) δ=160.4, 159.0, 149.5, 149.2, 139.6, 130.6, 130.2, 129.3 (×2), 129.2 (×2), 121.0, 115.6, 115.2, 115.0, 114.6, 106.5, 101.5, 71.5 (×2), 70.3, 70.2, 68.2, 52.6, 48.3, 37.6, 32.1, 30.6, 29.9 (×3), 29.8 (×2), 29.6 (×3), 28.5, 26.3, 23.0, 18.6, 14.3. Anal. Calc. for C115H164N2O16: C, 75.45; H, 9.03; N, 1.53. Found: C, 75.55; H, 9.14; N, 1.55.

Example 83

Preparation of [4-3,4-3,5]12G$_2$CH$_2$-Boc-L-Tyr-D-Ala-OMe

This dipeptide derivative has the following characteristics.
mp 92-93° C. [α]D$^{20}$=−1.6 (c. 0.05, THF). MALDI-TOF for C115H164N2O16 m/z calcd: 1853.53 [M+Na$^+$]; found 1854.13. HPLC:>99%.
$^1$H NMR (500 MHz, CDCl3) δ=7.34 (m, 8H), 7.11 (d, 2H, J=8.0 Hz), 7.03 (s, 2H), 6.92-6.85 (m, 14H), 6.65 (s, 2H), 6.52 (s, 1H), 6.40 (d, 1H, J=7.5 Hz), 5.04 (s, 8H), 4.96 (s, 2H), 4.90 (s, 4H), 4.53 (m, 1H), 4.31 (s, 1H), 3.94 (m, 8H), 3.71 (s, 3H), 3.08-2.91 (m, 2H), 1.81-1.72 (m, 8H), 1.45 (m, 8H), 1.41 (s, 9H), 1.36-1.25 (m, 67H), 0.88 (t, 12H, J=7.0 Hz).
$^{13}$C NMR (125 MHz, CDCl3) δ=160.4, 159.1, 149.4, 149.2, 139.5, 130.6, 130.2, 129.3 (×2), 129.2 (×2), 121.0, 115.6, 115.2, 115.1, 114.6, 106.4, 101.5, 71.5 (×2), 70.3, 70.2, 68.2, 52.6, 48.4, 37.6, 32.1, 30.6, 29.9 (×3), 29.8 (×2), 29.6 (×3), 28.5, 26.3, 23.0, 18.6, 14.3. C115H164N2O16 Anal. Calc: C, 75.45; H, 9.03; N, 1.53. Found: C, 75.50; H, 9.11; N, 1.54.

Example 84

Preparation of [4-3,4-3,5]12G$_2$CH$_2$-Boc-D-Tyr-L-Ala-OMe

This dipeptide derivative was prepared in a similar manner as that of Example 82.
mp 92-93.8° C. [α]D$^{20}$=+2.3 (c. 0.05, THF). MALDI-TOF for C115H164N2O16 m/z calcd: 1853.53 [M+Na$^+$]; found 1854.79. HPLC:>99%.
$^1$H NMR (500 MHz, CDCl3) δ=7.34 (m, 8H), 7.12 (d, 2H, J=8.0 Hz), 7.04 (s, 2H), 6.92-6.84 (m, 14H), 6.65 (s, 2H), 6.52 (s, 1H), 6.41 (d, 1H, J=7.5 Hz), 5.05 (s, 8H), 4.96 (s, 2H), 4.90 (s, 4H), 4.53 (m, 1H), 4.31 (s, 1H), 3.94 (m, 8H), 3.72 (s, 3H), 3.08-2.91 (m, 2H), 1.81-1.72 (m, 8H), 1.45 (m, 8H), 1.41 (s, 9H), 1.36-1.24 (m, 67H), 0.88 (t, 12H, J=7.0 Hz).
$^{13}$C NMR (125 MHz, CDCl3) δ=160.4, 159.1, 149.4, 149.2,139.5, 130.6, 130.1, 129.3 (×2), 129.2 (×2), 121.0, 115.6, 115.1, 115.0, 114.6, 106.4, 101.5, 71.5 (×2), 70.3, 70.1, 68.2, 52.6, 48.3, 37.6, 32.2, 30.6, 29.9 (×3), 29.8 (×2), 29.6 (×3), 28.5, 26.3, 23.1, 18.6, 14.3. C115H164N2O16 Anal. Calc: C, 75.45; H, 9.03; N, 1.53. Found: C, 75.49; H, 9.17; N, 1.58.

Example 85

Preparation of [4-3,4-3,5]12G$_2$CH$_2$-Boc-DL-Tyr-DL-Ala-OMe

This dipeptide derivative was prepared in a similar manner as that of Example 82.
mp 91-93° C. [α]D$^{20}$=0 (c. 0.05, THF). MALDI-TOF for C115H164N2O16 m/z calcd: 1853.53 [M+Na$^+$]; found 1853.19. HPLC:>99%.
$^1$H NMR (500 MHz, CDCl3) δ=7.32 (m, 8H), 7.11 (d, 2H, J=8.0 Hz), 7.03 (s, 2H), 6.93-6.84 (m, 14H), 6.65 (s, 2H), 6.52 (s, 1H), 6.37 (d, 1H, J=7.5 Hz), 5.05 (s, 8H), 4.96 (s, 2H), 4.90 (s, 4H), 4.52 (m, 1H), 4.30 (s, 1H), 3.94 (m, 8H), 3.70 (s, 3H), 3.06-2.94 (m, 2H), 1.76 (m, 8H), 1.44 (m, 8H), 1.41 (s, 9H), 1.36-1.24 (m, 67H), 0.88 (t, 12H, J=7.5 Hz).
$^{13}$C NMR (125 MHz, CDCl3) δ=160.4, 159.1, 149.4, 149.2, 139.5, 130.6, 130.1, 129.3 (×2), 129.2 (×2), 121.0, 115.6, 115.1, 115.0, 114.6, 106.4, 101.5, 71.5 (×2), 70.3, 70.1, 68.2, 52.6, 48.3, 37.6, 32.2, 30.6, 29.9 (×3), 29.8 (×2), 29.6 (×3), 28.5, 26.3, 23.1, 18.6, 14.3. C115H164N2O16 Anal. Calc: C, 75.45; H, 9.03; N, 1.53. Found: C, 75.51; H, 9.14; N, 1.56.

Example 86

Synthesis of [4-3,4-3,5]1G$_2$CH$_2$-Boc-Tyr-Ala-OMe

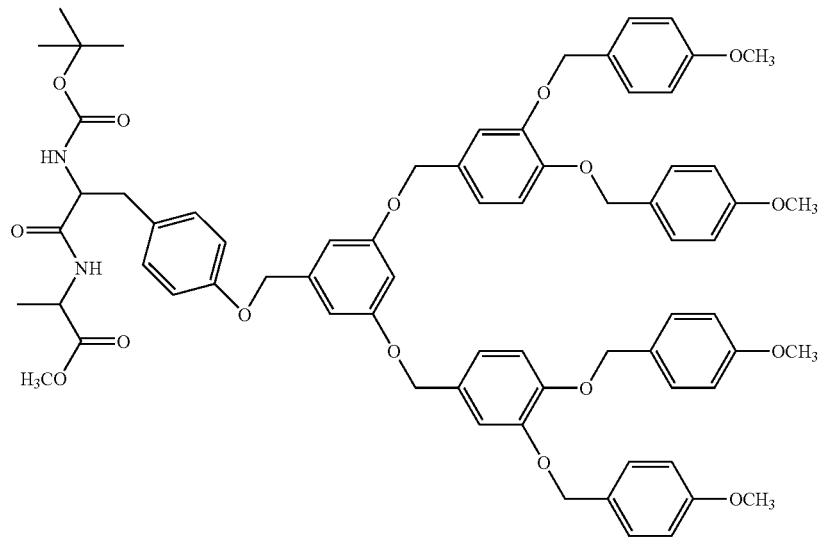

C$_{71}$H$_{76}$N$_2$O$_{16}$
Exact Mass: 1212.52
Mol. Wt.: 1213.37
C, 70.28; H, 6.31; N, 2.31; O, 21.10

This amphiphilic dendritic dipeptide was synthesized following the same general procedure as that for the preparation of [4-3,4-3,5]12G2CH2-Boc-Tyr-Ala-OMe; K2CO3 (94mg, 0.679mmol), Boc-Tyr(OH)-Ala-OMe (83 mg, 0.226 mmol), [4-3,4-3,5]1G2CH2Cl (200 mg, 0.226 mmol), DMF (10 mL). Purified by flash column chromatography: silica gel/1% MeOH in $CH_2Cl_2$, followed by precipitation in MeOH from minimal CH2Cl2 to give the title compound as a bluish solid.

150 mg (55%).

mp 70-73° C. $[\alpha]D^{20}$=−17.6 (c. 0.05, THF). MALDI-TOF for C71H76N2O16 m/z calcd: 1236.36 [M+Na$^+$]; found 1237.01. HPLC: >99%.

$^1$H NMR (500 MHz, CDCl3) δ=7.33 (d, 8H, J=9 Hz), 7.11 (d, 2H, J=8.5 Hz), 7.03 (s, 2H), 6.93-6.83 (m, 14H), 6.64 (s, 2H), 6.51 (s, 1H), 6.36 (d, 1H, J=7.5 Hz), 5.06 (s, 8H), 4.96 (s, 2H), 4.91 (s, 4H), 4.51 (m, 1H), 4.28 (s, 1H), 3.79 (d, 12H, J=6.5 Hz), 3.70 (s, 3H), 3.04-2.94 (m, 2H), 1.41 (s, 9H), 1.34 (d, 3H, J=7.0 Hz).

$^{13}$C NMR (125 MHz, CDCl3)δ=170.7, 160.2,159.4, 157.9, 149.4, 149.0, 139.4, 130.4, 130.1, 129.4, 129.3, 129.1, 129.0, 121.0, 115.5, 115.1(×2), 113.9, 106.4, 101.6, 71.3 (×2), 70.1, 70.0, 55.3, 52.4, 48.1, 37.5, 28.3, 18.4. C71H76N2O16 Anal. Calc: C, 70.28; H, 6.31; N, 2.31. Found: C, 70.33; H, 6.39; N, 2.36.

Example 87

Preparation of [4-3,4-3,5]10G$_2$CH$_2$-Boc-Tyr-Ala-OMe

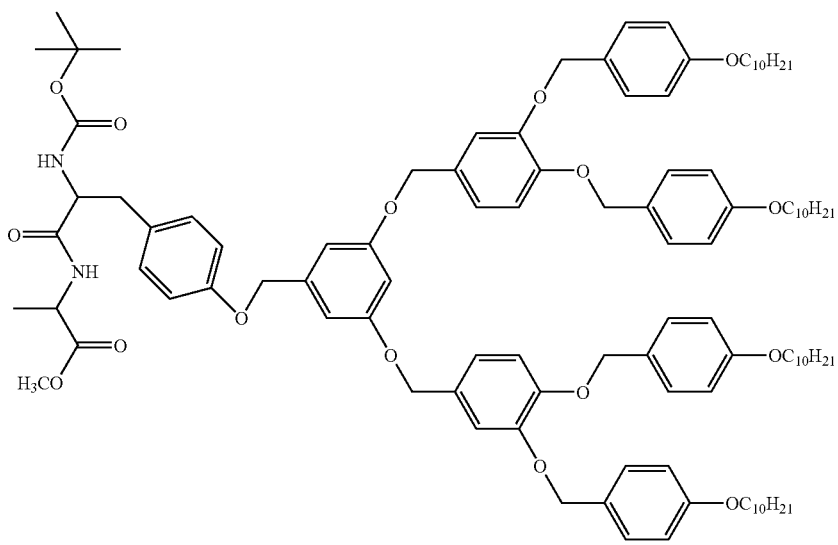

$C_{107}H_{144}N_2O_{16}$
Exact Mass: 1717.08
Mol. Wt.: 1718.32
C, 74.79; H, 8.68; N, 1.63; O, 14.90

This amphiphilic dendritic dipeptide was synthesized following the same general procedure as that for the preparation of [4-3,4-3,5]12G$_2$CH$_2$-Boc-Tyr-Ala-OMe; K2CO3 (72 mg, 0.518 mmol), Boc-Tyr(OH)-Ala-OMe (63 mg, 0.173 mmol), [4-3,4-3,5]10G2CH2Cl (240 mg, 0.173 mmol), DMF (10 mL). Purified by flash column chromatography: silica gel/1% MeOH in $CH_2Cl_2$ followed by precipitation in MeOH from minimal $CH_2Cl_2$ to give the title compound as a white solid.

Mass: 105 mg(35%). mp 88-90° C. $[\alpha]D^{20}$=−8.6 (c. 0.05, THF). MALDI-TOF for C107H148N2O16 m/z calcd: 1741.31 [M+Na$^+$]; found 1742.02. HPLC: >99%.

$^1$H NMR (500 MHz, CDCl3) δ=7.32 (m, 8H), 7.12 (d, 2H, J=8.5 Hz), 7.04 (s, 2H), 6.93-6.82 (m, 14H), 6.65 (s, 2H), 6.52 (s, 1H), 6.34 (d, 1H, J=7.5 Hz), 5.05 (s, 8H), 4.96 (s, 2H), 4.91 (s, 4H), 4.51 (m, 1H), 4.29 (s, 1H), 3.94 (m, 8H), 3.69 (s, 3H), 3.06-2.94 (m, 2H), 1.79-1.74 (m, 8H), 1.44 (m, 8H), 1.41 (s, 9H), 1.36-1.23 (m, 51H), 0.88 (t, 12H, J=7.5 Hz).

$^{13}$C NMR (125 MHz, CDCl3) δ=170.7, 160.2, 159.0, 157.9, 149.4, 149.1, 139.4, 130.4, 130.0, 129.2, 129.1, 129.0, 121.0, 115.6, 115.1, 114.5, 106.4, 101.5, 71.4, 71.3, 70.1, 70.0, 68.1, 52.4, 48.1, 31.9, 29.6, 29.4, 29.3, 28.3, 26.1, 22.7, 18.4, 14.1. C107H148N2O16 Anal. Calc: C, 74.79; H, 8.68; N, 1.63. Found: C, 74.80; H, 8.75; N, 1.65.

Example 88

Preparation of [4-3,4-3,5]14G-CH$_2$-Boc-Tyr-Ala-OMe

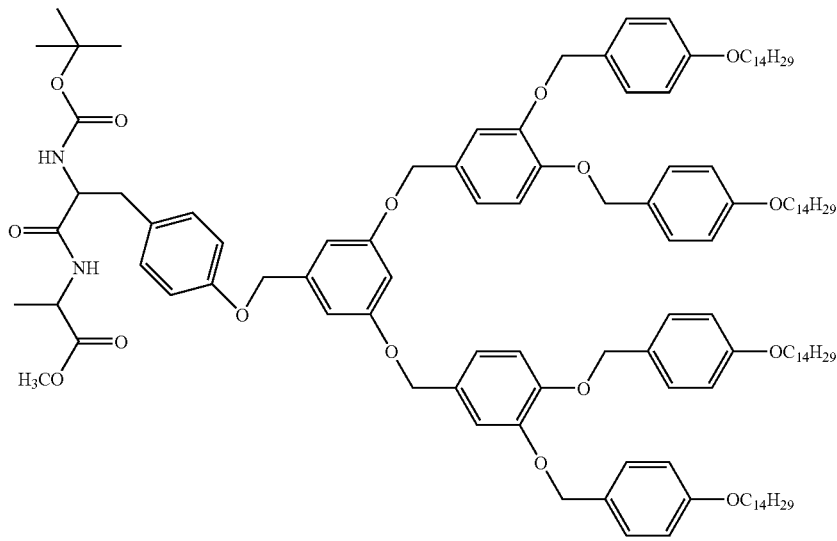

C$_{123}$H$_{180}$N$_2$O$_{16}$
Exact Mass: 1941.33
Mol. Wt.: 1942.75
C, 76.04; H, 9.34; N, 1.44; O, 13.18

This amphiphilic dendritic dipeptide was synthesized following the same general procedure as that for the preparation of [4-3,4-3,5]12G2CH2-Boc-Tyr-Ala-OMe; K2CO3 (46 mg, 0.333 mmol), Boc-Tyr(OH)-Ala-OMe (40 mg, 0.111 mmol), [4-3,4-3,5]14G2CH2Cl (179 mg, 0.111 mmol), DMF (8 mL). Purified by flash column chromatography: silica gel/ 1%MeOH/CH$_2$Cl$_2$, and precipitated in MeOH from minimal CH$_2$Cl$_2$ to give the title compound as a white solid. 120 mg (56%).

mp 100-101° C. [α]$_D^{20}$=−12.8 (c. 0.05, THF). MALDI-TOF for C123H180N2O16 m/z calcd: 1965.74 [M+Na$^+$]; found 1966.33. HPLC: >99%.

$^1$H NMR (500 MHz, CDCl3) δ=7.32 (m, 8H), 7.12 (d, 2H, J=8.5 Hz), 7.04 (s, 2H), 6.94-6.83 (m, 14H), 6.65 (s, 2H), 6.53 (s, 1H), 6.36 (d, 1H, J=7.5 Hz), 5.06 (s, 8H), 4.97 (s, 2H), 4.92 (s, 4H), 4.52 (m, 1H), 4.29 (s, 1H), 3.94 (m, 8H), 3.70 (s, 3H), 3.08-2.95 (m, 2H), 1.80-1.73 (m, 8H), 1.45 (m, 8H), 1.42 (s, 9H), 1.38-1.25 (m, 83H), 0.89 (t, 12H, J=7.0 Hz).

$^{13}$C NMR (125 MHz, CDCl3) δ=170.7, 160.2, 159.0 (×2), 149.4, 149.1, 139.4, 130.4 (×2), 130.1, 129.2, 129.1, 129.0, 121.0, 115.5, 115.1, 114.5, 106.4, 101.5, 71.4, 71.3, 70.1, 70.0, 68.1, 52.4, 48.1, 31.9, 29.7, 29.6, 29.4, 29.3, 28.3, 26.1, 22.7, 18.4, 14.1. C123H180N2O16 Anal. Calc: C, 76.04; H, 9.34; N, 1.44. Found: C, 76.09; H, 9.41; N, 1.47.

Example 89

Preparation of [4-3,4-3,5]16G$_2$CH$_2$-Boc-Tyr-Ala-OMe

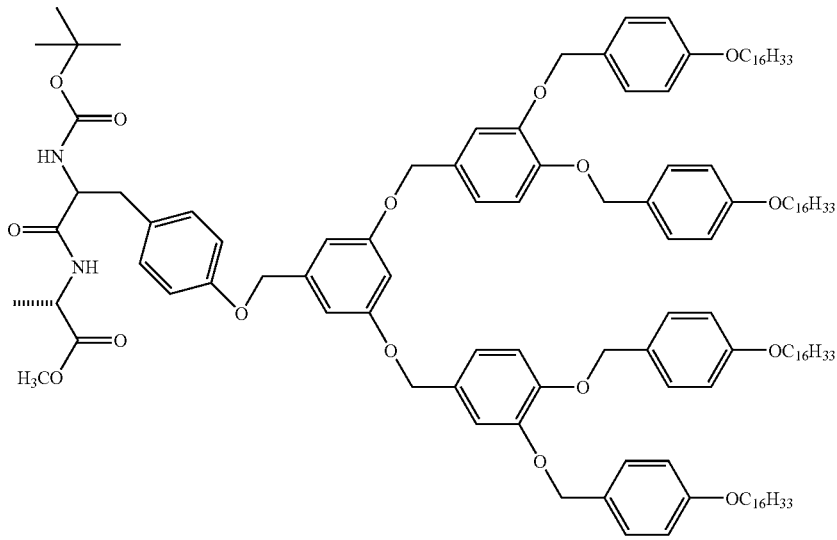

C$_{131}$H$_{198}$N$_2$O$_{16}$
Exact Mass: 2053.46
Mol. Wt.: 2054.96
C, 76.57; H, 9.61; N, 1.36; O, 12.46 as synthesized following the same general procedure as that for the preparation of [4-3,4-3,5]12G2CH2-Boc-Tyr-Ala-OMe; K2CO3 (48 mg, 0.348 mmol), Boc-Tyr(OH)-Ala-OMe (42 mg, 0.116 mmol), [4-3,4-3,5]16G2CH2Cl (200 mg, 0.116 mmol), DMF (8 mL). Purified by flash column chromatography: silica gel/1% MeOH in CH2Cl2 followed by precipitation in MeOH from minimal CH2Cl2 to give the title compound as a white solid, 125 mg (53%).

mp 101-103° C. [α]$D^{20}$=−8.4 (c. 0.05, THF). MALDI-TOF for C131H196N2O16 m/z calcd: 2077.95 [M+Na$^+$]; found 2077.95. HPLC: >99%.

$^1$H NMR (500 MHz, CDCl3) δ=7.33 (m, 8H), 7.12 (d, 2H, J=8.5 Hz), 7.05 (s, 2H), 6.95-6.84 (m, 14H), 6.66 (s, 2H), 6.54 (s, 1H), 6.35 (d, 1H, J=7.5 Hz), 5.06 (s, 8H), 4.97 (s, 2H), 4.92 (s, 4H), 4.53 (m, 1H), 4.30 (s, 1H), 3.96 (m, 8H), 3.71 (s, 3H), 3.08-2.95 (m, 2H), 1.82-1.75 (m, 8H), 1.47 (m, 8H), 1.42 (s, 9H), 1.37-1.25 (m, 99H), 0.89 (t, 12H, J=7.0 Hz).

$^{13}$C NMR (125 MHz, CDCl3) δ=170.7, 160.2, 159.0 (×2), 149.4, 149.1, 139.4, 130.4 (×2), 130.1, 129.2, 129.1 (×2), 129.0, 121.0, 115.6, 115.1, 114.5, 106.4, 101.5, 71.4 (×2), 70.1, 70.0, 68.1, 52.4, 48.1, 31.9, 29.7, 29.6 (×2), 29.4, 29.3 (×2), 28.3, 26.1, 22.7, 18.4, 14.1. Anal. Calc. for C131H196N2O16: C, 76.57; H, 9.61; N, 1.36. Found: C, 76.61; H, 9.68; N, 1.39.

Example 90

Preparation of [4-3,4-3,5]2G$_2$CH$_2$-Boc-Tyr-Ala-OMe

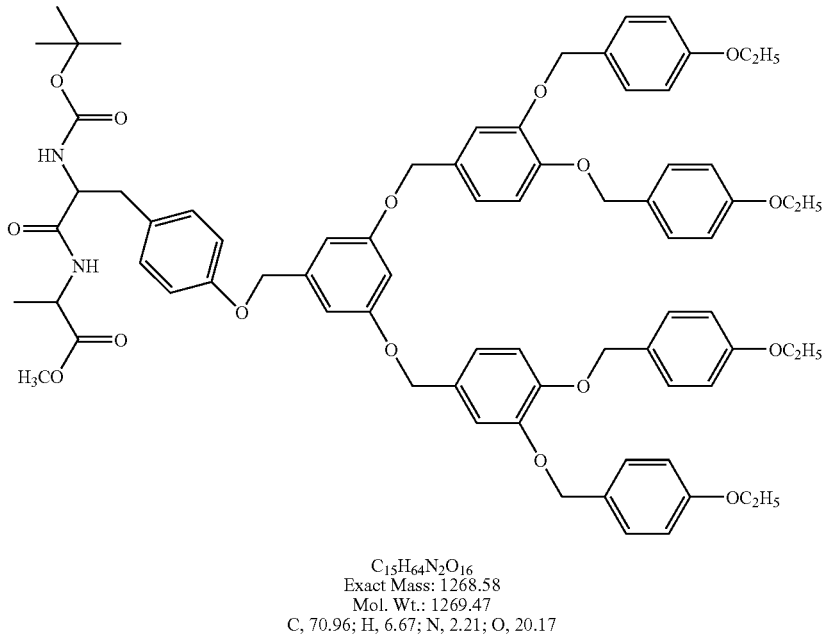

C$_{15}$H$_{64}$N$_2$O$_{16}$
Exact Mass: 1268.58
Mol. Wt.: 1269.47
C, 70.96; H, 6.67; N, 2.21; O, 20.17

PPh3 (68 mg, 0.261 mmol) was added in portions to a solution of Boc-Tyr(OH)-Ala-OMe (80 mg, 0.217 mmol), [4-3,4-3,5]2G2CH2OH (200 mg, 0.217 mmol), and diisopropyl azodicarboxylate (DIAD) (53 mg, 0.261 mmol) in dry THF (13 mL). The resulting mixture was allowed to stir at room temperature for 12 hours, after which the solvent was removed under reduced pressure and the residue purified by flash column chromatography: silica gel/2% MeOH in CH2Cl2, followed by precipitation in Et2O from minimal CH2Cl2, to give the title compound as a white solid 120 mg (44%).

mp 79-82° C. [α]$D^{20}$=−18.0 (c. 0.05, THF). MALDI-TOF for C75H84N2O16 m/z calcd: 1292.46 [M+Na$^+$]; found 1291.86. HPLC: >99%.

$^1$H NMR (500 MHz, CDCl3) δ=7.33 (d, 8H, J=6.5 Hz), 7.11 (d, 2H, J=8.5 Hz), 7.02 (s, 2H), 6.94-6.83 (m, 14H), 6.64 (s, 2H), 6.52 (s, 1H), 6.37 (d, 1H, J=7.5 Hz), 5.05 (s, 8H), 4.95 (s, 2H), 4.90 (s, 4H), 4.51 (m, 1H), 4.29 (s, 1H), 4.01 (m, 8H), 3.69 (s, 3H), 3.05-2.94 (m, 2H), 1.42-1.36 (m, 21H), 1.33 (d, 3H, J=7.5 Hz).

$^{13}$C NMR (125 MHz, CDCl3) δ=170.7, 160.2, 158.7 (×2), 149.4, 149.0, 139.4, 130.4, 130.0, 129.2, 129.1 (×2), 129.0, 121.0, 115.5, 115.1, 115.0, 114.4, 106.4, 101.5, 71.3 (×2), 70.0 (×2), 63.4, 52.4, 48.1, 37.4, 28.3, 18.4, 14.8. C75H84N2O16: Anal. Calc: C, 70.96; H, 6.67; N, 2.21. Found: C, 70.99; H, 6.71; N, 2.25.

Example 91

Preparation of [4-3,4-3,5]4G$_2$CH$_2$-Boc-Tyr-Ala-OMe

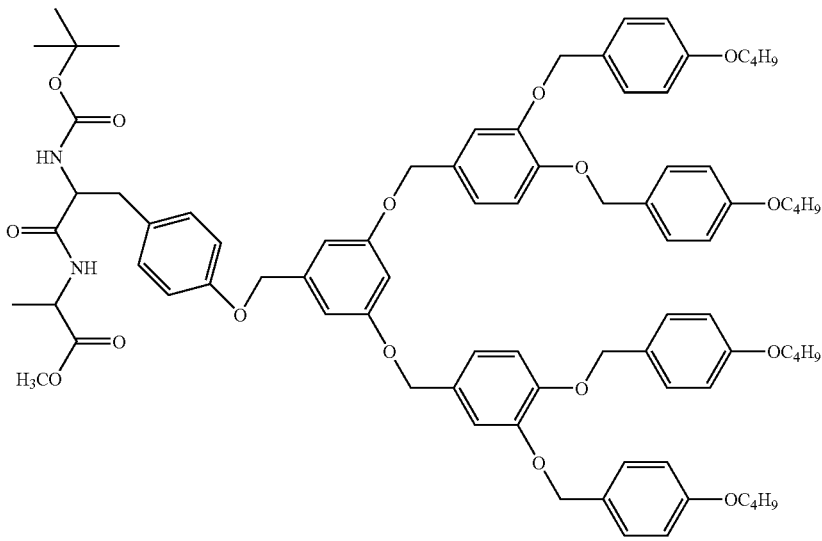

C$_{83}$H$_{100}$N$_2$O$_{16}$
Exact Mass: 1380.71
Mol. Wt.: 1381.69
C, 72.15; H, 7.30; N, 2.03; O, 18.53

This amphiphilic dendritic dipeptide was synthesized following the same general procedure as that for the preparation of [4-3,4-3,5]2G2CH2-Boc-Tyr-Ala-OMe; PPh3 (61 mg, 0.232 mmol), Boc-Tyr(OH)-Ala-OMe (71 mg, 0.194 mmol), [4-3,4-3,5]4G2CH2OH (200 mg, 0.194 mmol), DIAD (47 mg, 0.232 mmol), THF (10 mL). Crude product was purified by flash column chromatography: silica gel/1% MeOH in CH2Cl2, followed by precipitation in MeOH from minimal CH$_2$Cl$_2$, 110 mg (41%).

mp 84-87° C. [α]D$^{20}$=−13.4 (c. 0.05, THF). MALDI-TOF for C83H100N2O16 m/z calcd: 1404.68 [M+Na$^+$]; found 1404.09. HPLC: >99%.

$^1$H NMR (500 MHz, CDCl3) δ=7.33 (d, 8H, J=6.5 Hz), 7.11 (d, 2H, J=8.5 Hz), 7.02 (s, 2H), 6.94-6.83 (m, 14H), 6.64 (s, 2H), 6.52 (s, 1H), 6.37 (d, 1H, J=7.5 Hz), 5.05 (s, 8H), 4.95 (s, 2H), 4.90 (s, 4H), 4.51 (m, 1H), 4.29 (s, 1H), 3.95 (m, 8H), 3.69 (s, 3H), 3.09-2.94 (m, 2H), 1.75 (m, 8H), 1.49 (m, 8H), 1.41 (s, 9H), 1.33 (d, 3H, J=7.2 Hz).

$^{13}$C NMR (125 MHz, CDCl3)δ=172.8, 160.2, 159.0, 149.4, 149.0, 139.4, 130.4, 130.0, 129.2, 129.1 (×2), 129.0, 121.0, 115.5, 115.1, 114.5, 106.4, 101.5, 71.4, 71.3, 70.1, 70.0, 67.7, 52.4, 48.1, 37.4, 31.3, 28.3, 19.2, 18.4, 13.8. C83H100N2O16 Anal. Calc: C, 72.15; H, 7.30; N, 2.03. Found: C, 72.18; H, 7.38; N, 2.04.

Example 92

Preparation of [4-3,4-3,5]6G$_2$CH$_2$-Boc-Tyr-Ala-OMe

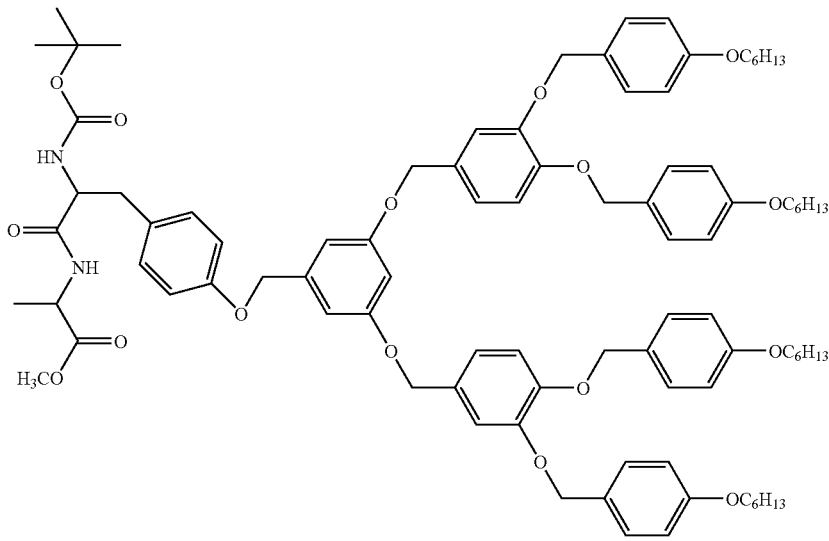

C$_{91}$H$_{116}$N$_2$O$_{16}$
Exact Mass: 1492.83
Mol. Wt.: 1493.90
C, 73.16; H, 7.83; N, 1.88; O, 17.14

This dendritic dipeptide was synthesized following the same general procedure as that for the preparation of [4-3,4-3,5]2G2CH2-Boc-Tyr-Ala-OMe; PPh3 (55 mg, 0.210 mmol), Boc-Tyr(OH)-Ala-OMe (64 mg, 0.175 mmol), [4-3,4-3,5]6G2CH2OH (200 mg, 0.175 mmol), DIAD (42 mg, 0.210 mmol), THF (10 mL). Crude product was purified by flash column chromatography: silica gel/1% MeOH in CH2Cl2, followed by precipitation in MeOH from minimal CH2Cl2, 127 mg (49%).

mp 62-64° C. $[\alpha]D^{20}$=−6.4 (c. 0.05, THF). MALDI-TOF for C91H116N2O16 m/z calcd: 1515.82 [M+Na$^+$]; found 1516.13. HPLC: >99%.

$^1$H NMR (500 MHz, CDCl3) δ=7.32 (m, 8H), 7.11 (d, 2H, J=8.0 Hz), 7.03 (s, 2H), 6.93-6.83 (m, 14H), 6.65 (s, 2H), 6.52 (s, 1H), 6.37 (d, 1H, J=7.0 Hz), 5.04 (s, 8H), 4.96 (s, 2H), 4.90 (s, 4H), 4.51 (m, 1H), 4.29 (s, 1H), 3.94 (m, 8H), 3.69 (s, 3H), 3.10-2.93 (m, 2H), 1.77 (m, 8H), 1.45 (m, 8H), 1.41 (s, 9H), 1.35-1.29 (m, 19H), 0.90 (m, 12H).

$^{13}$C NMR (125 MHz, CDCl3) δ=170.7, 160.2, 159.0, 158.9, 149.4, 149.0, 139.4, 130.4, 130.0, 129.1 (×2), 129.0, 121.0, 115.5, 115.0, 114.5, 106.3, 101.5, 71.3 (×2), 70.1, 70.0, 68.0, 52.4, 48.1, 37.4, 31.6, 29.7, 29.2, 28.2, 25.7, 22.6, 18.4, 14.0. C91H116N2O16: Anal. Calc: C, 73.16; H, 7.83; N, 1.88. Found: C, 73.20; H, 7.89; N, 1.90.

Example 93

Preparation of [4-3,4-3,5]8G$_2$CH$_2$-Boc-Tyr-Ala-OMe

This dendritic dipeptide was synthesized following the same general procedure as that for the preparation of [4-3,4-3,5]2G2CH2-Boc-Tyr-Ala-OMe; PPh3 (50 mg, 0.191 mmol), Boc-Tyr(OH)-Ala-OMe (58 mg, 0.159 mmol), [4-3,4-3,5]8G2CH2OH (200 mg, 0.159 mmol), DIAD (39 mg, 0.191 mmol), THF (10 mL). Crude product was purified by flash column chromatography: silica gel/1% MeOH in CH$_2$Cl$_2$, followed by precipitation in MeOH from minimal CH$_2$Cl$_2$, 100 mg (40%).

mp 79-80° C. $[\alpha]D^{20}$=−6.0 (c. 0.05, THF). MALDI-TOF for C99H132N2O16 m/z calcd: 1629.10 [M+Na$^+$]; found 1629.70. HPLC: >99%.

$^1$H NMR (500 MHz, CDCl3) δ=7.32 (m, 8H), 7.11 (d, 2H, J=8.5 Hz), 7.03 (s, 2H), 6.94-6.83 (m, 14H), 6.65 (s, 2H), 6.52 (s, 1H), 6.35 (d, 1H, J=7.0 Hz), 5.05 (s, 8H), 4.96 (s, 2H), 4.91 (s, 4H), 4.53 (m, 1H), 4.29 (s, 1H), 3.94 (m, 8H), 3.70 (s, 3H), 3.09-2.93 (m, 2H), 1.76 (m, 8H), 1.45 (m, 8H), 1.41 (s, 9H), 1.35-1.26 (m, 35H), 0.88 (t, 12H, J=6.5 Hz).

$^{13}$C NMR (125 MHz, CDCl3) δ=170.7, 160.2, 159.0, 158.9, 149.4, 149.1, 139.4, 130.4, 130.0, 129.2, 129.1 (×2), 129.0, 121.0, 115.5, 115.1, 114.5, 106.4, 101.5, 71.4, 71.3, 70.1, 70.0, 68.1, 52.4, 48.1, 31.8, 29.4, 29.3, 29.2, 28.3, 26.1, 22.6, 18.4, 14.1. C99H132N2O16 Anal. Calc: C, 74.03; H, 8.28; N, 1.74. Found: C, 74.05; H, 8.32; N, 1.77.

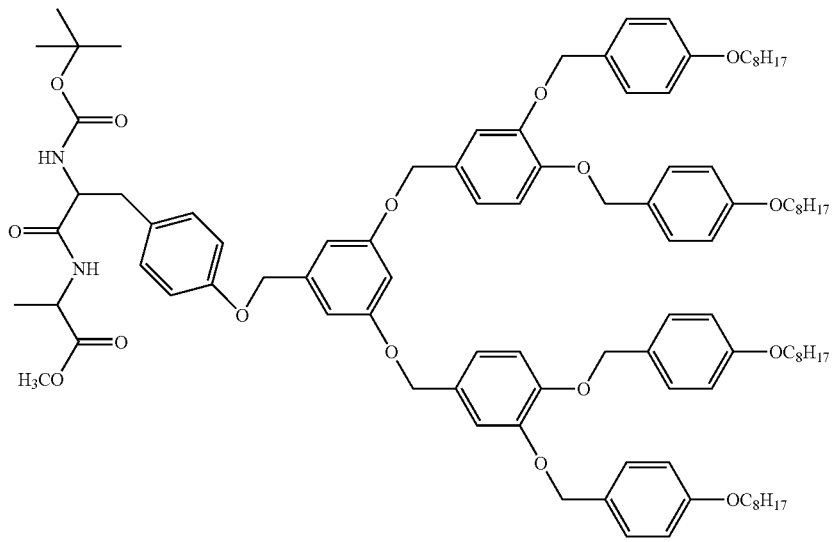

C$_{99}$H$_{132}$N$_2$O$_{16}$
Exact Mass: 1604.96
Mol. Wt.: 1606.11
C, 74.03; H, 8.28; N, 1.74; O, 15.94

Example 94

Preparation of [4-3,4-3,5]12G$_2$CH$_2$-Moc-Tyr-Ala-OMe

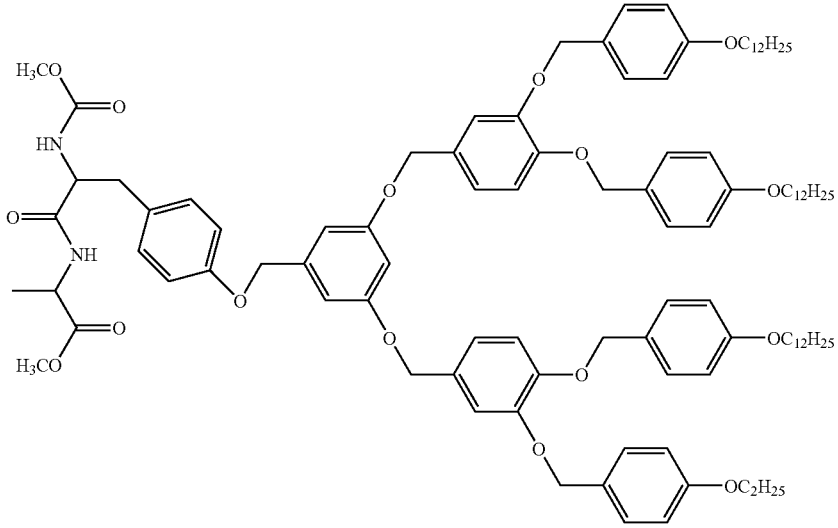

C$_{102}$H$_{152}$N$_2$O$_{16}$
Exact Mass: 1667.16
Mol. Wt.: 1668.35
C, 73.43; H, 9.55; N, 1.68; O, 15.34 as synthesized following the same general procedure as that for the preparation of [4-3,4-3,5]2G2CH2-Boc-Tyr-Ala-OMe; PPh3 (68 mg, 0.258 mmol), Moc-Tyr(OH)-Ala-OMe (70 mg, 0.215 mmol), [4-3,4-3,5]12G2CH2OH (318 mg, 0.215 mmol), DIAD (52 mg, 0.258 mmol), THF (10 mL). Crude product was purified by flash column chromatography: silica gel/1% MeOH in CH2Cl2, followed by precipitation in MeOH from minimal CH2Cl2, 156 mg (41%).

mp 110-113° C. [α]D$^{20}$=−9.6 (c. 0.05, THF). MALDI-TOF for C102H158N2O16 m/z calcd: 1691.34 [M+Na$^+$]; found 1691.30. HPLC: >99%. $^1$H NMR (500 MHz, CDCl3) δ=7.31 (m, 8H), 7.01 (d, 2H, J=8.5 Hz), 7.03 (s, 2H), 6.93-6.83 (m, 14H), 6.64 (s, 2H), 6.52 (s, 1H), 6.24 (d, 1H, J=7.5 Hz), 5.05 (s, 8H), 4.96 (s, 2H), 4.91 (s, 4H), 4.50 (m, 1H), 4.34 (s, 1H), 3.94 (m, 8H), 3.70 (s, 3H), 3.65 (s, 3H), 3.09-2.93 (m, 2H), 1.80-1.73 (m, 8H), 1.44 (m, 8H), 1.36-1.24 (m, 67H), 0.88 (t, 12H, J=7.0 Hz). $^{13}$C NMR (125 MHz, CDCl3) δ=160.2, 159.0, 158.9, 149.1, 139.6, 130.4, 130.1, 129.2, 129.1 (×2), 129.0, 121.0, 115.6, 115.2, 115.1, 114.5, 106.4, 101.6, 71.4, 71.3, 70.1, 70.0, 68.1, 48.2, 31.9, 29.7, 29.6 (×3), 29.4, 29.3 (×2), 26.1, 22.7, 18.3, 14.1. C102H158N2O16: Anal. Calc: C, 73.43; H, 9.55; N, 1.68. Found: C, 73.45; H, 9.59; N, 1.70.

Example 95

Preparation of [4-3,4-3,5]12G$_2$COO Boc-L-Tyr-L-Ala-OMe

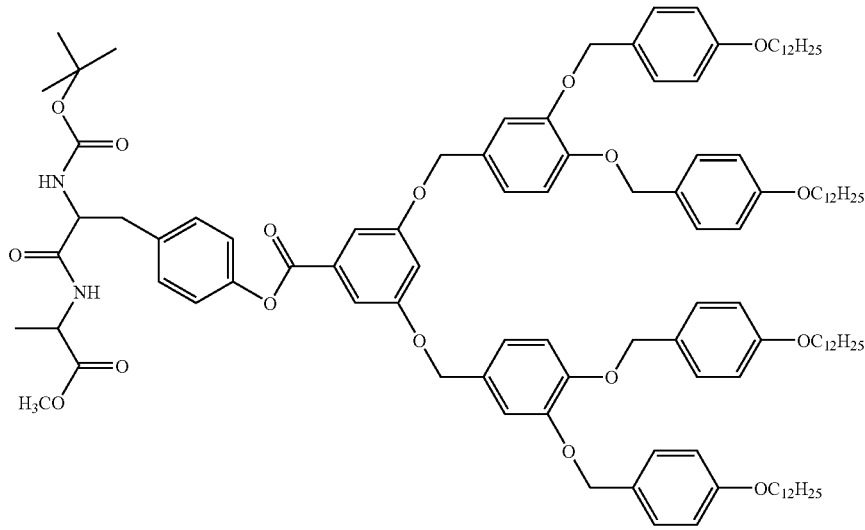

C$_{152}$H$_{162}$N$_2$O$_{16}$
Exact Mass: 1843.19
Mol. Wt.: 1844.52
C, 74.88; H, 8.85; N, 1.52; O, 14.75

A solution of [4-3,4-3,5]12G$_2$COOH[6] (200 mg, 0.134 mmol), Boc-L-Tyr(OH)-L-Ala-OMe (54 mg, 0.148 mmol) and catalytic pyridinium p-toluenesulfonate (PPTs) (20 mg, 10% wt.) were stirred in dry CH$_2$Cl$_2$ (5 mL) for 30 minutes at room temperature, after which was added DCC (55 mg, 0.268 mmol), and the reaction allowed to stir at room temperature for 16 hours, after which TLC (1% CH$_3$OH in CH$_2$Cl$_2$) showed completion. The urea salts were filtered and rinsed with CH$_2$Cl$_2$, the organic layer was washed with water and brine, dried over MgSO4 and concentrated. The crude product was purified by flash column chromatography: silica gel/ 1% CH3OH in CH2Cl2, followed by precipitation in CH3OH from minimal CH2Cl2 to give the title compound as a white solid 180 mg (73%).

mp 120-122° C. [α]D$^{20}$=−10.2 (c. 0.05, THF). MALDI-TOF for C115H162N2O17 m/z calcd: 1867.51 [M+Na$^+$]; found 1867.50. HPLC: >99%.

$^1$H NMR (500 MHz, CDCl3) δ=7.40 (d, 2H, J=2 Hz), 7.31 (m, 8H), 7.27 (d, 2H, J=8.5 Hz), 7.14 (d, 2H, J=8.5 Hz), 7.05 (s, 2H), 6.93 (s, 4H), 6.86 (m, 8H), 6.81 (m, 1H), 6.42 (d, 1H, J=7.5 Hz), 5.05 (s, 8H), 4.97 (s, 4H), 4.53 (m, 1H), 4.37 (s, 1H), 3.94 (m, 8H), 3.72 (s, 3H), 3.19-3.06 (m, 2H), 1.76 (m, 8H), 1.44 (m, 17H), 1.38-1.21 (r, 67H), 0.88 (t, 12H, J=6.5 Hz).

$^{13}$C NMR (125 MHz, CDCl3)δ=170.5, 160.0, 159.0, 149.2, 139.6, 130.5, 129.6, 129.1, 129.0 (×2), 121.8, 121.0, 115.5, 115.1, 114.5, 109.0, 71.3, 70.3, 68.1, 48.2, 31.9, 29.7, 29.6 (×3), 29.4, 29.3 (×2), 28.3, 26.1, 22.7, 18.4, 14.1. C115H162N2O17 Anal. Calc: C, 74.88; H, 8.85; N, 1.52. Anal. Found: C, 74.90; H, 8.89; N, 1.54.

Example 96

Test for Linear Dichroism

An L-L dendritic dipeptide film was obtained by depositing about 6-7 layers of a 0.2 mM solution of [4-3,4-3,5] 12G2CH2-Boc-L-Tyr-L-Ala-OMe in chloroform on a quartz plate. The film's CD was recorded at different cell angels. No linear dichroism was observed, only circular dichroism was observed at cell angles of −30°/60°; 0°/90°; and 30°/120°.

Example 97

Electron Diffraction and Imaging Studies

Transmission electron microscope images of unstained samples were recorded on Fuji image plates, using 100 and 120 kV (JEOL 100 CX and Philips EM400T) and low-dose procedures. Ultrathin (~50 to 100 nm thick) film samples for EM and ED were cast from dilute toluene solution onto hot (approximately 70° C.) distilled water surface. After evaporation of toluene, a thin film was retrieved on carbon-coated copper grids. To prevent dewetting during the following heat treatment, another layer of carbon film was deposited, creating a sandwich structure. These samples were heat treated and annealed, quenched and examined. Specifically, these samples were cooled slowly from the isotropic state to the hexagonal columnar phase (e.g., from 102° C. to 70° C. at a rate of 0.5° C./min), annealed (e.g., 4 hours at 70° C.) and quenched in air. This sample preparation procedure produces some homeotropic alignment of the columns, so that hexagonal diffraction and images may be observed at normal inci-

TABLE 1

Analysis of Dendritic Dipeptides
Thermal Transitions and Corresponding Enthalpy Changes of
[4-3,4-3,5]nG$_2$CH$_2$-Boc-L-Tyr-L-Ala-OMe
System where n = 1, 2, 4, 6, 8, 10, 12, 14, 16, as Determined by DSC.

| Tail length | heating | cooling |
|---|---|---|
| n = 1 | k 72 N$_c$[b] 82.2 (9.49$^f$)i[c]<br>g 44.2 N$_c$ 954 i | i 88.3 N$_c$ 35.2 g |
| n = 2 | N$_c$ 82.2 (11.21) i<br>g$^d$ 41.1 (1.01) N$_c$ | i 81.1 (11.21) N$_c$ |
| n = 4 | g 86.6 (5.47) k$_1$[e] 102.9 k$_2$ 109.5$^f$ (6.35) i<br>k$_3$ 43.4 (1.65) i | i 109.0 k$_3$ |
| n = 6 | k 64.2 (0.92) φ$_{h-i}$[g] 104.2 (8.84) i<br>φ$_h$ 63.7 (3.60) i | i 60.7 (3.68) φ$_h$[h] |
| n = 8 | K 80.3 (5.12) N$_c$ 93.0 (5.0) i<br>φ$_h$ 80.3 (7.32) i | i 76.3 (7.34) φ$_h$ |
| n = 10 | g 57.3 φ$_h$ 89.4 (4.53) i<br>g 60.2 φ$_h$ 89.4 (4.82) i | i 86.0 (5.33) φ$_h$ 58.4 g |
| n = 12 | g 56.1 φ$_h$ 96.1 (5.15) i<br>g 59.9 φ$_h$ 96.0 (5.14) i | i 93.4 (5.59) φ$_h$ 55.0 g |
| n = 14 | k 43.3 (10.94) φ$_h$ 100.3 (5.31) i<br>k 12.5 (5.21) g 63.1 φ$_h$ 100.2 (5.38) i | i 97.9 (5.74) φ$_h$ 54.3 g 7.43 (6.54) k |
| n = 16 | g$_a$[i] 55.0 (16.16) φ$_h$ 102.8 (5.49) i<br>k 35.1 (10.10) g 63.6 φ$_h$ 102.6 (5.51) i | i 99.9 (5.71) φ$_h$ 27.8 (10.85) k |

[a]Data from the first heating and cooling scans are on the first line and data from the second heating are on the second line.
[b]Nc = nematic columnar.
[c]i = isotropic.
[d]g = glass,
[e]k = crystalline.
[f]Peaks of phase transition are not fully resolved.
[g]φ$_{h-i}$ = columnar hexagonal (inverted).
[h]φ$_h$ = columnar hexagonal (normal).
[i]g$_a$ = amorphous glass.

dence. After an image was recorded, electron diffraction was observed to confirm that the electron dose used to record the image was small enough so as not to destroy the hexagonal phase by excessive dose.

Electron diffraction results indicate the presence of a hexagonal columnar mesophase. In contrast to similar molecules, which have an acid or ester unit at the apex, these dipeptide materials exhibit two significant differences. The higher-order diffraction peaks are relatively more intense and have comparable intensity. For acid or ester dendrons, there is a predominant peak, and all higher-order reflections are very weak in comparison. The second significant difference is that the column diameter is much larger: approximately (7 or 8) v. (4 or 5) nm. These two features are the result of a unique structure that is apparent from TEM images. A light (low-density) region appears in the center of each column, i.e. they appear hollow. Fourier analysis of the images demonstrated that astigmatism is absent and the image resolution is sufficiently high that the contrast transfer function has the same sign for each of the reflections. Thus, the relative phase of each of these reflections, i. e. +, –, and –, respectively, may be computed directly from Fourier analysis.

Electron diffraction results also show two more reflections. However, since these two reflections are absent from the Fourier transform of the image, the image resolution is insufficient for direct determination of the phase of these reflections also. These reflections are absent for two reasons. The primary reason is that the liquid crystalline phase formed by dipeptide dendron is extremely sensitive to the electron beam. Even the minimal dose for imaging is enough to damage the structure to a certain degree, thereby reducing the amplitude of these reflections.

Example 98

Absolute Value of Contrast Transfer Function

The absolute value of the contrast transfer function (CTF) for the TEM is a function of the spatial frequency u, which is the reciprocal of the d-spacing. Data points represent the absolute value of the Fourier transform of two regions in the same image (n=12): the hexagonal phase and a neighboring region where no lattice is detected. The spherical aberration coefficient of the objective lens was 6.7 mm, and its defocus –2.1 μm. All three peaks in the Fourier transform, the main reflections, coincide with the first broad peak in the CTF.

The amplitude of the reflections was also degraded at higher dose. The effect on these reflections was minimal, and their amplitude is approximately 80%, after Lorentz and CTF corrections. This amplitude is comparable to that measured by ED, which was obtained at a much lower dose. For images obtained at higher dose, for example, when the apparent amplitudes were degraded to approximately 20%, the phases determined from these images remain +, – and –, respectively. Since none of the TEM images contain the reflections, the phases of these components must be determined by trial evaluation of each possible combination: ––, ++, +– and –+. Fourier reconstructions of each of these possibilities, and based on the mass fractions of aliphatic, aromatic and peptide units, the peptide is likely to be near the center of the column, with aromatic and aliphatic portions at larger radii, as expected from the molecular shape. Of the possibilities a-d, c and d are the most unlikely, because the density exhibits wild oscillations both in the aromatic-peptide region as well as the aliphatic region. Case d is particularly unreasonable, because unlike the other possibilities, the high-density hexagons are arranged vertex-to-vertex, requiring huge variations in the extension and compression of the aliphatic periphery. Case ++ has fairly uniform aliphatic and aromatic density, but the high-density point in the center of the core is curious, and case –– is preferred since it possesses the most uniform aliphatic phase.

Example 99

Electron Density Maps of LL Dendritic Dipeptide

Electron density maps were calculated from the electron diffraction data with different phases for the peaks. The relative amplitudes of the main reflections were +1.00, –0.89, –0.85, ±0.44, ±0.31, respectively.

Example 100

Atomic Force Microscopy (AFM)

Samples for AFM were prepared by placing the powder material (n=12) between two graphite sheets and heating this sandwich first to 100° C. After quenching the sample to room temperature, the sandwich was split into two parts each having graphite substrate and a flat material layer on them. In some places, graphite was covered only by an ultrathin layer, which was approximately 3.7 nm thick, in others the material layer was 250-350 nm thick. Imaging was performed with a Dimension 5000 scanning probe microscope (Digital Instruments/Veeco Metrology Group), using etched Si probes with a stiffness of 1N/m. The AFM phase image presented in FIG. 3f of the manuscript was obtained on the surface of the thick layer after the sample was heated again to 95C and air-cooled to room temperature. The image shows a part of a liquid crystalline texture comprising parallel cylinders, whose spacing is 8.0 nm, as determined by Fourier analysis. This spacing represents the cylinder diameter a=2d10/√3, which is greater than 7.1 nm, as obtained by XRD measurement at 71° C. (cf. Table-ST1). AFM measurements at temperatures ranging from 25 to 85° C. indicate that the column diameter decreases (by approximately 1 nm) with increasing temperature.

Example 101

X-ray Diffraction (XRD) and Computational Studies

A—X-Ray Diffraction Experiments

Small- and wide-angle X-ray diffraction measurements of the bulk and oriented fiber samples were carried out with Cu—Kα1 radiation from a Bruker-Nonius FR-591 rotating anode X-ray source with a 0.2×2.0 mm² filament. The beam was collimated and focused by a single bent mirror and sagitally focusing Ge(111) monochromator, resulting in a 0.2× 0.2mm² spot on a Bruker-AXS Hi-Star multiwire area detector. To minimize attenuation and background scattering, an integral vacuum was maintained along the length of the flight tube and within the sample chamber. The samples were held in a temperature-controlled (±0.1° C.) oven. The raw two-dimensional diffraction patterns were processed and analyzed using the Datasqueeze software package. See, http://www.datasqueezesoftware.com. Small-angle X-ray diffraction measurements were carried out at room temperature, and at elevated temperature at which the peptide-attached dendrimers are expected to form a liquid crystalline phase. On cooling from isotropic phase, those with n=6 or higher ((4-3,4-3,5)nG2-CH$_2$-[Boc-L(D)-Tyr-L(D)-Ala-OMe], where n is the number of carbons in their alkyloxy groups and its values are 6,8,10,12,14 and 16; in short referred to as n-peptide-L-L hereafter) show sharp reflections with the lowest q-value (q=4π sin θ/λ) peak being very strong. They also show three more sharp reflections. The ratio of the reciprocal of the d-spacings (1/d1:1/d2:1/d3:1/d4), or the q-values (q1:q2:q3:q4) of these reflections are close to the expected values (1.0:1.73:2.00:2.65) for a 2d hexagonal columnar liquid crystal. The indices of the observed reflections are (10), (11), (20) and (21). The intensities of the higher order peaks, (11) and (20) are unusually enhanced relative to that observed in the usual filled-core hexagonal columnar systems like, for example, the same 4-3,4-3,5 dendron but attached with only CH2OH in the apex. See, Figure SF9. Further these peptide dendrons show the presence of a very weak peak. It may be noted that the inverse hexagonal (type-II) lyotropic liquid crystalline phases where the water channel in the core of the columns is surrounded by lipid molecules show much enhanced higher order peaks[11,12]. The lattice dimensions of these peptide-attached dendrimers range from 64.4 Å for n=6 to 87.0 Å for n=16, which also gives the diameter of the supramolecular cylindrical columns. See, Table 2 below. The column diameters are in good agreement with the length of the molecule calculated from the molecular models with some allowance for the possible tilt of these molecules, as shown by the oriented fiber measurements that are discussed later. In particular, the column diameter for a dendritic molecule with the same branching pattern ((4-3,4-3,5)12G2-CH2OH; n=12 alkyloxy chain) but without the peptide group in the core (FIG. 3b) is 53.4 Å. However for the peptide-attached dendrimer with n=12 alkyloxy chain it is 71.3 Å which shows that there is nearly an increase of 18 Å in the column diameter for the peptide-attached dendrimers.

B—X-ray Diffraction Patterns of LL Dendritic Dipeptide

The X-ray diffraction patterns in the 2D hexagonal columnar liquid crystalline phase for n-peptide-L-L dendrons with different chain lengths: (a) n=8, (b) n=12, (c) n=16. For comparison, the diffraction pattern of the dendron without the peptide group but with CH$_2$OH group ((4-3,4-3,5)12G2-CH2OH) in the apex that forms the usual, filled-core columns in the hexagonal columnar phase is shown. It may be noted that this molecule showed very weak (11) and (20) peaks and no (21) peak.

XRD data for dipeptide attached dendrons (A) with different alkyloxy chains but with the same stereochemistry (L-L) of the peptide groups and (B) with different stereochemistry but with the same alkyloxy chains (n=12), one with ester linkage (L-L ester), and one with Me group instead of Boc group (L-L Me), in the hexagonal columnar LC (φh) phase. The column diameter is the same as the lattice dimension of the 2D hexagonal lattice of hard cylinders, with the nearest neighbors touching each other. The lattice dimension is calculated from all the observed d-spacings $$a = 2d_{hk}\sqrt{(h^2+k^2+kh)}/\sqrt{3}.$$

TABLE 2

X-ray Data on Dendritic Dipeptides (A)

d-spacings (Å) and normalized integrated intensities of the observed reflections

| (hk) indices | n = 6 (55.0 C.) | n = 8 (75.0 C.) | n = 10 (69.5 C.) | n = 12 (71.0 C.) | n = 14 (72.0 C.) | n = 16 (74.0 C.) |
|---|---|---|---|---|---|---|
| (10) | 56.1/38 ± 1 | 59.4/44 ± 1 | 63.6/43 ± 1 | 61.6/46 ± 1 | 70.6/59 ± 1 | 75.3/61.1 ± 0.2 |
| (11) | 31.9/29.6 ± 0.5 | 34.0/28 ± 0.5 | 36.7/26 ± 3 | 35.5/24 ± 3 | 40.5/18 ± 3 | 43.5/17 ± 4 |
| (20) | 28.2/31 ± 1 | 29.4/25 ± 1 | 32.0/28 ± 3 | 30.8/27 ± 3 | 35.1/21 ± 5 | 37.5/22 ± 5 |
| (21) | 21.0/2 ± 1 | 22.2/3.4 ± 0.2 | 23.9/1 ± 1 | 23.4/3 ± 3 | 26.4/2 ± 2 | 28.6/1 ± 1 |
| column diameter (Å) | 64.4 ± 0.6 | 68.0 ± 0.4 | 73.5 ± 0.4 | 71.3 ± 0.2 | 81.2 ± 0.3 | 87.0 ± 0.3 |

(B)

d-spacings (Å) and normalized integrated intensities of the observed reflections

| (hk) indices | D—D (71.0 C.) | D-L (75.4 C.) | L-D (75.0 C.) | DL—DL (71.0 C.) | L—L ester (85.0 C.) | L—L Me (108.0 C.) |
|---|---|---|---|---|---|---|
| (10) | 62.8/50 ± 0.3 | 62.2/53.4 ± 0.4 | 61.6/43 ± 1 | 57.1/53 ± 1 | 62.2/66.5 ± 0.3 | 64.8/71 ± 1 |
| (11) | 36.1/24 ± 1 | 35.9/22.6 ± 0.4 | 35.7/26 ± 1 | 32.9/24 ± 1 | 35.7/17.3 ± 0.3 | 37.0/14 ± 1 |
| (20) | 314/25 ± 1 | 31.3/22.6 ± 0.4 | 30.8/29 ± 1 | 28.6/22 ± 1 | 30.1/15.2 ± 0.3 | 32.4/15 ± 1 |
| (21) | 23.8/1 ± 1 | 23.6/1.5 ± 0.2 | 23.4/2 ± 1 | 21.7/1 ± 1 | 23.4/1 ± 0.1 | 24.2/1 ± 1 |
| column diameter (Å) | 72.5 ± 0.2 | 72.0 ± 0.2 | 71.3 ± 0.2 | 66.0 ± 0.2 | 71 ± 1 | 74.4 ± 0.5 |

On cooling and below the glass transition temperature (Tg), for the molecules with n=14, 12, 10 the same reflections were observed but they became broad. The d-spacings of the reflections were again consistent with a 2d hexagonal columnar structure but with a large amount of disorder. Therefore the 2d hexagonal columnar liquid crystalline structure was frozen into columnar hexagonal glassy state below Tg. For n=4, the peptide-attached dendrimer forms only a crystalline phase and, for n=2 it formed only a columnar Nematic (Nc) phase. Thus at least alkyloxy chains longer than 4 units (n>4) are necessary to form a 2d hexagonal columnar liquid crystal, for these dendritic dipeptides.

Example 102

Electron Density Profile Analysis

Electron density profiles were computed for the peptide-attached dendrimers (n=6 to 16) with the integrated intensities obtained from the X-ray diffraction measurements in the 2d hexagonal columnar LC phase[13-15]. Due to their close similarity with the closed-core column forming supramolecular dendrimers we have studied earlier, the relative electron density profiles were analyzed in terms of a nanophase segregated model for different choices of the phases of the reflections. As noted above, the phase choice +--- for the (10), (11), (20) and (21) reflections exhibited a nearly flat and smooth periphery with low electron density corresponding to the aliphatic region of the supramolecular columns. However, for other choices of the phases for the (11), (20) and (21) reflections, the periphery of the columns showed considerable variation in the electron density appearing like a cluster of small hills of differing heights. We have shown earlier[14] that these variations seen in the liquid-like aliphatic regions do not satisfy the nanophase segregated model. The electron density profile for the +--- phase combination shows low electron density in the core that is lower than the aliphatic regions suggesting that the core is hollow. Unfortunately, quantitative analysis is limited by truncating the Fourier series at (21)[16]. Although even higher order reflections (30), (31) and (22) have been observed by ED, these weaker reflections cannot be measured here from bulk samples by powder XRD. Further more, the electron density reaches a maximum at the edge of the hollow core forming an annulus of high electron density region. This suggests that the aromatic and peptide parts of the dendrons organize in the annular region surrounding the hollow core with the aliphatic part lying in the low density periphery of the supramolecular columns. The relative electron density profiles also showed smaller diameter hollow core for the peptide-dendrimers with alkyloxy chain n=14 and n=16 corresponding to the relatively low observed intensities of the higher order peaks in the XRD patterns. See, Table 2 above.

In order to compare the features in the electron density profiles between dendrimers with different lengths of the alkyloxy chains, we developed a method to convert relative electron density values into absolute ones, e.g., electrons/Å$^3$. Although it is in principle possible to use the absolute scattered intensity in a small-angle x-ray scattering experiment to determine the absolute electron density[17], such experiments require highly precise measurements of many experimental factors, including incident beam intensity, sample absorption, detector sensitivity, and background corrections. Our approach is based on the observation that the mass density, and therefore the electron density, of the aliphatic region in a columnar liquid crystalline system is nearly constants. The overall average electron densities that are needed to convert the relative electron density values into the absolute ones were arrived at from the measured mass densities for the different peptide-attached dendrons and their column diameters obtained from the XRD measurements. The other unknown, namely, the scaling factor is calculated using the aliphatic mass density, 0.87 g/cm3, 0.30 electrons/Å3 obtained from our earlier studies[18], and the structural parameters. The absolute electron density profiles computed for the different dendritic dipeptides show low electron density in the core that is substantially below the average electron density. For shorter and medium chain length molecules (n=6, 10 and 12) the electron density in the center of the core is even lower than the lowest electron density in the aliphatic periphery. Thus it clearly establishes that the core of these columns is hollow and its size becomes smaller for longer chains.

Absolute electron density profiles of the column for (4-3, 4-3,5) nG$_2$-CH$_2$[Boc-L-Tyr-L-Ala-OMe] with different lengths ((a) n=6,10,12 and (b) n=12, 14 and 16) of the alkyloxy chain. The average aliphatic electron density is shown as a dotted horizontal line (black).

Example 103

Three Level Nanophase-Segregated Model

The analysis of the electron density profiles showed the hollow core, low density periphery and a high density intermediate region. The form factor was calculated for a cylinder with three level uniform electron density distributions that closely represents the features of the computed electron density profiles; a zero density core, a low density periphery corresponding to the aliphatic region and a high density intermediate region corresponding to the aromatic-peptide region. The form factor expression giving the amplitude of the diffraction pattern from the model was derived starting from that for a cylinder with constant electron density[19]:

$$F(q)=2\pi[(\rho ar-\rho al)(J1(qrar)rar/q)-\rho ar(J1(qrc)rc/q)+(\rho alJ1(qral)ral/q)],$$

wherein J1 is the first order Bessel function, ρar, ρal refer to the electron density of the aromatic-peptide and the aliphatic regions, respectively, and rc, rar, and ral to the radii of the core, aromatic-peptide, and the aliphatic regions, respectively. The amplitudes obtained from the experimental XRD intensities of the observed reflections (See, Table 2 above) along with their phases arrived at from electron density profile analysis were fit to the amplitudes calculated from the above expression by least-squares fit. The best fit was arrived at for a physically plausible combination of the radii of the aromatic-peptide and aliphatic regions and their electron densities used in the model by varying only some of all the variable parameters at a time during the least-squares fitting. The results of such fits for the n-peptide-L-L dendrimers (n=6 to 16) are summarized in Table 3 below with L-L stereochemistry for the dipeptide part.

TABLE 3

Three-Level Electron Density Model Fit Parameters (A)

| Fit Parameters | n = 6 (55.0 C.) | n = 8 (75.0 C.) | n = 10 (69.5 C.) | n = 12 (71.0 C.) | n = 14 (72.0 C.) | n = 16 (74.0 C.) |
|---|---|---|---|---|---|---|
| $\chi^2$ for the fit | 1.2 | 2.78 | 9.6 | 11.0 | 11.4 | 11.1 |
| Hole radius | 7.2 ± 0.4 Å | 7.0 ± 0.6 Å | 6.8 ± 0.9 Å | 6.4 ± 0.2 Å | 5.5 ± 13 Å | 4.3 ± 1.0 Å |
| Prefactor | 0.476 ± 0.02 | 0.55 ± 0.04 | 0.51 ± 0.07 | 0.52 ± 0.05 | 0.552 ± 0.1 | 0.528 ± 0.15 |
| Aromatic region's outer radius | 22.8 ± 0.4 Å | 23.8 ± 0.4 Å | 24.4 ± 0.7 Å | 23.6 ± 0.5 Å | 25.8 ± 0.8 Å | 25.6 ± 0.3 Å |
| Aliphatic region's outer radius | 31.9 ± 1 Å | 35.4 ± 0.8 Å | 35.5 ± 3.2 Å | 35.7 ± 0.5 Å | 38.8 ± 1.4 Å | 39.4 ± 2.1 Å |

(B)

| Fit Parameters | D—D (71.0 C.) | D-L (75.4 C.) | L-D (75.0 C.) | DL—DL (71.0 C.) | L—L ester (85.0 C.) | L—L Me (108.0 C.) |
|---|---|---|---|---|---|---|
| $\chi^2$ for the fit | 20.4 | 20.0 | 30.9 | 16.2 | 16.6 | 15.2 |
| Hole radius | 6.8 ± 0.5 Å | 6.4 ± 1.5 Å | 6.7 ± 0.9 Å | 6.4 ± 0.4 Å | 6.2 ± 0.6 Å | 5.1 ± 1 Å |
| Prefactor | 0.548 ± 0.1 | 0.56 ± 0.06 | 0.48 ± 0.1 | 0.577 ± 0.04 | 0.581 ± 0.08 | 0.572 ± 0.06 |
| Aromatic region's outer radius | 23.6 ± 0.6 Å | 23.5 ± 1.0 Å | 23.3 ± 1.2 Å | 23.3 ± 0.8 Å | 21.1 ± 0.8 Å | 23.8 ± 0.4 Å |
| Aliphatic region's outer radius | 36.2 ± 1.9 Å | 35.6 ± 1.5 Å | 33.9 ± 1 Å | 36.0 ± 3 Å | 33.7 ± 0.6 Å | 35.9 ± 0.9 Å |

The fit results show that the pore diameter of the core decreases as the alkyl chain length becomes larger. It also shows that the pore diameter for the supramolecular dendrimers with different stereochemistry of the dipeptide units (D-D, D-L and DL-DL) and is nearly the same as that of L-L. Form-factor fits to a three-level electron density distribution model for the molecular organization of (4-3,4-3,5)nG$_2$-CH$_2$ [Boc-L-Tyr-L-Ala-OMe] (A) with different lengths of alkyloxy chains and (B) of (4-3,4-3,5)12G$_2$-CH$_2$X with X=[Boc-D-Tyr-D-Ala-OMe], called D-D, and with different stereochemistry of the Tyrosine and Alanine groups, namely, D-L, L-D, DL-DL, in the hexagonal columnar LC (φh) phase. It also includes one with ester linkage (L-L ester), and one with Me group instead of Boc group (L-L Me).

Example 104

Absolute Electron Density Reconstructions From the Three Level Model

Absolute electron density profiles were calculated from the diffraction amplitudes obtained from the form factor fits to the three level electron distribution model described above in order to compare it with the electron density profiles computed from the x-ray diffraction intensity data. For 12-peptide-L-L dendrimer, there is a slight mismatch between the profiles calculated from the model and that from the x-ray data only in the core and peripheral regions (Figure SF11a). In the core region, the model profile gives a slightly higher electron density (at the very center ~0.165 e/Å$^3$), whereas the experimental profile has slightly lower density (~0.135 e/Å$^3$). However as one moves away from the center the difference becomes smaller and the difference becomes very small. For 10-peptide-L-L dendrimer, however, one cannot distinguish between the experimental profile and the model profile in the core region, and well into the aromatic region. The difference is seen only in the peripheral regions and the extent of mismatch is almost same as that for n=12, as can be seen from Figure SF11b. In the case of 6-peptide-L-L dendrimer the overall agreement is quite good; the profiles match in most of the regions. Only in a small region near the core and the periphery there is a relatively smaller mismatch. The electron density levels obtained from the model fits for 12-peptide-L-L dendrimer and 6-peptide-L-L dendrimer show a slightly larger, by ~10%, electron density than the maximum of the experimental ones; in the aliphatic regions it is slightly lower than expected. However, for 10-peptide-L-L the model electron density value is slightly lower than the maximum of the experimental profile. These profiles show that, overall, the form factor fits adequately reproduce the experimental electron density profiles. As noted earlier, the observed mismatches may arise from the fact the liquid crystalline systems show smaller number of observed reflections than the crystalline phases[16].

Example 105

Comparison of Model and Experimental Electron Density Profiles

The electron density profiles computed from the model (red) intensities shown along with that calculated from the XRD data. The electron density values used in the core, aromatic and aliphatic regions in the form factor fits are shown in dotted lines.

Example 106

X-ray Fiber Diffraction

X-ray patterns from oriented fibers were recorded for the dendritic dipeptide samples in order to gain insight into the molecular arrangement in the columnar liquid crystalline phase since many of these supramolecular structures (n=10, 12 and 14) froze into an ordered glassy liquid crystalline state. The diffraction patterns showed two sets of X-like pattern of spots; the set that subtends a large angle between its arms arises from the tilted arrangement of the molecules (spots "B" in FIG. 3c, main manuscript); half of this angle is the average tilt of the long axis of the molecule from the normal to the column axis. This feature is similar to that seen in the fiber pattern of a highly tapered dendron that we have investigated earlier[15] which shows only a single, unsplit meridional (on the line passing through the origin of the diffraction pattern and parallel to the fiber axis) spot. Tilt angle of the molecular long axis was obtained by curve fitting the X-profile through these tilt spots. In addition the pattern shows split meridional spots forming a stretched X-like pattern that can be attributed to the short-range helical arrangement of the peptide-dendrimers. Both the tilt and short-range helical features were observed in the oriented fiber patterns of charge-transfer complexes of donor/acceptor functionalized dendron-jacketed conductive polymers[20] we have studied earlier. The short-range helical pitch was calculated from these spots. For n=12 peptide dendrimer with L-L stereochemistry the tilt angle is 61±1°. Although the outer radius of the peptide-aromatic region (29.7 Å) calculated from the molecular models for the conformation with the dendron and the dipeptide parts lying nearly in a plane agrees closely with that calculated from the experimental overall density for the material and the density of the aliphatic part, the tilt of the dendron in that conformation is only less than 10°. This small tilt present in this conformation shows that the peptide part will have to be at some distance from the core of the columns in order for the dendron part to develop the observed large tilt. For the 12-peptide with D-D stereochemistry, the tilt angle obtained from the diffraction patterns is 47±3°. For n=10 and n=14 with L-L stereochemistry it is 41±1°, 52°±1°, respectively. Therefore the observed tilt angles are substantially higher than that found from the flat-conformation molecular model. Thus the observed tilt angles corroborate the conclusions drawn from the electron density profile analysis and form factor fits that the core of these supramolecular columns is hollow. The short-range helical pitch for the 12-peptide-L-L, 12-peptide-D-D, 10-peptide-L-L and 14-peptide-L-L are: 4.4±0.1 Å, 4.1±0.1 Å, 4.5±0.2 Å, and 3.7±0.1 Å, respectively.

Example 107

Molecular Modeling

Molecular models were investigated in order to gain insights into how the dendron and the dipeptide parts organize into hollow core columns. Models were built with molecular modeling software, Macromodel 7.2 (Columbia University, NY, U.S.A) and the software suite, Materials Studio (Accelrys Inc, San Diego, Calif., U.S.A). Different models for the self-assembly of the peptide-attached dendrons were considered with a view to obtain supramolecular columns with a hollow core. A total of eight models (four non-helical and four helical) were considered which fall into two classes depending on the relative orientation of the peptide part and the dendron part. Within each class two types of arrangement of the neighboring layers were considered; one in which the peptide parts in the neighboring layers do not interdigitate and the other in which they interdigitate substantially. Since the fiber diffraction analysis and the CD experiments show that there is a helical arrangement of the molecules and, further, the fiber patterns show a substantial tilt of the dendron part, two kinds of models to obtain helical arrangement of the peptide-attached dendrons were explored. One of them is the one in which the large part of the peptide region is almost parallel to the long axis of the dendron part of the molecule (parallel conformation). The other one has the peptide part nearly perpendicular to the long-axis or the molecular plane of the dendron part of the molecule (perpendicular conformation). Single layer of assemblies were constructed with the hydrogen bonds between the peptide parts of the neighboring molecules and their organization into a single column was explored. In the parallel conformation, the neighboring layers stacked nearly periodically one over the other due to the hydrogen bonding pattern and the interior of the peptide region was sterically severely restricted which in turn allowed only loose-packing of the dendron parts leaving empty space in between the neighboring dendrons. Further, they formed much larger diameter columns than experimentally measured values due to their inability to sustain the required tilt of the dendron part of the molecule. However, during energy minimization, the perpendicular conformation assembly developed a large tilt of the dendron part with the peptide part of a single molecule forming two hydrogen bonds on each side to the peptide part of the neighboring molecules. The development of the large tilt is facilitated by the $CH_2O$ linkage that connects the phenyl from the peptide and the dendron part. In this conformation the dendron part can have varying tilts without affecting the orientation of the peptide part. Thus they form a hydrogen-bond stabilized channel in the core with the tilted dendron part. It was found that such an arrangement of the dendrons can form a single layer with both helical and non-helical arrangements. However, since the CD experiments and the oriented fiber diffraction studies show the existence of helical arrangements, the non-helical arrangement was discarded. Assemblies of layers of such hydrogen-bonded, tilted, helical configurations were relaxed with energy minimization routines in order to obtain the final structure of the columns. The resulting model has hydrogen bonding between the neighboring layers as well, thus stabilizing the entire column. A similar model was arrived at for L-D peptide dendrons that has a lesser number of hydrogen bonds between the peptide units due to the steric hindrance imposed by the methyl attached to the chiral carbon of the D-Alanine group. This may explain the observed lower isotropization temperature for L-D peptide dendrimer. The methyl groups at one end of the peptide part form the interior wall of the column making them hydrophobic. This arrangement suggests that by suitable modification of this methyl group it should be possible to design super hydrophobic channels. The peptide part was nearly vertical and the dendrons part had a large tilt. In this conformation the dendrons organize into hollow core columns with the hydrogen-bonded dipeptides in the core.

Hydrogen bonding pattern between the peptides in the core of the columns showed the hydrogen-bonded Boc-L-Tyr-L-Ala-OMe peptides from two neighboring layers of the supramolecular column. The hydrogen bonding between the bottom layer (carbons in green) and the top layer (carbons in blue) can also be seen which stabilizes the column. In the bottom, the H-bonding is between the peptides within the bottom layer is between its NH and the carbonyl groups. In the middle there are two hydrogen bonds due to the NH and the carbonyl groups of the peptides in the bottom layer and the oxygen (adjacent to Boc group) from the peptides in the top layer. The hydrogen-bonded Boc-L-Tyr-D-Ala-OMe peptides from two neighboring layers of the supramolecular showed hydrogen bonding between the bottom layer (carbons in green) and the top layer (carbons in blue) may also be seen which stabilizes the column. Between the layers, there were two hydrogen bonds due to the NH and the carbonyl groups of the peptides in the bottom layer and the oxygen (adjacent to Boc group) from the peptides in the top layer. In a single layer, the peptide forms, on one side, only one hydrogen bond with its neighbor within the same layer.

Example 108

Crystal Structure of L-L Dipeptide Without the Dendron Attached 100 mg/ml of L-L dipeptide were dissolved in a mixture of chloroform (1.95 ml) and methanol (0.05 ml) using a vortex mixer. The dipeptide (L-L) crystals were grown by keeping the solution at room temperature for 7 days with spontaneous evaporation of the solvent. The excess solvent was removed by pipette to isolate single crystals of dipeptide. The structure of such a crystal was determined from single crystal diffraction data (Table 4 below) which shows how the L-L dipeptide molecules pack in the crystal. It crystallizes into an orthorhombic lattice with the dimensions: a=9.7260(14)Å, b=9.655 (2)Å, and c=20.865(3)Å. The Tyrosine and Alanine regions developed a c-like fold rather than retain a largely linear conformation. In the crystal, the molecule forms one intramolecular and two intermolecular hydrogen bonds. The Alanine part had an intra-molecular hydrogen bond (2.38 Å) between the NH and the C=O (hydrogen attached to N1 and the oxygen $O_5$). The oxygen ($O_3$) in the C=O of the Tyrosine forms an intermolecular hydrogen bond (2.02 Å) with the terminal OH group of the phenyl of the Tyrosine of the neighboring dipeptide (hydrogen attached to O6 in Figure SF15a). The oxygen (O1 in Figure SF15a) in the C=O of Alanine forms an intramolecular hydrogen bond with the NH of the Tyrosine (N2). It may be noted that the conformation of the dipeptide in the crystal structure is different from the one arrived at in the molecular models of the hollow-core columnar assemblies of the peptide dendrons discussed earlier. In particular the Tyrosine and Alanine units form a largely linear conformation in the molecular models of the dipeptide dendrons whereas the dipeptide shows a c-like fold in the crystal structure. Conformation and Packing of L-L Dipeptide in the Crystal were seen from the conformation of the single molecule in the crystal, and a single unit cell of the crystal showed the intermolecular (one) and intramolecular (two) hydrogen bonds formed by a single molecule.

TABLE 4

Single Crystal Structural Data for L—L Dipeptide

| | |
|---|---|
| Formula: | $C_{18}H_{26}N_2O_6$ |
| Formula weight: | 366.41 |
| Crystal class: | orthorhombic |
| Space group: | $P2_12_12_1$ (#19) |
| Z | 4 |
| Cell constants: | |
| a | 9.7260(14) Å |
| b | 9.655(2) Å |
| c | 20.865(3) Å |
| V | 1959.2(5) Å$^3$ |
| μ | 0.93 cm$^{-1}$ |
| crystal size, mm | 0.40 × 0.27 × 0.10 |
| $D_{calc}$ | 1.242 g/cm$^3$ |
| F(000) | 784 |
| Radiation: | Mo-K$_\alpha$ (λ = 0.71070 Å) |
| 2θ range | 5.72–50.7° |
| hkl collected: | −11 ≦ h ≦ 11; −9 ≦ k ≦ 11; −25 ≦ l ≦ 17 |
| No. reflections measured: | 11983 |
| No. unique reflections: | 3510 ($R_{int}$ = 0.0218) |
| No. observed reflections | 3239 (F > 4σ) |

TABLE 4-continued

Single Crystal Structural Data for L—L Dipeptide

| | |
|---|---|
| No. reflections used in refinement | 3510 |
| No. parameters | 241 |
| R indices (F > 4σ) | $R_1$ = 0.0335; $wR_2$ = 0.0792 |
| R indices (all data) | $R_1$ = 0.0380; $wR_2$ = 0.0810 |
| GOF: | 1.050 |
| Final Difference Peaks, e/Å$^3$ | +0.139, −0.177 |

Example 109

X-ray Diffraction & Differential Scanning Calorimetry of Lipid-Dendritic Dipeptide Mixtures and Liposomes Containing Dendritic Dipeptides The phase behavior and molecular organization of lipid-dendron mixtures and of lipid vesicles dispersed with the dendritic dipeptide were investigated by Differential Scanning Calorimetric (DSC) and small- and wide-angle X-ray diffraction studies, respectively. The peptide-attached dendrons (4-3,4-3,5)12G2CH2-(Boc-L-Tyr-L-Ala-OMe) that were investigated for self-assembly in solution (main text) were mixed in various mass ratios in dichloro methane (DCM) or cyclohexane with the lipid (L-α-phosphatidylcholine P5638 from Sigma 20032004) that was used in the preparation of vesicles and then dried under the flow of Argon. Analysis of the dried mixtures by DSC (Figure SF16a) showed, on first heating, a very small endothermic peak for the lipid:dendron weight ratio of 14:1 at 91.9° C., suggesting that this peak could correspond to the 2D hexagonal columnar LC to the isotropic transition for the pure peptide-attached dendron (ϕh□i transition at 96.1° C. for n=12, table ST1). A slightly enhanced, small peak was observed at a slightly higher temperature, 93.8° C. for the 7:1 mixture as well (Figure SF16b). However, on cooling, a small peak was observed at almost the same temperature (89.0° C. and 89.1° C. for the 14:1 and 7:1 mixture, respectively) for both mixtures corresponding to the isotropic to the 2D hexagonal columnar LC phase transition (i→Φh transition at 93.4° C. for n=12). See, Table 1 above. Further the enthalpy of this phase transition for the 14:1 mixture is nearly 30% smaller than that for the 7:1 mixture. The phase behavior of the pure lipid was also investigated with the DSC in the similar temperature range with the same heating and cooling rates. However, the DSC traces did not show any peak either on heating or cooling showing that the pure lipid does not have any first-order phase transition in this temperature range. It may also be noted that the peak observed on first cooling and second heating is enhanced versus that observed in the first heating for both mixtures. This analysis demonstrates that the presence of the lipid facilitates the self-assembly of the dendritic dipeptide regardless of the nature of the solvent. In addition, the overall thermal behavior of these mixtures and the pure lipid suggests that during heating there is either a molecular reorganization into a better ordered lattice structure and/or an enhanced phase-segregation of the self-assembled dendritic dipeptide from the lipid matrix as shown by the X-ray diffraction studies described below. The differential scanning calorimeter traces of the first heating, and the first cooling runs of the dried mixtures of lipid with the peptide-attached dendron, (4-3,4-3,5)12G2CH2-Boc-L-Tyr-L-Ala-OMe done at the rate of 10°/minute.

The small-angle X-ray diffraction patterns recorded for the dried solvent-mixed lipid-dendritic dipeptide mixture (weight ratio 14:1) showed a very strong peak and five very weak peaks at 25° C. In all cases, the peak positions were found after curve-fitting the peak profiles taking into account the background using Datasqueeze data analysis software. The observed peaks could be indexed to two 2D hexagonal columnar structures with different lattice dimensions. The strong peak was indexed as the (10) reflection corresponding to a column diameter of 59.5 Å with the three weak peaks indexed to the (11), (20) and (21) reflections from the same lattice. This column diameter is close to the expected value since the measured membrane thickness of the vesicles formed by these lipid molecules is 56.0 Å. Among the other two very weak peaks observed, one occurred at a smaller q-value than the strong peak observed from the lipids. These peaks could be indexed to the (10) and (11) reflections of a 2D hexagonal columnar lattice corresponding to a column diameter of 72.6 Å. Note that the (11) peak from the lipid lattice falls almost at the same position as the (20) peak from the lattice self-organized from the supramolecular columns self-assembled from the dendritic dipeptide. On heating to 75° C., the (10) peak of the peptide-dendron lattice becomes slightly enhanced and relatively narrower and the (11) peak is seen relatively easily, corresponding to a column diameter of 71.1 Å. However at 110° C., the dendritic dipeptide columns transform to the isotropic phase. Since the dendritic dipeptide columns are very small in concentration and the intensity of the reflection in the isotropic phase is much smaller than the (10) peak in the LC phase, the intensity of the peak in the isotropic phase in this 1:14 (dendritic dipeptide to lipid) mixture is expected to be quite small. On cooling to 75° C., the (10), (11) and (20) peaks of the dendritic dipeptide lattice becomes enhanced and the (11) and (20) peaks are easily seen. The (10) peak position corresponds to a column diameter of 74.8 Å that is nearly 4 Å larger than that observed on the first heating at the same temperature suggesting that there is a slight reorganization of the columns. The fact that the intensity of the (10) peak is significantly larger than that seen at the same temperature on first heating shows that there is enhanced phase-segregation of the self-assembled columns from the lipid matrix in the isotropic phase of the supramolecular columns and reorganization in the isotropic phase leading to a better ordered structure on cooling. Similar enhancement of the peptide-dendron peaks is also observed in the case of the 1:7 (dendritic dipeptide to lipid) as to be expected. Further the enhancement of the higher order peaks suggests that the core of the dendritic dipeptide columns is similar to that in the pure dendritic dipeptide columnar system. In fact, the calculated integrated intensities of the (10), (11) and (20) peaks for the 1:7 mixture turn out to be 57±2, 24±10, 19±10, respectively (compare with Table 2-B above), showing that the molecular organization of the dendritic dipeptide in the mixture is similar to that seen in their pure system. At 25° C., the peaks of the supramolecular columns generated from the dendritic dipeptide are slightly reduced in intensity and broadened as to be expected for the LC columnar glassy state exhibited by the pure peptide-dendrons. In summary, these X-ray studies show that the dendritic dipeptide is self-assembled in supramolecular porous columns in the presence of the lipid. They also indicate that the dendritic dipeptide when first mixed with lipid is partially phase segregated (disordered supramolecular columns) yet mainly dispersed molecularly (i.e. unassembled) and/or as individual columns. However, once heated to the isotropic phase there is enhanced phase-segregation of the supramolecular columns, and a reorganization of the supramolecular columns into more-ordered columns as seen from their 2D LC phase. The structure of the supramolecular columns formed in the lipid is similar to that formed on their own as a single phase system, i.e. in bulk, or in cyclohexane solution. Small-angle XRD patterns from the 1:14 mixture of peptide dendron with lipids. Patterns were recorded on first heating at 25° C., 75° C., ands also at 110° C. on first heating and then cooling to 75° C.

Vesicles formed from a 1:14 (mass ratio dendritic dipeptide to lipid) mixture were dried at 22° C. under a flow of Ar or Nitrogen and small-angle x-ray diffraction was carried out with these samples. The dried sample shows in the XRD pattern at 25° C., a fairly sharp, strong peak corresponding to a d-spacing of 55.1 Å. The pattern also shows a weak peak which occurs as a shoulder on the low-q side of this strong peak corresponding to a d-spacing of approximately 66 Å. No other weak peaks are observed unlike in the case of the dried mixture of peptide-dendron with lipid, discussed earlier. The fact that the d-spacing of the strong peak is very close to the bilayer thickness, 56.0 Å, measured in the pure vesicles shows that the curved bilayer shell of the vesicle collapses into a lamellar arrangement of the flattened bilayers. The layer thickness of the lipid lamellae decreases slightly on heating and remains nearly the same on cooling. The intensity of this peak decreases after thermal treatment, indicating a decrease in electron density contrast, which is likely due to a loss of water. The d-spacing of the observed weak peak is very close to the d-spacing of the (10) peak of the pure peptide-dendron in the 2D hexagonal columnar phase. In fact it yields a column diameter of approximately 76 Å which is slightly larger than that of the column generated from the pure dendritic dipeptide (a=71.3 Å, see, Table 2-B above). The column diameter remains approximately the same size as the sample is heated and cooled. No evidence of phase segregation is observed. The process of heating to 110° C. and cooling it down does not give rise to either the enhancement or appearance of the higher order peaks from the peptide-dendron columnar structure. This is in contrast with the behavior observed in the case of dried mixtures of lipid with peptide-dendron. This shows that, perhaps, there is hardly any enhancement in the phase-segregation of the self-assembled supramolecular columns from the lipid bilayer. In other words the microstructure of the dendritic dipeptide phase in the dried vesicles is almost unchanged even after heating to the isotropic phase. This demonstrates that the liposome stabilizes the individual dispersion of the supramolecular columns.

These X-ray studies showed that the mixture of lipid and dendritic dipeptide contains mostly self-assembled dendritic columns dispersed at the molecular level in the lipid and to a much lesser extent as self-organized assemblies of columns (column lattice). The self-assembly process seems to be independent of the nature of the solvent used. For example, methylene chloride mediates the self-assembly of the dendritic dipeptide in the presence of the lipid. However, pure methylene chloride does not facilitate the self-assembly process in the absence of the lipid (main manuscript text). The sonication process to form lipid vesicles largely disaggregates the lattice of supramolecular columns and disperses individual supramolecular columns in the vesicle bilayer. However, the sonication process does not disassemble the supramolecular columns. This can be explained by the stronger intra-column interactions versus inter-columns interactions. Moreover, at high temperature there is no enhanced phase-segregation of the supramolecular columns from the dried vesicles, as is the case in their bulk mixture, even when heated to the isotropic phase of the columnar structure. This indicates that the bilayer structure of the liposome largely favors the individual supramolecular dendritic columns dispersed at the molecular level in the lipid bilayer versus their aggregated-lattice that is favored in the bulk state of the lipid.

Small-angle XRD patterns from the dried dendritic dipeptide dispersed vesicle from the 1:14 mixture of dried, peptide-dendron dispersed lipid vesicles. Patterns were recorded on first heating at 25° C., 75° C, 110° C., and then cooling to 75° C., and 25° C. The same patterns shown enlarged in order to see the weak (10) peak from the peptide-dendrons.

Example 110

Membrane Transport Experiment

Procedure for Liposome Preparation

The method for the preparation of liposomes followed the procedure described by Finikova and references cited therein. 30 mg of soy bean phospholipid (L-α-phosphatidylcholine, Catalog Sigma 2003-2004, Cat #P5638) and 1 mg of the (4-3,4-3,5)12$G_2$-$CH_2$(Boc-L-Tyr-L-Aka-OMe) were dissolved in 2 ml of $CH_2Cl_2$, $CHCl_3$ or cyclohexane in a 10 ml cone-shaped flask. In control experiments, the mixture contained only the phospholipids (no dendron was added). The solvent was removed on a rotary evaporator at 20° C. under rapid spinning, making sure the lipid layer is uniformly dispersed on the flask walls. The residue was dried in vacuum for 2 hrs at 20° C. In some experiments the sample was gradually heated on a water bath up to 100° C., kept at 100° C. for 1 h and cooled back also gradually to 20° C. A 2 ml buffer solution consisting of 10 mM K2HPO4, 50mM KCl solution in water (pH 7.0) were added to the flask and the lipid was left to re-hydrate for 2 h at 20° C. For proton-jumps experiments, the buffer solution also contained a pH-sensitive membrane impermeable fluorescent dye (porphyrin-dendrimer H2P-$Glu^4OH$). The amount of dye in solution was adjusted so that the value of absorption in the Q-band maximum of the porphyrin ($\lambda max$=517 nm) was approximately 1.8-2.0 OD. Such high concentration was necessary to make sure that the fluorescence signal from the liposomes had sufficient intensity after removal of the excess untrapped dye. Following lipid re-hydration, the liposomes (average size 30 nm) were prepared by ultra-sonication using a microtip in pulsed mode (4×60, output 4:40%. sonicator Vibracell, Sonic & Materials. Inc.) with intermediate cooling of the mixture on ice. For DSC, CD and X-ray experiments the liposomes not containing dye, were dried under a flow of Argon at 20° C., while for proton jumps experiments the liposomes were purified from the outside dye on a Sephadex G200 (Sigma) column ($\phi$1.5 cm ×10 cm) with 2 cm layer of QAE Sepharose A50 (Pharmacia) anion-exchange resin at the bottom. Most of the dye was excluded by gel-filtration on Sephadex, while the remaining dye was captured by the resin. QAE A50 resin has a very high affinity to H2P-$Glu^4OH$ due to its polyanionic structure (FIG. 10).

Example 111

Liposomal Fluorescence Experiments

These experiments were conducted in accordance to Hamamatsu employing a Fluorolog-2 and R2658P PMT. The measurements were conducted using a standard 1 cm quartz cell, equipped with a stirrer and a pH mini-electrode. pH changes inside the vesicles after addition of small aliquots (10-15 μL) of acid (1M HCl) or base (1M KOH) (the amounts were pre-calibrated to produce approximately 1 pH jumps in 4.5 mL-cell volume) were monitored using right angle detection and ratio of fluorescence intensities at 647 and 670 nm. Gramicidin (0.4 μg/mL, final concentration) was added directly to the cell as the measurements progressed, from a stock solution in DMSO. The amount of DMSO added (5 μL) did not affect the proton permeability of the liposomes.

Calculation of Number of Channels per Vesicle

Molar and Mass Ratio of Dendron and Lipid

Referring to FIG. 5:
MW(Dendron)=1800 Da MW (Lipid)=650 Da
The lipid used was a mixture of many lipids with one phosphatidylcholine and two $C_{14}$ alkyls on average.
2 channels per vesicle intended
200 dendron molecules per 8000 lipid molecules~Molar Ratio 1:40

| Channels intended per vesicle | Molar Ratio (Dendron:Lipid) | Mass Ratio (Dendron:Lipid) |
|---|---|---|
| 4 | 1:20 | 1:7 |
| 2 | 1:40 | 1:14 |
| 1 | 1:80 | 1:30 |

The following references are considered relevant to an understanding of the inventive subject matter, and their inclusion for such purpose is not an admission that such documents are material to patentability of the claimed subject matter, nor an admission that such documents are prior art. Documents considered material to patentability will be separately identified by Information Disclosure Statement.

REFERENCES

Stang, P. J., Andreson, A. G., J. Org. Chem. 41, 3034-3036 (1976).
Cronin, J. S., Ginah, F. O., Murray, A. R., Copp, J. D., Synthetic Comm. 26, 3491-3494, (1996).
Percec, V., et al., J. Am. Chem. Soc. 120, 8619-8631, (1998).
Percec, V., Johansson, G., Ungar, G., Abramic, D., J. Chem. Soc. Perkin 1, 4, 447-450 (1994).
Weissflog, W., et al., Liq. Cryst. 5, 111-122, (1989).
Percec, V., et al., J. Am. Chem. Soc. 123, 1302-1315 (2001).
Percec, V., et al., J. Am. Chem. Soc. 122, 10273-10281 (2000).
Gacel, G., et al., J. Med. Chem. 24, 11191124 (1981).
Wardrop, D., Basak, A., Org. Lett. 3, 1053-1056 (2001).
Jang, W-D., et al., J. Am. Chem. Soc. 122, 3232-3233 (2000).
Turner, D. C., and Gruner, S. M., Biochemistry 31, 1340-1355(1992).
Rappolt, M., et al., Biophys. J. 84, 3111-3122 (2003).
Hudson, S. D. et al., Science 278, 449-452 (1997)
Balagurusamy, V. S. K., Ungar, G., Percec, V., Johansson, G., J. Am. Chem. Soc. 119, 1539-1555 (1997).
Percec, V., et al., Angew. Chem. Int .Ed. 42, 4338-4342 (2003).
Zeng, X., and Ungar, G., Polymer 39, 4523-4533 (1998).
Endres, A., et al., Rev. Sci. Instr. 68, 4009 (1997).
Ungar, G., Abramic, D., Percec, V. and Heck, J. A., Liq. Cryst. 21, 73 (1996).
Vainshtein, B. K. Diffraction of X-rays by chain molecules (Elsevier, New York 1966).
Percec, V., et al., Nature 419, 384-387(2002).
Fihikova, O. S., et al., J. Am. Chem. Soc. 125, 4882-4893 (2003).

Klug, A., From macromolecules to biological assemblies. Angew. Chem. Int. Ed. Engl.
Doyle, D. A. et al., The structure of the potassium channel: molecular basis of K$^+$
Murata, K. et al., Nature, 427, 36-44(2004).
Ishii, D. et al., Nature, 423, 628-632(2003).
Bayley, H. & Cremer, P. S., Stochastic sensors inspired by biology. Nature 413, 226-230(2001).
Fernandez-Lopez, S. et al., Nature 412, 452-455(2001).
Ghadiri, M. R., et al., Nature 366, 324-327(1993).
Schmitt, J.-L., et al., Helv. Chim. Acta 86, 1598-1624(2003).
22, 565-582(1983).
conduction and selectivity. Science 280, 69-77(1998).
Nature 407, 599-605(2000).
Lehn, J.-M., Supramolecular Chemistry. Concepts and Perspectives. (VCH, Weinheim, 1995) p. 118.
Bong, D. T., et al., Angew. Chem. Int. Ed. 40, 989-1011 (2001).
Hill, D. J., et al., Chem. Rev. 101, 3893-4011(2001).
Sakai, N. & Matile S., Chem. Commun. 2003, 2514-2523.
Percec, V. et al., Nature 391, 161-164(1998).
Percec, V. et al. Self-organization of supramolecular helical dendrimers into complex electronic materials. Nature 419, 384-387(2002).
Percec, V., et al. Synthesis and NaOTf mediated self-assembly of monodendritic crown-ethers. Chem. Eur. J. 8, 2011-2025(2002).
Hudson, et al., Science 278, 449-452(1997).
Percec, V., et al., J. Am. Chem. Soc. 123, 1302-1315(2001).
Nelson, J. C., et al., Science 277, 1793-1796(1997).
Brunsveld, L., et al., J. Am. Chem. Soc. 122, 6175-6182 (2000).
Chan, H. S., et al., Phil. Trans. R. Soc. Lond. B. 348, 61-70 (1995).
Engelkamp, H. et al., Science 284, 785-788(2001).
Hirschberg et al., Nature 407, 167-170(2000).
Balagurusamy, V. S. K. et al., J. Am. Chem. Soc.119, 1539-1555(1997).
Hummer, G., et al., Nature, 414, 188-190(2001).
Cornelissen, J. L. M et al. b-Helical polymers from isocyanopeptides. Science 293, 676-680(2001).
Rigaud et al., Biochim. Biophys. Acta 1231, 223-246(1995).
Ghadiri et al., Nature 369, 301-304(1994).
Finikova et al., J. Am. Chem. Soc. 125, 4882-4893(2003).
Emrick & Fréchet, Curr. Opin. Coll Interf. Sci.4,15-23 (1999).

The invention now being fully described, it will be apparent to one of ordinary skill in the art that many changes and modifications can be made thereto without departing from the spirit or scope of the invention as set forth herein.

What is claimed as novel and unobvious in United States Letters Patent is:

1. A pharmaceutical formulation comprising
an amphiphilic dendritic dipeptide, said amphiphilic dendritic dipeptide comprising at least one dipeptide having one or more of a naturally occurring or synthetic non-polar amino acid, a polar amino acid, an aromatic amino acid and/or a sulfur-containing amino acid; and a dendron, said dipeptide and said dendron being assembled into a pore-comprising amphiphilic dendritic dipeptide; and
a pharmaceutically acceptable carrier.

2. An encapsulation formulation comprising an amphiphilic dendritic dipeptide, said amphiphilic dendritic dipeptide comprising at least one dipeptide having one or more of a naturally occurring or synthetic non-polar amino acid, a polar amino acid, an aromatic amino acid and/or a sulfur-containing amino acid; and a dendron, said encapsulation formulation comprising a reverse encapsulation formulation.

3. The encapsulation formulation of claim 2, further comprising a pharmaceutically, veterinarily or agriculturally active agent(s).

4. The composition of claim 3, wherein the agent(s) comprise(s) an anti-viral, anti-bacterial and/or anti-fungal agent(s).

5. A stochastic sensor comprising an amphiphilic dendritic dipeptide, said amphiphilic dendritic dipeptide comprising at least one dipeptide having one or more of a naturally occurring or synthetic non-polar amino acid, a polar amino acid, an aromatic amino acid and/or a sulfur-containing amino acid; and a dendron.

6. A method for making an amphiphilic dendritic dipeptide, comprising
obtaining a dendron comprising one or more arms;
obtaining a dipeptide comprising a polar or non-polar amino acid(s) and/or an aromatic or sulfur-containing amino acid(s);
contacting the dendron and the dipeptide under conditions effective for operatively attaching the dipeptide to the dendron and allowing their self assembly into a pore-comprising amphiphilic dendritic dipeptide; and
allowing the pore-comprising amphiphilic dendritic dipeptide to self assemble into a synthetic trans-membrane channel, and
incorporating the dendritic dipeptide into a pharmaceutically, veterinarily or agriculturally active composition.

7. The method of claim 6, wherein the composition comprises an encapsulation composition.

8. The method of claim 7, wherein the composition comprises a reversible encapsulation composition.

9. A method for making an amphiphilic dendritic dipeptide, comprising
obtaining a dendron comprising one or more arms;
obtaining a dipeptide comprising a polar or non-polar amino acid(s) and/or an aromatic or sulfur-containing amino acid(s);
contacting the dendron and the dipeptide under conditions effective for operatively attaching the dipeptide to the dendron and allowing their self-assembly into a pore-comprising amphiphilic dendritic dipeptide; and
incorporating the dendritic dipeptide into a composition for stochastic sensing.

* * * * *